(12) United States Patent
Miwa et al.

(10) Patent No.: US 7,495,104 B2
(45) Date of Patent: Feb. 24, 2009

(54) QUINOLINE OR QUINAZOLINE DERIVATIVES INHIBITING AUTO-PHOSPHORYLATION OF FIBROBLAST GROWTH FACTOR RECEPTORS

(75) Inventors: Atsushi Miwa, Takasaki (JP); Tetsuya Yoshino, Takasaki (JP); Tatsushi Osawa, Gunma (JP); Teruyuki Sakai, Takasaki (JP); Toshiyuki Shimizu, Takasaki (JP); Yasunari Fujiwara, Shibuya-Ku (JP)

(73) Assignee: Kirin Beer Kabushiki Kaisha, Tokyo-to (JP)

( * ) Notice: Subject to any disclaimer, the term of this patent is extended or adjusted under 35 U.S.C. 154(b) by 172 days.

(21) Appl. No.: 10/491,898

(22) PCT Filed: Oct. 17, 2002

(86) PCT No.: PCT/JP02/10803

§ 371 (c)(1),
(2), (4) Date: Sep. 20, 2004

(87) PCT Pub. No.: WO03/033472

PCT Pub. Date: Apr. 24, 2003

(65) Prior Publication Data

US 2005/0049264 A1    Mar. 3, 2005

(30) Foreign Application Priority Data

Oct. 17, 2001  (JP) .............................. 2001-319826
Jun. 7, 2002   (JP) .............................. 2002-167652

(51) Int. Cl.
C07D 215/38  (2006.01)
C07D 239/72  (2006.01)
A61K 31/47   (2006.01)

(52) U.S. Cl. .................. 546/157; 546/163; 544/283; 514/312; 514/313; 514/257

(58) Field of Classification Search .......... 546/157, 546/163; 544/283; 514/312, 313, 258
See application file for complete search history.

(56) References Cited

U.S. PATENT DOCUMENTS 6,143,764 A  * 11/2000 Kubo et al. .............. 514/312
6,630,489 B1 * 10/2003 Crawley .................. 514/311
6,797,823 B1 *  9/2004 Kubo et al. .............. 544/287
6,821,987 B2 * 11/2004 Kubo et al. .............. 514/312

FOREIGN PATENT DOCUMENTS

| EP | 0 860 433 | 8/1998 |
|---|---|---|
| JP | 11-158149 | 6/1999 |
| JP | 2002-030083 | 1/2002 |
| WO | 96/09294 | 3/1996 |
| WO | 00/43366 | 7/2000 |
| WO | 01/21594 | 3/2001 |
| WO | 01/21596 | 3/2001 |
| WO | 02/32872 | 4/2002 |
| WO | 02/088110 | 11/2002 |

OTHER PUBLICATIONS

Yanong D. Wang, et al., "Inhibitors of Src Tyrosine Kinase: the preparation and structure-activity relationship of 4-anilino-3-cyanoquinolines and 4-anilinoquinazolines", Bioorganic & Medicinal Chemistry Letters, vol. 10, pp. 2477-2480, 2000.
U.S. Appl. No. 11/432,407, filed May 12, 2006, Sakai et al.
U.S. Appl. No. 10/491,898, filed Sep. 20, 2004, Miwa et al.
U.S. Appl. No. 10/491,898, filed Apr. 16, 2004, Miwa, et al.
U.S. Appl. No. 10/480,632, filed Dec. 22, 2003, Fujiwara, et al.
U.S. Appl. No. 10/168,392, filed Oct. 25, 2002, filed Sakai, et al.
Y. Wang, et al., "Inhibitors of Src Tyrosine Kinase: The Preparation and Structure-Activity Relationship of 4-Anilino-3-cyanoquinolines and 4-Anilinoquinazolines", Bioorganic & Medicinal Chemistry Letters, vol. 10, 2000, pp. 2477-2480.

* cited by examiner

Primary Examiner—D. Margaret Seaman
(74) Attorney, Agent, or Firm—Oblon, Spivak, McClelland, Maier & Neustadt, P.C.

(57) ABSTRACT

An objective of the present invention is to provide novel compounds which have inhibitory activity against autophosphorylation of an FGF receptor family and, when orally or intraveneously administered, can suppress the growth of cancer cells. The compounds of the present invention are represented by formula (I) or a pharmaceutically acceptable salt or solvate thereof:

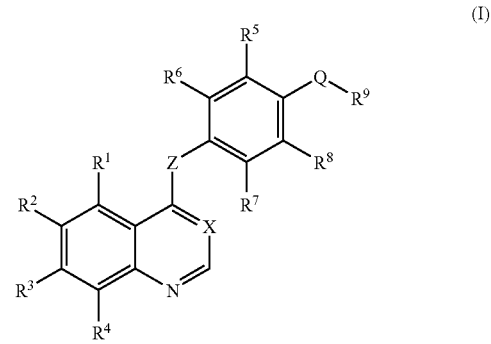

(I)

wherein X represents CH or N; Z represents O or S; Q represents $NR^{10}$, $CR^{11}R^2$, carbonyl, O, $S(=O)m$, wherein m is 0 to 2, or urea; $R^1$ to $R^3$ each independently represent H, OH, halogen, nitro, amino, alkyl, alkoxy or the like in which the alkyl and alkoxy groups are optionally substituted; $R^4$ represents H; $R^5$ to $R^8$ each independently represent H, halogen, alkyl, or alkoxy; and $R^9$ represents an optionally substituted carbocyclic or heterocyclic group.

21 Claims, No Drawings

QUINOLINE OR QUINAZOLINE DERIVATIVES INHIBITING AUTO-PHOSPHORYLATION OF FIBROBLAST GROWTH FACTOR RECEPTORS

BACKGROUND OF THE INVENTION

1. Field of the Invention

The present invention relates to quinoline derivatives and quinazoline derivatives which have antitumor activity. More particularly, the present invention relates to quinoline derivatives and quinazoline derivatives which have inhibitory activity against the autophosphorylation of fibroblast growth factor receptors and have inhibitory activity against abnormal cell proliferation.

2. Background Art

Growth factors such as epithelial growth factors, platelet-derived growth factors, insulin-like growth factors, and basic fibroblast growth factors (hereinafter abbreviated to "bFGF") play an important role in cell proliferation. Among others, bFGF is known to accelerate cell proliferation and migration of vascular endothelial cells, fibloblasts and the like, and is also known to be involved in angiogenesis and wound healing (Trends. Pharmacol. Sci. April; 22 (4): 201–7, 2001).

Further, the expression of bFGF, or FGFR1 (hereinafter referred to as "Flg"), FGFR2 (hereinafter referred to as "Bek") and the like belonging to a fibroblast growth factor receptor family is reported to be found in various cancers such as brain tumors, lung cancer, breast cancer, gastric cancer, head and neck cancer, and prostatic cancer (Proc. Natl. Acad. Sci. USA, 87: 5710–5714, 1990 Oncogene. 1997 Aug. 14; 15 (7): 817–26 Cancer Res. 1994 Jan. 15; 54 (2): 523–30. Cancer Res. 1992 Feb. 1; 52 (3): 571–7). In particular, it is reported for gastric cancer that overexpression of Bek correlates with poor prognosis mainly in poorly differentiated cancers such as scirrhus gastric cancers (Clin Cancer Res. 1996 August; 2 (8): 1373–81. J Cancer Res Clin Oncol. 2001 April; 127 (4): 207–16. Int Rev Cytol. 2001; 204: 49–95.).

There is a plurality of reports on small molecule compounds having inhibitory activity against the autophosphorylation of Flg (J Pharmacol Exp Ther. 1998 July; 286 (1): 569–77. Invest New Drugs. 1999; 17 (2): 121–35. Cancer Res. 2001 Feb. 15; 61 (4): 1464–8.). On the other hand, there is no report on compounds capable of inhibiting the autophosphorylation of Bek which is considered to be deeply involved in the progression of gastric cancer.

SUMMARY OF THE INVENTION

The present inventors have found that a certain group of quinoline derivatives and quinazoline derivatives have Bek-autophosphorylation inhibitory activity and, at the same time, have antitumor effect.

An object of the present invention is to provide compounds having potent antitumor activity, more specifically novel compounds which have inhibitory activity against the auto-phosphorylation of members of an FGF receptor family including Bek and, when orally or intraveneously administered, can suppress the growth of cancer cells.

According to the present invention, there is provided a compound represented by formula (I) or a pharmaceutically acceptable salt or solvate thereof:

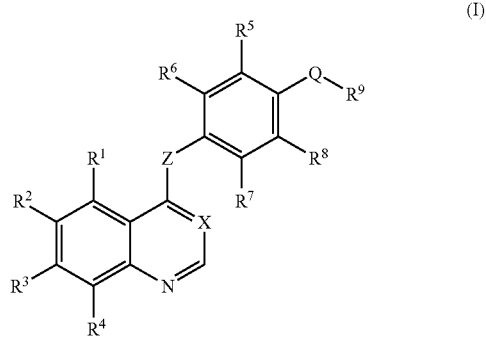

wherein
X represents CH or N;
Z represents O or S;
Q represents
—N(—$R^{10}$)— wherein $R^{10}$ represents a hydrogen atom or $C_{1-4}$ alkyl,
—C(—$R^{11}$)(—$R^{12}$)— wherein $R^{11}$ and $R^{12}$, which may be the same or different, represent a hydrogen atom or $C_{1-6}$ alkylcarbonyloxy,
—C(=O)—,
—O—,
—S(=O)m- wherein m is 0, 1, or 2, or
—NH—C(=O)—NH—;
$R^1$, $R^2$, and $R^3$, which may be the same or different, represent
a hydrogen atom,
hydroxyl,
a halogen atom,
nitro,
amino,
$C_{1-6}$ alkyl,
$C_{2-6}$ alkenyl,
$C_{2-6}$ alkynyl, or
$C_{1-6}$ alkoxy,
in which the $C_{1-6}$ alkyl, $C_{2-6}$ alkenyl, $C_{2-6}$ alkynyl, and $C_{1-6}$ alkoxy groups, which may be represented by $R^1$, $R^2$, and $R^3$, are optionally substituted by hydroxyl; a halogen atom; $C_{1-6}$ alkoxy; $C_{1-6}$ alkylcarbonyl; carboxyl; $C_{1-6}$ alkoxycarbonyl; —(C=O)—$NR^{14}R^{15}$ wherein $R^{14}$ and $R^{15}$, which may be the same or different, represent a hydrogen atom or $C_{1-4}$ alkyl optionally substituted by hydroxyl, or alternatively $R^{14}$ and $R^{15}$ may combine with the nitrogen atom attached thereto to form a saturated five- or six-membered heterocyclic group; amino in which one or two hydrogen atoms on the amino group are optionally substituted by $C_{1-6}$ alkyl or a saturated or unsaturated three- to eight-membered carbocyclic or heterocyclic group, and the $C_{1-6}$ alkyl group is optionally substituted by hydroxyl, $C_{1-6}$ alkoxy, or a saturated or unsaturated three- to eight-membered carbocyclic or heterocyclic group; or a saturated or unsaturated three- to eight-membered carbocyclic or heterocyclic group in which (i) the carbocyclic or heterocyclic group is optionally substituted by hydroxyl, an oxygen atom, $C_{1-6}$ alkyl, $C_{2-6}$ alkenyl, $C_{2-6}$ alkynyl, $C_{1-6}$ alkoxy, $C_{1-6}$ alkoxycarbonyl, or a saturated or unsaturated three- to eight-membered carbocyclic or heterocyclic group; the $C_{1-6}$ alkyl, $C_{2-6}$ alkenyl, and $C_{2-6}$ alkynyl groups are optionally substituted by hydroxyl, $C_{1-6}$ alkoxy, or a saturated or unsaturated three- to eight-membered carbocyclic or heterocyclic group; (ii) when the carbocyclic or heterocyclic group is substituted by two $C_{1-6}$ alkyl groups, the two alkyl groups may combine together to form an alkylene chain; and (iii) the carbocyclic or heterocyclic group may be condensed with another saturated or unsaturated five- to seven-membered carbocyclic or heterocyclic group to form a bicyclic group;

one or two hydrogen atoms on the amino group, which may be represented by $R^1$, $R^2$, and $R^3$, are optionally substituted by $C_{1-6}$ alkyl which is optionally substituted by hydroxyl or $C_{1-6}$ alkoxy;

$R^4$ represents a hydrogen atom;

$R^5$, $R^6$, $R^7$, and $R^8$, which may be the same or different, represent a hydrogen atom, a halogen atom, $C_{1-4}$ alkyl, $C_{1-4}$ alkoxy, nitro, or amino; and $R^9$ represents $C_{1-10}$ alkyl or a saturated or unsaturated three- to eight-membered carbocyclic or heterocyclic group in which the three- to eight-membered carbocyclic or heterocyclic group is optionally substituted by an oxygen atom, $C_{1-6}$ alkyl, $C_{2-6}$ alkenyl, $C_{2-6}$ alkynyl, $C_{1-6}$ alkoxy, a halogen atom, or a saturated or unsaturated three- to eight-membered carbocyclic or heterocyclic group, and the $C_{1-6}$ alkyl, $C_{2-6}$ alkenyl, $C_{2-6}$ alkynyl, and $C_{1-6}$ alkoxy groups are optionally substituted by a halogen atom or a saturated or unsaturated three- to eight-membered carbocyclic or heterocyclic group, provided that, when Q represents —C(=O)—, $R^2$ and $R^3$ do not simultaneously represent methoxy.

The compounds according to the present invention can be used for the theraphy and prophylaxis of a disease for which the inhibition of Bek-autophosphorylation is effective therapeutically or prophylactically.

DETAILED DESCRIPTION OF THE INVENTION

Compound

The terms "alkyl," "alkoxy," "alkenyl," and "alkynyl" as used herein as a group or a part of a group respectively mean straight chain or branched chain alkyl, alkoxy, alkenyl, and alkynyl.

$C_{1-6}$ alkyl is preferably $C_{1-4}$ alkyl.

$C_{1-6}$ alkoxy is preferably $C_{1-4}$ alkoxy.

$C_{2-6}$ alkenyl is preferably $C_{2-4}$ alkenyl.

$C_{2-6}$ alkynyl is preferably $C_{2-4}$ alkynyl.

Examples of $C_{1-6}$ alkyl include methyl, ethyl, n-propyl, isopropyl, n-butyl, i-butyl, s-butyl, t-butyl, n-pentyl, and n-hexyl.

Examples of $C_{1-6}$ alkoxy include methoxy, ethoxy, n-propoxy, i-propoxy, n-butoxy, i-butoxy, s-butoxy, and t-butoxy.

Examples of $C_{2-6}$ alkenyl include allyl, butenyl, pentenyl, and hexenyl.

Examples of $C_{2-6}$ alkynyl include 2-propynyl, butynyl, pentynyl, and hexynyl.

The expression "alkyl optionally substituted by" as used herein refers to alkyl, in which one or more hydrogen atoms on the alkyl group have been substituted by one or more substituents which may be the same or different, and unsubstituted alkyl. It will be apparent to a person having ordinary skill in the art that the maximum number of substituents may be determined depending upon the number of substitutable hydrogen atoms on the alkyl group. This is true of a group having a substituent other than the alkyl group.

The term "halogen atom" means a fluorine, chlorine, bromine, or iodine atom.

The saturated or unsaturated three- to eight-membered carbocyclic ring is preferably a four- to seven-membered, more preferably five- or six-membered, saturated or unsaturated carbocyclic ring. Examples of saturated or unsaturated three- to eight-membered carbocyclic rings include phenyl, cyclopropyl, cyclobutyl, cyclopentyl, cyclohexyl, and cycloheptyl.

The saturated or unsaturated three- to eight-membered heterocyclic ring contains at least one hetero-atom selected from oxygen, nitrogen, and sulfur atoms. The saturated or unsaturated three- to eight-membered heterocyclic ring preferably contains one, two or three hetero-atoms with the remaining ring-constituting atoms being carbon atoms. The saturated or unsaturated three- to eight-membered heterocyclic ring is preferably a saturated or unsaturated four- to seven-membered heterocyclic ring, more preferably a saturated or unsaturated five- or six-membered heterocyclic ring. Examples of saturated or unsaturated three- to eight-membered heterocyclic groups include thienyl, pyridyl, 1,2,3-triazolyl, thiazolyl, imidazolyl, isoxazolyl, pyrazolyl, piperazinyl, piperazino, piperidyl, piperidino, morpholinyl, morpholino, homopiperazinyl, homopiperazino, thiomorpholinyl, thiomorpholino, tetrahydropyrrolyl, and azepanyl.

The saturated or unsaturated carboxylic and heterocyclic groups may condense with another saturated or unsaturated five- to seven-membered carbocyclic or heterocyclic ring to form a bicyclic group, preferably a saturated or unsaturated nine- to twelve-membered bicyclic carbocyclic or heterocyclic group. Such bicyclic groups include naphthyl, quinolyl, 1,2,3,4-tetrahydroquinolyl, 1,4-benzoxanyl, indanyl, indolyl, 1,2,3,4-tetrahydronaphthyl, and phthalimide.

When the carbocyclic or heterocyclic group is substituted by two $C_{1-6}$ alkyl groups, the two alkyl groups may combine together to form an alkylene chain, preferably a $C_{1-3}$ alkylene chain. Carbocyclic or heterocyclic groups having this crosslinked structure include azabicyclo[2.2.2]octanyl, bicyclo[2.2.2]octanyl and norbornanyl.

$R^1$ preferably represents a hydrogen atom.

Preferably, $R^2$ and $R^3$ may be the same or different and represent a group other than a hydrogen atom.

More preferably, $R^2$ represents unsubstituted $C_{1-6}$ alkoxy, still more preferably unsubstituted methoxy, and $R^3$ represents hydroxyl or optionally substituted $C_{1-6}$ alkoxy, or alternatively $R^2$ represents hydroxyl or optionally substituted $C_{1-6}$ alkoxy and $R^3$ represents unsubstituted $C_{1-6}$ alkoxy, still more preferably unsubstituted methoxy.

$R^3$, and $R^{103}$ which will be described later preferably represent —O—(CH$_2$)p-$R^{13}$ wherein p is an integer of 0 to 6, —(CH$_2$)p- is optionally substituted by $C_{1-6}$ alkyl, hydroxyl, or a halogen atom, and $R^{13}$ represents a hydrogen atom; hydroxyl; a halogen atom; $C_{1-6}$ alkoxy; $C_{1-6}$ alkylcarbonyl; carboxyl; $C_{1-6}$ alkoxycarbonyl; —(C=O)—NR$^{14}$R$^{15}$ wherein $R^{14}$ and $R^{15}$, which may be the same or different, represent a hydrogen atom or $C_{1-4}$ alkyl optionally substituted by hydroxyl, or alternatively $R^{14}$ and $R^{15}$ may combine with the nitrogen atom attached thereto to form a saturated five- or six-membered heterocyclic group; amino in which one or two hydrogen atoms on the amino group are optionally substituted by $C_{1-6}$ alkyl or a saturated or unsaturated three- to eight-membered carbocyclic or heterocyclic group, and the $C_{1-6}$ alkyl group is optionally substituted by hydroxyl, $C_{1-6}$ alkoxy, or a saturated or unsaturated three- to eight-membered carbocyclic or heterocyclic group; or a saturated or unsaturated three- to eight-membered carbocyclic or heterocyclic group in which the carbocyclic or heterocyclic group is optionally substituted by hydroxyl, an oxygen atom, $C_{1-6}$ alkyl, $C_{2-6}$ alkenyl, $C_{2-6}$ alkynyl, $C_{1-6}$ alkoxy, $C_{1-6}$ alkoxycarbonyl, or a saturated or unsaturated three- to eight-membered carbocyclic or heterocyclic group; the $C_{1-6}$ alkyl, $C_{2-6}$ alkenyl, and $C_{2-6}$ alkynyl groups are optionally substituted by hydroxyl, $C_{1-6}$ alkoxy, or a saturated or unsaturated three- to eight-membered carbocyclic or heterocyclic group; when the carbocyclic or heterocyclic group is substituted by two $C_{1-6}$ alkyl groups, the two alkyl groups may combine together to form an alkylene chain; and the carbocyclic or heterocyclic group may be condensed with another saturated or unsaturated five- to seven-membered carbocyclic or heterocyclic group to form a bicyclic group. When p=0, —(CH$_2$)p- represents a bond.

All of $R^5$, $R^6$, $R^7$, and $R^8$ preferably represent a hydrogen atom, or any one or two of $R^5$, $R^6$, $R^7$, and $R^8$ represent a group other than a hydrogen atom with all the remaining groups representing a hydrogen atom.

$R^9$ preferably represents a saturated or unsaturated four- to seven-membered carbocyclic or heterocyclic group.

Preferred substituents of the carbocyclic or heterocyclic group represented by $R^9$ include an oxygen atom, $C_{1-4}$ alkyl, $C_{2-4}$ alkenyl, $C_{1-4}$ alkoxy, a halogen atom, or a saturated or unsaturated four- to seven-membered carbocyclic or heterocyclic group, and the $C_{1-4}$ alkyl, $C_{2-4}$ alkenyl, and $C_{1-4}$ alkoxy groups are optionally substituted by a halogen atom or saturated or unsaturated four- to seven-membered carbocyclic or heterocyclic group.

$R^9$, and $R^{109}$ which will be described later preferably represent phenyl of which the p-position is substituted by $C_{1-4}$ alkyl or a saturated or unsaturated four- to seven-membered carbocyclic or heterocyclic group.

$R^9$, and $R^{409}$ which will be described later preferably represent $C_{1-4}$ alkyl substituted by t-butyl; or a saturated five- to seven-membered carbocyclic group optionally substituted by one, two, or three of $C_{1-4}$ alkyl groups. The $C_{1-4}$ alkyl substituted by t-butyl preferably represents —(CH$_2$)t-$R^{51}$ wherein t is an integer of 1 to 4 and $R^{51}$ represents t-butyl.

When Q represents —NH—(C=O)—NH—, $R^9$ preferably represents $C_{1-4}$ alkyl substituted by t-butyl; or a saturated five- to seven-membered carbocyclic group optionally substituted by one, two, or three of $C_{1-4}$ alkyl groups.

Examples of preferred compounds according to the present invention include compounds represented by formula (100):

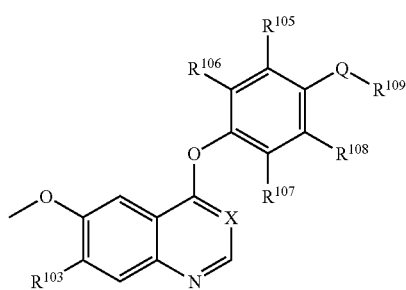

(100)

wherein

X represents CH or N;

Q represents

—N(—$R^{110}$)— wherein $R^{110}$ represents a hydrogen atom or $C_{1-4}$ alkyl, —C(—$R^{111}$)(—$R^{112}$)— wherein $R^{111}$ and $R^{112}$, which may be the same or different, represent a hydrogen atom or $C_{1-4}$ alkylcarbonyloxy, or

—O—;

$R^{103}$ represents hydroxyl or $C_{1-6}$ alkoxy in which the $C_{1-6}$ alkoxy group is optionally substituted by hydroxyl; a halogen atom; $C_{1-6}$ alkoxy; $C_{1-6}$ alkylcarbonyl; carboxyl; $C_{1-6}$ alkoxycarbonyl; —(C=O)—NR$^{14}$R$^{15}$ wherein R$^{14}$ and R$^{15}$, which may be the same or different, represent a hydrogen atom or $C_{1-4}$ alkyl optionally substituted by hydroxyl, or alternatively $R^{14}$ and $R^{15}$ may combine with the nitrogen atom attached thereto to form a saturated five- or six-membered heterocyclic group; amino in which one or two hydrogen atoms on the amino group are optionally substituted by $C_{1-6}$ alkyl or a saturated or unsaturated three- to eight-membered carbocyclic or heterocyclic group, and the $C_{1-6}$ alkyl group is optionally substituted by hydroxyl, $C_{1-6}$ alkoxy, or a saturated or unsaturated three- to eight-membered carbocyclic or heterocyclic group; or a saturated or unsaturated three- to eight-membered carbocyclic or heterocyclic group in which the carbocyclic or heterocyclic group is optionally substituted by hydroxyl, an oxygen atom, $C_{1-6}$ alkyl, $C_{2-6}$ alkenyl, $C_{2-6}$ alkynyl, $C_{1-6}$ alkoxy, $C_{1-6}$ alkoxycarbonyl, or a saturated or unsaturated three- to eight-membered carbocyclic or heterocyclic group; the $C_{1-6}$ alkyl, $C_{2-6}$ alkenyl, and $C_{2-6}$ alkynyl groups are optionally substituted by hydroxyl, $C_{1-6}$ alkoxy, or a saturated or unsaturated three- to eight-membered carbocyclic or heterocyclic group; when the carbocyclic or heterocyclic group is substituted by two $C_{1-6}$ alkyl groups, the two alkyl groups may combine together to form an alkylene chain; and the carbocyclic or heterocyclic group may be condensed with another saturated or unsaturated five- to seven-membered carbocyclic or heterocyclic group to form a bicyclic group;

all of $R^{105}$, $R^{106}$, $R^{107}$, and $R^{108}$ represent a hydrogen atom, or any one or two of $R^{105}$, $R^{106}$, $R^{107}$, and $R^{108}$ represent a halogen atom, $C_{1-4}$ alkyl, $C_{1-4}$ alkoxy, nitro, or amino with all the remaining groups representing a hydrogen atom; and $R^{109}$ represents a saturated or unsaturated four- to seven-membered carbocyclic or heterocyclic group in which the four- to seven-membered carbocyclic or heterocyclic group is optionally substituted by an oxygen atom, $C_{1-4}$ alkyl, $C_{2-4}$ alkenyl, $C_{1-4}$ alkoxy, a halogen atom, or a saturated or unsaturated four- to seven-membered carbocyclic or heterocyclic group, and the $C_{1-4}$ alkyl, $C_{2-4}$ alkenyl, and $C_{1-4}$ alkoxy groups are optionally substituted by a halogen atom or saturated or unsaturated four- to seven-membered carbocyclic or heterocyclic group.

Examples of more preferred compounds according to the present invention include compounds represented by formula (200):

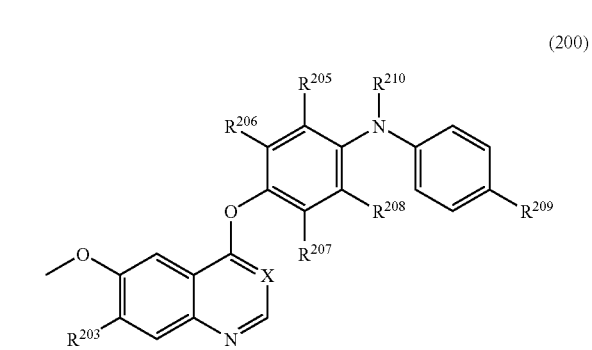

(200)

wherein

X represents CH or N;

$R^{203}$ represents —O—(CH$_2$)p-$R^{13}$ wherein p is an integer of 0 to 6, —(CH$_2$)p- is optionally substituted by $C_{1-6}$ alkyl, hydroxyl, or a halogen atom, and $R^{13}$ represents a hydrogen atom; hydroxyl; a halogen atom; $C_{1-6}$ alkoxy; $C_{1-6}$ alkylcarbonyl; carboxyl; $C_{1-6}$ alkoxycarbonyl; —(C=O)—NR$^{14}$R$^{15}$ wherein $R^{14}$ and $R^{15}$, which may be the same or different, represent a hydrogen atom or $C_{1-4}$ alkyl optionally substituted by hydroxyl, or alternatively $R^{14}$ and $R^{15}$ may combine with the nitrogen atom attached thereto to form a saturated five- or six-membered heterocyclic group; $C_{1-6}$ alkoxycarbonyl; amino in which one or two hydrogen atoms on the amino group are optionally substituted by $C_{1-6}$ alkyl or a saturated or unsaturated three- to eight-membered carbocyclic or heterocyclic group, and the $C_{1-6}$ alkyl group is optionally substituted by hydroxyl, $C_{1-6}$ alkoxy, or a saturated or unsaturated three- to eight-membered carbocyclic or heterocyclic group; or a saturated or unsaturated three- to eight-membered carbocyclic or heterocyclic group in which the carbocyclic or heterocyclic group is optionally substituted by hydroxyl, an oxygen atom, $C_{1-6}$ alkyl, $C_{2-6}$ alkenyl, $C_{2-6}$ alkynyl, $C_{1-6}$ alkoxy, $C_{1-6}$ alkoxycarbonyl, or a saturated or unsaturated three- to eight-membered carbocyclic or heterocyclic group; the $C_{1-6}$ alkyl, $C_{2-6}$ alkenyl, and $C_{2-6}$ alkynyl groups are optionally substituted by hydroxyl, $C_{1-6}$ alkoxy, or a saturated or unsaturated three- to eight-membered carbocyclic or heterocyclic group; when the carbocyclic or heterocyclic group is substituted by two $C_{1-6}$ alkyl groups, the two alkyl groups may combine together to form an alkylene chain; and the carbocyclic or heterocyclic group may be condensed with another saturated or unsaturated five- to seven-membered carbocyclic or heterocyclic group to form a bicyclic group;

all of $R^{205}$, $R^{206}$, $R^{207}$, and $R^{208}$ represent a hydrogen atom, or any one or two of $R^{205}$, $R^{206}$, $R^{207}$, and $R^{208}$ represent a halogen atom, $C_{1-4}$ alkyl, $C_{1-4}$ alkoxy, nitro, or amino with all the remaining groups representing a hydrogen atom; and $R^{209}$ represents $C_{1-4}$ alkyl or a saturated or unsaturated four- to seven-membered carbocyclic or heterocyclic group and $R^{210}$ represents a hydrogen atom or $C_{1-4}$ alkyl.

Examples of preferred compounds according to the present invention include compounds represented by formula (300):

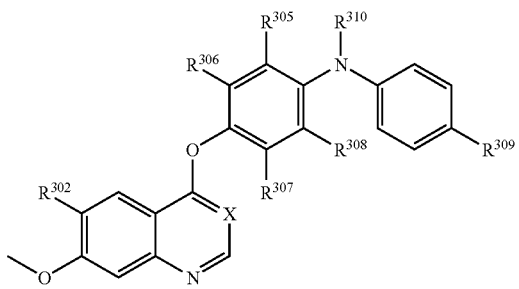

(300)

wherein

X represents CH or N;

$R^{302}$ represents —O—$(CH_2)$p-$R^{13}$ wherein p is an integer of 0 to 6, —$(CH_2)$p- is optionally substituted by $C_{1-6}$ alkyl, hydroxyl, or a halogen atom, and $R^{13}$ represents a hydrogen atom; hydroxyl; a halogen atom; $C_{1-6}$ alkoxy; $C_{1-6}$ alkylcarbonyl; carboxyl; $C_{1-6}$ alkoxycarbonyl; —(C=O)—$NR^{14}R^{15}$ wherein $R^{14}$ and $R^{15}$, which may be the same or different, represent a hydrogen atom or $C_{1-4}$ alkyl optionally substituted by hydroxyl, or alternatively $R^{14}$ and $R^{15}$ may combine with the nitrogen atom attached thereto to form a saturated five- or six-membered heterocyclic group; $C_{1-6}$ alkoxycarbonyl; amino in which one or two hydrogen atoms on the amino group are optionally substituted by $C_{1-6}$ alkyl or a saturated or unsaturated three- to eight-membered carbocyclic or heterocyclic group, and the $C_{1-6}$ alkyl group is optionally substituted by hydroxyl, $C_{1-6}$ alkoxy, or a saturated or unsaturated three- to eight-membered carbocyclic or heterocyclic group; or a saturated or unsaturated three- to eight-membered carbocyclic or heterocyclic group in which the carbocyclic or heterocyclic group is optionally substituted by hydroxyl, an oxygen atom, $C_{1-6}$ alkyl, $C_{2-6}$ alkenyl, $C_{2-6}$ alkynyl, $C_{1-6}$ alkoxy, $C_{1-6}$ alkoxycarbonyl, or a saturated or unsaturated three- to eight-membered carbocyclic or heterocyclic group; the $C_{1-6}$ alkyl, $C_{2-6}$ alkenyl, and $C_{2-6}$ alkynyl groups are optionally substituted by hydroxyl, $C_{1-6}$ alkoxy, or a saturated or unsaturated three- to eight-membered carbocyclic or heterocyclic group; when the carbocyclic or heterocyclic group is substituted by two $C_{1-6}$ alkyl groups, the two alkyl groups may combine together to form an alkylene chain; and the carbocyclic or heterocyclic group may be condensed with another saturated or unsaturated five- to seven-membered carbocyclic or heterocyclic group to form a bicyclic group;

all of $R^{305}$, $R^{306}$, $R^{307}$, and $R^{308}$ represent a hydrogen atom, or any one or two of $R^{305}$ $R^{306}$ $R^{307}$ and $R^{308}$ represent a halogen atom, $C_{1-4}$ alkyl, $C_{1-4}$ alkoxy, nitro, or amino with all the remaining groups representing a hydrogen atom; and $R^{309}$ represents $C_{1-4}$ alkyl or a saturated or unsaturated four- to seven-membered carbocyclic or heterocyclic group and $R^{310}$ represents a hydrogen atom or $C_{1-4}$ alkyl.

Examples of preferred compounds according to the present invention include compounds represented by formula (400):

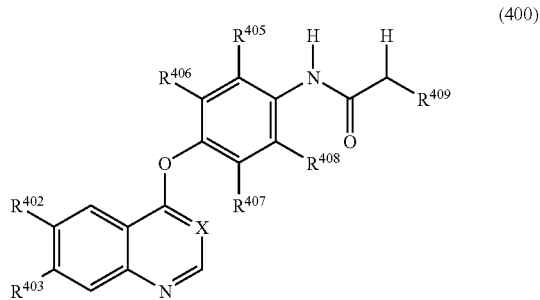

(400)

wherein

X represents CH or N;

$R^{402}$ and $R^{403}$, which may be the same or different, represent —O—$(CH_2)$p-$R^{13}$ wherein p is an integer of 0 to 6, —$(CH_2)$p- is optionally substituted by $C_{1-6}$ alkyl, hydroxyl, or a halogen atom, and $R^{13}$ represents a hydrogen atom; hydroxyl; a halogen atom; $C_{1-6}$ alkoxy; $C_{1-6}$ alkylcarbonyl; carboxyl; $C_{1-6}$ alkoxycarbonyl; —(C=O)—$NR^{14}R^{15}$ wherein $R^{14}$ and $R^{15}$, which may be the same or different, represent a hydrogen atom or $C_{1-4}$ alkyl optionally substituted by hydroxyl, or alternatively $R^{14}$ and $R^{15}$ may combine with the nitrogen atom attached thereto to form a saturated five- or six-membered heterocyclic group; $C_{1-6}$ alkoxycarbonyl; amino in which one or two hydrogen atoms on the amino group are optionally substituted by $C_{1-6}$ alkyl or a saturated or unsaturated three- to eight-membered carbocyclic or heterocyclic group, and the $C_{1-6}$ alkyl group is optionally substituted by hydroxyl, $C_{1-6}$ alkoxy, or a saturated or unsaturated three- to eight-membered carbocyclic or heterocyclic group; or a saturated or unsaturated three- to eight-membered carbocyclic or heterocyclic group in which the carbocyclic or heterocyclic group is optionally substituted by hydroxyl, an oxygen atom, $C_{1-6}$ alkyl, $C_{2-6}$ alkenyl, $C_{2-6}$ alkynyl, $C_{1-6}$ alkoxy, $C_{1-6}$ alkoxycarbonyl, or a saturated or unsaturated three- to eight-membered carbocyclic or heterocyclic group; the $C_{1-6}$ alkyl, $C_{2-6}$ alkenyl, and $C_{2-6}$ alkynyl groups are optionally substituted by hydroxyl, $C_{1-6}$ alkoxy, or a saturated or unsaturated three- to eight-membered carbocyclic or heterocyclic group; when the carbocyclic or heterocyclic group is substituted by two $C_{1-6}$ alkyl groups, the two alkyl groups may combine together to form an alkylene chain; and the carbocyclic or heterocyclic group may be condensed with another saturated or unsaturated five- to seven-membered carbocyclic or heterocyclic group to form a bicyclic group;

all of $R^{405}$, $R^{406}$, $R^{407}$, and $R^{408}$ represent a hydrogen atom, or any one or two of $R^{405}$, $R^{406}$, $R^{407}$, and $R^{408}$ represent a halogen atom, $C_{1-4}$ alkyl, $C_{1-4}$ alkoxy, nitro, or amino with all the remaining groups representing a hydrogen atom; and $R^{409}$ represents $C_{1-4}$ alkyl substituted by t-butyl; or a saturated five- to seven-membered carbocyclic group optionally substituted by one, two, or three of $C_{1-4}$ alkyl groups.

Preferably, any one of $R^{402}$ and $R^{403}$ represents unsubstituted alkoxy, and the other represents a group other than unsubstituted alkoxy.

Examples of preferred compounds according to the present invention include compounds described in working examples.

Particularly preferred compounds according to the present invention include compounds 37, 59, 70, 71, 79, 81, and 102 described in working examples.

The compounds according to the present invention may form pharmaceutically acceptable salts thereof. Preferred examples of such salts include: alkali metal or alkaline earth metal salts such as sodium salts, potassium salts or calcium salts; hydrohalogenic acid salts such as hydrofluoride salts, hydrochloride salts, hydrobromide salts, or hydroiodide salts; inorganic acid salts such as nitric acid salts, perchloric acid salts, sulfuric acid salts, or phosphoric acid salts; lower alkylsulfonic acid salts such as methanesulfonic acid salts, trifluoromethanesulfonic acid salts, or ethanesulfonic acid salts; arylsulfonic acid salts such as benzenesulfonic acid salts or p-toluenesulfonic acid salts; organic acid salts such as fumaric acid salts, succinic acid salts, citric acid salts, tartaric acid salts, oxalic acid salts, maleic acid salts, acetic acid salts, malic acid salts, lactic acid salts, or ascorbic acid salts; and amino acid salts such as glycine salts, phenylalanine salts, glutamic acid salts, or aspartic acid salts.

The compounds according to the present invention may form solvates. Such solvates include, for example, hydrates, alcoholates, for example, methanolates and ethanolates, and etherates, for example, diethyl etherate.

Production of Compounds

Compounds according to the present invention may be produced, for example, according to schemes 1 to 14. Starting compounds necessary for the synthesis of the compounds according to the present invention are commercially available or alternatively can be easily produced by conventional methods. In the schemes, $R^1$ to $R^{10}$ are as defined in formula (I).

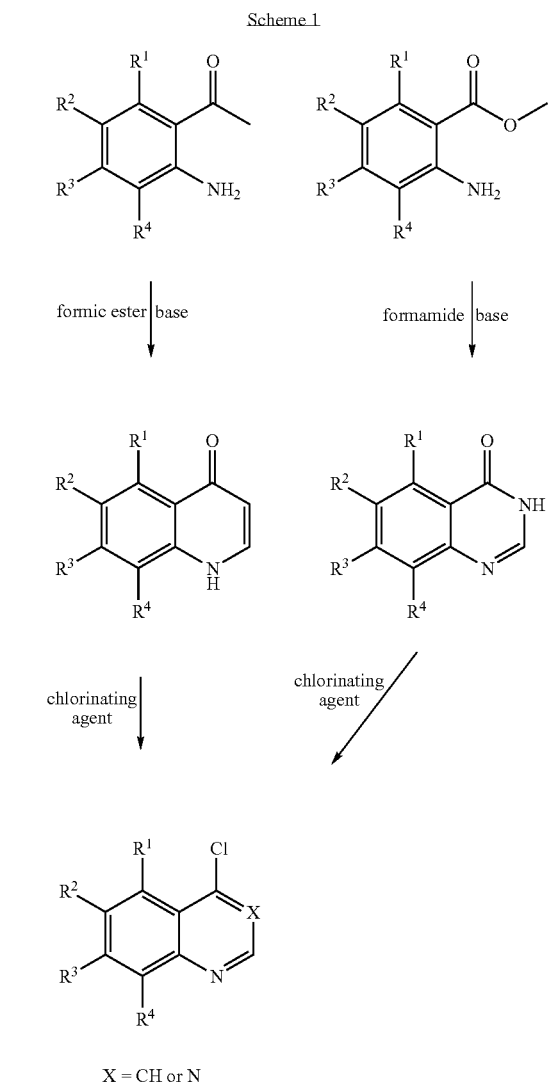

For example, a 4-chloroquinoline derivative can be synthesized by a conventional method as described, for example, in Org. Synth. Col. Vol. 3, 272 (1955), Acta Chim. Hung., 112, 241 (1983), or WO 98/47873. Scheme 1 shows an example of the synthesis of the 4-chloroquinoline derivative. A quinolone derivative is produced by reacting a 2-aminoacetophenone derivative with a formic ester, for example, ethyl formate, in a suitable solvent, for example, tetrahydrofuran, in the presence of a base, for example, sodium methoxide. The 4-chloroquinoline derivative is produced by reacting the quinolone derivative in the presence of a chlorinating agent, for example, phosphorus oxychloride.

For example, a 4-chloroquinazoline derivative can be produced as follows. A quinazolone derivative is produced by reacting a 2-amino-benzoate acid derivative with formamide in a suitable solvent, for example, a mixed solvent composed of N,N-dimethylformamide and methanol, in the presence of a base, for example, sodium methoxide. The 4-chloroquinazoline derivative is produced by reacting the quinazolone derivative in the presence of a chlorinating agent, for example, phosphorus oxychloride.

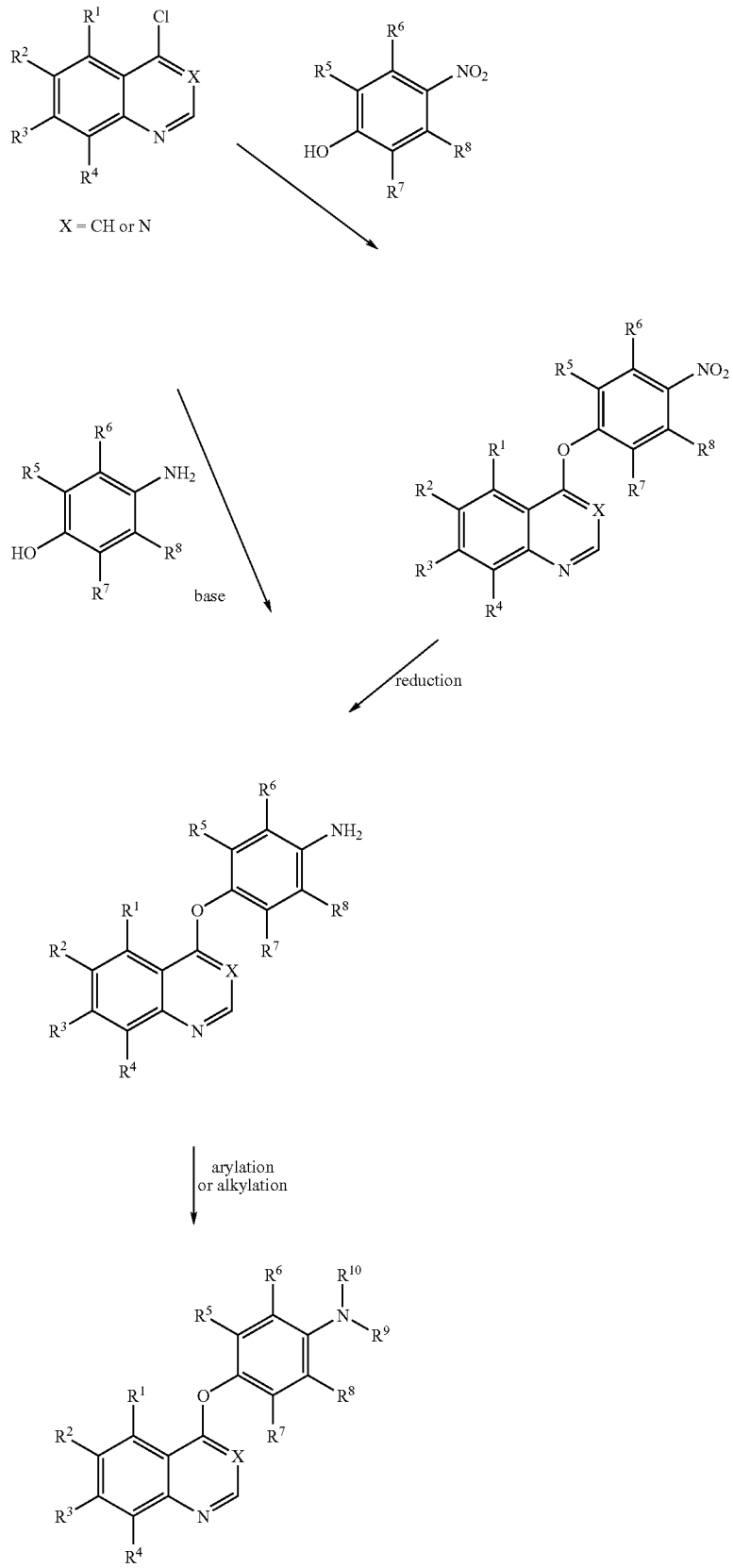
Scheme 2

A 4-(aminophenoxy)quinoline derivative or a corresponding quinazoline derivative is produced by reacting a nitrophenol derivative with the 4-chloroquinoline derivative or corresponding quinazoline derivative in a suitable solvent, for example, chlorobenzene, to synthesize a 4-(nitrophenoxy)quinoline derivative or a corresponding quinazoline derivative and then reacting the 4-(nitrophenoxy)quinoline derivative or corresponding quinazoline derivative in a suitable solvent, for example, N,N-dimethyl formamide, in the presence of a catalyst, for example, palladium hydroxide-carbon or palladium-carbon, under a hydrogen atmosphere. The nitro group can also be reduced with zinc, iron or the like.

Alternatively, the 4-(aminophenoxy)quinoline derivative or corresponding quinazoline derivative can be produced by reacting an aminophenol derivative with the 4-chloroquinoline derivative or corresponding quinazoline derivative in a suitable solvent, for example, dimethyl sulfoxide, in the presence of a base, for example, sodium hydride. Alternatively, the 4-(aminophenoxy)quinoline derivative can also be produced by dissolving an aminophenol derivative in an aqueous sodium hydroxide solution and subjecting the solution to a two-phase reaction with a solution of the 4-chloroquinazoline derivative in a suitable organic solvent, for example, ethyl methyl ketone, in the presence of a phase transfer catalyst, for example, tetra-n-butylammonium chloride, or in the absence of the catalyst.

The corresponding aniline derivative can be produced by subjecting an anilino group in a 4-(aminophenoxy)quinoline derivative or a quinazoline derivative to arylation under suitable conditions (e.g., mixed solvent in the presence of copper (II) acetate) or alkylation under suitable conditions (e.g., condensing the anilino group with a ketone derivative in N,N-dimethylformamide and then reacting the condensate with sodium borohydride acetate).

A quinoline derivative or a corresponding quinazoline derivative having a hydroxyl group at its 6- or 7-position can be produced by dissolving a 6,7-dimethoxy-4-(nitrophenoxy)quinoline derivative or a corresponding quinazoline derivative in a suitable solvent (for example, chloroform) and heating the solution under reflux in the presence of a suitable Lewis acid (for example, aluminum trichloride). A 4-(nitrophenoxy)quinoline derivative or corresponding quinazoline derivative containing a specific substituent introduced at its 6- or 7-position can be produced by introducing a desired substituent into the introduced hydroxyl group, or by protecting the hydroxyl group with a protective group. The hydroxyl group can be protected by reacting an unpurified solid of the derivative with benzyl chloride in N,N-dimethylformamide in the presence of potassium carbonate and then conducting separation and purification.

Scheme 3

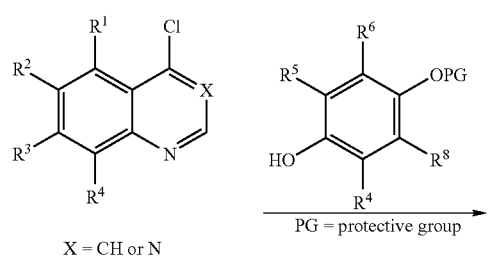

X = CH or N

PG = protective group

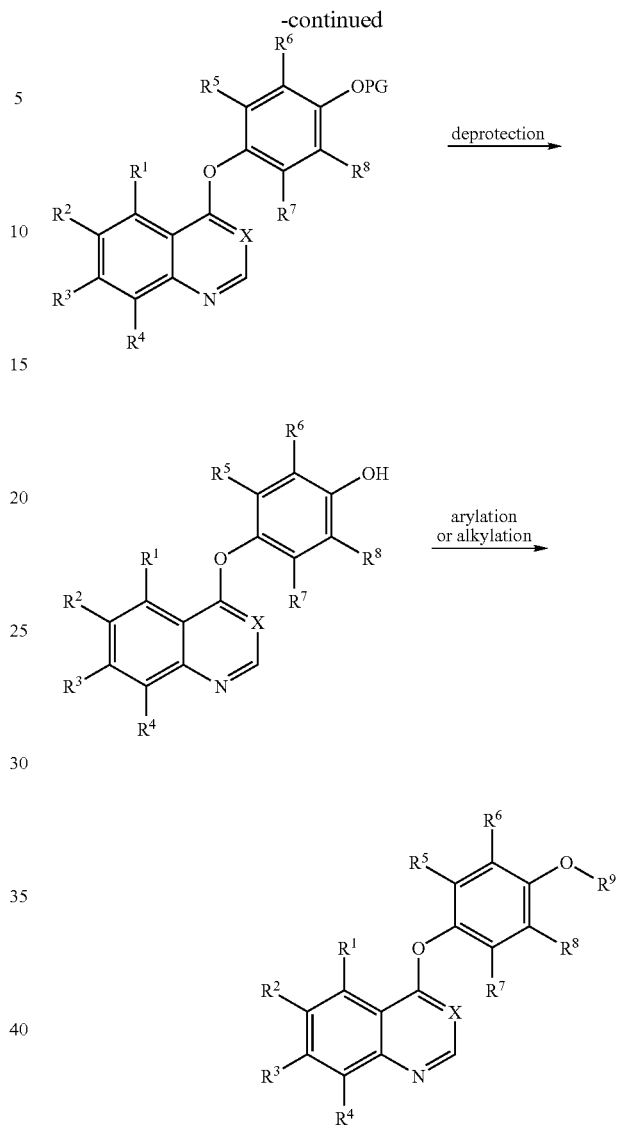

A 4-(hydroxyphenoxy)quinoline derivative or a corresponding quinazoline derivative is produced by reacting a phenol derivative with the 4-chloroquinoline derivative or corresponding quinazoline derivative in a suitable solvent, for example, chlorobenzene, to synthesize a 4-phenoxyquinoline derivative or a corresponding quinazoline derivative and then removing the protective group of the hydroxyl group under suitable conditions (for example, when the protective group is benzyl, for example, a reaction is allowed to proceed in N,N-dimethylformamide in the presence of palladium hydroxide-carbon or palladium-carbon in a hydrogen atmosphere). A corresponding ether derivative is produced by subjecting a hydroxy group in the 4-(hydroxyphenoxy)quinoline derivative or quinazoline derivative to arylation under suitable conditions (e.g., reacting the hydroxy group with an aryl borate derivative in a chloroform-triethylamine mixed solvent in the presence of copper(II) acetate) or alkylation under suitable conditions (e.g., reacting the hydroxy group with an alkyl halide in N,N-dimethylformamide in the presence of potassium carbonate.

Scheme 4

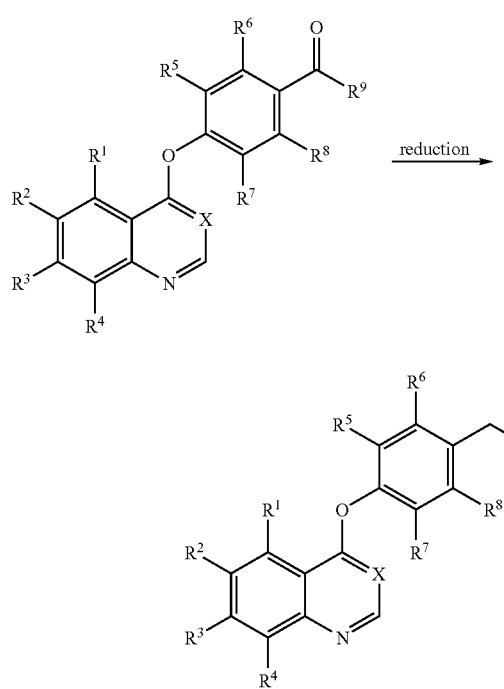

A corresponding ketone derivative is produced by reacting an acylphenol derivative with a 4-chloroquinoline derivative or a corresponding quinazoline derivative in a suitable solvent (for example, chlorobenzene). A corresponding methylene derivative is produced by reducing the carbonyl group in the ketone derivative under suitable conditions. The acylphenol derivative is commercially available or can easily be produced by a conventional method. For example, an acyl-containing phenol derivative is produced by reacting a phenol derivative containing a protective hydroxyl group with an acid chloride derivative in a suitable solvent (for example, nitromethane) in the presence of a Lewis acid (for example, ytterbium(III) triflate), and a corresponding acylphenol derivative is produced by further removing the protective group of the hydroxyl group under suitable conditions.

Scheme 5

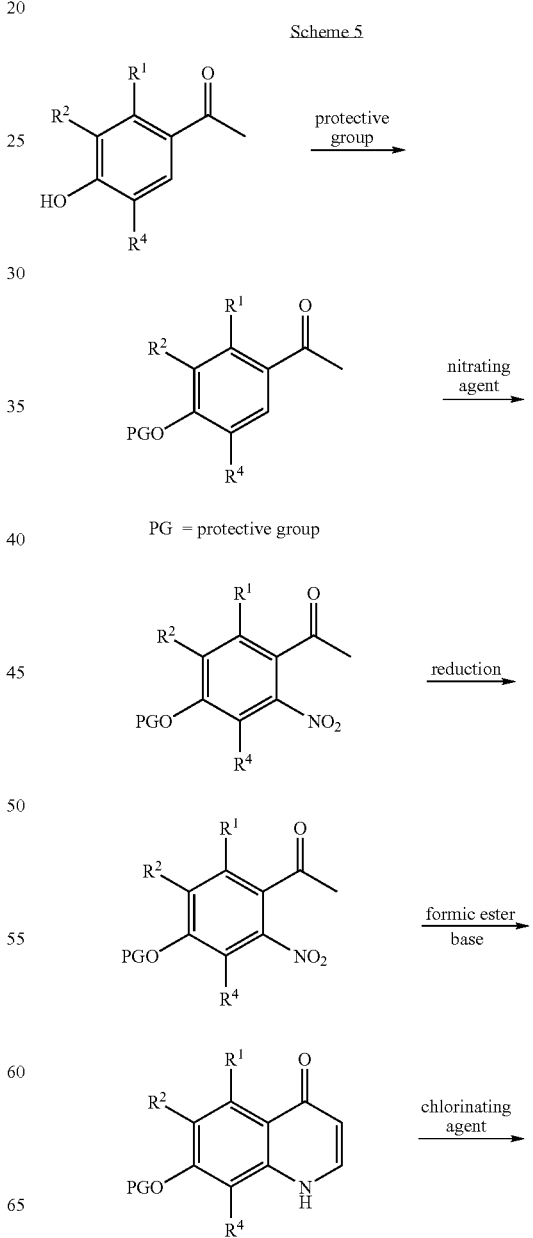

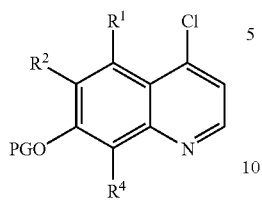

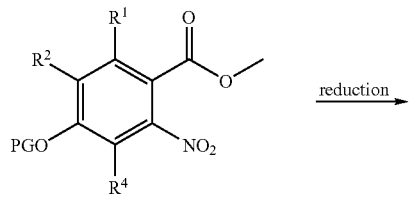

For example, an intermediate for synthesizing a derivative having a specific substituent at the 7-position of the quinoline ring can be produced according to scheme 5. A nitro group can be introduced by protecting a commercially available 4'-hydroxyacetophenone derivative with a suitable substituent, for example, benzyl, and then reacting the protected 4'-hydroxyacetophenone derivative with a nitrating agent, for example, fuming nitric acid-acetic acid. The later steps of scheme 5 are carried out as shown in scheme 1. Specifically, the nitro group is reduced to an amino group which is then reacted with a formic ester in the presence of a base to give a quinolone ring. Next, the quinolone ring is reacted with a chlorinating agent to give a 4-chloroquinoline derivative. In the chlorination reaction, when phosphorus oxychloride is used as the chlorinating agent, the yield can be improved by adding a base, for example, N,N-diisopropylethylamine.

An intermediate for synthesizing a derivative having a specific substituent at the 6-position of the quinoline ring can be produced by using a 3'-hydroxyacetophenone derivative instead of the 4'-hydroxyacetophenone derivative.

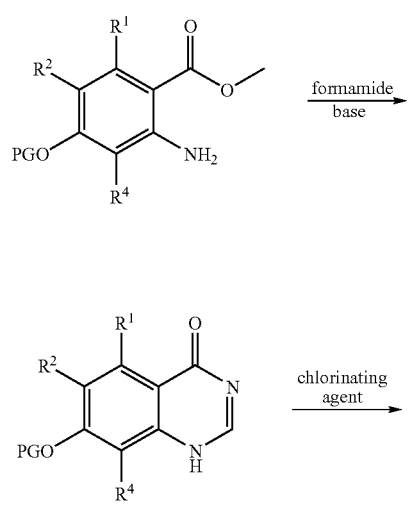

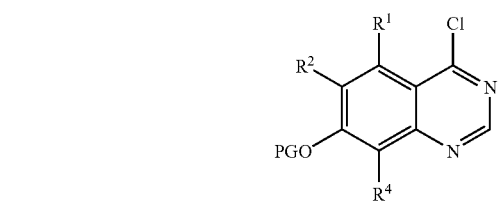

Scheme 6

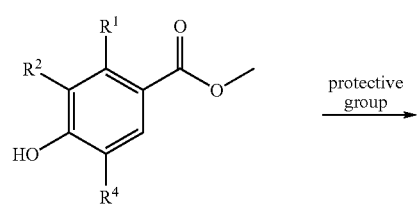

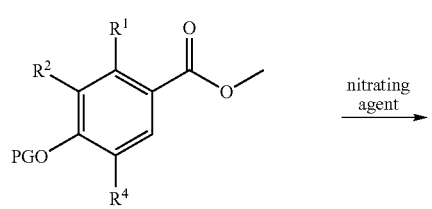

PG = protective group

For example, an intermediate for synthesizing a derivative having a specific substituent at the 7-position of the quinazoline ring can be produced according to scheme 6. A nitro group can be introduced by protecting a hydroxyl group in a commercially available 4'-hydroxybezoic ester derivative with a suitable substituent, for example, benzyl, and then reacting the product with a nitrating agent, for example, fuming nitric acid-acetic acid. The later steps of scheme 6 are carried out as shown in scheme 1. Specifically, a quinazolone ring is formed by reducing the nitro group to an amino group and then reacting the product with formamide in the presence of a base. Next, a 4-chloroquinazoline derivative can be produced by reacting the product with a chlorinating agent. In the chlorination reaction, when phosphorus oxychloride is used as a chlorinating agent, the addition of a base, for example, N,N-diisopropylethylamine can improve the yield.

An intermediate for synthesizing a derivative having a specific substituent at the 6-position of the quinazoline ring can be produced by using a 3'-hydroxybenozic ester derivative instead of the 4'-hydroxybenzoic ester derivative.

Scheme 7
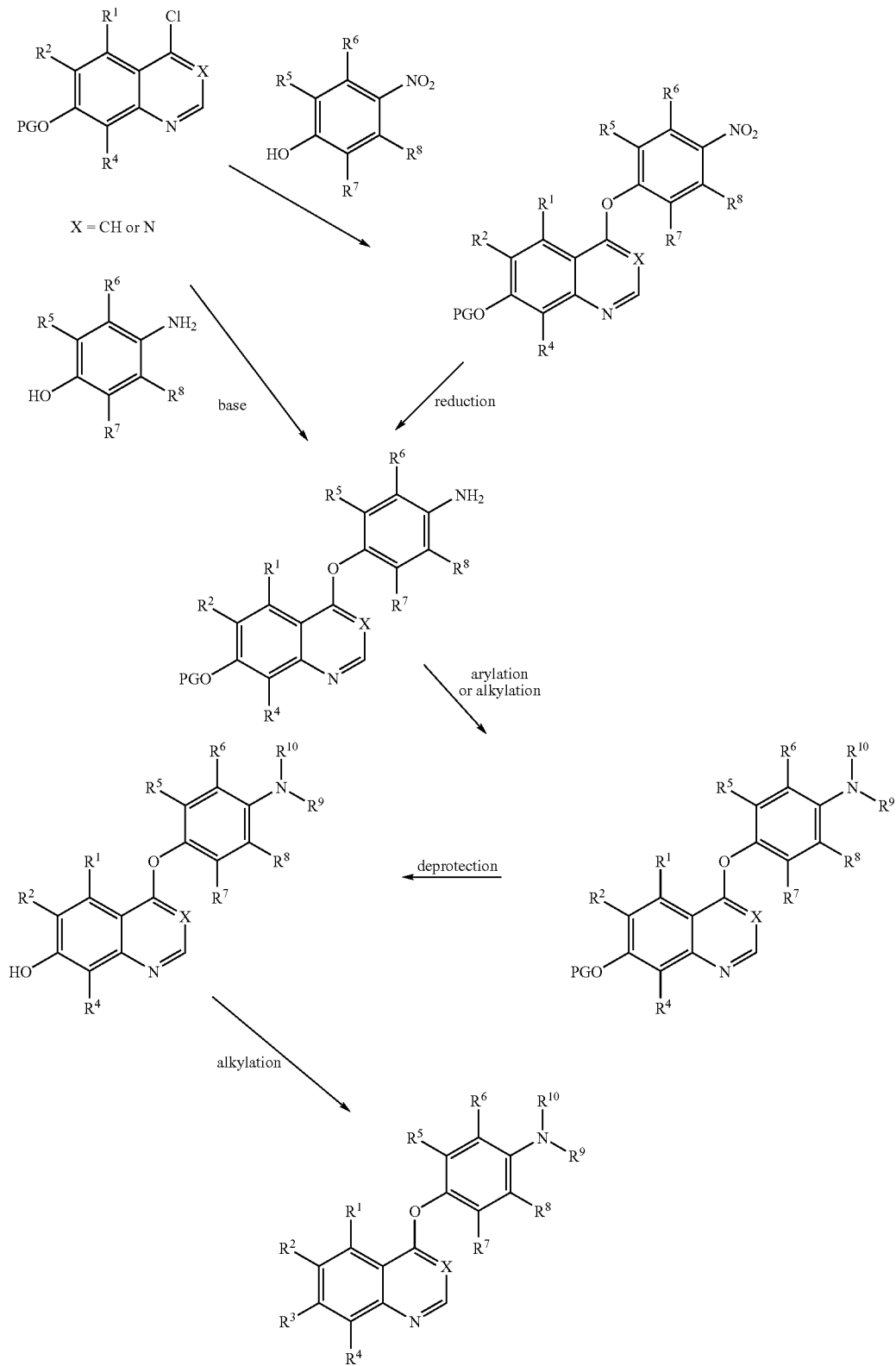
$R^3$ = optionally substituted $C_{1-6}$ alkoxy

An aniline derivative having a specific substituent at the 7-position of the quinoline or quinazoline ring can be produced, for example, according to scheme 7. Specifically, a 4-(aminophenoxy)quinoline derivative or a corresponding quinazoline derivative is produced by reacting the 4-chloroquinoline derivative or quinazoline derivative produced in scheme 5 or scheme 6 with a nitrophenol derivative in a suitable solvent, for example, chlorobenzene, to synthesize a 4-(nitrophenoxy)quinoline derivative or a corresponding quinazoline derivative and then reacting the 4-(nitrophenoxy) quinoline derivative or corresponding quinazoline derivative in a suitable solvent, for example, N,N-dimethyl formamide, in the presence of a catalyst, for example, palladium hydroxide-carbon or palladium-carbon, under a hydrogen atmosphere. The nitro group can also be reduced with zinc, iron or the like. Alternatively, the 4-(aminophenoxy)quinoline derivative or corresponding quinazoline derivative may be produced by reacting an aminophenol derivative with the 4-chloroquinoline derivative or corresponding quinazoline derivative in a suitable solvent, for example, dimethyl sulfoxide, in the presence of a base, for example, sodium hydride. Alternatively, the 4-(aminophenoxy)quinazoline derivative may also be produced by dissolving an aminophenol derivative in an aqueous sodium hydroxide solution and subjecting the solution to a two-phase reaction with a solution of the 4-chloroquinazoline derivative in a suitable organic solvent, for example, ethyl methyl ketone, in the presence of a phase transfer catalyst, for example, tetra-n-butylammonium chloride, or in the absence of the catalyst. A corresponding aniline derivative, in which the hydroxyl group at the 7-position of quinoline or quinazoline has been protected, is produced by subjecting an anilino group in a 4-(aminophenoxy)quinoline derivative or a quinazoline derivative to arylation under suitable conditions (e.g., reacting the anilino group with an aryl borate derivative in a chloroform-triethylamine mixed solvent in the presence of copper(II) acetate) or alkylation under suitable conditions (e.g., condensing the anilino group with a ketone derivative in N,N-dimethylformamide and then reacting the condensate with sodium borohydride acetate). A 7-hydroxyquinoline derivative or a corresponding 7-hydroxyquinazoline derivative is produced by removing the protective group of the hydroxyl group in the aniline derivative under suitable conditions (for example, when the protective group is benzyl, for example, a reaction is allowed to proceed in N,N-dimethylformamide in the presence of palladium hydroxide-carbon or palladium-carbon in a hydrogen atmosphere). Next, an aniline derivative having a specific substituent at the 7-position of the quinoline or quinazoline ring is produced by alkylating the 7-hydroxyquinoline derivative or corresponding 7-hydroxyquinazoline derivative under suitable conditions (e.g., reacting the derivative with an alkyl halide in N,N-dimethylformamide in the presence of potassium carbonate).

A method for synthesizing the compound according to the present invention having a substituent at the 7-position of the quinoline ring or the quinazoline ring is disclosed in scheme 7. When a quinoline derivative or quinazoline derivative containing a protective group introduced into its 6-position is used as a starting compound, the compound according to the present invention having a substituent at the 6-position of the quinoline ring or quinazoline ring can be synthesized. The quinoline derivative or quinazoline derivative containing a protective group introduced at the 6-position to be used as the starting compound can be synthesized, for example, according to scheme 18 which will be described later.

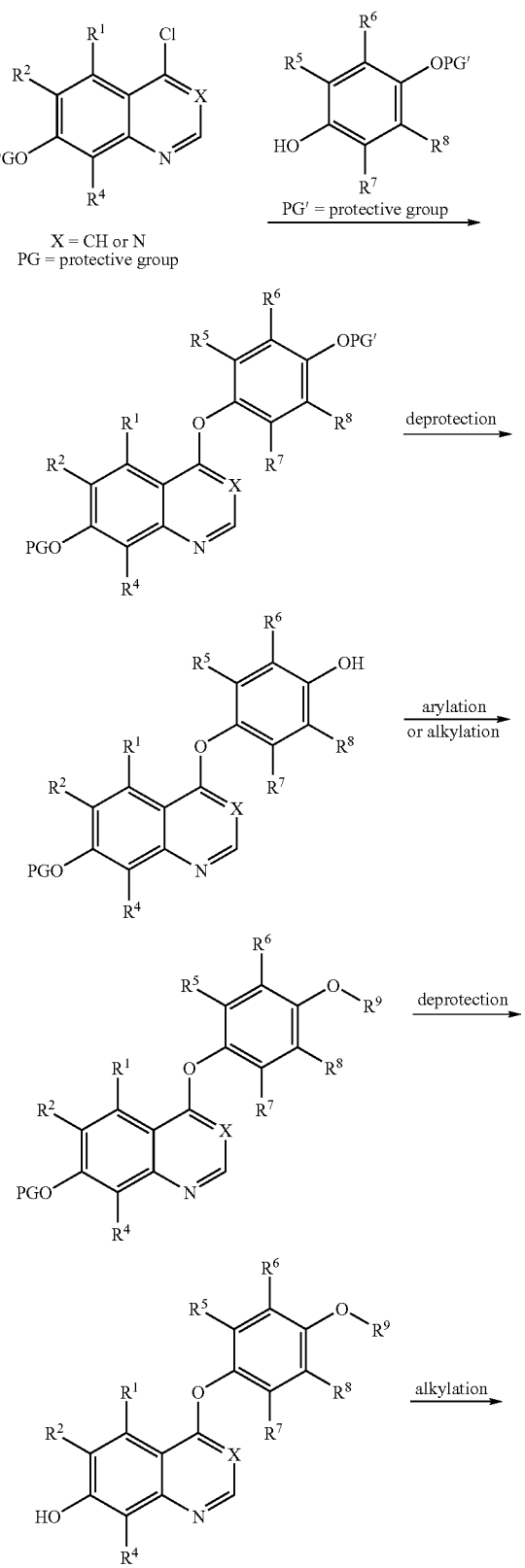

-continued

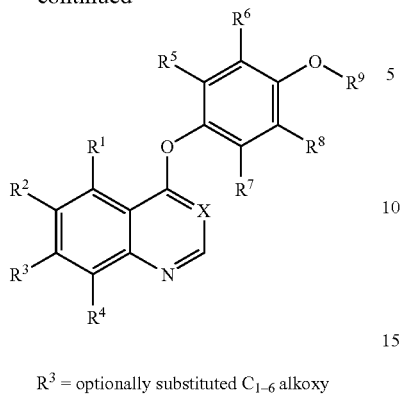

R³ = optionally substituted C₁₋₆ alkoxy

An ether derivative having a specific substituent at the 7-position of the quinoline ring or quinazoline ring can be produced, for example, according to scheme 8. Specifically, a 4-(hydroxyphenoxy)quinoline derivative or a corresponding quinazoline derivative is produced by reacting a phenol derivative with the 4-chloroquinoline derivative or quinazoline derivative produced in scheme 5 or 6 in a suitable solvent, for example, chlorobenzene, to synthesize a 4-phenoxyquinoline derivative or a corresponding quinazoline derivative and then removing the protective group of the hydroxyl group under suitable conditions (for example, when the protective group is benzyl, for example, a reaction is allowed to proceed in N,N-dimethylformamide in the presence of palladium hydroxide-carbon or palladium-carbon in a hydrogen atmosphere). A corresponding ether derivative having a protected hydroxyl group at the 7-position of quinoline or quinazoline is produced by subjecting a hydroxy group in the 4-(hydroxyphenoxy)quinoline derivative or quinazoline derivative to arylation under suitable conditions (e.g., reacting the hydroxy group with an aryl borate derivative in a chloroform-triethylamine mixed solvent in the presence of copper(II) acetate) or alkylation under suitable conditions (e.g., reacting the hydroxy group with an alkyl halide in N,N-dimethylformamide in the presence of potassium carbonate). A 7-hydroxyquinoline derivative or a corresponding 7-hydroxyquinazoline derivative is produced by removing the protective group of the hydroxyl group in the ether derivative under suitable conditions (for example, when the protective group is benzyl, for example, a reaction is allowed to proceed in N,N-dimethylformamide in the presence of palladium hydroxide-carbon or palladium-carbon in a hydrogen atmosphere). Next, an ether derivative having a specific substituent at the 7-position of the quinoline or quinazoline ring is produced by alkylating the 7-hydroxyquinoline derivative or corresponding 7-hydroxyquinazoline derivative under suitable conditions (e.g., reacting the derivative with an alkyl halide in N,N-dimethylformamide in the presence of potassium carbonate).

A method for synthesizing the compound according to the present invention having a substituent at the 7-position of the quinoline ring or the quinazoline ring is disclosed in scheme 8. When a quinoline derivative or quinazoline derivative containing a protective group introduced into its 6-position is used as a starting compound, the compound according to the present invention having a substituent at the 6-position of the quinoline ring or quinazoline ring can be synthesized. The quinoline derivative or quinazoline derivative containing a protective group introduced at the 6-position to be used as the starting compound can be synthesized, for example, according to scheme 18 which will be described later.

Scheme 9

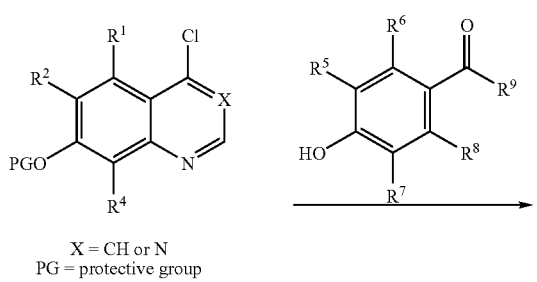

X = CH or N
PG = protective group

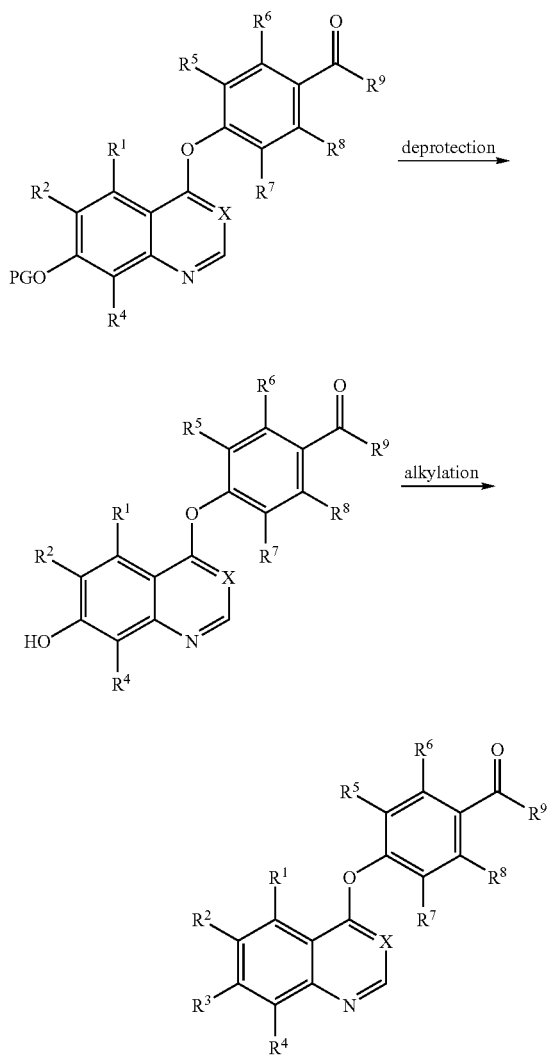

R³ = optionally substituted C₁₋₆ alkoxy

A ketone derivative having a specific substituent at the 7-position of the quinoline or quinazoline ring can be produced, for example, according to scheme 9. Specifically, a ketone derivative having a protected hydroxyl group at the 7-position of quinoline or quinazoline is produced by reacting the 4-chloroquinoline derivative or quinazoline derivative produced in scheme 5 or scheme 6 with an acylphenol derivative in a suitable solvent, for example, chlorobenzene. A 7-hydroxyquinoline derivative or a corresponding 7-hydroxyquinazoline derivative is produced by removing the protective group of the hydroxyl group in the ketone derivative under suitable conditions (for example, when the protective group is benzyl, for example, a reaction is allowed to proceed in N,N-dimethylformamide in the presence of palladium hydroxide-carbon or palladium-carbon in a hydrogen atmosphere). Next, a ketone derivative having a specific substituent at the 7-position of the quinoline or quinazoline ring is produced by alkylating the 7-hydroxyquinoline derivative or corresponding 7-hydroxyquinazoline derivative under suitable conditions (e.g., reacting the derivative with an alkyl halide in N,N-dimethylformamide in the presence of potassium carbonate).

A method for synthesizing the compound according to the present invention having a substituent at the 7-position of the quinoline ring or the quinazoline ring is disclosed in scheme 9. When a quinoline derivative or quinazoline derivative containing a protective group introduced into its 6-position is used as a starting compound, the compound according to the present invention having a substituent at the 6-position of the quinoline ring or quinazoline ring can be synthesized. The quinoline derivative or quinazoline derivative containing a protective group introduced at the 6-position to be used as the starting compound can be synthesized, for example, according to scheme 18 which will be described later.

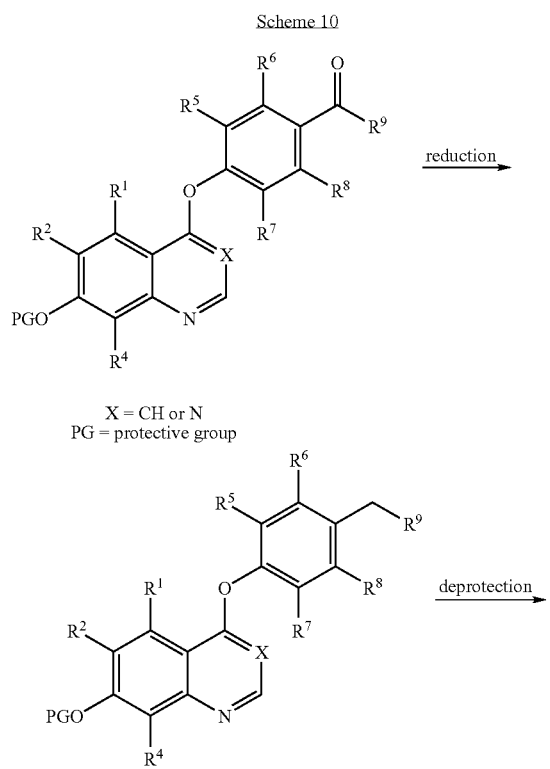

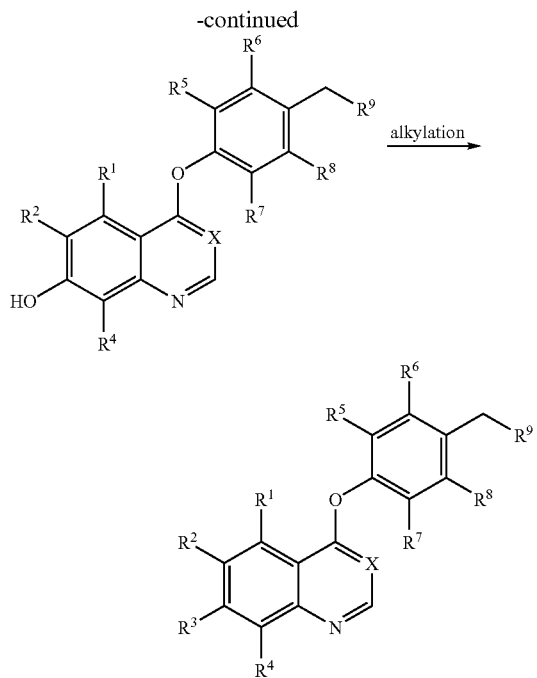

$R^3$ = optionally substituted $C_{1-6}$ alkoxy

A methylene derivative having a specific substituent at the 7-position of the quinoline or quinazoline ring can be produced, for example, according to scheme 10. Specifically, a corresponding methylene derivative is produced by reducing the carbonyl group of the ketone derivative having a protected hydroxyl group at the 7-position of quinoline or quinazoline produced in scheme 9 under suitable conditions. A 7-hydroxyquinoline derivative or a corresponding 7-hydroxyquinazoline derivative is produced by removing the protective group of the hydroxyl group in the methylene derivative under suitable conditions (for example, when the protective group is benzyl, for example, a reaction is allowed to proceed in N,N-dimethylformamide in the presence of palladium hydroxide-carbon or palladium-carbon in a hydrogen atmosphere). Next, a methylene derivative having a specific substituent at the 7-position of the quinoline or quinazoline ring is produced by alkylating the 7-hydroxyquinoline derivative or corresponding 7-hydroxyquinazoline derivative under suitable conditions (e.g., reacting the derivative with an alkyl halide in N,N-dimethylformamide in the presence of potassium carbonate).

A method for synthesizing the compound according to the present invention having a substituent at the 7-position of the quinoline ring or the quinazoline ring is disclosed in scheme 10. When a quinoline derivative or quinazoline derivative containing a protective group introduced into its 6-position is used as a starting compound, the compound according to the present invention having a substituent at the 6-position of the quinoline ring or quinazoline ring can be synthesized. The quinoline derivative or quinazoline derivative containing a protective group introduced at the 6-position to be used as the starting compound can be synthesized, for example, according to scheme 18 which will be described later.

Scheme 11

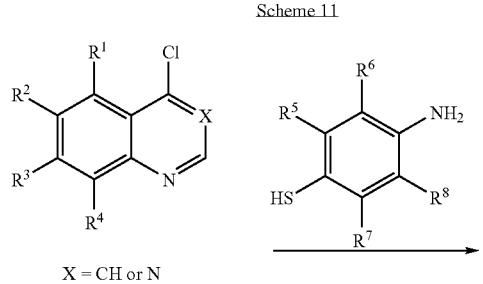

X = CH or N

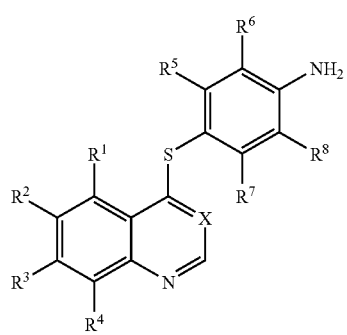

A 4-(quinolylsulfanyl)aniline derivative or a 4-(quinazolinylsulfanyl)aniline derivative (a compound represented by formula (I) in which Z represents S) is produced by reacting an aminothiophenol derivative with a 4-chloroquinoline derivative or a corresponding quinazoline derivative in a suitable solvent, for example, chlorobenzene.

Scheme 12

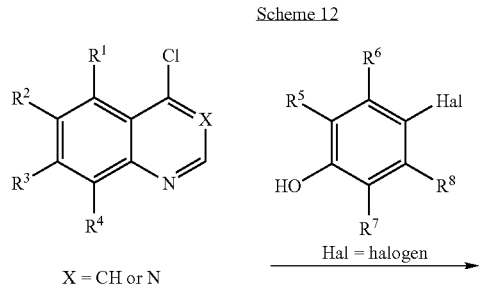

X = CH or N

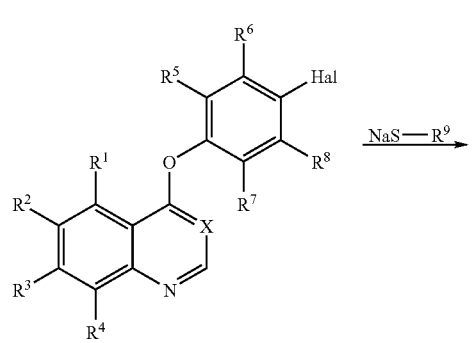

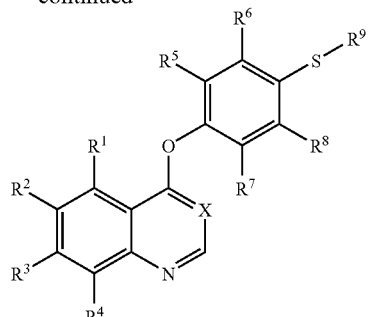

A compound represented by formula (I), wherein Q represents S, is produced by reacting a phenol derivative with a 4-chloroquinoline derivative or a corresponding quinazoline derivative in a suitable solvent, for example, chlorobenzene, to synthesize a 4-phenoxyquinoline derivative or a corresponding quinazoline derivative and then reacting the 4-phenoxyquinoline derivative or corresponding quinazoline derivative with NaS—$R^9$ in a suitable solvent, for example, ethylene glycol, in the presence of a catalyst, for example, a nickel catalyst.

Scheme 13

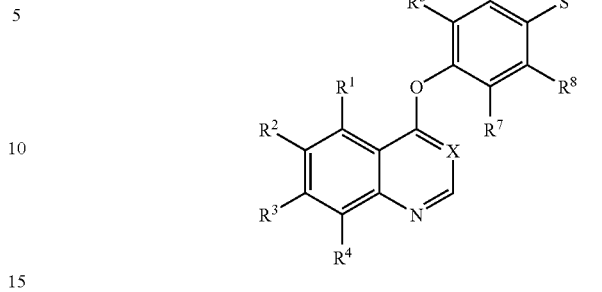

X = CH or N

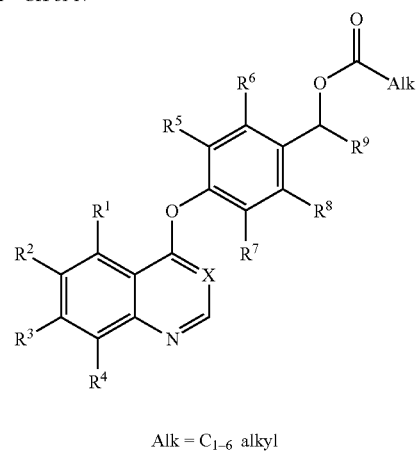

Alk = $C_{1-6}$ alkyl

An ester derivative (a compound represented by formula (I) wherein $R^{11}$ or $R^{12}$ represents $C_{1-6}$ alkylcarbonyloxy) is produced, for example, by allowing sodium borohydride to act in ethanol to give an alcohol derivative and then reacting the alcohol derivative with an acylating agent, for example, acetic anhydrie, in a suitable solvent, for example, N,N-dimethylformamide in the presence of a base, for example, triethylamine.

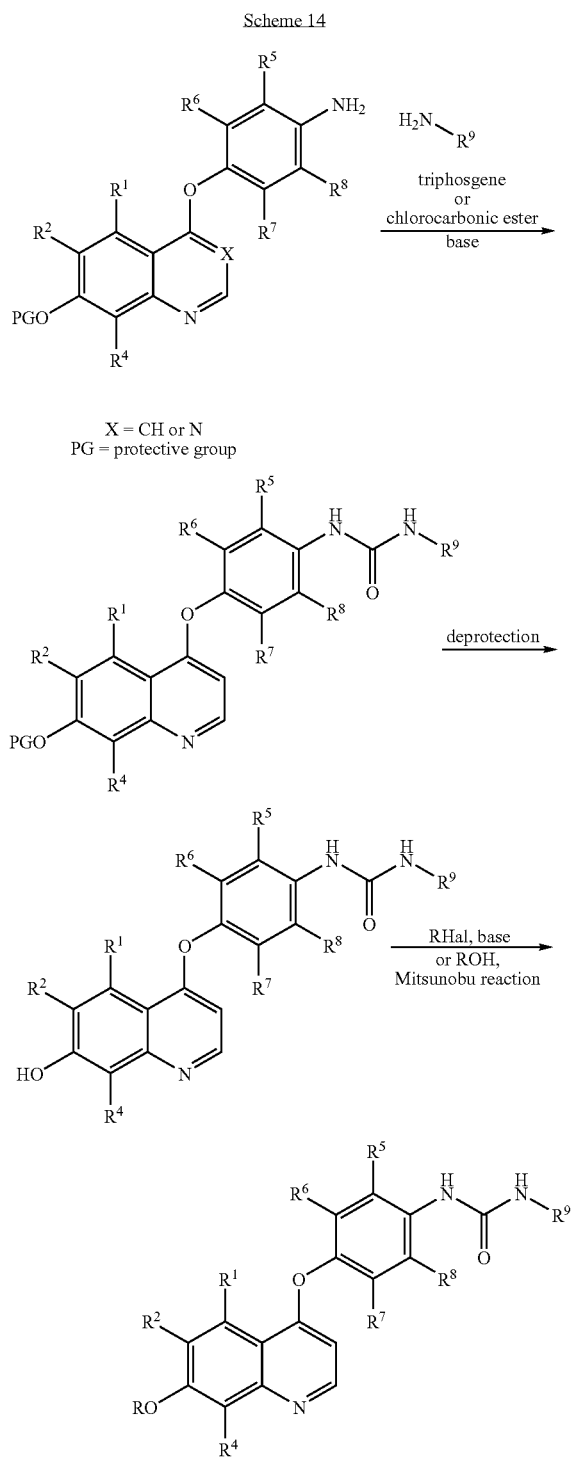

R = optionally substituted $C_{1-6}$ alkyl

A urea derivative having a specific substituent at the 6- or 7-position of the quinoline or quinazoline ring can be produced, for example, according to scheme 14. Specifically, a urea derivative having a protected hydroxyl group at the 7-position of quinoline or quinazoline can be produced by dissolving the 4-(aminophenoxy)quinoline derivative or corresponding quinazoline derivative produced in scheme 7 in a suitable solvent, for example, chloroform to prepare a solution, adding triphosgene or a chloroformic ester to the solution in the presence of a suitable base, for example, triethylamine, and reacting the mixture with a suitable alkylamine. A 7-hydroxyquinoline derivative or a corresponding quinazoline derivative can be produced by deprotecting the hydroxyl group of the urea derivative under suitable conditions. For example, when the protective group is benzyl, the urea derivative is reacted in a hydrogen atmosphere in N,N-dimethylformamide in the presence of palladium hydroxide-carbon or palladium-carbon. Next, a urea derivative having a specific substituent at the 7-position of quinoline or quinazoline can be produced by alkylating the 7-hydroxyquinoline derivative or corresponding quinazoline derivative under suitable conditions (for example, reacting the 7-hydroxyquinoline derivative or corresponding quinazoline derivative with an alkyl halide (RHal) in N,N-dimethylformamide in the presence of potassium carbonate, or reacting the 7-hydroxyquinoline derivative or corresponding quinazoline derivative with an alkyl alcohol (ROH) by a Mitsunobu reaction).

A quinoline derivative or corresponding quinazoline derivative having a hydroxyl group at the 6- or 7-position of quinoline or quinazoline can be produced by dissolving a 6,7-dimethoxy-4-(nitrophenoxy)quinoline derivative or corresponding quinazoline derivative having a specific substituent at the 6- or 7-position of the quinoline ring or quinazoline ring in a suitable solvent, for example, chloroform, to prepare a solution and heating the solution under reflux in the presence of a suitable Lewis acid, for example, aluminum trichloride. A 4-(nitrophenoxy)quinoline derivative or corresponding quinazoline derivative having a protective group at its 6- or 7-position can be produced by protecting the hydroxyl group of this derivative under suitable conditions and then conducting separation and purification. The hydroxyl group may be protected, for example, with a benzyl group, and the benzyl group can be introduced by reacting the derivative with benzyl chloride in N,N-dimethylformamide in the presence of potassium carbonate. A 4-(aminophenoxy)quinoline derivative or a corresponding quinazoline derivative can be derived from the derivative thus obtained in the same manner as in scheme 7. A urea derivative having a specific substituent at the 6- or 7-position of the quinoline ring or quinazoline ring can be produced from this derivative according to scheme 14.

A method for synthesizing the compound according to the present invention having a substituent at the 7-position of the quinoline ring or the quinazoline ring is disclosed in scheme 14. When a quinoline derivative or quinazoline derivative containing a protective group introduced into its 6-position is used as a starting compound, the compound according to the present invention having a substituent at the 6-position of the quinoline ring or quinazoline ring can be synthesized. The quinoline derivative or quinazoline derivative containing a protective group introduced at the 6-position to be used as the starting compound can be synthesized, for example, according to scheme 18, which will be described later, and scheme 7.

A urea derivative having a specific substituent at the 7-position of the quinoline ring or at the 7-position of the quinazoline ring can also be synthesized according to the method described in WO 00/43366.

Use of Compounds/Pharmaceutical Composition

Overexpression of Bek, overexpression of Bek variants and the like in poorly differentiated gastric cancers, mainly scirrhus gastric cancers, are reported, and Bek signals are considered to be involved in malignancy of cancer cells (Biochem. Biophys. Res. Commun. 265, 739–745, 1999, Surg Oncol. 2000 July; 9 (1): 5–11.). Further, as with VEGF, bFGF is reported to accelerate angiogenesis (Am J Surg. 1997 November; 174 (5): 540–4. Arterioscler Thromb Vasc Biol. 2000 May; 20 (5): 1250–6.) and is considered to be involved in angiogenesis in cancers. Therefore, the growth of cancer cells and angiogenesis can be suppressed by inhibiting the autophosphorylation of Bek.

The compounds according to the present invention inhibited in vitro the Bek-autophosphorylation which constitutively occurs in human gastric cancer cells (OCUM-2MD3) bFGF-independently (see Pharmacological Test Example 1).

Further, the compounds according to the present invention actually exhibited in vivo tumor growth inhibitory activity against human gastric cancer cells (OCUM-2MD3) (see Pharmacological Test Examples 2 and 3).

Accordingly, the compounds according to the present invention are useful for the treatment or prophylaxis of a disease for which the inhibition of Bek-autophosphorylation is effective therapeutically or prophylactically.

Diseases for which the inhibition of Bek-autophosphorylation is effective therapeutically or prophylactically include malignant tumors such as brain tumors, colon cancer, pancreatic cancer, lung cancer, renal cancer, ovarian cancer, and prostatic cancer, preferably solid tumors.

According to the present invention, there is provided a pharmaceutical composition comprising the compound according to the present invention. The pharmaceutical composition according to the present invention can be used for the treatment or prophylaxis of diseases for which the inhibition of Bek-autophosphorylation is effective therapeutically or prophylactically.

Further, according to the present invention, there is provided a method for treating or preventing a disease for which the inhibition of Bek-autophosphorylation is effective therapeutically or prophylactically, said method comprising the step of administering a therapeutically or prophylactically effective amount of the compound according to the present invention together with a pharmaceutically acceptable carrier to a mammal.

According to the present invention, there is provided use of the compound according to the present invention, for the manufacture of an agent for use in the treatment or prophylaxis of a disease for which the inhibition of Bek-autophosphorylation is effective therapeutically or prophylactically.

The compounds according to the present invention can be administered to human and non-human animals orally or parenterally by administration routes, for example, intravenous administration, intramuscular administration, subcutaneous administration, rectal administration, or percutaneous administration. Therefore, the pharmaceutical composition comprising as an active ingredient the compound according to the present invention is formulated into suitable dosage forms according to the administration routes.

Specifically, oral preparations include tablets, capsules, powders, granules, and syrups, and parental preparations include injections, suppositories, tapes, and ointments.

These various preparations may be prepared by conventional methods, for example, with commonly used excipients, disintegrants, binders, lubricants, colorants, and diluents.

Excipients include, for example, lactose, glucose, corn starch, sorbit, and crystalline cellulose. Disintegrants include, for example, starch, sodium alginate, gelatin powder, calcium carbonate, calcium citrate, and dextrin. Binders include, for example, dimethylcellulose, polyvinyl alcohol, polyvinyl ether, methylcellulose, ethylcellulose, gum arabic, gelatin, hydroxypropylcellulose, and polyvinyl pyrrolidone. Lubricants include, for example, talc, magnesium stearate, polyethylene glycol, and hydrogenated vegetable oils.

In preparing the injections, if necessary, for example, buffers, pH adjustors, stabilizers, tonicity agents, and preservatives may be added.

The content of the compound according to the present invention in the pharmaceutical composition according to the present invention may vary depending upon the dosage form. In general, however, the content is 0.5 to 50% by weight, preferably 1 to 20% by weight, based on the whole composition.

The dose may be appropriately determined in consideration of, for example, the age, weight, sex, difference in diseases, and severity of condition of individual patients, preferably in the range of 1 to 100 mg/kg. This dose is administered at a time daily or divided doses of several times daily.

The compound according to the present invention may be administered in combination with other medicament, for example, a carcinostatic agent. In this case, the compound according to the present invention may be administered simultaneously with or after or before the administration of other medicament. The type, administration intervals and the like of the carcinostatic agent may be determined depending upon the type of cancer and the condition of patients.

EXAMPLES

The present invention is further illustrated by the following Examples that are not intended as a limitation of the invention.

Necessary starting compounds were produced as described in WO 97/17329, WO 98/47873, WO 00/43366, and Japanese Patent Laid-Open No. 328782/1997. Starting compounds not described in these publications were produced as described in Preparation Examples below.

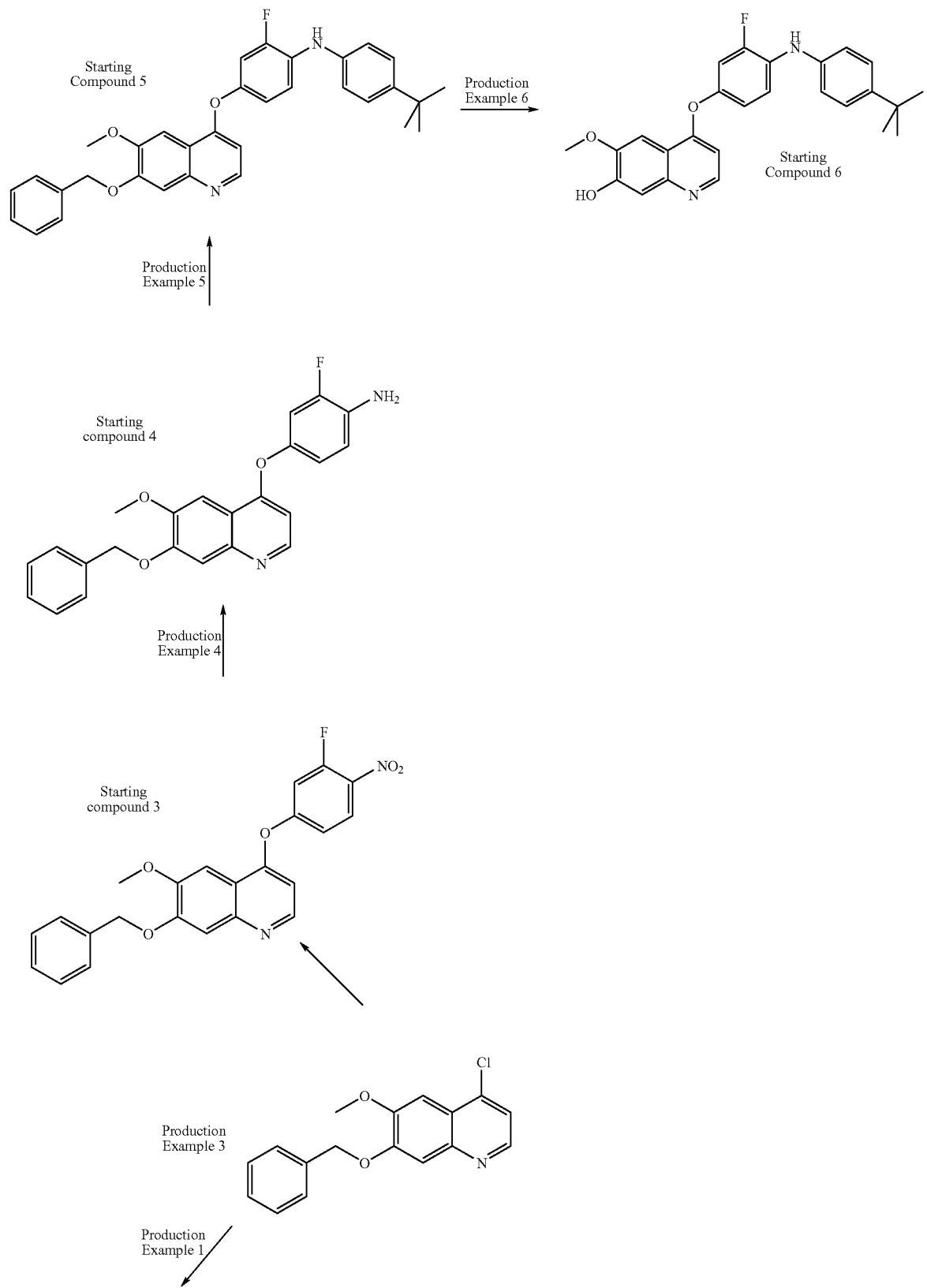
Scheme 15

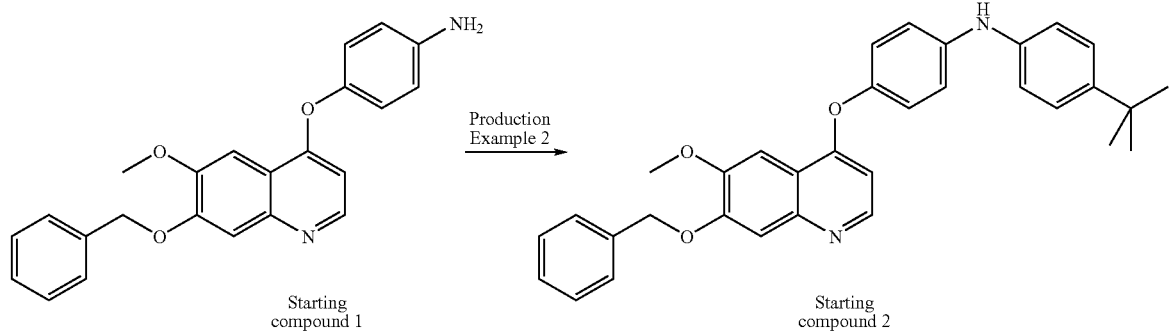
Scheme 16
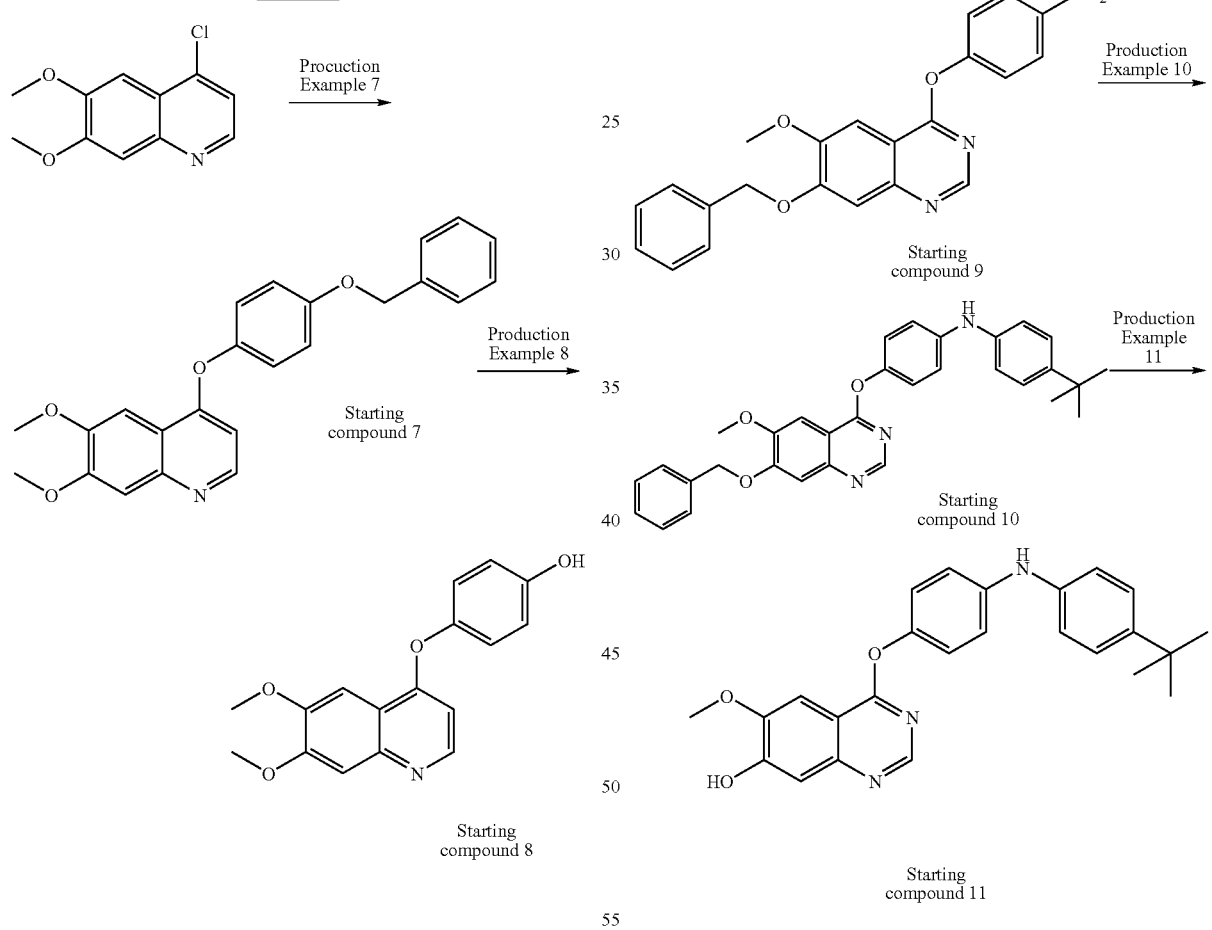
Scheme 17
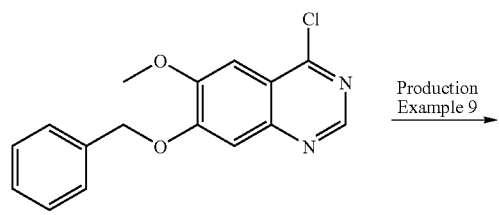
Scheme 18
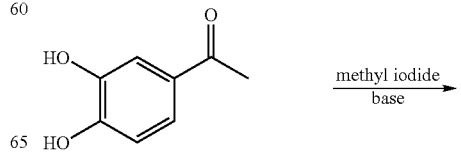

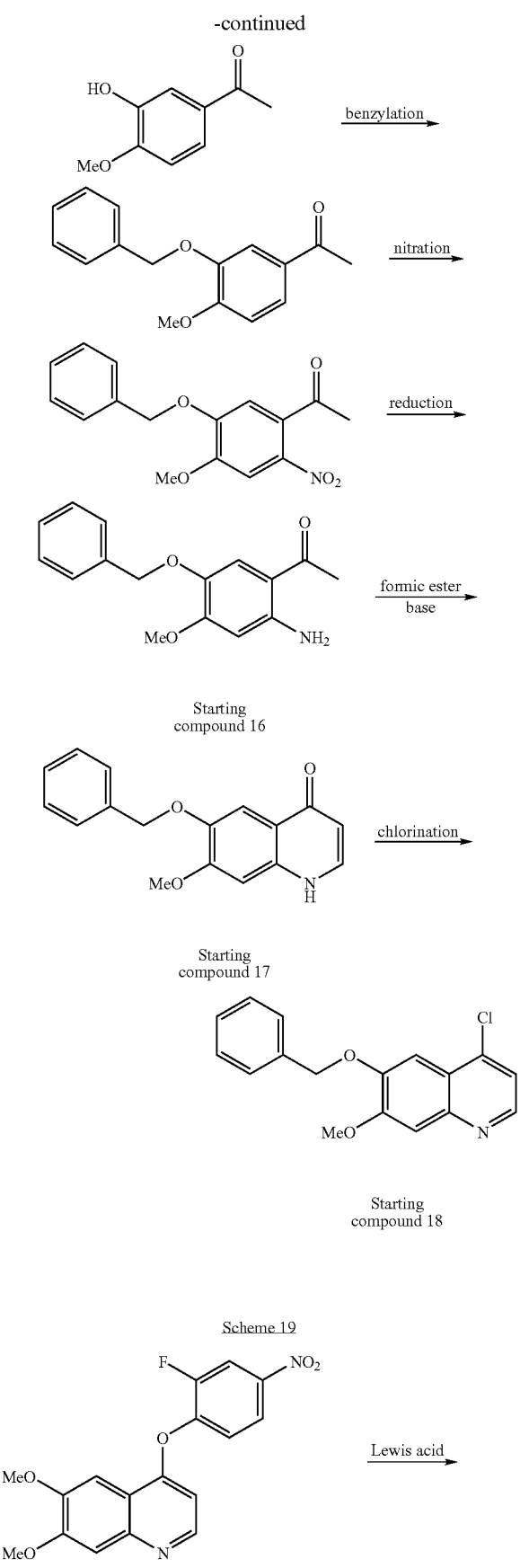
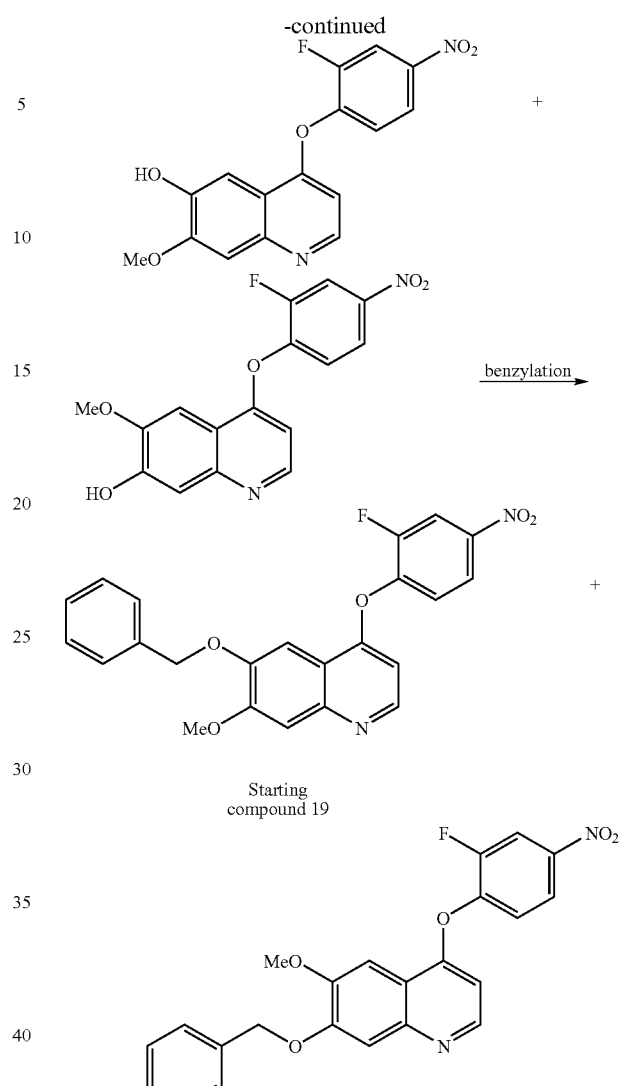

Preparation Example 1 (Starting Compound 1)

4-Aminophenol (12.21 g) and sodium methoxide (28% methanol solution, 21.07 g) were dissolved in N,N-dimethylacetamide (140 ml) to prepare a solution which was then stirred at room temperature for one hr. The solvent was removed by evaporation under the reduced pressure. 7-(Benzyloxy)-4-chloro-6-methoxyquinoline (21.00 g) and N,N-dimethylacetamide (210 ml) were added to the residue, and the mixture was stirred at 120° C. for 22 hr. The solvent was removed by evaporation under the reduced pressure. Water (300 ml) was added to the residue, and the mixture was stirred at room temperature for 4 hr. The resultant precipitate was collected by filtration and was dried to give the target compound (24.90 g, yield 96%).

Preparation Example 2 (Starting Compound 2)

4-{[7-(Benzyloxy)-6-methoxy-4-quinolyl]oxy}aniline (18.60 g), 4-tert-butylphenylboronic acid (17.8 g), copper(II) acetate (22.7 g), and triethylamine (50 ml) were added to chloroform, and the mixture was stirred at room temperature for 96 hr. Water was added to the reaction solution, and the mixture was extracted with chloroform. The chloroform layer was dried over sodium sulfate. The solvent was removed by evaporation under the reduced pressure. The crude was purified by chromatography on silica gel using chloroform/acetone for development to give the target compound (7.89 g, yield 31%).

Preparation Example 3 (Starting Compound 3)

7-(Benzyloxy)-4-chloro-6-methoxyquinoline (9.00 g) and 3-fluoro-4-nitrophenol (5.66 g) were added to chlorobenzene (60 ml), and the mixture was stirred at 120° C. for 21 hr. Chloroform (100 ml) and an aqueous sodium hydroxide solution (prepared by dissolving sodium hydroxide (2.4 g) in water (100 ml)) were added to the reaction solution, and the mixture was stirred at room temperature overnight. The organic layer was extracted with chloroform, and the chloroform layer was washed with an aqueous saturated sodium hydrogencarbonate solution and saturated brine. The chloroform layer was dried over sodium sulfate. The solvent was removed by evaporation under the reduced pressure. The crude thus obtained was washed with hexane/ethyl acetate (1/1), then the target compound was collected by filtration, dried and given (10.39 g, yield 82%).

Preparation Example 4 (Starting Compound 4)

7-(Benzyloxy)-4-(3-fluoro-4-nitrophenoxy)-6-methoxyquinoline (4.11 g), ammonium chloride (2.62 g), and zinc (12.80 g) were added to methanol (80 ml), and the mixture was stirred at 100° C. for 3 hr. The reaction solution was filtered, and the filtrate was concentrated. An aqueous saturated sodium hydrogencarbonate solution was added to the crude thus obtained, and the mixture was stirred at room temperature overnight. Chloroform was added to the solution, and the mixture was extracted. The chloroform layer was dried over sodium sulfate. The solvent was removed by evaporation under the reduced pressure to give the target compound (1.80 g, yield 47%).

Preparation Example 5 (Starting Compound 5)

4-{[7-(Benzyloxy)-6-methoxy-4-quinolyl]oxy}-2-fluoroaniline (1.78 g), 4-tert-butylphenylboronic acid (1.62 g), copper(II) acetate (2.07 g), and triethylamine (6 ml) were added to chloroform (100 ml), and the mixture was stirred at room temperature overnight. Further, 4-tert-butylboronic acid (0.81 g) and copper(II) acetate (1.03 g) were added thereto, and the mixture was stirred at room temperature overnight. Water was added to the reaction solution, and the mixture was extracted with chloroform. The chloroform layer was dried over sodium sulfate. The solvent was removed by evaporation under the reduced pressure to give a crude which was then purified by chromatography on silica gel using chloroform/acetone for development to give the target compound (1.94 g, yield 82%).

Preparation Example 6 (Starting Compound 6)

N-(4-{[7-(Benzyloxy)-6-methoxy-4-quinolyl]oxy}-2-fluorophenyl)-N-[4-(tert-butyl)phenyl]amine (1.94 g) and methanesulfonic acid (1 ml) were added to trifluoroacetic acid (20 ml), and the mixture was heated under reflux for one hr. The solvent in the reaction solution was removed by evaporation under the reduced pressure. An aqueous saturated sodium hydrogencarbonate solution was added to the crude thus obtained, and the mixture was extracted with chloroform. The chloroform layer was dried over anhydrous sodium sulfate, and the solvent was removed by evaporation under the reduced pressure to give a crude which was then purified by chromatography on silica gel using chloroform/methanol for development to give the target compound (1.28 g, yield 80%).

Preparation Example 7 (Starting Compound 7)

6,7-Dimethoxy-4-chloroquinoline (4.00 g) and 4-benzyloxyphenol (7.15 g) were added to chlorobenzene (4 ml), and the mixture was heated under reflux overnight. Chloroform and an aqueous sodium hydroxide solution were added to the reaction solution, and the mixture was stirred at room temperature. The organic layer was extracted with chloroform, and the chloroform layer was washed with an aqueous saturated sodium hydrogencarbonate solution. The chloroform layer was then dried over sodium sulfate. The solvent was removed by evaporation under the reduced pressure to give a crude which was then purified by chromatography on silica gel using hexane/acetone/dichloromethane for development to give the target compound (4.04 g, yield 58%).

Preparation Example 8 (Starting Compound 8)

4-[4-(Benzyloxy)phenoxy]-6,7-dimethoxyquinoline (3.00 g) and palladium hydroxide (600 mg) were added to N,N-dimethylformamide (150 ml), and the mixture was stirred in a hydrogen atmosphere at 60° C. overnight. The reaction solution was filtered through Celite. The solvent was removed by evaporation under the reduced pressure. The crude thus obtained was washed with methanol, followed by filtration and drying to quantitatively give the target compound.

Preparation Example 9 (Starting Compound 9)

7-(Benzyloxy)-4-chloro-6-methoxyquinazoline (500 mg) and tetra-n-butylammonium chloride (230 mg) were added to ethyl methyl ketone (20 ml) (solution A). 4-Aminophenol (270 mg) and sodium hydroxide (99 mg) were added to water (10 ml) (solution B). Solution A and solution B were mixed together, and the mixture was heated under reflux for 2 hr. Ethyl methyl ketone was removed by evaporation under the reduced pressure, and the crude was extracted with chloroform. The chloroform layer was washed with an aqueous saturated sodium carbonate solution and saturated brine and was then dried over anhydrous sodium sulfate. The solvent was removed by evaporation under the reduced pressure to give a crude which was then purified by chromatography on silica gel using chloroform/acetone for development to quantitatively give the target compound.

Preparation Example 10 (Starting Compound 10)

4-{[7-(Benzyloxy)-6-methoxy-4-quinazolinyl]oxy}aniline (620 mg), 4-tert-butylphenylboronic acid (530 mg), copper(II) acetate (660 mg), and triethylamine (2 ml) were added to chloroform (30 ml), and the mixture was stirred at room temperature overnight. Water was added to the reaction solution, and the mixture was extracted with chloroform. The chloroform layer was dried over sodium sulfate. The solvent was removed by evaporation under the reduced pressure to give a crude which was purified by chromatography on silica gel using chloroform/acetone for development to give the target compound (0.45 g, yield 54%).

Preparation Example 11 (Starting Compound 11)

N-(4-{[7-(Benzyloxy)-6-methoxy-4-quinazolinyl]oxy}phenyl)-N-[4-(tert-butyl)phenyl]amine (0.45 g) and methanesulfonic acid (0.5 ml) were added to trifluoroacetic acid (10 ml), and the mixture was heated under reflux for one hr. The solvent in the reaction solution was removed by evaporation under the reduced pressure. An aqueous saturated sodium hydrogencarbonate solution was added to the crude thus obtained, and the mixture was extracted with chloroform. The chloroform layer was dried over anhydrous sodium sulfate, and the solvent was removed by evaporation under the reduced pressure to give a crude which was then purified by chromatography on silica gel using chloroform/acetone for development to give the target compound (0.20 g, yield 54%).

Preparation Example 12

Production of 2-amino-5-benzyloxy-4-methoxyacetophenone (Starting Compound 16)

3',4'-Dihydroxyacetophenone (20.1 g) was dissolved in N,N-dimethylformamide (320 ml) to prepare a solution. Lithium carbonate (24.4 g) and methyl iodide (20.5 ml) were added to the solution, and the mixture was stirred at 55° C. overnight. The reaction solution was ice-cooled and was acidified by the addition of a 10% aqueous hydrochloric acid solution. Chloroform was added to the solution, and the mixture was extracted twice. The extract was washed with saturated brine, was dried over sodium sulfate, and was then evaporated to dryness. The solid was dissolved in N,N-dimethylformamide (200 ml). Potassium carbonate (21.8 g), tetrabutylammonium iodide (4.8 g), and benzyl bromide (18.9 ml) were added to the solution, and the mixture was stirred at 100° C. for one hr. Water was added thereto, and the mixture was extracted twice with chloroform. The extract was washed with saturated brine, was dried over sodium sulfate, and was then evaporated to dryness. The solid was dissolved in acetic acid (95 ml). Fuming nitric acid (13.6 ml) was added to the solution by portions under ice cooling, and the mixture was stirred at room temperature for 3 hr. Under ice cooling, the mixture was neutralized by the addition of a 10% aqueous sodium hydroxide solution. Chloroform was added thereto to dissolve the resultant solid. The reaction solution was extracted twice with chloroform. The extract was washed with saturated brine, was dried over sodium sulfate, and was then evaporated to dryness. Ethanol was added to the solid, and the mixture was heated to 100° C. to dissolve the solid in ethanol. Water (20 ml), ammonium chloride (21.1 g), and zinc powder (112 g) were added to the solution, and the mixture was stirred at 100° C. for one hr. The reaction solution was filtered while hot, and the filtrate was washed with a chloroform-methanol mixed solution. The mother liquor was concentrated. Ethyl acetate and 10% sodium hydroxide were added to the residue, the mixture was vigorously stirred, and the insolubles were then removed by filtration. The mother liquor was extracted with ethyl acetate, and the extract was washed with saturated brine, was dried over sodium sulfate, and was then evaporated to dryness. The solid thus obtained was purified by chromatography on silica gel using hexane/ethyl acetate/dichloromethane for development to give the title compound (13.1 g, yield 37%) (4 steps).

$^1$H-NMR (CDCl$_3$, 400 MHz): 2.39 (s, 3H), 3.89 (s, 3H), 5.05 (s, 2H), 6.25 (s, 1H), 7.15 (s, 1H), 7.29–7.45 (m, 5H)

Preparation Example 13

Production of 6-benzyloxy-7-methoxy-4-quinolone (Starting Compound 17)

2-Amino-5-benzyloxy-4-methoxyacetophenone (13.1 g), tetrahydrofuran (anhydrous) (200 ml), and sodium methoxide (5 eq, 13.1 g) were added, and the mixture was stirred at room temperature for 30 min. Ethyl formate (5 eq, 19.4 ml) was added thereto, and the mixture was further stirred at room temperature for one hr. Water was added thereto, and the mixture was stirred at room temperature for one hr, followed by concentration under the reduced pressure. The concentrate was rendered weakly acidic by the addition of 10% aqueous hydrochloric acid. Chloroform was added thereto, the mixture was extracted with chloroform, and the extract was washed with saturated brine, was dried over sodium sulfate, and the solvent was then removed by evaporation under the reduced pressure. The crude thus obtained was purified by chromatography on silica gel using chloroform/methanol for development to give the title compound (11.5 g, yield 85%).

$^1$H-NMR (CDCl$_3$, 400 MHz): δ 3.97 (s, 3H), 5.19 (s, 2H), 6.28 (d, J=7.3 Hz, 1H), 7.02 (s, 1H), 7.29–7.41 (m, 3H), 7.47–7.51 (m, 2H), 7.71 (s, 1H), 7.86 (d, J=7.3 Hz, 1H)

Preparation Example 14

Production of 6-benzyloxy-4-chloro-7-methoxy-quinoline (Starting Compound 18)

6-Benzyloxy-7-methoxy-4-quinolone (2.4 g), diisopropylamine (5 eq, 7.4 ml), and phosphorus oxychloride (2.5 eq, 2.0 ml) were added, and the mixture was stirred at 110° C. for one hr. The stirred mixture was concentrated under the reduced pressure. Chloroform and iced water were then added to the concentrate. The mixture was rendered weakly alkaline by the addition of 28% aqueous ammonia, followed by extraction with chloroform. The extract was washed with saturated brine and was dried over sodium sulfate, and the solvent was then removed by evaporation under the reduced pressure. The crude thus obtained was purified by chromatography on silica gel using chloroform/methanol for development to give the title compound (1.6 g, yield 63%).

$^1$H-NMR (CDCl$_3$, 400 MHz): δ 4.04 (s, 3H), 5.32 (s, 2H), 7.32–7.44 (m, 4H), 7.45 (s, 1H), 7.49 (s, 1H), 7.51–7.55 (m, 2H), 8.57 (d, J=4.9 Hz, 1H)

Mass spectrometric value (ESI-MS, m/z): 300 (M+1)

Preparation Example 15

Production of 4-[(6-benzyloxy-7-methoxy-4-quinolyl)oxy]-3-fluoro-nitrobenzene (Starting Compound 19)

4-[(6,7-Dimethoxy-4-quinolyl)oxy]-3-fluoro-nitrobenzene (4.3 g) was dissolved in chloroform (200 ml) to prepare a solution. Aluminium chloride (10 g) was added to the solution, and the mixture was heated under reflux for 2 hr. The solvent was removed by evaporation before water (200 ml) was carefully added to the residue. The precipitated crude crystal (6.5 g) was collected by filtration. This crude crystal was dissolved in dimethylformamide (150 ml). Potassium carbonate (9.0 g) and benzyl chloride (4.5 g) were added to the solution, and the mixture was stirred at room temperature for 5 hr. The mixture was extracted with ethyl acetate. The extract was then washed with saturated brine and was dried over anhydrous sodium sulfate, and the solvent was removed by evaporation under the reduced pressure. The residue was purified by column chromatography on silica gel, and the title compound (1.4 g, yield 27%) was obtained from the fraction of n-hexane:ethyl acetate (1:4).

$^1$H-NMR (CDCl$_3$, 400 MHz): 4.04 (s, 3H), 5.26 (s, 2H), 6.57 (d, J=5.1 Hz, 1H), 7.15–7.47 (m, 6H), 7.33 (s, 1H), 7.47 (s, 1H), 8.02–8.05 (m, 1H), 8.13–8.16 (m, 1H), 8.57 (d, J=5.1 Hz, 1H)

Compound 5: (4-Tert-butylphenyl)-[4-(6,7-dimethoxyquinolin-4-yloxy)phenyl]amine

4-[(6,7-Dimethoxy-4-quinolyl)oxy]aniline (689 mg) (starting compound A) and 4-t-butylphenylboronic acid (450 mg) (starting compound B) were dissolved in a mixed solution composed of dichloromethane (50 ml) and triethylamine (0.7 ml) to prepare a solution. Copper(II) acetate (450 mg) was added to the solution, and the mixture was stirred at room temperature for 16 hr. The mixture was filtered, and the filtrate was then concentrated to give a crude which was then purified by chromatography on silica gel to give the title compound (500 mg, yield 50%).

$^1$H-NMR (CDCl$_3$, 400 MHz): 1.24 (s, 9H), 4.13 (s, 3H), 4.15 (s, 3H), 5.75 (brs, 1H), 6.41 (d, J=5.4 Hz, 1H), 6.96–7.06 (m, 6H), 7.22–7.26 (m, 2H), 7.34 (s, 1H), 7.51 (s, 1H), 8.40 (d, J=5.1 Hz, 1H)

Mass spectrometric value (m/z): 429 [M+H]$^+$

Compound 20: (4-Tert-butylphenyl)-[4-(6.7-dimethoxyquinolin-4-yloxy)phenyl]-methylamine

[4-(6,7-Dimethoxy-4-quinolyloxy)phenyl]methylamine (100 mg) was dissolved in chloroform (10 ml) to prepare a solution. Triethylamine (0.3 ml), 4-tert-butylphenylboranic acid (100 mg), and copper(II) acetate (50 mg) were then added to the solution, and the mixture was stirred at room temperature for 3 days. The insolubles were removed by filtration, and the solvent was then removed by evaporation under the reduced pressure. The residue was purified by thin-layer chromatography on silica gel using chloroform/acetone for development to give the title compound (21 mg, yield 15%).

$^1$H-NMR (CDCl$_3$, 400 MHz): δ 8.49 (m, 1H), 7.59 (s, 1H), 7.44 (s, 1H), 7.34 (d, J=8.8 Hz, 2H), 7.07 (d, J=9.0 Hz, 2H), 7.04 (d, J=8.8 Hz, 2H), 7.02 (d, J=9.3 Hz, 2H), 6.50 (d, J=4.4 Hz, 1H), 4.05 (s, 3H), 4.05 (s, 3H), 3.34 (s, 3H), 1.33 (s, 9H)

Mass spectrometric value (m/z): 443 [M+H]$^+$

Compound 21: 4-[4-(4-Tert-butylphenylamino)phenoxy]-6-methoxy-quinolin-7-ol

[4-(7-Benzyloxy-6-methoxy-4-quinolyloxy)phenyl](4-tert-butylphenyl)amine (starting compound 2) (400 mg) was dissolved in N,N-dimethylformamide (10 ml) to prepare a solution. Triethylamine (2 ml) and 20% palladium hydroxide (0.58 g) were then added to the solution, and the mixture was stirred in a hydrogen atmosphere at room temperature overnight. The insolubles were removed by filtration, and the solvent was then removed by evaporation under the reduced pressure. Water and ethyl acetate were added to the crude, and the mixture was extracted with ethyl acetate. The extract was washed with saturated brine and was dried over sodium sulfate. The solvent was removed by evaporation under the reduced pressure, and the residue was purified by chromatography on silica gel using chloroform/acetone for development to give the title compound (205 mg, yield 62%).

$^1$H-NMR (CDCl$_3$, 400 MHz): δ 8.49 (d, J=5.2 Hz, 1H), 7.60 (s, 1H), 7.52 (s, 1H), 7.32 (d, J=8.5 Hz, 2H), 7.12 (d, J=8.8 Hz, 2H), 7.07 (d, J=9.3 Hz, 2H), 7.05 (d, J=8.8 Hz, 2H), 6.45 (d, J=5.4 Hz, 1H), 5.68 (s, 1H), 4.08 (s, 3H), 1.32 (s, 9H)

Mass spectrometric value (m/z): 415 [M+H]$^+$

Compound 22: (4-Tert-butylphenyl)-{4-[7-(2-chloroethoxy)-6-methoxyquinolin-4-yloxy]phenyl}amine 4-[4-(4-Tert-butylphenylamino)phenoxy]-6-methoxyquinolin-7-ol (Compound 21) (60 mg) (starting compound A) was dissolved in N,N-dimethylformamide (2 ml) to prepare a solution. Potassium carbonate (200 mg) and 1-bromo-2-chloroethylene (0.1 ml) (starting compound B) were then added to the solution, and the mixture was stirred at room temperature for 8 hr. Water and ethyl acetate were added to the reaction solution, and the mixture was extracted with ethyl acetate. The extract was washed with saturated brine and was dried over sodium sulfate. The solvent was removed by evaporation under the reduced pressure, and the crude was washed with methanol for purification to give the title compound (22 mg, yield 32%).

$^1$H-NMR (CDCl$_3$, 400 MHz): δ 8.49 (d, J=5.1 Hz, 1H), 7.60 (s, 1H), 7.41 (s, 1H), 7.33 (d, J=8.6 Hz, 2H), 7.12 (d, J=8.6 Hz, 2H), 7.07 (d, J=8.3 Hz, 2H), 7.06 (d, J=8.6 Hz, 2H), 6.49 (d, J=5.4 Hz, 1H), 5.69 (s, 1H), 4.45 (t, J=6.1 Hz, 2H), 4.05 (s, 3H), 3.96 (t, J=6.3 Hz, 2H), 1.33 (s, 9H)

Mass spectrometric value (m/z): 975 [2M+Na]$^+$

Compound 24: (4-Tert-butylphenyl)-{4-[6-methoxy-7-(3-morpholin-4-ylpropoxy)quinolin-4-yloxy]phenyl}amine (4-Tert-butylphenyl)-{4-[7-(3-chloropropoxy)-6-methoxy-4-quinolyloxy]phenyl}amine (40 mg) (starting compound A) was dissolved in N,N-dimethylformamide (1 ml) to prepare a solution. Morpholine (30 µl) (starting compound B) was then added to the solution, and the mixture was stirred at 70° C. for 2 days. Water and ethyl acetate were added to the reaction solution, and the mixture was extracted with ethyl acetate. The extract was washed with saturated brine and was dried over sodium sulfate. The solvent was removed by evaporation under the reduced pressure, and the residue was purified by thin-layer chromatography on silica gel using chloroform/methanol for development to give the title compound (12 mg, yield 27%).

$^1$H-NMR (CDCl$_3$, 400 MHz): δ 8.47 (d, J=5.4 Hz, 1H), 7.57 (s, 1H), 7.43 (s, 1H), 7.32 (d, J=8.8 Hz, 2H), 7.11 (d, J=9.0 Hz, 2H), 7.07 (d, J=9.3 Hz, 2H), 7.05 (d, J=8.8 Hz, 2H), 6.47 (d, J=5.4 Hz, 1H), 5.71 (s, 1H), 4.27 (t, J=6.6 Hz, 2H), 4.03 (s, 3H), 3.72 (m, 4H), 2.58 (t, J=7.1 Hz, 2H), 2.49 (m, 4H), 2.13 (tt, J=6.8, 7.1 Hz, 2H), 1.32 (s, 9H)

Mass spectrometric value (m/z): 542 [M+H]$^+$

Compound 30: 4-[4-(4-Tert-butylphenoxy)phenoxy]-6,7-dimethoxyquinoline 4-(6,7-Dimethoxy-4-quinolyloxy)phenol (starting compound 8) (24 mg) was dissolved in chloroform (2 ml) to prepare a solution. Triethylamine (0.3 ml), 4-tert-butylphenylboranic acid (50 mg), and copper(II) acetate (90 mg) were added to the solution, and the mixture was stirred at room temperature for 4 days. The insolubles were removed by filtration, and the solvent was then removed by evaporation under the reduced pressure. The residue was purified by thin-layer chromatography on silica gel using chloroform/acetone for development to give the title compound (20 mg, yield 58%).

$^1$H-NMR (CDCl$_3$, 400 MHz): δ 8.50 (d, J=5.1 Hz, 1H), 7.57 (s, 1H), 7.44 (s, 1H), 7.38 (d, J=8.8 Hz, 2H), 7.15 (d, J=8.8 Hz, 2H), 7.09 (d, J=9.0 Hz, 2H), 6.99 (d, J=8.8 Hz, 2H), 6.48 (d, J=5.4 Hz, 1H), 4.05 (s, 3H), 4.05 (s, 3H), 1.34 (s, 9H)

Mass spectrometric value (m/z): 430 [M+H]$^+$

Compound 31: (4-Tert-butylphenyl)-[4-(6,7-dimethoxyquinolin-4-yloxy)phenyl]methyl acetate

[4-(Tert-butyl)phenyl]{4-[(6,7-dimethoxy-4-quinolyl)oxy]phenyl}-methanone (111 mg) and sodium boron hydride (76 mg) were added to ethanol (15 ml), and the mixture was stirred at room temperature for 3 hr. Water was added to the reaction solution, and the mixture was extracted with chloroform. The chloroform layer was dried over anhydrous sodium sulfate. Chloroform was removed by evaporation under the reduced pressure to give a crude which was then purified by thin-layer chromatography on silica gel using chloroform/ethyl acetate for development to give (4-tert-butylphenyl)-[4-(6,7-dimethoxy-4-quinolyloxy)phenyl]methanol (108 mg, yield 97%).

(4-Tert-butylphenyl)-[4-(6,7-dimethoxy-4-quinolyloxy)phenyl]-methanol (51 mg) was dissolved in N,N-dimethylformamide (10 ml). Triethylamine (1 ml) and acetic anhydride (0.5 ml) were then added to the solution, and the mixture was stirred at room temperature overnight. Water and ethyl acetate were added to the reaction solution, and the mixture was extracted with ethyl acetate. The extract was washed with saturated brine and was dried over sodium sulfate. The solvent was removed by evaporation under the reduced pressure, and the residue was purified by thin-layer chromatography on silica gel using chloroform/acetone for development to give the title compound (35 mg, yield 63%).

$^1$H-NMR (CDCl$_3$, 400 MHz): δ 8.50 (m, 1H), 7.54 (s, 1H), 7.52 (s, 1H), 7.45 (d, J=8.8 Hz, 2H), 7.39 (d, J=8.3 Hz, 2H), 7.29 (d, J=8.6 Hz, 2H), 7.16 (d, J=8.5 Hz, 2H), 6.91 (s, 1H), 6.52 (d, J=5.2 Hz, 1H), 4.06 (s, 3H), 4.03 (s, 3H), 2.19 (s, 3H), 1.32 (s, 9H)

Mass spectrometric value (m/z): 486 [M+H]$^+$

Compound 32: 4-[4-(4-Tert-butylbenzyl)phenoxy]-6,7-dimethoxyquinoline (4-Tert-butylphenyl)-[4-(6,7-dimethoxy-4-quinolyloxy)phenyl]-methyl acetate (Compound 31) (26 mg) was dissolved in N,N-dimethylformamide (3 ml) to prepare a solution. Triethylamine (0.5 ml) and 20% palladium hydroxide (200 mg) were then added to the solution, and the mixture was stirred in a hydrogen atmosphere at room temperature for 2 hr. The reaction solution was filtered, water and ethyl acetate were added to the filtrate, and the mixture was extracted with ethyl acetate. The extract was washed with saturated brine and was dried over sodium sulfate. The solvent was removed by evaporation under the reduced pressure to give the title compound (18 mg, yield 79%).

$^1$H-NMR (CDCl$_3$, 400 MHz): δ 8.48 (d, J=5.1 Hz, 1H), 7.55 (s, 1H), 7.42 (s, 1H), 7.34 (d, J=8.0 Hz, 2H), 7.28 (d, J=8.3 Hz, 2H), 7.15 (d, J=8.0 Hz, 2H), 7.10 (d, J=8.3 Hz, 2H), 6.47 (d, J=5.1 Hz, 1H), 4.05 (s, 3H), 4.04 (s, 3H), 4.00 (s, 2H), 1.32 (s, 9H)

Mass spectrometric value (m/z): 428 [M+H]$^+$

Compound 37: (4-Tert-butylphenyl)-{4-[6-methoxy-7-(2-morpholin-4-ylethoxy)quinolin-4-yloxy]phenyl}amine N,N-Dimethylformamide (2 ml) was added to 4-{4-[4-(tert-butyl)anilino]phenoxy}-6-methoxy-7-quinolinol (compound 21) (100 mg), potassium carbonate (167 mg), and 4-(2-chloroethyl)morpholine hydrochloride (70 mg), and the mixture was stirred at 75 to 80° C. for 6 hr. Water and ethyl acetate were added to the reaction solution, and the mixture was extracted with ethyl acetate. The extract was washed with saturated brine and was dried over sodium sulfate, and the solvent was then removed by evaporation under the reduced pressure. The crude thus obtained was purified by thin-layer chromatography on silica gel using chloroform/methanol for development to give the title compound (102 mg, yield 81%).

$^1$H-NMR (CDCl$_3$, 400 MHz): δ 8.48 (d, J=5.1 Hz, 1H), 7.58 (s, 1H), 7.41 (s, 1H), 7.33 (d, J=8.8 Hz, 2H), 7.04–7.13 (m, 6H), 6.48 (d, J=5.1 Hz, 1H), 5.69 (br, 1H), 4.34 (t, J=6.0 Hz, 2H), 4.03 (s, 3H), 3.73–3.77 (m, 4H), 2.96 (t, J=6.1 Hz, 2H), 2.62–2.66 (m, 4H), 1.33 (s, 9H)

Mass spectrometric value (m/z): 528 [M+H]$^+$

Compound 42: (4-Tert-butylphenyl)-{4-[6-methoxy-7-(1-propylpiperidin-4-ylmethoxy)quinolin-4-yloxy]phenyl}amine 4-Hydroxymethyl piperidine (1.8 g) was dissolved in chloroform (30 ml) to prepare a solution. Triethylamine (4 ml) and di-tert-butyl dicarbonate (3.28 g) were then added to the solution, and the mixture was stirred at room temperature for one hr. The solvent was removed by evaporation under the reduced pressure. The crude thus obtained was then dissolved in ethyl acetate, and the solution was washed with saturated brine and was dried over sodium sulfate. The solvent was removed by evaporation under the reduced pressure, and the residue was washed with hexane to give tert-butyl-4-(hydroxymethyl)-1-piperidine carboxylate (2.67 g, yield 83%).

(4-Tert-butylphenyl)-[4-(6-methoxy-7-hydroxy-4-quinolyloxy)-phenyl]amine (compound 21) (0.8 g) (starting compound A), tert-butyl-4-(hydroxymethyl)-1-piperidine carboxylate (0.59 g) (starting compound B), and triphenylphosphine (0.85 g) were dissolved in tetrahydrofuran (25 ml), and the solution was stirred at room temperature for 20 min. Under ice cooling, 40% diethyl azodicarboxylate (1.5 ml) was added to the reaction solution, and the mixture was stirred at room temperature overnight. Water and ethyl acetate were added to the reaction solution. The mixture was extracted with ethyl acetate, and the extract was washed with saturated brine and was dried over sodium sulfate. The solvent was removed by evaporation under the reduced pressure. The crude was dissolved in a 30% trifluoroacetic acid/chloroform solution (15 ml), and the solution was stirred at room temperature for 30 min. The solvent was removed by evaporation under the reduced pressure, and the residue was then purified by chromatography on silica gel using chloroform/acetone for development to give (4-tert-butylphenyl)-{4-[6-methoxy-7-(4-piperidinylmethoxy)-4-quinolyloxy]phenyl}amine (0.84 g, yield 86%).

(4-Tert-butylphenyl)-{4-[6-methoxy-7-(4-piperidinylmethoxy)-4-quinolyloxy]phenyl}amine (150 mg) was dissolved in N,N-dimethylformamide (3 ml) to prepare a solution. Potassium carbonate (300 mg) and 1-bromopropane (0.15 ml) were then added to the solution, and the mixture was stirred at room temperature for 4 hr. Water and ethyl acetate were added to the reaction solution, and the mixture was extracted with ethyl acetate. The extract was washed with saturated brine and was dried over sodium sulfate. The solvent was removed by evaporation under the reduced pressure, and the residue was purified by thin-layer chromatography on silica gel using chloroform/acetone for development to give the title compound (12 mg, yield 7%).

$^1$H-NMR (CDCl$_3$, 400 MHz): δ 8.47 (d, J=5.4 Hz, 1H), 7.57 (s, 1H), 7.38 (s, 1H), 7.32 (d, J=8.8 Hz, 2H), 7.12 (d, J=9.0 Hz, 2H), 7.07 (d, J=8.8 Hz, 2H), 7.05 (d, J=8.5 Hz, 2H), 6.47 (d, J=5.4 Hz, 1H), 4.06 (m, 2H), 4.02 (s, 3H), 3.12 (m, 2H), 2.44 (m, 2H), 2.22–1.94 (m, 5H), 1.64 (m, 4H), 1.32 (s, 9H), 0.93 (t, J=7.4 Hz, 3H)

Mass spectrometric value (m/z): 588 [M+Cl]$^-$

Compound 44: [4-(6,7-Dimethoxyquinolin-4-yloxy)phenyl]-(4-morpholin-4-ylphenyl)amine 4-[(6,7-Dimethoxy-4-quinolyl)oxy]aniline (100 mg) and 4-bromophenylboronic acid (80 mg) were dissolved in a mixed solution composed of dichloromethane (5 ml) and triethylamine (0.07 ml) to prepare a solution. Copper(II) acetate (50 mg) was added to the solution, and the mixture was stirred at room temperature for 16 hr. The stirred mixture was filtered, and the filtrate was then concentrated. The crude thus obtained was purified by chromatography on silica gel to give (4-bromophenyl)-[4-(6,7-dimethoxy-4-quinolyloxy)phenyl]amine (70 mg).

Palladium acetate (18 mg) and (+)-BINAP (70 mg) were dissolved in toluene (1.5 ml), and the solution was stirred at room temperature for 5 min. (4-Bromophenyl)-[4-(6,7-dimethoxy-4-quinolyloxy)phenyl]amine (100 mg), morpholine (0.15 ml), and cesium carbonate (200 mg) were added in that order to the reaction solution, and the mixture was stirred at 80° C. overnight. The insolubles were removed by filtration, and the solvent was then removed by evaporation under the reduced pressure. The residue was purified by thin-layer chromatography on silica gel using chloroform/acetone to give the title compound (10 mg, yield 9%).

$^1$H-NMR (CDCl$_3$, 400 MHz): δ 8.47 (d, J=5.6 Hz, 1H), 7.59 (s, 1H), 7.51 (s, 1H), 7.32–6.70 (m, 8H), 6.51 (d, J=5.6 Hz, 1H), 4.06 (s, 3H), 4.06 (s, 3H), 3.88 (m, 4H), 3.74–3.38 (m, 4H)

Mass spectrometric value (m/z): 458 [M+H]$^+$

Compound 59: 1-{4-[4-(4-Tert-butyl-phenylamino)phenoxy]-6-methoxyquinolin-7-yloxy}-3-morpholin-4-ylpropan-2-ol N,N-Dimethylformamide (2 ml) was added to 4-[4-(4-tert-butylphenylamino)phenoxy]-6-methoxyquinolin-7-ol (compound 21) (150 mg) (starting compound A) and potassium carbonate (250 mg). Epibromohydrin (46 μl) was added dropwise thereto, and the mixture was stirred at room temperature for 24 hr. Morpholine (95 μl) (starting compound B) was added dropwise to the reaction solution, and the mixture was stirred at 70 to 75° C. for 5 hr. The stirred mixture was extracted with ethyl acetate, and the extract was washed with saturated brine and was dried over sodium sulfate. The solvent was then removed by evaporation under the reduced pressure. The crude thus obtained was purified by thin-layer chromatography on silica gel using chloroform/methanol for development to give the title compound (179 mg, yield 89%).

$^1$H-NMR (CDCl$_3$, 400 MHz): δ 8.48 (d, J=5.4 Hz, 1H), 7.58 (s, 1H), 7.43 (s, 1H), 7.33 (d, J=8.8 Hz, 2H), 7.04–7.14 (m, 6H), 6.48 (d, J=5.1 Hz, 1H), 5.69 (br, 1H), 4.25–4.32 (m, 1H), 4.15–4.24 (m, 2H), 4.02 (s, 3H), 3.69–3.79 (m, 4H), 2.66–2.72 (m, 2H), 2.60–2.64 (m, 2H), 2.48–2.54 (m, 2H), 1.32 (s, 9H)

Mass spectrometric value (m/z): 558 [M+H]$^+$

Compound 70: (R)-1-{4-[4-(4-Tert-butylphenylamino)phenoxy]-6-methoxyquinolin-7-yloxy}-3-morpholin-4-ylpropan-2-ol 4-[4-(4-Tert-butylphenylamino)phenoxy]-6-methoxyquinolin-7-ol (compound 21) (230 mg) was dissolved in N,N-dimethylformamide (8 ml) to prepare a solution. Potassium carbonate (300 mg) and p-toluenesulfonic acid (2R)-(–)-glycidyl (0.22 g) were then added to the solution, and the mixture was stirred at room temperature overnight. Morpholine (0.5 ml) was added to the reaction solution, and the mixture was further stirred at 70° C. overnight. Water and ethyl acetate were added to the reaction solution, and the mixture was extracted with ethyl acetate. The extract was washed with saturated brine and was dried over sodium sulfate. The solvent was removed by evaporation under the reduced pressure, and the residue was purified by thin-layer chromatography on silica gel using chloroform/acetone for development to give the title compound (200 mg, yield 65%).

$^1$H-NMR (CDCl$_3$, 400 MHz): δ 8.48 (d, J=5.4 Hz, 1H), 7.58 (s, 1H), 7.43 (s, 1H), 7.33 (d, J=8.8 Hz, 2H), 7.04–7.14 (m, 6H), 6.48 (d, J=5.1 Hz, 1H), 5.69 (br, 1H), 4.25–4.32 (m, 1H), 4.15–4.24 (m, 2H), 4.02 (s, 3H), 3.69–3.79 (m, 4H), 2.66–2.72 (m, 2H), 2.60–2.64 (m, 2H), 2.48–2.54 (m, 2H), 1.32 (s, 9H)

Mass spectrometric value (m/z): 558 [M+H]$^+$

Compound 71: (s)-1-{4-[4-(4-Tert-butylphenylamino)phenoxy]-6-methoxyquinolin-7-yloxy}-3-morpholin-4-ylpropan-2-ol 4-[4-(4-Tert-butylphenylamino)phenoxy]-6-methoxyquinolin-7-ol (compound 21) (210 mg) was dissolved in N,N-dimethylformamide (10 ml) to prepare a solution. Potassium carbonate (500 mg) and p-toluenesulfonic acid (2S)-(+)-glycidyl (0.31 g) were then added to the solution, and the mixture was stirred at room temperature overnight. Morpholine (0.5 ml) was added to the reaction solution, and the mixture was stirred at 70° C. for additional 9 hr. Water and ethyl acetate were added to the reaction solution, and the mixture was extracted with ethyl acetate. The extract was washed with saturated brine and was dried over sodium sulfate. The solvent was removed by evaporation under the reduced pressure, and the residue was purified by thin-layer chromatography on silica gel using chloroform/acetone for development to give the title compound (180 mg, yield 64%).

$^1$H-NMR (CDCl$_3$, 400 MHz): δ 8.48 (d, J=5.4 Hz, 1H), 7.58 (s, 1H), 7.43 (s, 1H), 7.33 (d, J=8.8 Hz, 2H), 7.04–7.14 (m, 6H), 6.48 (d, J=5.1 Hz, 1H), 5.69 (br, 1H), 4.25–4.32 (m, 1H), 4.15–4.24 (m, 2H), 4.02 (s, 3H), 3.69–3.79 (m, 4H), 2.66–2.72 (m, 2H), 2.60–2.64 (m, 2H), 2.48–2.54 (m, 2H), 1.32 (s, 9H)

Mass spectrometric value (m/z): 558 [M+H]$^+$

Compound 75: [4-(6,7-Dimethoxyquinolin-4-yloxy)phenyl]-(4,5-dimethylthiazol-2-yl)amine 4-[(6,7-Dimethoxy-4-quinolyl)oxy]aniline (200 mg) was dissolved in ethanol (30 ml) to prepare a solution. 4-Chlorobenzoyl isothiocyanate (173 mg) was added to the solution, and the mixture was stirred at room temperature for 3 hr. After the completion of the reaction, the solvent was removed by evaporation. The crude thus obtained was purified by chromatography on silica gel using chloroform/acetone for development to give N-(4-chlorobenzoyl)-N'-4-[(6,7-dimethoxy-4-quinolyl)oxy]phenyl]thiourea (313 mg, yield 94%).

This compound was added to a 3 N aqueous sodium hydroxide solution (10 ml), and the mixture was stirred with heating at 100° C. for 10 min. The heating was stopped, and the reaction solution was acidified by the addition of concentrated hydrochloric acid and was then rendered weakly alkaline by the addition of aqueous ammonia. The precipitate in the solution was collected by filtration while washing with water to give N-{4-[(6,7-dimethoxy-4-quinolyl)oxy]phenyl}thiourea (200 mg, yield 89%).

N-{4-[(6,7-Dimethoxy-4-quinolyl)oxy]phenyl}thiourea (50 mg) was dissolved in dimethylformamide (5 ml) to prepare a solution. Triethylamine (43 mg) and 3-bromo-2-butanone (43 mg) were added to the solution, and the mixture was stirred at room temperature for 3 hr. Water and ethyl acetate were added to the reaction solution, and the mixture was extracted with ethyl acetate. The extract was then washed with saturated brine and was dried over anhydrous sodium sulfate, and the solvent was removed by evaporation under the reduced pressure. The crude thus obtained was purified by column chromatography on silica gel using chloroform/methanol for development to give the title compound (42 mg, yield 73%).

$^1$H-NMR (CDCl$_3$, 400 MHz): 2.14 (s, 2H), 2.18 (s, 4H), 3.97 (s, 3H), 3.98 (s, 3H), 6.39 (d, J=5.4 Hz, 1H), 7.07 (d, J=8.8 Hz, 2H), 7.35 (s, 1H), 7.35 (d, J=8.8 Hz, 2H), 7.50 (s, 1H), 8.40 (d, J=5.4 Hz, 1H)

Mass spectrometric value (m/z): 408 [M+1]$^+$

Compound 76: 5-[4-(6,7-Dimethoxyquinolin-4-yloxy)phenylamino]-3-phenyl-3H-[1,3,4]oxazol-2-one 4-(6,7-Dimethoxy-4-quinolyloxy)aniline (310 mg) was dissolved in triethylamine/chloroform (5 ml/20 ml) to prepare a solution. Triphosgene (350 mg) was then added to the solution, and the mixture was stirred at room temperature for 30 min. Phenylhydrazine hydrochloride (180 mg) was added to the reaction solution, and the mixture was stirred at room temperature for additional 30 min. Water and ethyl acetate were added to the reaction solution, and the mixture was extracted with ethyl acetate. The extract was washed with saturated brine and was dried over sodium sulfate. The solvent was removed by evaporation under the reduced pressure, and the residue was purified by thin-layer chromatography on silica gel using chloroform/acetone for development to give N1-{4-[(6,7-dimethoxy-4-quinolyl)oxy]phenyl}-2-phenyl-1-hydrazinecarboxamide (270 mg, yield 60%).

N1-{4-[(6,7-Dimethoxy-4-quinolyl)oxy]phenyl}-2-phenyl-1-hydrazinecarboxamide (34 mg) was dissolved in chloroform (5 ml) to prepare a solution. Triethylamine (1 ml) and triphosgene (77 mg) were then added to the solution, and the mixture was stirred at room temperature for 2 hr. Water and ethyl acetate were added to the reaction solution, and the mixture was extracted with ethyl acetate. The extract was washed with saturated brine and was dried over sodium sulfate. The solvent was removed by evaporation under the reduced pressure, and the residue was purified by thin-layer chromatography on silica gel using chloroform/methanol for development to give the title compound (6 mg, yield 17%).

$^1$H-NMR (DMSO-d$_6$, 400 MHz): δ 8.52 (d, J=5.1 Hz, 1H), 7.72–7.66 (m, 4H), 7.50 (s, 1H), 7.45 (m, 2H), 7.41 (s, 1H), 7.39 (d, J=9.0 Hz, 2H), 7.20 (m, 1H), 6.60 (d, J=5.1 Hz, 1H), 3.96 (s, 3H), 3.94 (s, 3H)

Mass spectrometric value (m/z): 455 [M−H]$^−$

Compound 77: (4-Tert-butylcyclohexyl)-[4-(6,7-dimethoxyquinolin-4-yloxy)phenyl]amine 4-(6,7-Dimethoxy-4-quinolyloxy)aniline (300 mg) was dissolved in N,N-dimethylformamide (10 ml) to prepare a solution. 4-Tert-butylcyclohexanone (200 mg) was then added to the solution, and the mixture was stirred at 60° C. for one hr. The reaction solution was cooled to room temperature before sodium triacetoxy borohydride (400 mg) was added thereto. The mixture was then stirred at room temperature for 3 hr. Water and ethyl acetate were added to the reaction solution, and the mixture was extracted with ethyl acetate. The extract was washed with saturated brine and was dried over sodium sulfate. The solvent was removed by evaporation under the reduced pressure, and the residue was purified by chromatography on silica gel using chloroform/acetone for development to give the title compound (50 mg, yield 11%).

$^1$H-NMR (CDCl$_3$, 400 MHz): δ 8.45 (m, 1H), 7.59 (s, 1H), 7.48 (s, 1H), 7.02–6.96 (m, 2H), 6.70–6.62 (m, 2H), 6.48 (m, 1H), 4.05 (s, 6H), 3.18 (m, 1H), 2.25–1.05 (m, 9H), 0.88 (m, 9H)

Mass spectrometric value (m/z): 435 [M+H]$^+$

Compound 78: (4-Tert-butylphenyl)-{4-[6-methoxy-7-(2-morpholin-4-ylethoxy)quinazolin-4-yloxy]phenyl}amine 4-{4-[4-(Tert-butyl)anilino]phenoxy}-6-methoxy-7-quinazolinol (starting compound 11) (100 mg), potassium carbonate (50 mg), and 4-(2-chloroethyl)morpholine hydrochloride (67 mg) were added to N,N-dimethylformamide (2 ml), and the mixture was stirred at 80° C. overnight. Water was added to the reaction solution, and the mixture was extracted with ethyl acetate. The ethyl acetate layer was washed with saturated brine and was dried over sodium sulfate. The solvent was then removed by evaporation under the reduced pressure. The crude thus obtained was purified by thin-layer chromatography on silica gel using chloroform/methanol for development to give the title compound (120 mg, yield 94%).

$^1$H-NMR (DMSO-d$_6$, 400 MHz): δ 8.54 (s, 1H), 8.09 (s, 1H), 7.55 (s, 1H), 7.41 (s, 1H), 7.28 (d, J=8.5 Hz, 2H), 7.12 (m, 4H), 7.04 (d, J=8.8 Hz, 2H), 4.32 (t, J=5.6 Hz, 2H), 3, 97 (s, 3H), 3.60 (m, 4H), 2.80 (t, J=5.9 Hz, 2H), 2.53 (m, 4H), 1.27 (s, 9H)

Mass spectrometric value (m/z): 527 [M−H]$^−$

Compound 79: (4-Tert-butylphenyl)-{2-fluoro-4-[6-methoxy-7-(2-morpholin-4-ylethoxy)quinolin-4-yloxy]phenyl}amine 4-{4-[4-(Tert-butyl)anilino]-3-fluorophenoxy}-6-methoxy-7-quinolinol (starting compound 6) (1.75 g), potassium carbonate (2.80 g), and 4-(2-chloroethyl)morpholine hydrochloride (1.13 g) were added to N,N-dimethylformamide (20 ml), and the mixture was stirred at 80° C. overnight. Water was added to the reaction solution, and the mixture was extracted with ethyl acetate. The ethyl acetate layer was washed with saturated brine and was dried over sodium sulfate. The solvent was then removed by evaporation under the reduced pressure. The crude thus obtained was purified by chromatography on silica gel using chloroform/methanol for development to give the title compound (1.44 g, yield 64%).

$^1$H-NMR (CDCl$_3$, 400 MHz): δ 8.50 (d, J=5.4 Hz, 1H), 7.53 (s, 1H), 7.41 (s, 1H), 7.31–7.38 (m, 3H), 7.09 (d, J=8.5 Hz, 2H), 6.97 (m, 1H), 6.88 (m, 1H), 6.51 (d, J=5.4 Hz, 1H), 5.74 (br, 1H), 4.34 (t, J=5.9 Hz, 2H), 4.03 (s, 3H), 3.76 (m, 4H), 2.96 (t, J=5.9 Hz, 2H), 2.64 (m, 4H), 1.33 (s, 9H)

Mass spectrometric value (m/z): 546 [M+H]$^+$

Compound 87: 1-(3,3-Dimethyl-butyl)-3-{2-fluoro-4-[6-methoxy-7-(2-morpholin-4-yl-ethoxy)-quinolin-4-yloxy]-phenyl}-urea 4-[(7-Benzyloxy-6-methoxy-4-quinolyl)oxy]-2-fluoroaniline (3.0 g) was dissolved in anhydrous chloroform (100 ml) to prepare a solution. Triethylamine (3.9 g) was added to the solution, and a solution of triphosgene (2.3 g) in anhydrous chloroform (5 ml) was then added thereto. The mixture was stirred at room temperature for 30 min. Subsequently, a solution of 3,3-dimethylbutylamine (1.6 g) in anhydrous chloroform (5 ml) was added thereto, and the mixture was stirred at room temperature for additional 1 hr. A saturated sodium hydrogencarbonate solution was added thereto, and the mixture was stirred. The organic layer was then separated, was washed with saturated brine, and was dried over anhydrous sodium sulfate. The solvent was removed by evaporation under the reduced pressure. The residue was purified by column chromatography on silica gel, and 1-[4-([7-benzyloxy-6-methoxy-quinolin-4-yloxy]-2-fluorophenyl)-3-(3,3-dimethyl-butyl)urea (3.9 g, yield 97%) was obtained from the fraction of chloroform: methanol (98:2).

$^1$H-NMR (CDCl$_3$, 400 MHz): 0.93 (s, 9H), 1.43–1.47 (m, 2H), 3.26–3.31 (m, 2H), 4.01 (s, 3H), 4.78 (brs, 1H), 5.30 (s, 2H), 6.45 (d, J=5.4 Hz, 1H), 6.57 (brs, 1H), 6.88–6.95 (m, 2H), 7.28–7.49 (m, 5H), 7.44 (s, 1H), 7.50 (s, 1H), 8.14 (t, J=8.8 Hz, 1H), 8.45 (d, J=5.4 Hz, 1H)

1-[4-([7-Benzyloxy-6-methoxy-quinolin-4-yloxy]-2-fluorophenyl)-3-(3,3-dimethyl-butyl)urea (11 g) prepared above was suspended in trifluoroacetic acid (20 ml) and methanesulfonic acid (1 ml), and the suspension was heated under reflux for 1 hr. The solvent was removed by evaporation under the reduced pressure. Water was added to the residue, and the solution was adjusted to a pH value of substantially 7 by the addition of a 10% sodium hydroxide solution. The resultant precipitate was collected by filtration to give 1-(3,3-dimethyl-butyl)-3-[2-fluoro-4-(7-hydroxy-6-methoxy-quinolin-4-yloxy)-phenyl]-urea. Next, N,N-dimethylformamide (2 ml) was added to the urea (103 mg) (starting compound A), potassium carbonate (166 mg), and 4-(2-chloroethyl)morpholine hydrochloride (69 mg) (starting compound B), and the mixture was stirred at 75 to 80° C. for 16 hr. Water and ethyl acetate were added to the reaction solution, and the mixture was extracted with ethyl acetate. The extract was washed with saturated brine and was dried over sodium sulfate, and the solvent was then removed by evaporation under the reduced pressure. The crude thus obtained was purified by thin-layer chromatography on silica gel using chloroform/methanol for development to give the title compound (47.7 mg, yield 37%).

$^1$H-NMR (CDCl$_3$+CD$_3$OD, 400 MHz): 0.96 (s, 9H), 1.45–1.51 (m, 2H), 2.72 (br, 4H), 3.02 (t, J=5.6 Hz, 2H), 3.28–3.34 (m, 2H), 3.78–3.81 (m, 4H), 4.02 (s, 3H), 4.40 (t, J=5.6 Hz, 2H), 5.16 (br, 1H), 6.51 (d, J=5.6 Hz, 1H), 6.89 (dd, J=2.7, 11.2 Hz, 1H), 6.91 (br, 1H), 6.95–6.97 (m, 1H), 7.52 (s, 1H), 7.55 (s, 1H), 8.24 (dd, J=9.0, 9.0 Hz, 1H), 8.46 (d, J=5.6 Hz, 1H)

Mass spectrometric value (ESI-MS, m/z): 541 (M$^+$+1)

1-(3,3-Dimethyl-butyl)-3-{2-fluoro-4-[6-methoxy-7-(2-morpholin-4-yl-ethoxy)-quinolin-4-yloxy]-phenyl}-urea hydrochloride 1-(3,3-Dimethyl-butyl)-3-{2-fluoro-4-[6-methoxy-7-(2-morpholin-4-yl-ethoxy)-quinolin-4-yloxy]-phenyl}-urea (42.7 mg) was dissolved in chloroform (1 ml) and methanol (1 ml) to prepare a solution. To the solution was added 10 drops of 10% hydrogen chloride-methanol with a Pasteur pipette. The mixture was concentrated by an evaporator, and the concentrate was dried by means of a vacuum pump to give a hydride compound (48.9 mg).

$^1$H-NMR (CDCl$_3$+CD$_3$OD, 400 MHz): 0.96 (s, 9H), 1.45–1.51 (m, 2H), 3.22–3.32 (m, 4H), 3.71–3.80 (m, 4H), 4.00–4.10 (m, 5H), 4.18–4.28 (m, 2H), 4.94 (br, 2H), 6.84 (d, J=5.1 Hz, 1H), 6.97 (d, J=9.0 Hz, 2H), 7.64 (s, 1H), 8.01 (s, 1H), 8.38 (t, J=9.0 Hz, 1H), 8.57 (d, J=4.6 Hz, 1H)

Mass spectrometric value (ESI-MS, m/z): 563 (M+Na)$^+$

Compound 99: 1-(3,3-Dimethyl-butyl)-3-{2-fluoro-4-[6-methoxy-7-(2-piperidin-1-yl-ethoxy)-quinolin-4-yloxy]-phenyl}-urea A crude product of 1-(3,3-dimethyl-butyl)-3-[2-fluoro-4-(7-hydroxy-6-methoxy-quinolin-4-yloxy)-phenyl]-urea was dissolved in dimethylformamide (100 ml) to prepare a solution. Potassium carbonate (18 g) and 1-bromo-2-chloroethane (11 g) were added to the solution, and the mixture was stirred at room temperature for 20 hr. The mixture was extracted with ethyl acetate, was then washed with saturated brine, and was dried over anhydrous sodium sulfate. The solvent was removed by evaporation under the reduced pressure. The residue was washed with a mixed solvent of n-hexane: ethyl acetate (2:1) and was then collected by filtration to give 1-{4-[7-(2-chloroethoxy)-6-methoxy-quinolin-4-yloxy]-2-fluorophenyl}-3-(3,3-dimethyl-butyl)urea (7.7 g, yield 74%).

$^1$H-NMR (CDCl$_3$, 400 MHz): 0.94 (s, 3H), 1.44–1.48 (m, 2H), 3.26–3.32 (m, 2H), 3.91–3.95 (m, 2H), 4.01 (s, 3H), 4.41–4.45 (m, 2H), 4.79–4.81 (m, 1H), 6.47 (d, J=5.4 Hz, 1H), 6.55–6.57 (m, 1H), 6.89–6.96 (m, 2H), 7.40 (s, 1H), 7.51 (s, 1H), 8.10 (t, J=8.8 Hz, 1H), 8.47 (d, J=5.4 Hz, 1H)

N,N-Dimethylformamide (80 ml) was added to the urea (1.98 g) (starting compound A), potassium carbonate (5 eq, 2.82 g), and piperidine (5 eq, 2.02 ml) (starting compound B), and the mixture was stirred at 70 to 75° C. for 17 hr. Piperidine (2 eq, 0.8 ml) (starting compound B) was added thereto. The mixture was further stirred at 70 to 75° C. for 23 hr. Water and ethyl acetate were added to the reaction solution, and the mixture was extracted with ethyl acetate. The extract was washed with saturated brine and was dried over sodium sulfate, and the solvent was then removed by evaporation under the reduced pressure. The crude thus obtained was purified by chromatography on alumina (grade III) using chloroform/methanol for development to give the title compound (1.69 g, yield 78%).

$^1$H-NMR (CDCl$_3$, 400 MHz): δ 0.95 (s, 9H), 1.43–1.52 (m, 4H), 1.62–1.70 (m, 4H), 2.53–2.62 (m, 4H), 2.92 (t, J=5.9 Hz, 2H), 3.24–3.31 (m, 2H), 4.02 (s, 3H), 4.32 (t, J=5.9 Hz, 2H), 6.48 (d, J=5.4 Hz, 1H), 6.87–6.97 (m, 2H), 7.38 (s, 1H), 7.52 (s, 1H), 8.19–8.26 (m, 1H), 8.43 (d, J=5.4 Hz, 1H)

Mass spectrometric value (ESI-MS, m/z): 539 (M+1)

1-(3,3-Dimethyl-butyl)-3-{2-fluoro-4-[6-methoxy-7-(2-piperidin-1-yl-ethoxy)-quinolin-4-yloxy]-phenyl}-urea hydrochloride Methanol (20 ml) and chloroform (2 ml) were added to 1-(3,3-dimethyl-butyl)-3-{2-fluoro-4-[6-methoxy-7-(2-piperidin-1-yl-ethoxy)-quinolin-4-yloxy]-phenyl}-urea to prepare a solution. Hydrogen chloride-methanol was added to the solution, and the mixture was acidified and was concentrated. Diethyl ether was added to the residue, and mixture was filtrated to give the title compound (1.75 g, yield 91%).

$^1$H-NMR (CDCl$_3$, 400 MHz): δ 0.93 (s, 9H), 1.46–1.52 (m, 2H), 1.78–1.96 (m, 4H), 2.13–2.27 (m, 2H), 3.03–3.12 (m, 2H), 3.21–3.27 (m, 2H), 3.68–3.83 (m, 4H), 4.05 (s, 3H), 4.87–4.94 (m, 2H), 6.82 (d, J=6.6 Hz, 1H), 6.87–6.96 (m, 2H), 7.58 (s, 1H), 7.97 (s, 1H), 8.30–8.33 (m, 1H), 8.56 (d, J=6.8 Hz, 1H)

Mass spectrometric value (ESI-MS, m/z): 539 (M+1)

Compound 101: 1-[4-(6,7-Dimethoxy-quinolin-4-yloxy)-phenyl]-3-(3,3-dimethyl-butyl)-urea 4-[(6,7-Dimethoxy-quinolyl)oxy]aniline (2 g) was dissolved in chloroform (100 ml) (starting compound A) to prepare a solution. Triethylamine (2 ml) was added to the solution. A solution of triphosgene (1 g) in chloroform (4 ml) was added dropwise thereto, and the mixture was stirred at room temperature for 30 min. 3,3-Dimethylbutylamine (750 mg) (starting compound B) was added thereto, and the mixture was stirred at room temperature for 5 hr. Water and chloroform were added to the reaction solution, and the mixture was extracted with chloroform. The extract was washed with saturated brine and was dried over sodium sulfate. The solvent was then removed by evaporation under the reduced pressure. The crude thus obtained was purified by chromatography on silica gel using chloroform/acetone for development to give the title compound (1.70 g, yield 59%).

$^1$H-NMR (CDCl$_3$, 400 MHz): 0.93 (s, 9H), 1.42–1.46 (m, 2H), 3.27–3.32 (m, 2H), 4.03 (s, 3H), 4.03 (s, 3H), 5.03 (br, 1H), 6.44 (d, J=5.3 Hz, 1H), 7.11 (d, J=9.0 Hz, 2H), 7.41 (s, 1H), 7.43 (d, J=8.8 Hz, 2H), 7.55 (s, 1H), 8.46 (d, J=5.1 Hz, 1H), 8.84 (br, 1H)

Mass spectrometric value (ESI-MS, m/z): 424 (M$^+$+1)

1-[4-(6,7-Dimethoxy-quinolin-4-yloxy)-phenyl]-3-(3,3-dimethyl-butyl)-urea hydrochloride Methanol (20 ml) and chloroform (2 ml) were added to 1-[4-(6,7-dimethoxy-quinolin-4-yloxy)-phenyl]-3-(3,3-dimethyl-butyl)-urea to prepare a solution. The solution was acidified by the addition of hydrogen chloride-methanol, and the acidified solution was concentrated. Diethyl ether was added to the residue, and the mixture was filtrated to give the title compound (1.75 g, yield 91%).

$^1$H-NMR (CDCl$_3$, 400 MHz): 0.92 (s, 9H), 1.45–1.49 (m, 2H), 3.24–3.30 (m, 2H), 4.10 (s, 3H), 4.14 (s, 3H), 5.98 (br, 1H), 6.48 (d, J=6.6 Hz, 1H), 7.02 (d, J=9.0 Hz, 2H), 7.65 (s, 1H), 7.72 (d, J=9.0 Hz, 2H), 7.88 (s, 1H), 8.18 (d, J=6.6 Hz, 1H), 8.84 (br, 1H)

Mass spectrometric value (ESI-MS, m/z): 424 (M$^+$+1)

Compounds 5, 20, 21, 22, 24, 30, 31, 32, 37, 42, 44, 59, 70, 71, 75, 76, 77, 78, 79, 87, 99 and 101 had the following respective chemical structures.

| Compound No. | Structure of compound |
|---|---|
| 5 | 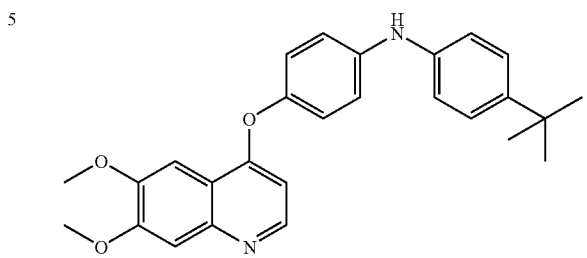 |
| 20 | 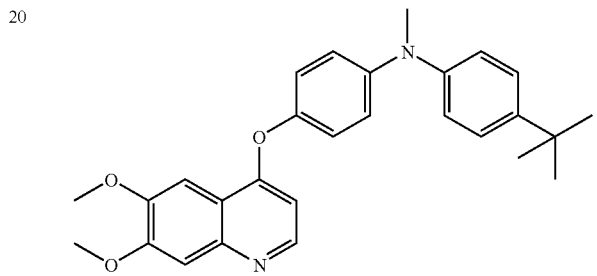 |

-continued
| Compound No. | Structure of compound |
|---|---|
| 21 | 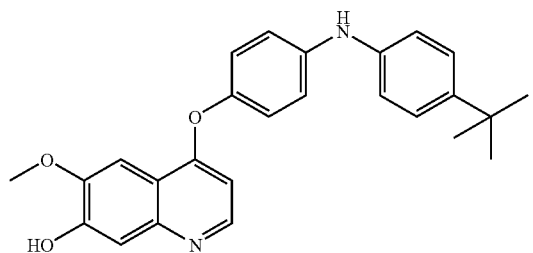 |
| 22 | 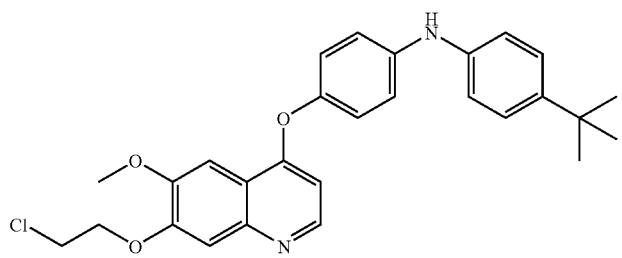 |
| 24 | 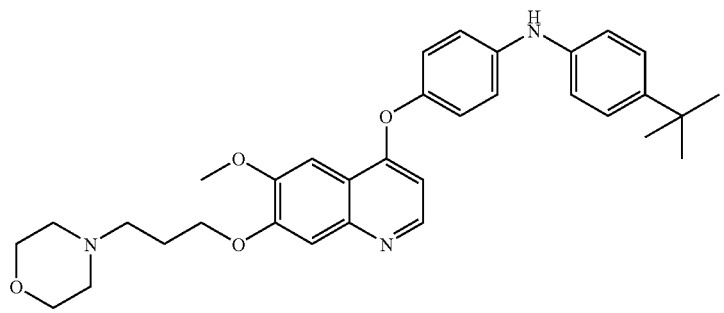 |
| 30 | 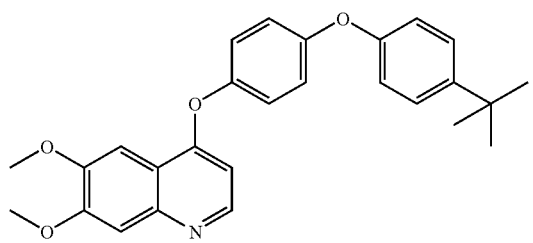 |
| 31 | 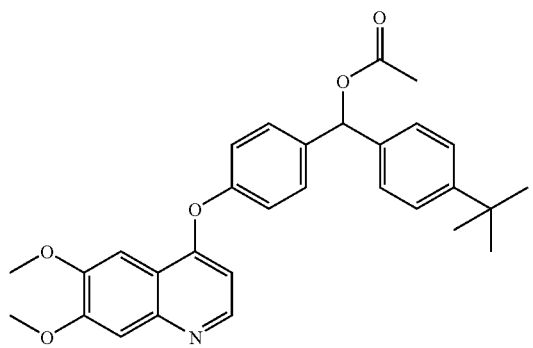 |

-continued
| Compound No. | Structure of compound |
|---|---|
| 32 | 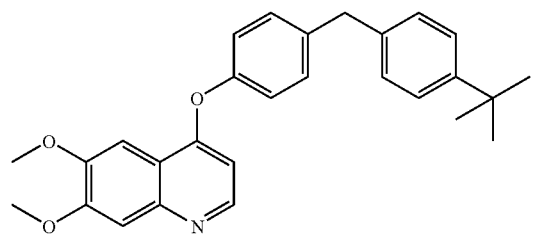 |
| 37 | 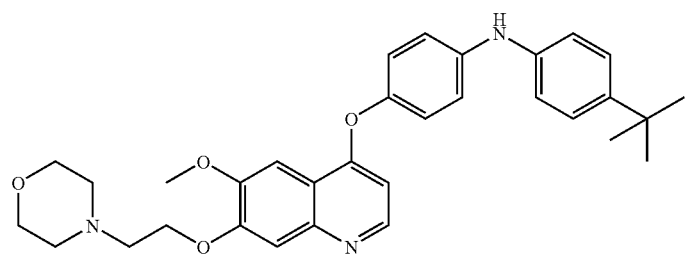 |
| 42 | 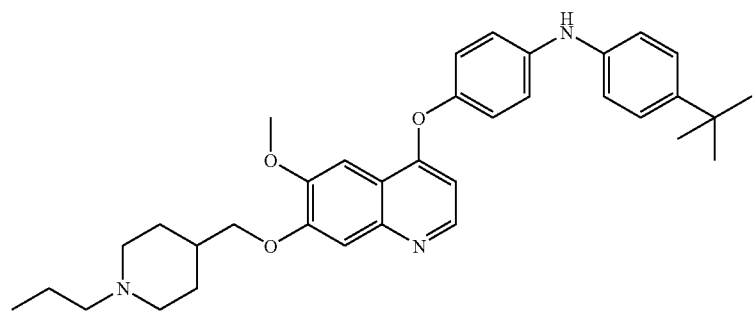 |
| 44 | 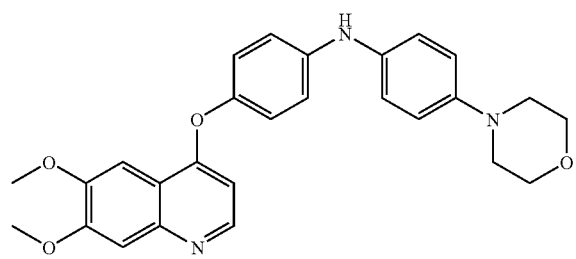 |
| 59 | 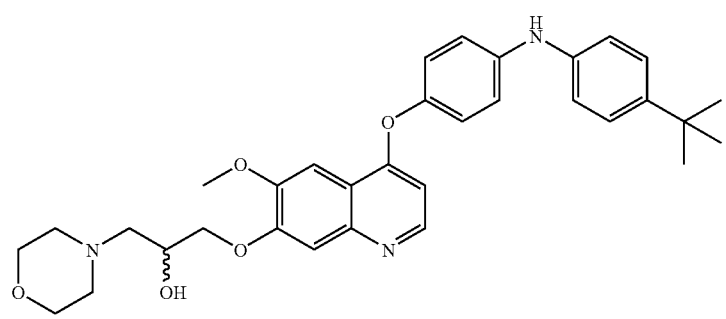 |

-continued

| Compound No. | Structure of compound |
|---|---|
| 70 | |
| 71 | |
| 75 | |
| 76 | |
| 77 | |

-continued

| Compound No. | Structure of compound |
|---|---|
| 78 | |
| 79 | |
| 87 | |
| 99 | |
| 101 | |

The following compounds were synthesized in the same manner as in the Synthesis Examples of the above compounds.

Compound No. Name of Compound

1: [4-(6,7-Dimethoxyquinolin-4-yloxy)phenyl]-(4-methoxyphenyl)-amine
2: [4-(6,7-Dimethoxyquinolin-4-yloxy)phenyl]-(4-vinylphenyl)amine
3: Biphenyl-4-yl-[4-(6,7-dimethoxyquinolin-4-yloxy)phenyl]amine
4: [4-(6,7-Dimethoxyquinolin-4-yloxy)phenyl]-(4-fluorophenyl)amine
6: [4-(6,7-Dimethoxyquinolin-4-yloxy)phenyl]-(4-trifluoromethoxy-phenyl)amine
7: (4-Benzyloxyphenyl)-[4-(6,7-dimethoxyquinolin-4-yloxy)phenyl]-amine
8: (4-Butylphenyl)-[4-(6,7-dimethoxyquinolin-4-yloxy)phenyl]amine
9: [4-(6,7-Dimethoxyquinolin-4-yloxy)phenyl]-(4-isopropylphenyl)-amine
10: (4-Cyclohexylphenyl)-[4-(6,7-dimethoxyquinolin-4-yloxy)phenyl]-amine
11: (4-Tert-butylphenyl)-[2-chloro-4-(6,7-dimethoxyquinolin-4-yloxy)phenyl]amine
12: (4-Tert-butylphenyl)-[3-chloro-4-(6,7-dimethoxyquinolin-4-yloxy)phenyl]amine
13: (4-Tert-butylphenyl)-[4-(6,7-dimethoxyquinolin-4-yloxy)-2-methylphenyl]amine
14: (4-Tert-butylphenyl)-[4-(6,7-dimethoxyquinolin-4-yloxy)-2-methoxyphenyl]amine
15: (4-Tert-butylphenyl)-[4-(6,7-dimethoxyquinolin-4-yloxy)-3-methoxyphenyl]amine
16: (4-Tert-butylphenyl)-[4-(6,7-dimethoxyquinolin-4-yloxy)-2,3-dimethylphenyl]amine
17: (4-Tert-butylphenyl)-[4-(6,7-dimethoxyquinolin-4-yloxy)-2,5-dimethylphenyl]amine
18: (4-Tert-butylphenyl)-[4-(6,7-dimethoxyquinolin-4-yloxy)-3-fluorophenyl]amine
19: (4-Tert-butylphenyl)-[4-(6,7-dimethoxyquinolin-4-yloxy)-2-fluorophenyl]amine
23: (4-Tert-butylphenyl)-{4-[7-(3-chloropropoxy)-6-methoxyquinolin-4-yloxy]phenyl}amine
25: (4-Tert-butylphenyl)-{4-[6-methoxy-7-(4-morpholin-4-ylbutoxy)-quinolin-4-yloxy]phenyl}amine
26: 3-{4-[4-(4-Tert-butylphenylamino)phenoxy]-6-methoxyquinolin-7-yloxy}propionamide
27: (4-Tert-butylphenyl)-(4-{6-methoxy-7-[2-(1-methylpyrrolidin-2-yl)ethoxy]quinolin-4-yloxy}phenyl)amine
28: (4-Tert-butylphenyl)-{4-[6-methoxy-7-(2-methylthiazol-4-ylmethoxy)quinolin-4-yloxy]phenyl}amine
29: (4-Tert-butylphenyl)-(4-{6-methoxy-7-[4-(4-methylpiperazin-1-yl)butoxy]quinolin-4-yloxy}phenyl)amine
33: (4-Tert-butylphenyl)-(4-{6-methoxy-7-[2-(4-methylpiperazin-1-yl)ethoxy]quinolin-4-yloxy}phenyl)amine
34: (4-Tert-butylphenyl)-{4-[6-methoxy-7-(3-piperidin-1-ylpropoxy)-quinolin-4-yloxy]phenyl}amine
35: (4-Tert-butylphenyl)-(4-{6-methoxy-7-[3-(4-methylpiperazin-1-yl)propoxy]quinolin-4-yloxy}phenyl)amine
36: (4-Tert-butylphenyl)-{4-[6-methoxy-7-(4-piperidin-1-ylbutoxy)-quinolin-4-yloxy]phenyl}amine
38: (4-Tert-butylphenyl)-{4-[6-methoxy-7-(2-piperidin-1-ylethoxy)-quinolin-4-yloxy]phenyl}amine
39: (4-Tert-butylphenyl)-{4-[6-methoxy-7-(2-pyrrolidin-1-ylethoxy)-quinolin-4-yloxy]phenyl}amine
40: N1-[4-(Tert-butyl)phenyl]-4-({7-[2-(dimethylamino)ethoxy]-6-methoxy-4-quinolyl}oxy)aniline
41: N1-[4-(Tert-butyl)phenyl]-4-({7-[2-(diethylamino)ethoxy]-6-methoxy-4-quinolyl}oxy)aniline
43: (3,4-Dimethoxyphenyl)-[4-(6,7-dimethoxyquinolin-4-yloxy)-phenyl]amine
45: (4-Tert-butylphenyl)-(4-{6-methoxy-7-[2-(4-methyl-[1,4]diazepin-1-yl)ethoxy]quinolin-4-yloxy}phenyl)amine
46: N1-[4-(Tert-butyl)phenyl]-4-({7-[3-(dimethylamino)propoxy]-6-methoxy-4-quinolyl}oxy)aniline
47: N1-[4-(Tert-butyl)phenyl]-4-({7-[3-(diethylamino)propoxy]-6-methoxy-4-quinolyl}oxy)aniline
48: 2-[(2-{4-[4-(4-Tert-butyl-phenylamino)phenoxy]-6-methoxy-quinolin-7-yloxy}ethyl)-(2-hydroxyethyl)amino]ethanol
49: 2-[(2-{4-[4-(4-Tert-butyl-phenylamino)phenoxy]-6-methoxy-quinolin-7-yloxy}ethyl)methylamino]ethanol
50: {4-[7-(2-Azepan-1-ylethoxy)-6-methoxyquinolin-4-yloxy]phenyl}-(4-tert-butylphenyl)amine
51: 2-[(3-{4-[4-(4-Tert-butylphenylamino)phenoxy]-6-methoxy-quinolin-7-yloxy}propyl)-(2-hydroxyethyl)amino]ethanol
52: 2-[(3-{4-[4-(4-Tert-butylphenylamino)phenoxy]-6-methoxy-quinolin-7-yloxy}propyl)methylamino]ethanol
53: (4-Tert-butylphenyl)-{4-[6-methoxy-7-(3-pyrrolidin-1-ylpropoxy)-quinolin-4-yloxy]phenyl}amine
54: {4-[7-(3-Azepan-1-ylpropoxy)-6-methoxyquinolin-4-yloxyl]-phenyl}-(4-tert-butylphenyl)amine
55: (4-Tert-butylphenyl)-{4-[6-methoxy-7-(1-methylpiperidin-2-ylmethoxy)quinolin-4-yloxy]phenyl}amine
56: (4-Tert-butylphenyl)-{4-[6-methoxy-7-(1-methylpiperidin-3-ylmethoxy)quinolin-4-yloxy]phenyl}amine
57: (4-Tert-butylphenyl)-{4-[6-methoxy-7-(5-vinyl-1-azabicyclo-[2.2.2]oct-2-ylmethoxy)quinolin-4-yloxy]phenyl}amine
58: (4-Tert-butylphenyl)-{4-[6-methoxy-7-(1-methylpyrrolidin-2-ylmethoxy)quinolin-4-yloxy]phenyl}amine
60: 1-{4-[4-(4-Tert-butyl-phenylamino)phenoxy]-6-methoxyquinolin-7-yloxy}-3-diethylaminopropan-2-ol
61: 1-{4-[4-(4-Tert-butyl-phenylamino)phenoxy]-6-methoxyquinolin-7-yloxy}-3-pyrrolidin-1-ylpropan-2-ol
62: 1-{4-[4-(4-Tert-butyl-phenylamino)phenoxy]-6-methoxyquinolin-7-yloxy}-3-piperidin-1-ylpropan-2-ol
63: 1-Azepan-1-yl-3-{4-[4-(4-tert-butylphenylamino)phenoxy]-6-methoxyquinolin-7-yloxy}propan-2-ol
64: 1-{4-[4-(4-Tert-butylphenylamino)phenoxy]-6-methoxyquinolin-7-yloxy}-3-(4-methylpiperazin-1-yl)propan-2-ol
65: 1-{4-[4-(4-Tert-butylphenylamino)phenoxy]-6-methoxyquinolin-7-yloxy}-3-(4-methyl-[1,4]diazepin-1-yl)propan-2-ol
66: 1-{4-[4-(4-Tert-butylphenylamino)phenoxy]-6-methoxyquinolin-7-yloxy}-3-ethylaminopropan-2-ol
67: 1-{4-[4-(4-Tert-butylphenylamino)phenoxy]-6-methoxyquinolin-7-yloxy}-3-dimethylaminopropan-2-ol
68: (4-Tert-butylphenyl)-(4-{7-[2-(2,6-dimethylmorpholin-4-yl)ethoxy]-6-methoxyquinolin-4-yloxy}phenyl)amine
69: (4-Tert-butylphenyl)-(4-{7-[3-(2,6-dimethylmorpholin-4-yl)propoxy]-6-methoxyquinolin-4-yloxy}phenyl)amine
72: [4-(6,7-Dimethoxyquinazolin-4-yloxy)phenyl]-(4-isopropyl-phenyl)amine
73: [4-(6,7-Dimethoxyquinolin-4-yloxy)phenyl]thiophen-3-ylamine
74: (4-Tert-butylphenyl)-[4-(6,7-dimethoxyquinazolin-4-yloxy)-phenyl]amine
80: (4-Tert-butylphenyl)-{4-[6-methoxy-7-(3-morpholin-4-ylbutoxy)-quinolin-4-yloxy]phenyl}amine 81: [1-(2-{4-[4-(4-Tert-butylphenylamino)phenoxy]-6-methoxy-quinolin-7-yloxy}ethyl)piperidin-4-yl]methanol
82: 1-(2-{4-[4-(4-Tert-butylphenylamino)phenoxy]-6-methoxy-quinolin-7-yloxy}ethyl)piperidin-4-ol
83: 4-{2-[(4-{4-[4-(Tert-butyl)anilino]phenoxy}-6-methoxy-7-quinolyl)-oxy]ethyl}-1,4-oxazinan-4-ium-4-oleate
84: N-[4-(Tert-butyl)phenyl]-N-(3-chloro-4-{[6-methoxy-7-(2-morpholinoethoxy)-4-quinolyl]oxy}phenyl)amine
85: 2-({2-[(4-{4-[4-(Tert-butyl)anilino]phenoxy}-6-methoxy-7-quinolyl)oxy]ethyl}amino)-1-ethanol
86: 1-[(4-{4-[4-(Tert-butyl)anilino]phenoxy}-7-methoxy-6-quinolyl)-oxy]-3-morpholino-2-propanol
88: 1-(3,3-Dimethyl-butyl)-3-{2-fluoro-4-[6-methoxy-7-(3-morpholin-4-yl-propoxy)-quinolin-4-yloxy]-phenyl}-urea hydrochloride
89: 1-(3,3-Dimethyl-butyl)-3-{2-fluoro-4-[7-(2-hydroxy-3-morpholin-4-yl-propoxy)-6-methoxy-quinolin-4-yloxy]-phenyl}-urea hydrochloride
90: 1-(3,3-Dimethyl-butyl)-3-{4-[7-methoxy-6-(2-morpholin-4-yl-ethoxy)-quinolin-4-yloxy]-phenyl}-urea
91: 1-(3,3-Dimethyl-butyl)-3-{4-[6-methoxy-7-(2-piperidin-1-yl-ethoxy)-quinolin-4-yloxy]-phenyl}-urea hydrochloride
94: 1-(3,3-Dimethyl-butyl)-3-(4-{7-[3-(4-hydroxymethyl-piperidin-1-yl)-propoxy]-6-methoxy-quinolin-4-yloxy}-phenyl)-urea
96: 1-(3,3-Dimethyl-butyl)-3-(4-{7-[3-(4-hydroxy-piperidin-1-yl)-propoxy]-6-methoxy-quinolin-4-yloxy}-phenyl)-urea
97: 1-(3,3-Dimethyl-butyl)-3-(4-{7-[2-(2,6-dimethyl-morpholin-4-yl)-ethoxy]-6-methoxy-quinolin-4-yloxy}-2-fluoro-phenyl)-urea
98: 1-(3,3-Dimethyl-butyl)-3-{3-fluoro-4-[6-methoxy-7-(2-morpholin-4-yl-ethoxy)-quinolin-4-yloxy]-phenyl}-urea
100: 1-{2-Chloro-4-[6-methoxy-7-(2-piperidin-1-yl-ethoxy)-quinolin-4-yloxy]-phenyl}-3-(3,3-dimethyl-butyl)-urea
102: 1-[4-(6,7-Dimethoxy-quinolin-4-yloxy)-3-fluorophenyl]-3-(3,3-dimethyl-butyl)-urea
103: 1-[2-Chloro-4-(6,7-dimethoxyquinolin-4-yloxy)-phenyl]-3-(3,3-dimethyl-butyl)-urea
105: 1-[4-(6,7-Dimethoxy-quinolin-4-yloxy)-phenyl]-3-(3,3,5-trimethyl-cyclohexyl)-urea
106: 1-[4-(6,7-Dimethoxy-quinolin-4-yloxy)-2-fluoro-phenyl]-3-(3,3,5-trimethyl-cyclohexyl)-urea
107: 1-[2-Chloro-4-(6,7-dimethoxy-quinolin-4-yloxy)-phenyl]-3-(3,3,5-tri methyl-cyclohexyl)-urea
108: 1-[4-(6,7-Dimethoxy-quinolin-4-yloxy)-phenyl]-3-(3,3-dimethyl-cyclohexyl)-urea
109: 1-[4-(6,7-Dimethoxy-quinolin-4-yloxy)-2-fluoro-phenyl]-3-(3,3-dimethyl-cyclohexyl)-urea
110: 1-[2-Chloro-4-(6,7-dimethoxy-quinolin-4-yloxy)-phenyl]-3-(3,3-dimethyl-cyclohexyl)-urea
111: 1-[4-(6,7-Dimethoxy-quinolin-4-yloxy)-2-fluoro-phenyl]-3-(3,3-dimethyl-butyl)-urea
112: 1-(3,3-Dimethyl-butyl)-3-{4-[6-methoxy-7-(2-morpholin-4-yl-ethoxy)-quinolin-4-yloxy]-phenyl}-urea hydrochloride
113: 1-(3,3-Dimethyl-butyl)-3-(4-{6-methoxy-7-[2-(4-methyl-piperazin-1-yl)-ethoxy]-quinolin-4-yloxy}-phenyl)-urea hydrochloride
114: 1-{2-Chloro-4-[6-methoxy-7-(2-morpholin-4-yl-ethoxy)-quinolin-4-yloxy]-phenyl}-3-(3,3-dimethyl-butyl)-urea
115: 1-(2-Chloro-4-{6-methoxy-7-[2-(4-methyl-piperazin-1-yl)-ethoxy]-quinolin-4-yloxy}-phenyl)-3-(3,3-dimethyl-butyl)-urea
116: 1-(2-Chloro-4-{7-[2-(2,6-dimethyl-morpholin-4-yl)-ethoxy]-6-methoxy-quinolin-4-yloxy}-phenyl)-3-(3,3-dimethyl-butyl)-urea
117: 1-(2-Chloro-4-{6-methoxy-7-[2-(4-methyl-piperidin-1-yl)-ethoxy]-quinolin-4-yloxy}-phenyl)-3-(3,3-dimethyl-butyl)-urea
119: 1-(3,3-Dimethyl-butyl)-3-(4-{7-[2-(2,6-dimethyl-morpholin-4-yl)-ethoxy]-6-methoxy-quinolin-4-yloxy}-phenyl)-urea
120: 1-(3,3-Dimethyl-butyl)-3-(4-{7-[2-(3,5-dimethyl-piperidin-1-yl)-ethoxy]-6-methoxy-quinolin-4-yloxy}-phenyl)-urea
121: 1-(3,3-Dimethyl-butyl)-3-(4-{6-methoxy-7-[2-(4-phenyl-piperidin-1-yl)-ethoxy]-quinolin-4-yloxy}-phenyl)-urea
122: 1-(4-{7-[2-(4-Benzyl-piperidin-1-yl)-ethoxy]-6-methoxy-quinolin-4-yloxy}-phenyl)-3-(3,3-dimethyl-butyl)-urea
123: 1-{4-[7-(2-[1,4']bipiperidineyl-1'-yl-ethoxy)-6-methoxy-quinolin-4-yloxy]-phenyl}-3-(3,3-dimethyl-butyl)-urea
124: 1-(3,3-Dimethyl-butyl)-3-(4-{6-methoxy-7-[2-(4-pyrrolidin-1-yl-piperidin-1-yl)-ethoxy]-quinolin-4-yloxy}-phenyl)-urea
125: 1-(2-Chloro-4-{7-[2-(2,6-dimethyl-morpholin-4-yl)-ethoxy]-6-methoxy-quinolin-4-yloxy}-phenyl)-3-(3,3-dimethyl-butyl)-urea
126: 1-{3-Chloro-4-[6-methoxy-7-(2-morpholin-4-yl-ethoxy)-quinolin-4-yloxy]-phenyl}-3-(3,3-dimethyl-butyl)-urea
127: 1-(3-Chloro-4-{7-[2-(2,6-dimethyl-morpholin-4-yl)-ethoxy]-6-methoxy-quinolin-4-yloxy}-phenyl)-3-(3,3-dimethyl-butyl)-urea
128: 1-(3,3-Dimethyl-butyl)-3-(4-{7-[2-(2,6-dimethyl-morpholin-4-yl)-ethoxy]-6-methoxy-quinolin-4-yloxy}-3-fluoro-phenyl)-urea
129: 1-(3,3-Dimethyl-butyl)-3-{3-fluoro-4-[6-methoxy-7-(2-piperidin-1-yl-ethoxy)-quinolin-4-yloxy]-phenyl}-urea
130: 1-(3,3-Dimethyl-butyl)-3-(4-{7-[2-(2,6-dimethyl-piperidin-1-yl)-ethoxy]-6-methoxy-quinolin-4-yloxy}-2-fluoro-phenyl)-urea
131: 1-(3,3-Dimethyl-butyl)-3-(2-fluoro-4-{6-methoxy-7-[2-(2,2,6,6-tetramethyl-piperidin-1-yl)-ethoxy]-quinolin-4-yloxy}-phenyl)-urea
132: 1-(3,3-Dimethyl-butyl)-3-(4-{7-[2-(2,6-dimethyl-piperidin-1-yl)-ethoxy]-6-methoxy-quinolin-4-yloxy}-3-fluoro-phenyl)-urea
133: 1-(3,3-Dimethyl-cyclohexyl)-3-{2-fluoro-4-[6-methoxy-7-(2-morpholin-4-yl-ethoxy)-quinolin-4-yloxy]-phenyl}-urea
134: 1-(3,3-Dimethyl-cyclohexyl)-3-(4-{7-[2-(2,6-dimethyl-morpholin-4-yl)-ethoxy]-6-methoxy-quinolin-4-yloxy}-2-fluoro-phenyl)-urea For these compounds, chemical structures, starting compounds, synthesis methods, and data for identifying the compounds are as follows. The numeral described in the column of the synthesis method indicates that the indicated compound has been synthesized according to the Synthesis Example of the indicated compound number.

| Compound No. | Structure of compound | Starting compound A |
|---|---|---|
| 1 | | |
| 2 | | |
| 3 | | |
| 4 | | |
| 6 | | |

| Compound No. | Starting compound B | Mass spectrometric value (m/z) | Synthesis method |
|---|---|---|---|
| 1 | | 403 [M + H]$^+$ | 5 |

-continued
| | | | |
|---|---|---|---|
| 2 | 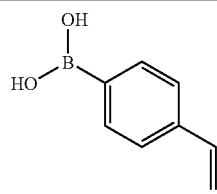 | 399 [M + H]+ | 5 |
| 3 | 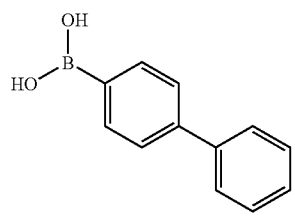 | 449 [M + H]+ | 5 |
| 4 | 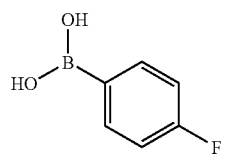 | 391 [M + H]+ | 5 |
| 6 | 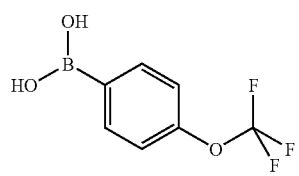 | 457 [M + H]+ | 5 |
| Compound No. | Structure of compound | Starting compound A |
|---|---|---|
| 7 | 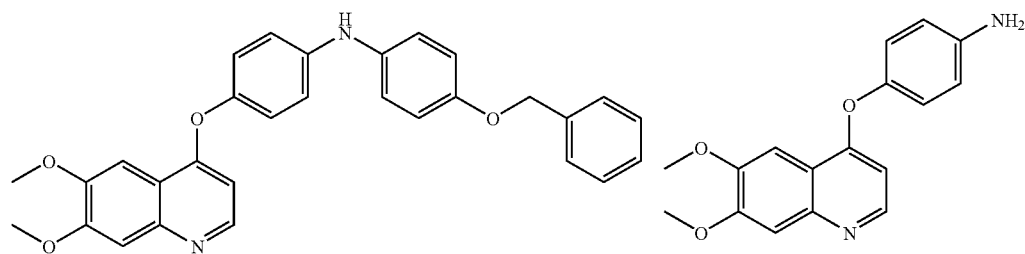 | |
| 8 | 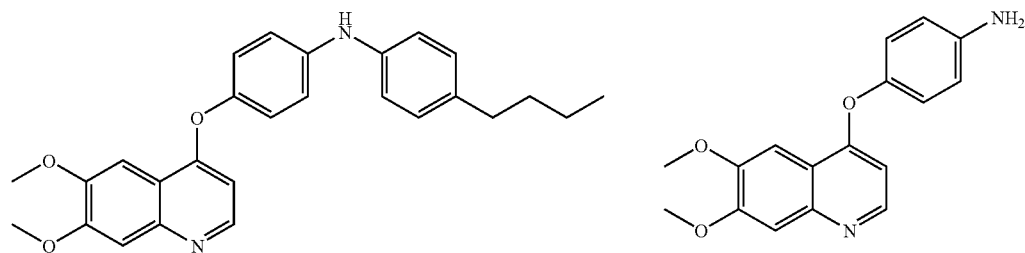 | |
| 9 | 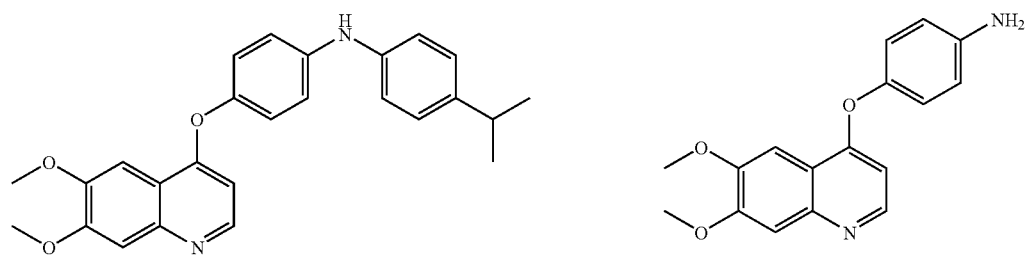 | |

-continued

| Compound No. | Starting compound B | Mass spectrometric value (m/z) | Synthesis method |
|---|---|---|---|
| 7 | (4-benzyloxyphenyl)boronic acid | 479 [M + H]⁺ | 5 |
| 8 | (4-butylphenyl)boronic acid | 429 [M + H]⁺ | 5 |
| 9 | (4-isopropylphenyl)boronic acid | 415 [M + H]⁺ | 5 |
| 10 | (4-cyclohexylphenyl)boronic acid | 455 [M + H]⁺ | 5 |
| 11 | (4-tert-butylphenyl)boronic acid | 497 [M + Cl]⁻ | 5 |

-continued

| Compound No. | Structure of compound | Starting compound A |
|---|---|---|
| 12 | | |
| 13 | | |
| 14 | | |
| 15 | | |
| 16 | | |

-continued
| Compound No. | Starting compound B | Mass spectrometric value (m/z) | Synthesis method |
|---|---|---|---|
| 12 | (HO)₂B-C₆H₄-C(CH₃)₃ | 497 [M + Cl]⁻ | 5 |
| 13 | (HO)₂B-C₆H₄-C(CH₃)₃ | 478 [M + Cl]⁻ | 5 |
| 14 | (HO)₂B-C₆H₄-C(CH₃)₃ | 493 [M + Cl]⁻ | 5 |
| 15 | (HO)₂B-C₆H₄-C(CH₃)₃ | 493 [M + Cl]⁻ | 5 |
| 16 | (HO)₂B-C₆H₄-C(CH₃)₃ | 491 [M + Cl]⁻ | 5 |
| Compound No. | Structure of compound | Starting compound A |
|---|---|---|
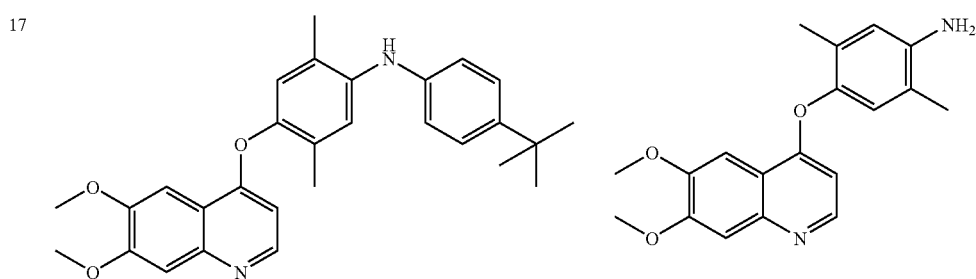
17

-continued
| | | |
|---|---|---|
| 18 | 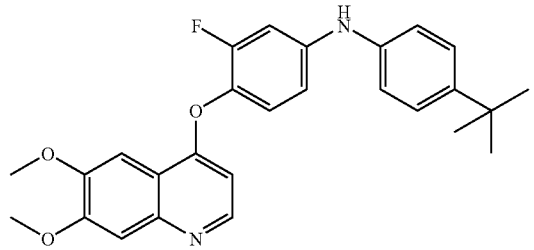 | 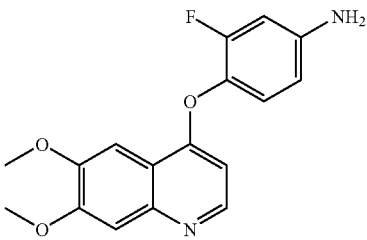 |
| 19 | 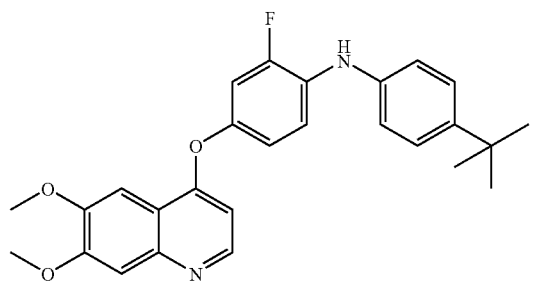 | 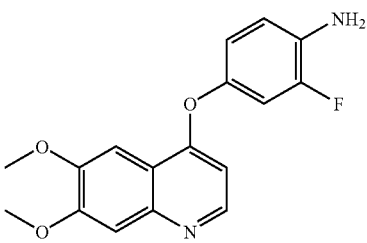 |
| 23 | 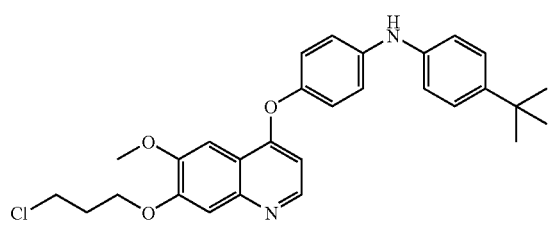 | 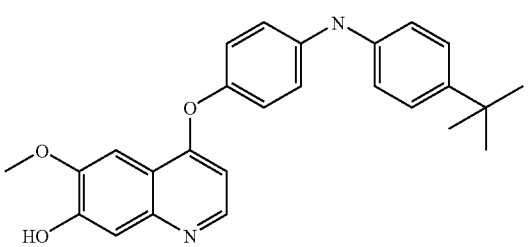 |
| 25 | 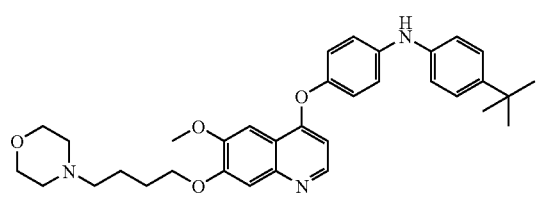 | 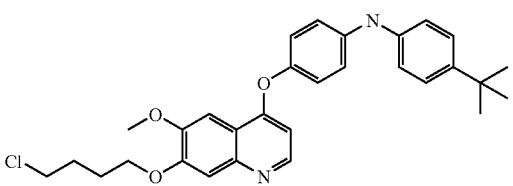 |
| Compound No. | Starting compound B | Mass spectrometric value (m/z) | Synthesis method |
|---|---|---|---|
| 17 | 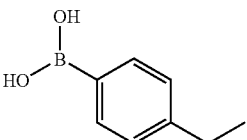 | 491 [M + Cl]⁻ | 5 |
| 18 |  | 455 [M − H]⁻ | 5 |

-continued
| | | | |
|---|---|---|---|
| 19 | 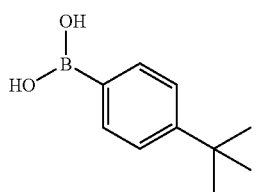 | 445 [M − H]⁻ | 5 |
| 23 | 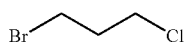 | 491 [M + H]⁺ | 22 |
| 25 | 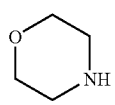 | 556 [M + H]⁺ | 24 |
| Compound No. | Structure of compound | Starting compound A |
|---|---|---|
| 26 | 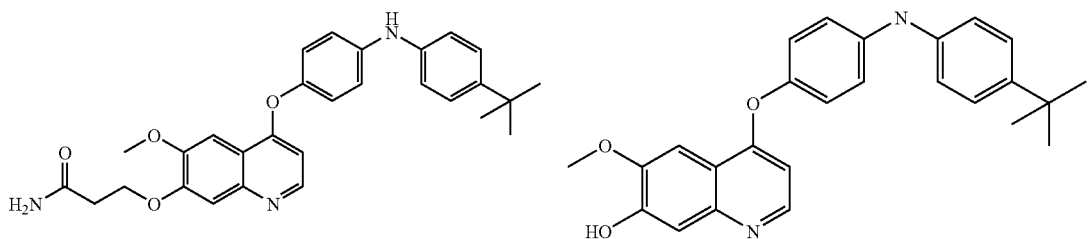 | |
| 27 | 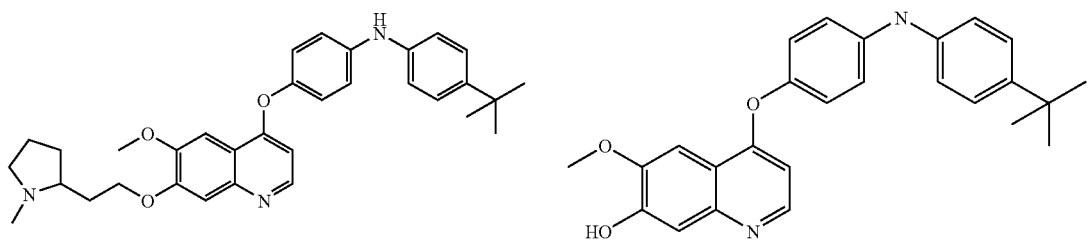 | |
| 28 | 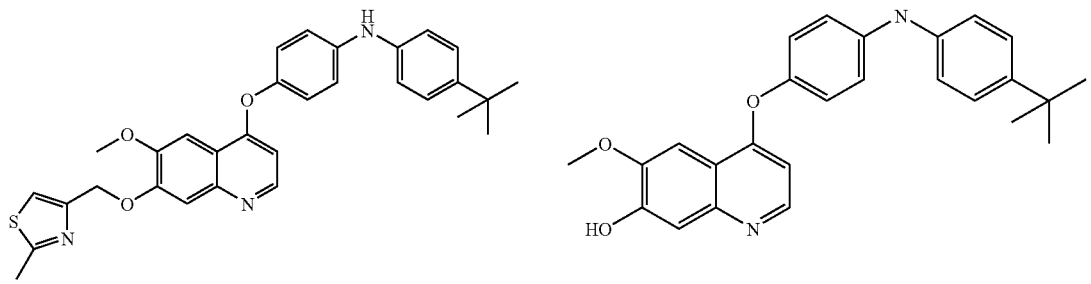 | |
| 29 | 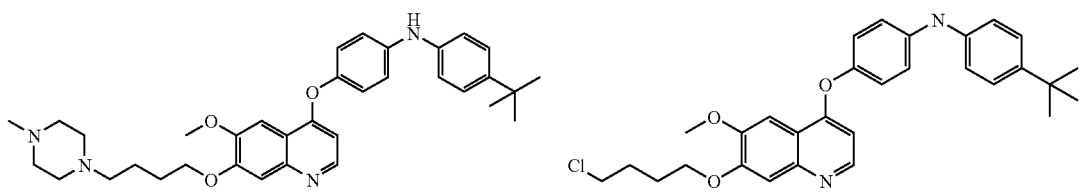 | |

-continued
| 33 | | 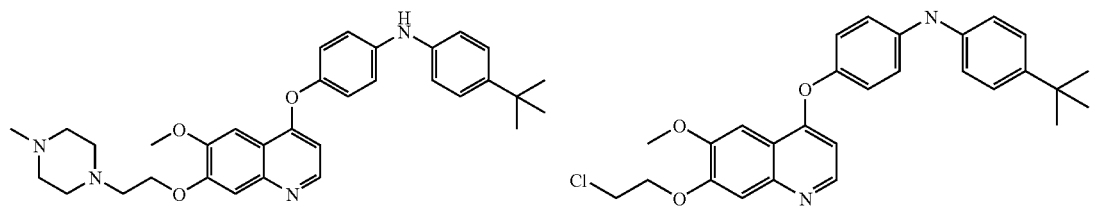 | |
| Compound No. | Starting compound B | Mass spectrometric value (m/z) | Synthesis method |
|---|---|---|---|
| 26 | 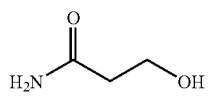 | 508 [M + Na]+ | 42 |
| 27 | 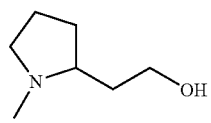 | 526 [M + H]+ | 42 |
| 28 | 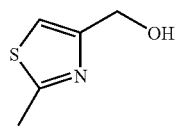 | 526 [M + H]+ | 42 |
| 29 | 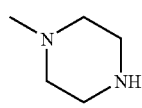 | 569 [M + H]+ | 24 |
| 33 | 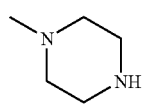 | 563 [M + Na]+ | 24 |
| Compound No. | Structure of compound | Starting compound A |
|---|---|---|
| 34 | | 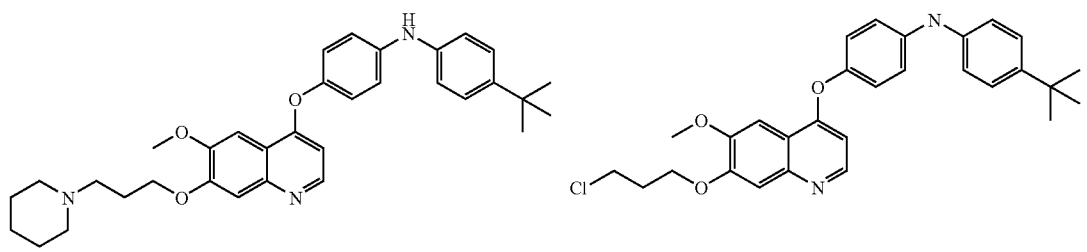 |
| 35 | | 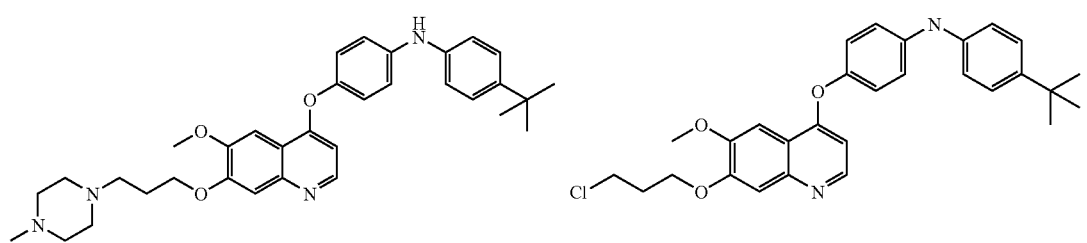 |

-continued
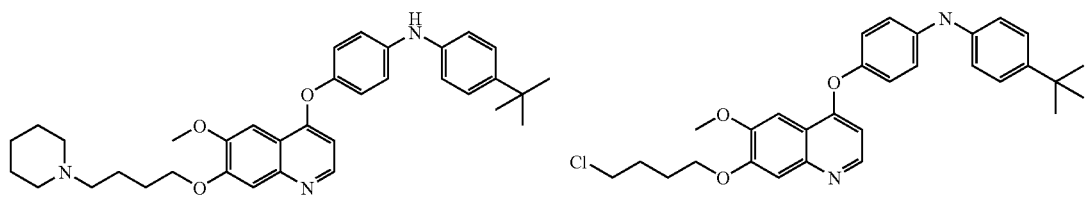
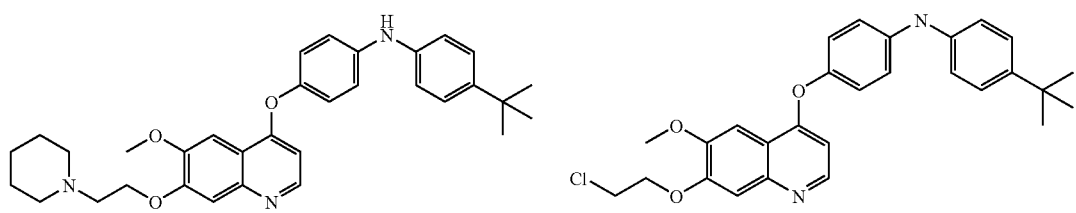
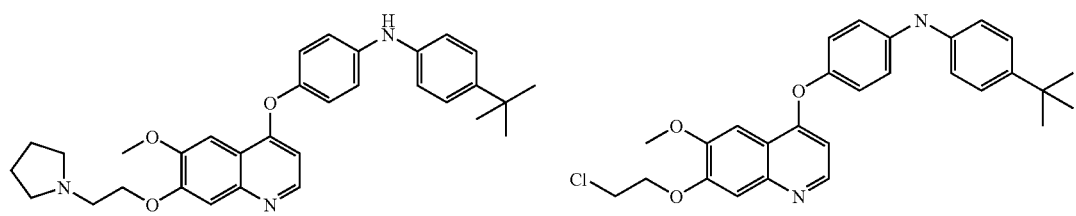
| Compound No. | Starting compound B | Mass spectrometric value (m/z) | Synthesis method |
|---|---|---|---|
| 34 | piperidine (NH) | 540 [M + H]+ | 24 |
| 35 | 1-methylpiperazine | 555 [M + H]+ | 24 |
| 36 | piperidine (NH) | 554 [M + H]+ | 24 |
| 38 | piperidine (NH) | 526 [M + H]+ | 24 |
| 39 | pyrrolidine | 512 [M + H]+ | 24 |
| Compound No. | Structure of compound | Starting compound A |
|---|---|---|
| 40 | | |

-continued
| 41 | 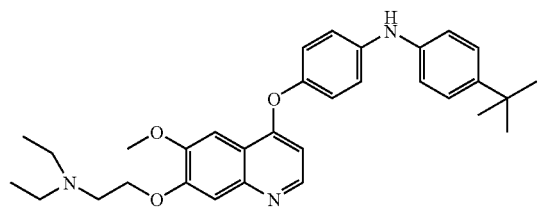 | 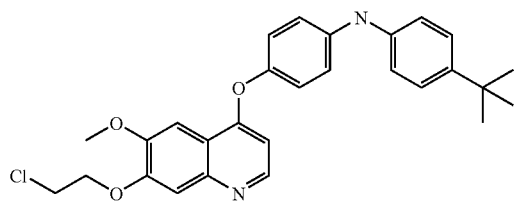 |
| 43 | 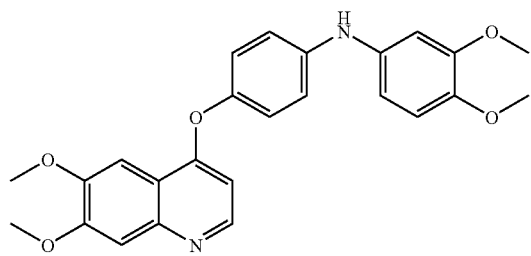 | 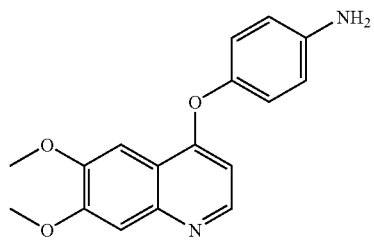 |
| 45 | 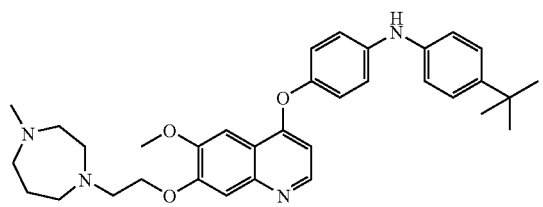 | 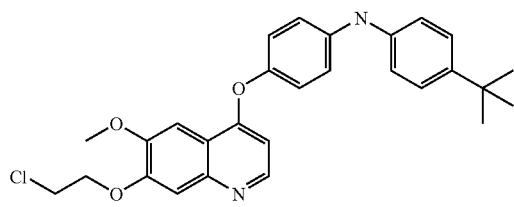 |
| 46 | 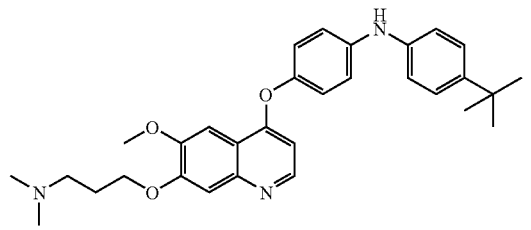 | 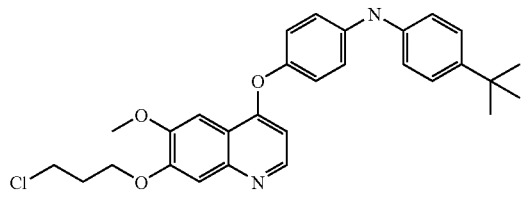 |
| Compound No. | Starting compound B | Mass spectrometric value (m/z) | Synthesis method |
|---|---|---|---|
| 40 |  | 486 [M + H]$^+$ | 24 |
| 41 | 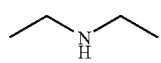 | 514 [M + H]$^+$ | 24 |
| 43 | 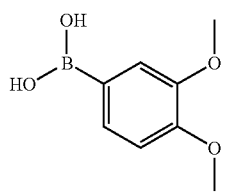 | 467 [M + Cl]$^-$ | 5 |
| 45 | 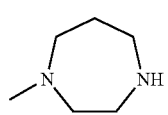 | 555 [M + H]$^+$ | 24 |
| 46 |  | 500 [M + H]$^+$ | 24 |

-continued

| Compound No. | Structure of compound | Starting compound A |
|---|---|---|
| 47 | | |
| 48 | | |
| 49 | | |
| 50 | | |
| 51 | | |

| Compound No. | Starting compound B | Mass spectrometric value (m/z) | Synthesis method |
|---|---|---|---|
| 47 | | 528 [M + H]$^+$ | 24 |
| 48 | | 546 [M + H]$^+$ | 24 |
| 49 | | 516 [M + H]$^+$ | 24 |
| 50 | | 540 [M + H]$^+$ | 24 |

-continued

| | | | |
|---|---|---|---|
| 51 | HO~N(H)~OH (diethanolamine) | 560 [M + H]⁺ | 24 |

| Compound No. | Structure of compound | Starting compound A |
|---|---|---|
| 52 | | |
| 53 | | |
| 54 | | |
| 55 | | |
| 56 | | |

| Compound No. | Starting compound B | Mass spectrometric value (m/z) | Synthesis method |
|---|---|---|---|
| 52 | MeNH-CH₂CH₂-OH | 530 [M + H]⁺ | 24 |

-continued

| | | | |
|---|---|---|---|
| 53 | pyrrolidine (structure) | 526 [M + H]+ | 24 |
| 54 | azepane (structure) | 554 [M + H]+ | 24 |
| 55 | (1-methylpiperidin-2-yl)methanol (structure) | 526 [M + H]+ | 42 |
| 56 | (1-methylpiperidin-3-yl)methanol (structure) | 526 [M + H]+ | 42 |

| Compound No. | Structure of compound | Starting compound A |
|---|---|---|
| 57 | (quinuclidine-substituted quinoline structure) | (7-hydroxy-6-methoxyquinoline structure) |
| 58 | (N-methylpyrrolidine-substituted quinoline structure) | (7-hydroxy-6-methoxyquinoline structure) |
| 60 | (diethylaminopropanol-substituted quinoline structure) | (7-hydroxy-6-methoxyquinoline structure) |
| 61 | (pyrrolidinylpropanol-substituted quinoline structure) | (7-hydroxy-6-methoxyquinoline structure) |

-continued
| 62 | 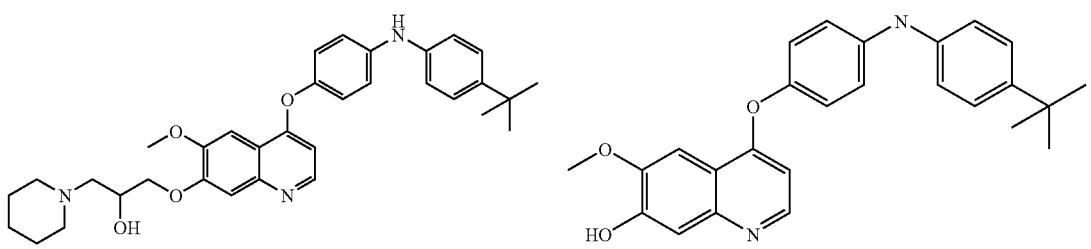 | | |
| Compound No. | Starting compound B | Mass spectrometric value (m/z) | Synthesis method |
|---|---|---|---|
| 57 | 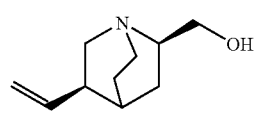 | 564 [M + H]+ | 42 |
| 58 | 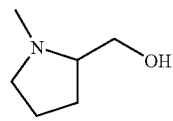 | 512 [M + H]+ | 42 |
| 60 | 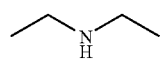 | 544 [M + H]+ | 59 |
| 61 |  | 542 [M + H]+ | 59 |
| 62 | 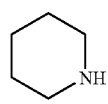 | 556 [M + H]+ | 59 |
| Compound No. | Structure of Compound | Starting compound A |
|---|---|---|
| 63 | 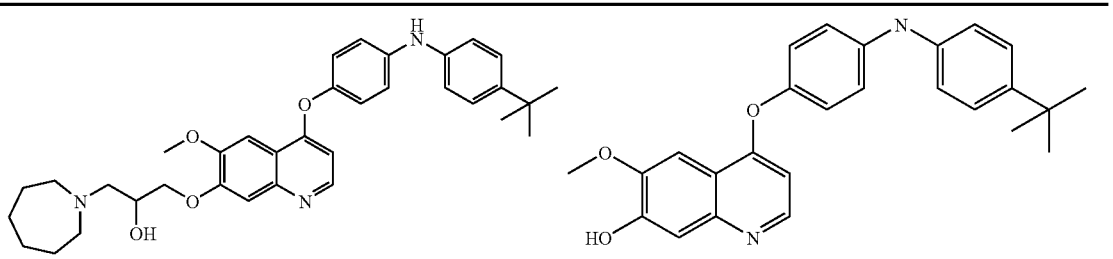 | |
| 64 | 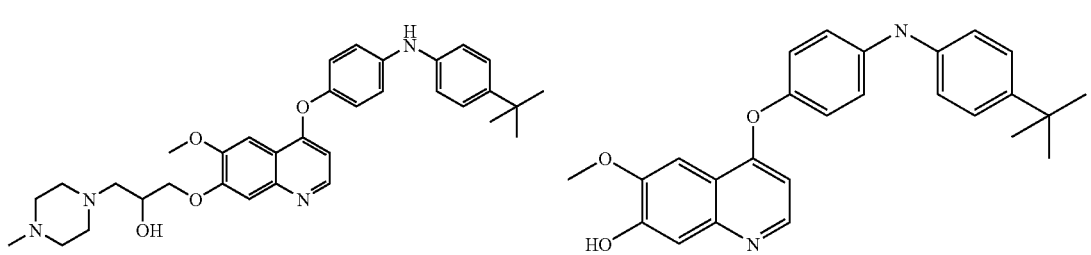 | |

-continued
65 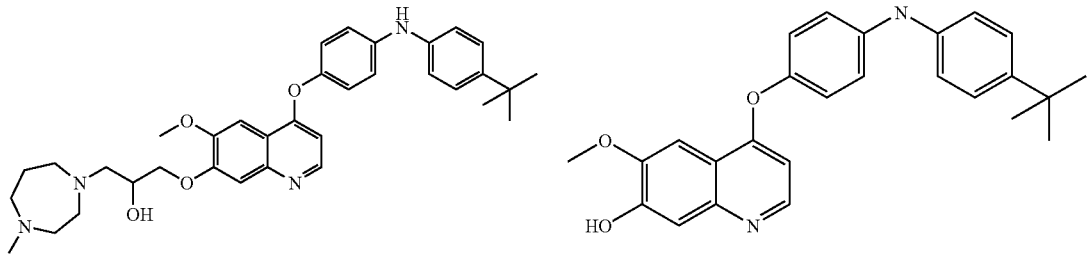
66 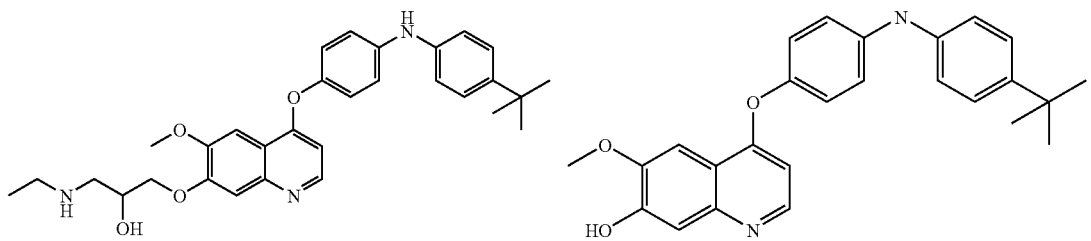
67 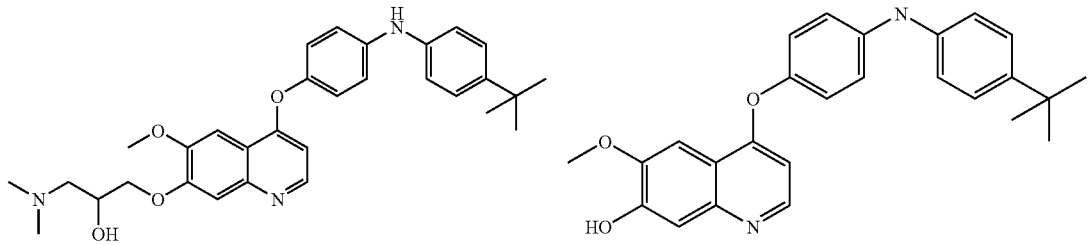
| Compound No. | Starting compound B | Mass spectrometric value (m/z) | Synthesis method |
|---|---|---|---|
| 63 | | 570 [M + H]⁺ | 59 |
| 64 | | 571 [M + H]⁺ | 59 |
| 65 | | 585 [M + H]⁺ | 59 |
| 66 | | 516 [M + H]⁺ | 59 |
| 67 | | 516 [M + H]⁺ | 59 |
| Compound No. | Structure of compound | Starting compound A |
|---|---|---|
68 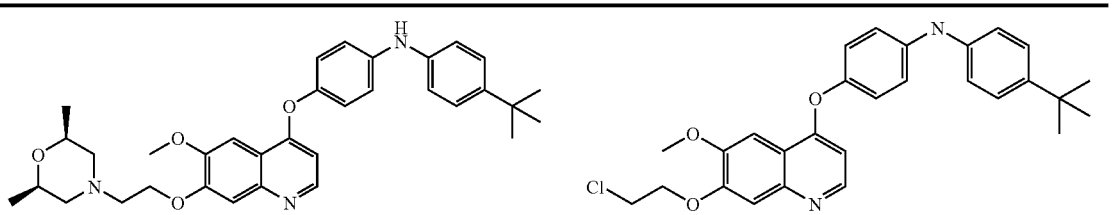

-continued
69 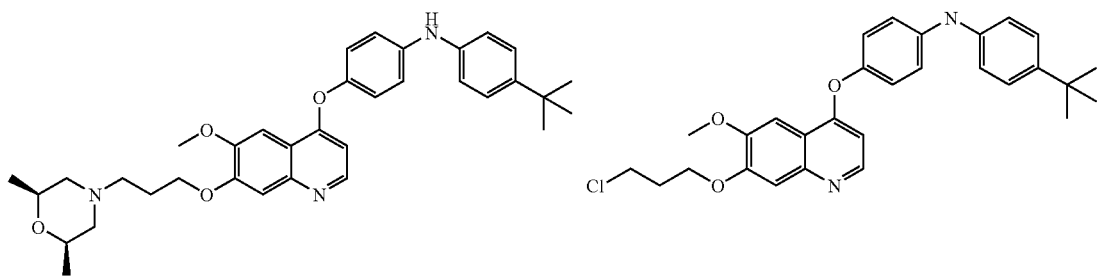
72 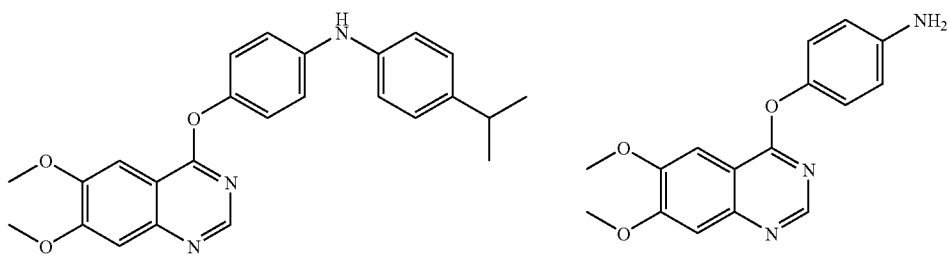
73 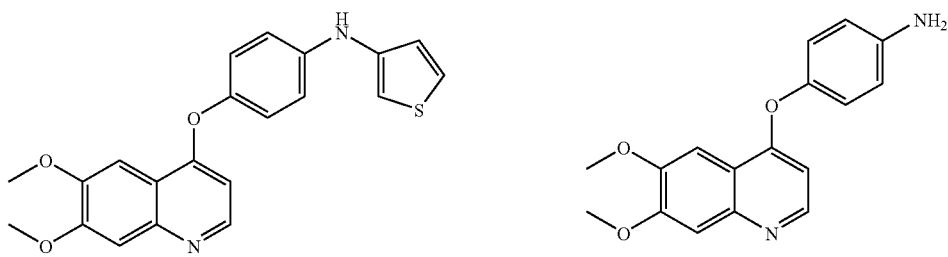
74 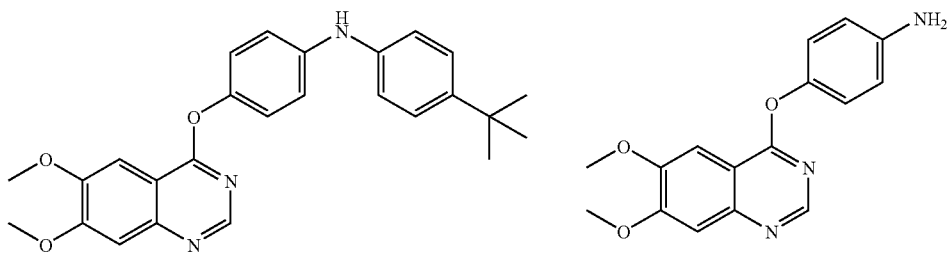
| Compound No. | Starting compound B | Mass spectrometric value (m/z) | Synthesis method |
|---|---|---|---|
| 68 | 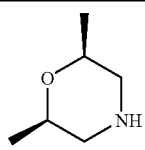 | 556 [M + H]+ | 24 |
| 69 | 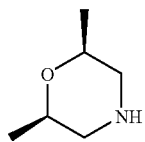 | 570 [M + H]+ | 24 |
| 72 | 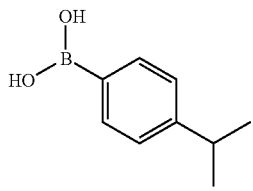 | 416 (M + H)+ | 5 |

-continued
| | | | |
|---|---|---|---|
| 73 | 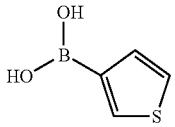 | 379 (M + H)+ | 5 |
| 74 | 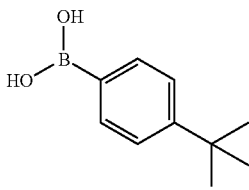 | 430 (M + H)+ | 5 |
| Compound No. | Structure of compound | Starting compound A |
|---|---|---|
| 80 | 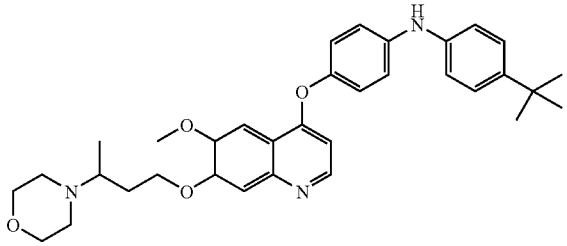 | 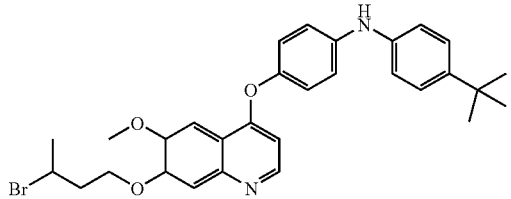 |
| 81 | 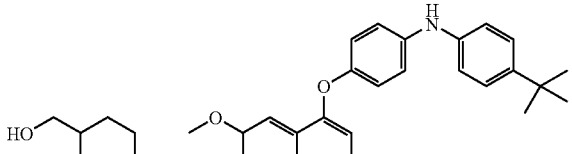 | 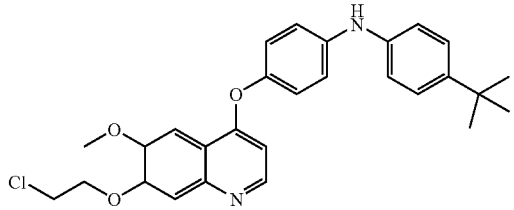 |
| 82 | 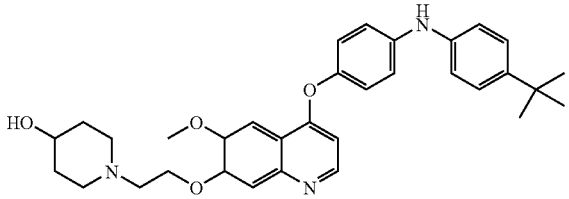 | 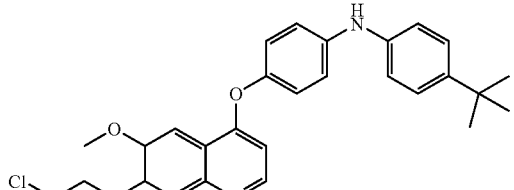 |
| Compound No. | Starting compound B | Mass spectrometric value (m/z) | Synthesis method |
|---|---|---|---|
| 80 |  | 556 (M + H)+ | 24 |
| 81 | 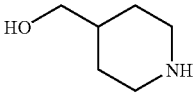 | 556 (M + H)+ | 24 |
| 82 | 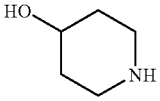 | 542 (M + H)+ | 24 |

-continued

| Compound No. | Structure of compound | Starting compound A |
|---|---|---|
| 83 | | |
| 84 | | |
| 85 | | |
| 86 | | |
| 88 | | |

| Compound No. | Starting compound B | Synthesis method |
|---|---|---|
| 83 | | 24 |
| 84 | | 24 |
| 85 | | 24 |

-continued
| | | | |
|---|---|---|---|
| 86 | 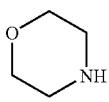 | 59 | |
| 88 | 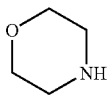 | 99 | |
| Compound No. | Structure of compound |
|---|---|
| 89 | 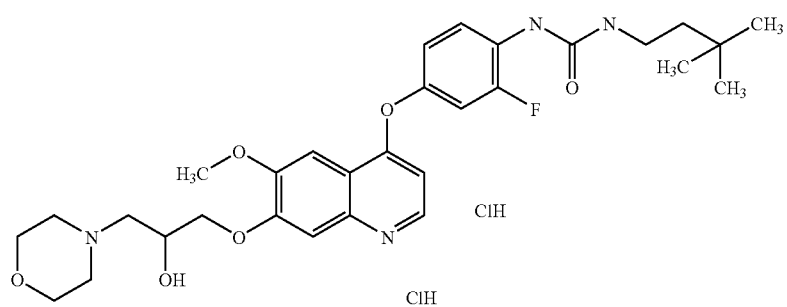 |
| 90 | 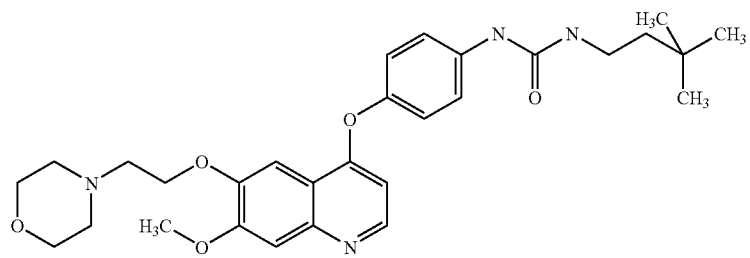 |
| 91 | 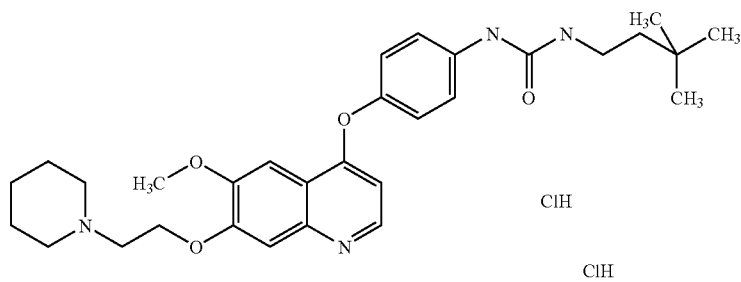 |
| 94 | 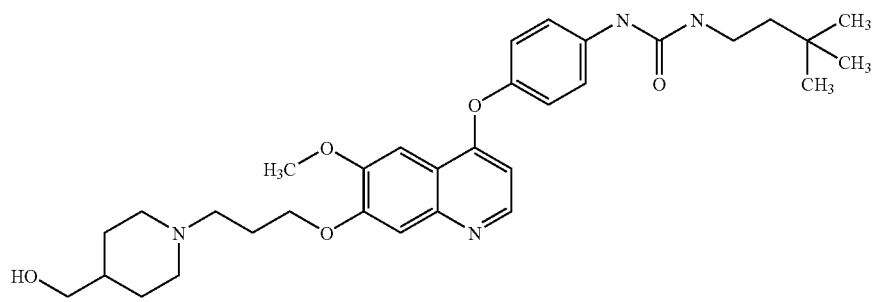 |

96 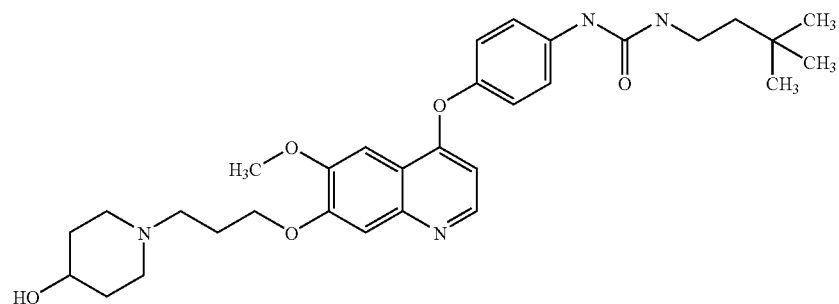
| Compound No. | Starting compound A |
|---|---|
| 89 | 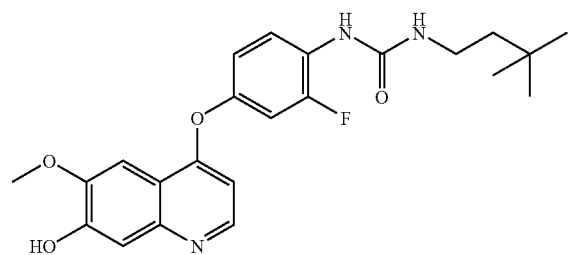 |
| 90 | 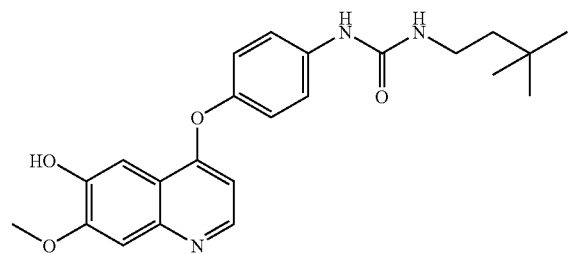 |
| 91 | 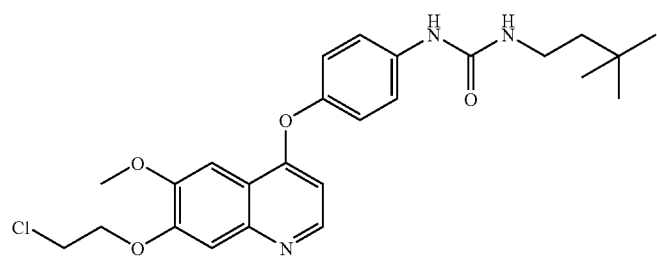 |
| 94 | 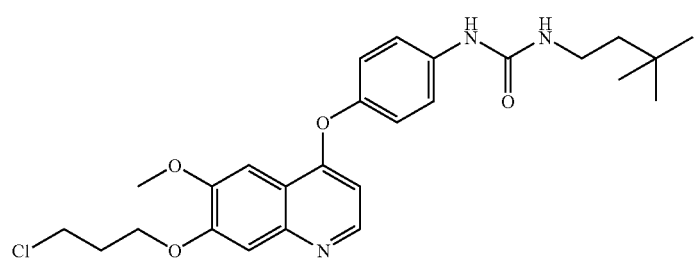 |

-continued
| | 96 | |
|---|---|---|
| | 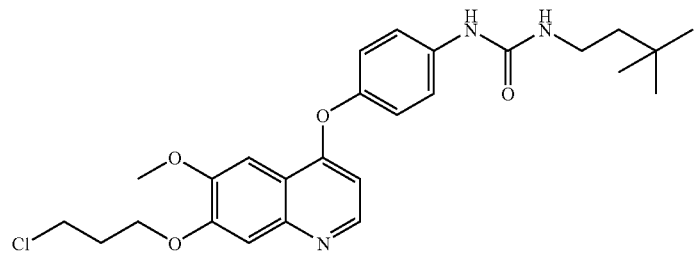 | |
| Compound No. | Starting compound B | Synthesis method |
|---|---|---|
| 89 | 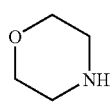 | 59 |
| 90 | 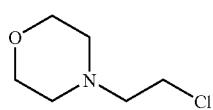 | 87 |
| 91 | 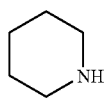 | 99 |
| 94 | 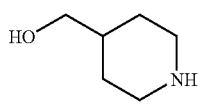 | 99 |
| 96 | 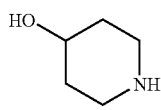 | 99 |
| Compound No. | Structure of compound |
|---|---|
| 97 | 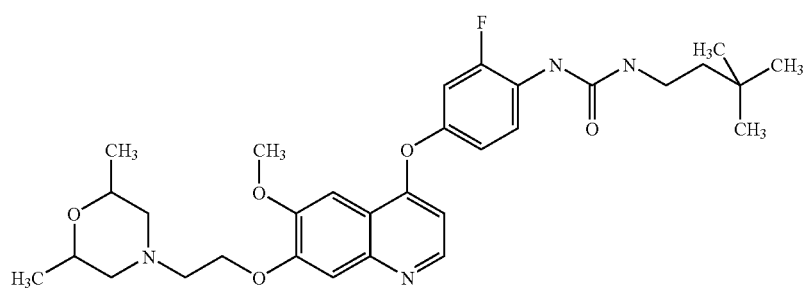 |
| 98 | 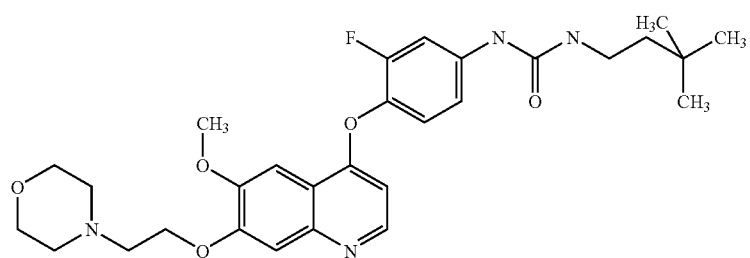 |

-continued
100 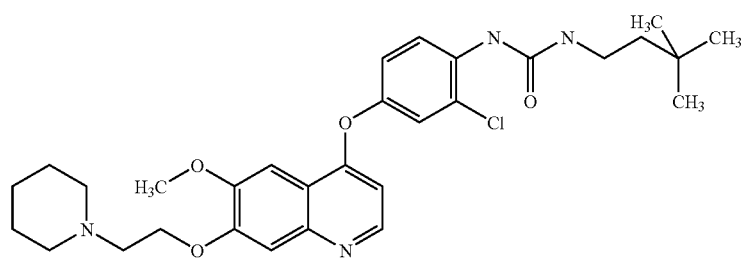
102 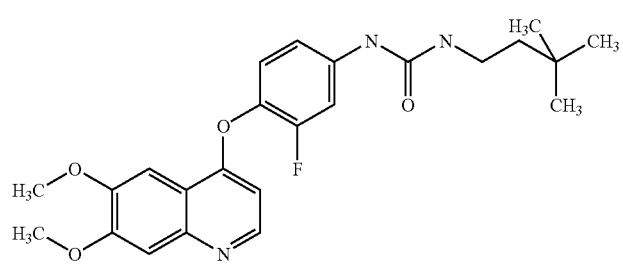
103 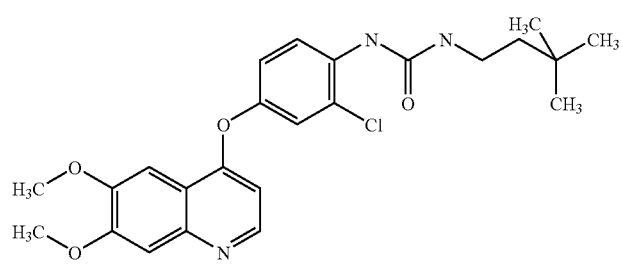
| Compound No. | Starting compound A |
|---|---|
| 97 | 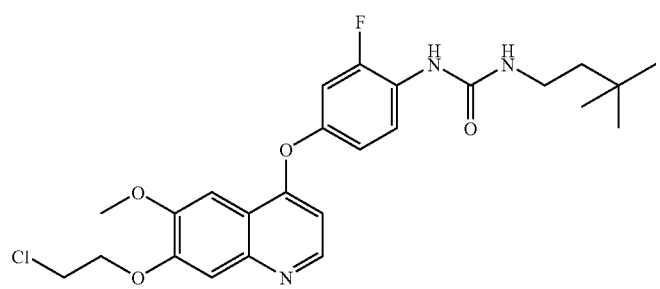 |
| 98 | 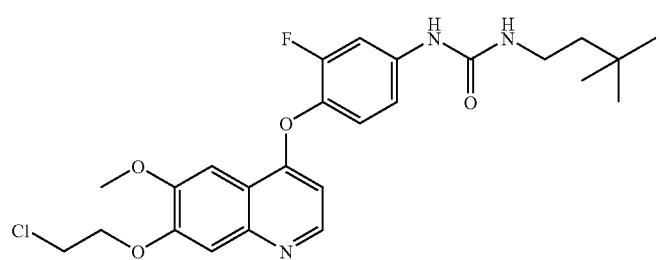 |

-continued
100 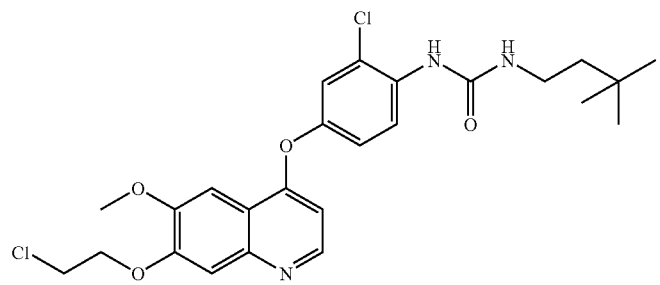
102 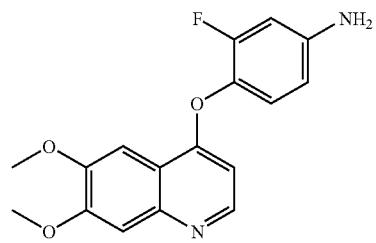
103 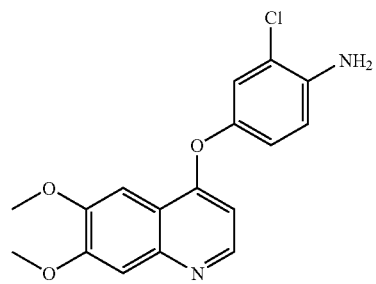
| Compound No. | Starting compound B | Synthesis method |
|---|---|---|
| 97 | 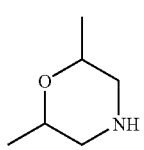 | 99 |
| 98 | 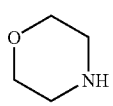 | 99 |
| 100 | 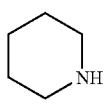 | 99 |
| 102 | 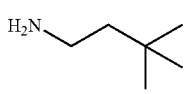 | 101 |
| 103 | 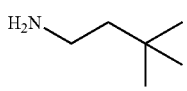 | 101 |

-continued

| Compound No. | Structure of compound | Starting compound A |
|---|---|---|
| 105 | | |
| 106 | | |
| 107 | | |
| 108 | | |
| 109 | | |

-continued

| Compound No. | Starting compound B | Synthesis method |
|---|---|---|
| 105 | H₂N-(3,3,5-trimethylcyclohexyl) | 101 |
| 106 | H₂N-(3,3,5-trimethylcyclohexyl) | 101 |
| 107 | H₂N-(3,3,5-trimethylcyclohexyl) | 101 |
| 108 | H₂N-(3,3-dimethylcyclohexyl) | 101 |
| 109 | H₂N-(3,3-dimethylcyclohexyl) | 101 |

| Compound No. | Structure of compound | Starting compound A |
|---|---|---|
| 110 | 6,7-dimethoxyquinolin-4-yl-oxy-(2-chlorophenyl)-NHC(O)NH-(3,3-dimethylcyclohexyl) | 4-(4-amino-3-chlorophenoxy)-6,7-dimethoxyquinoline |
| 111 | 6,7-dimethoxyquinolin-4-yl-oxy-(2-fluorophenyl)-NHC(O)NH-CH₂CH₂-C(CH₃)₃ | 4-(4-amino-2-fluorophenoxy)-6,7-dimethoxyquinoline |
| 112 | 7-(2-morpholinoethoxy)-6-methoxyquinolin-4-yl-oxy-phenyl-NHC(O)NH-CH₂CH₂-C(CH₃)₃ · 2 HCl | 4-(4-aminophenoxy)-7-(2-chloroethoxy)-6-methoxyquinoline |

-continued
113 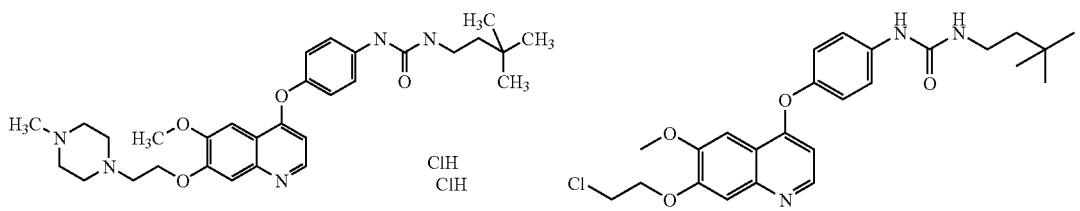
114 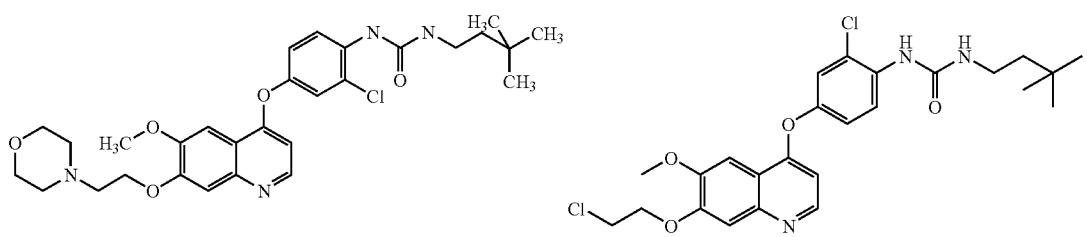
| Compound No. | Starting compound B | Synthesis method |
|---|---|---|
| 110 | 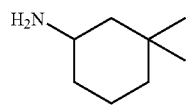 | 101 |
| 111 | 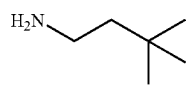 | 101 |
| 112 | 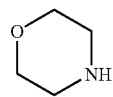 | 99 |
| 113 | 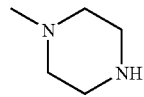 | 99 |
| 114 | 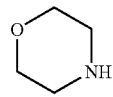 | 99 |
| Compound No. | Structure of compound |
|---|---|
| 115 | 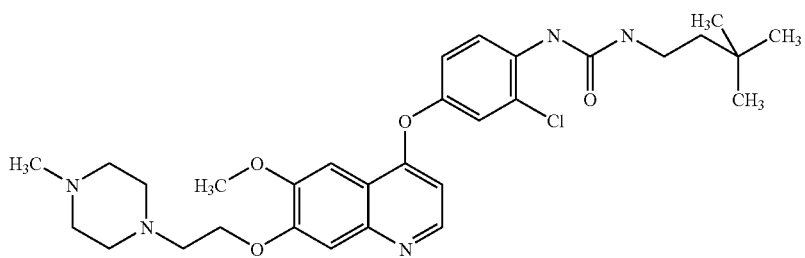 |

-continued
116
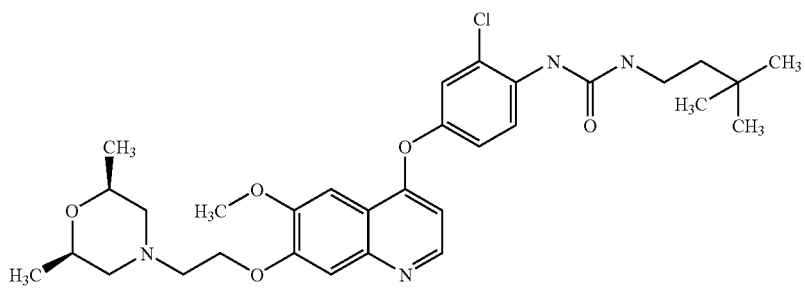
117
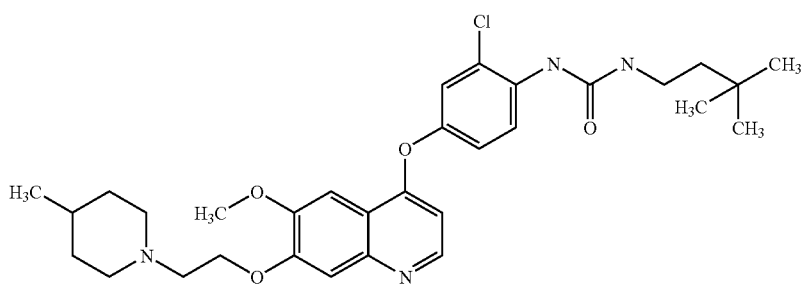
119
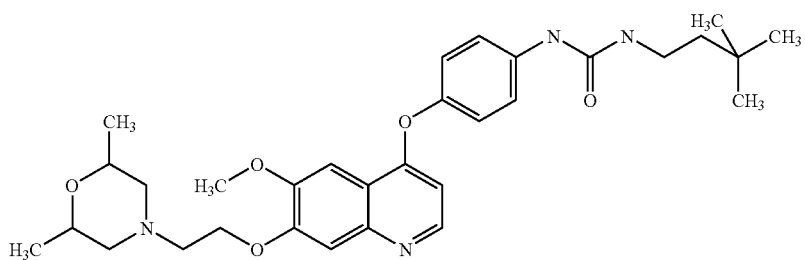
120
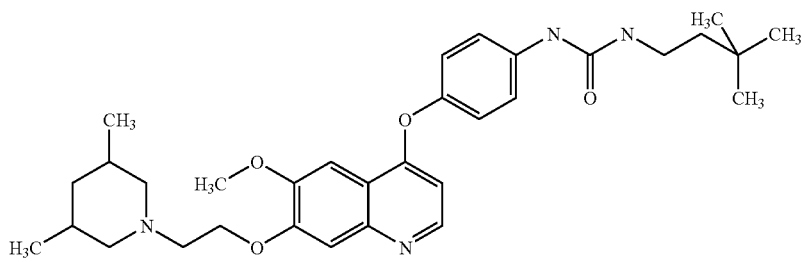
| Compound No. | Starting compound A |
|---|---|
| 115 | 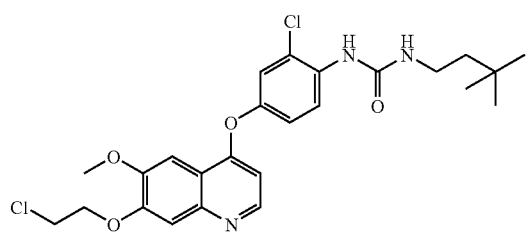 |

-continued
| | | |
|---|---|---|
| | 116 | 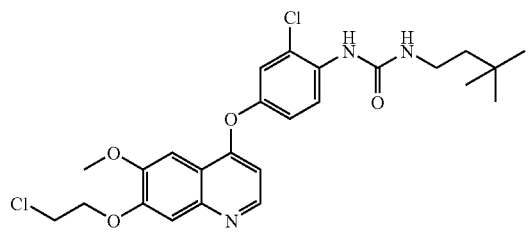 |
| | 117 | 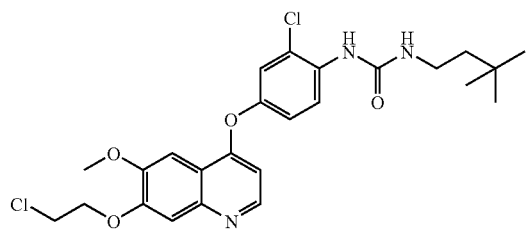 |
| | 119 | 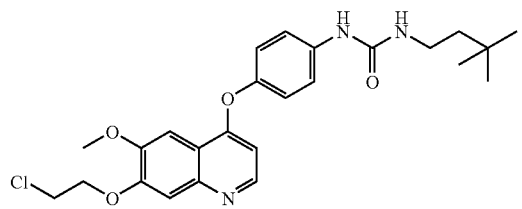 |
| | 120 | 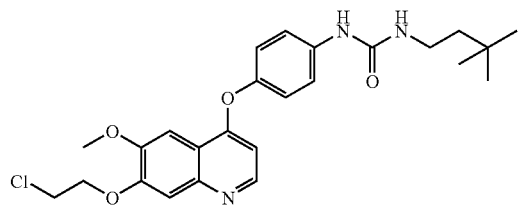 |
| Compound No. | Starting compound B | Synthesis method |
|---|---|---|
| 115 | 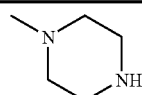 | 99 |
| 116 | 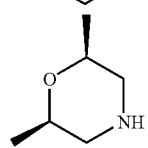 | 99 |
| 117 | 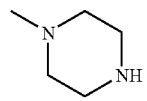 | 99 |
| 119 | 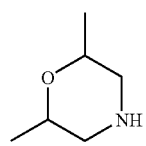 | 99 |
| 120 | 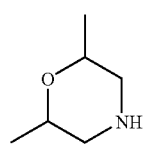 | 99 |

-continued

| Compound No. | Structure of compound |
|---|---|
| 121 | |
| 122 | |
| 123 | |
| 124 | |
| 125 | |

-continued

| Compound No. | Starting compound A |
|---|---|
| 121 | 6-methoxy-7-(2-chloroethoxy)quinoline-4-yloxy-phenyl urea with 3,3-dimethylbutyl group |
| 122 | 6-methoxy-7-(2-chloroethoxy)quinoline-4-yloxy-phenyl urea with 3,3-dimethylbutyl group |
| 123 | 6-methoxy-7-(2-chloroethoxy)quinoline-4-yloxy-phenyl urea with 3,3-dimethylbutyl group |
| 124 | 6-methoxy-7-(2-chloroethoxy)quinoline-4-yloxy-phenyl urea with 3,3-dimethylbutyl group |
| 125 | 6-methoxy-7-(2-chloroethoxy)quinoline-4-yloxy-(2-chloro)phenyl urea with 3,3-dimethylbutyl group |

| Compound No. | Starting compound B | Synthesis method |
|---|---|---|
| 121 | 4-phenylpiperidine | 99 |
| 122 | 4-benzylpiperidine | 99 |

| | | |
|---|---|---|
| 123 | 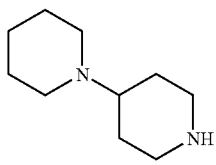 | 99 |
| 124 | 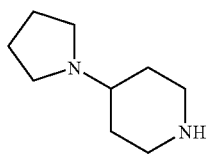 | 99 |
| 125 | 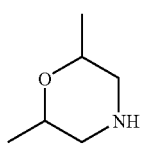 | 99 |
| Compound No. | Structure of compound |
|---|---|
| 126 | 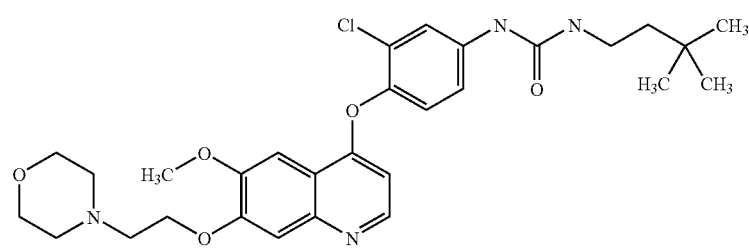 |
| 127 | 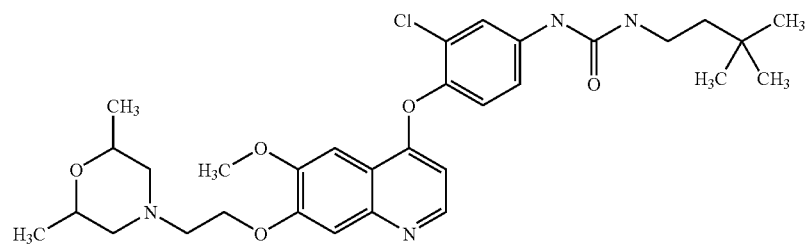 |
| 128 | 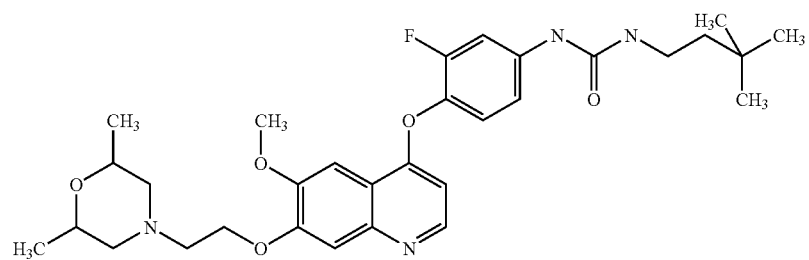 |

-continued
129 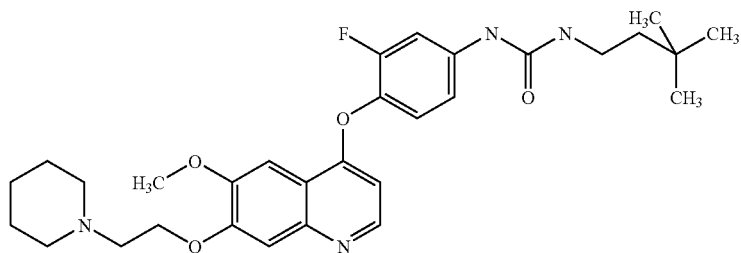
130 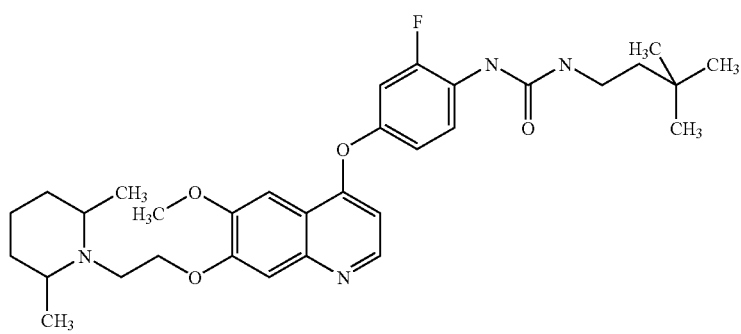
| Compound No. | Starting compound A |
|---|---|
126 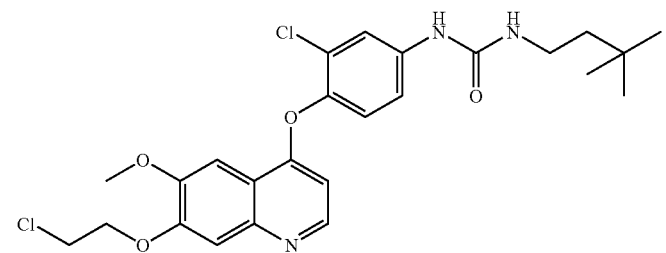
127 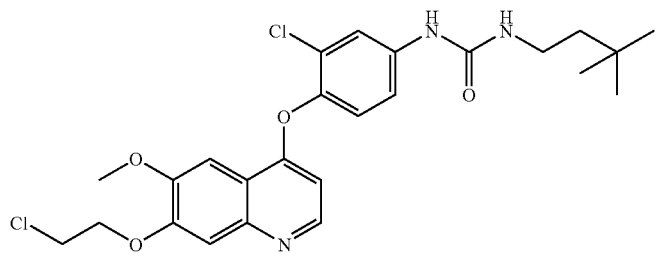
128 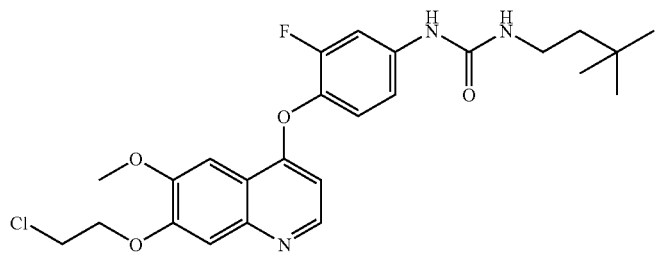

-continued
129
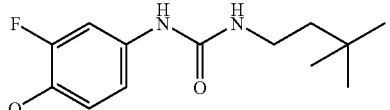
130
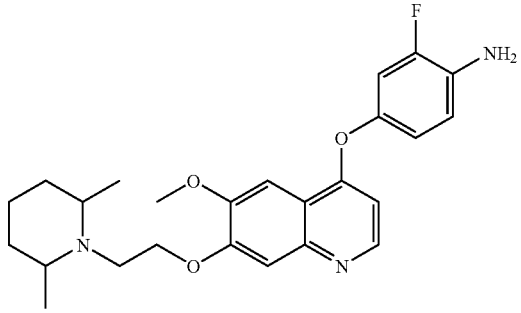
| Compound No. | Starting compound B | Synthesis method |
|---|---|---|
| 126 | morpholine | 99 |
| 127 | 2,6-dimethylmorpholine (cis) | 99 |
| 128 | 2,6-dimethylmorpholine | 99 |
| 129 | piperidine | 99 |
| 130 | H₂N-CH₂CH₂-C(CH₃)₃ | 101 |
| Compound No. | Structure of compound |
|---|---|
| 131 |  |

-continued
| | |
|---|---|
| 132 | 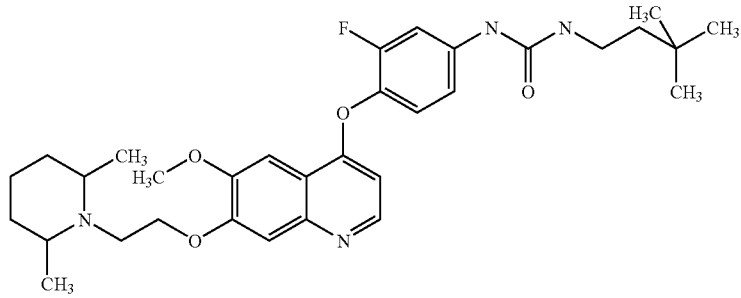 |
| 133 | 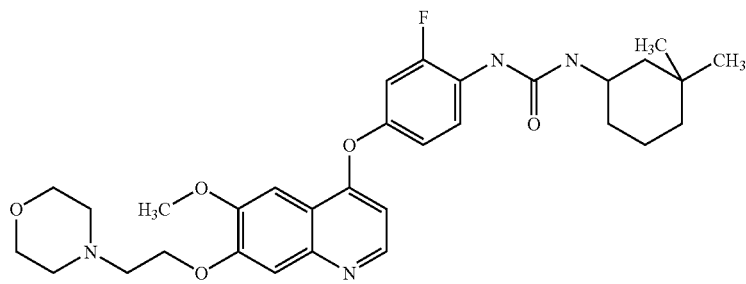 |
| 134 | 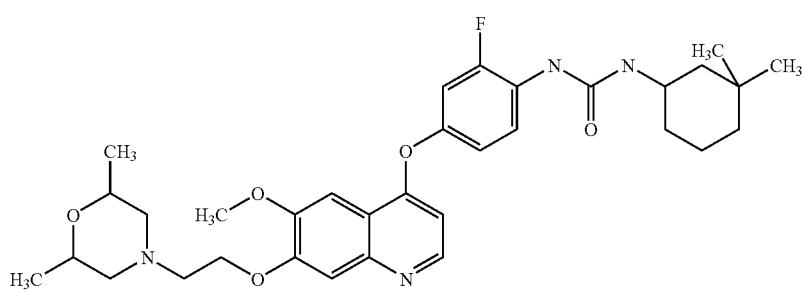 |
| Compound No. | Starting compound A |
|---|---|
| 131 | 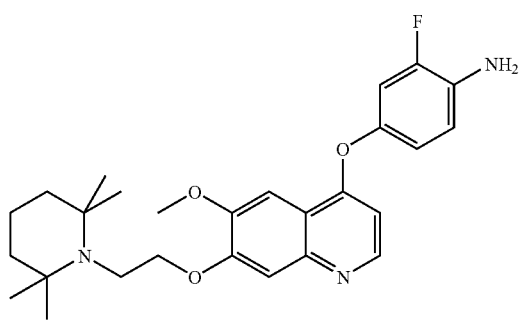 |
| 132 | 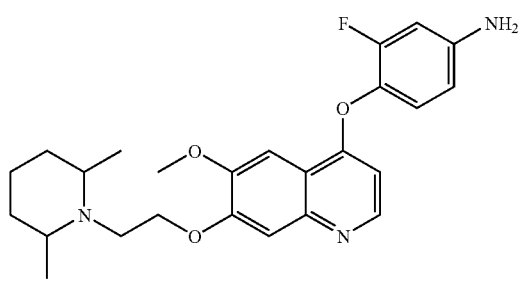 |

-continued

| | | |
|---|---|---|
| 133 | 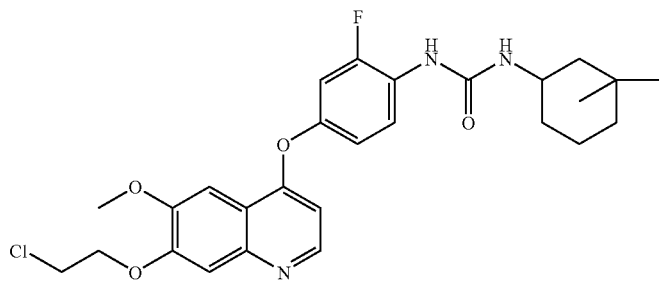 | |
| 134 | 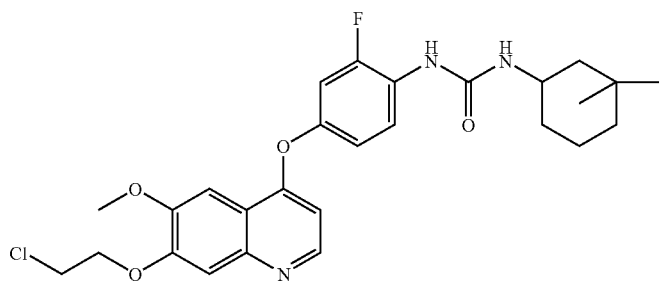 | |

| Compound No. | Starting compound B | Synthesis method |
|---|---|---|
| 131 | 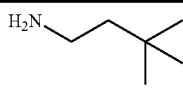 | 101 |
| 132 | 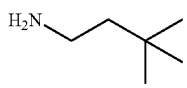 | 101 |
| 133 | 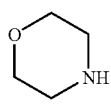 | 99 |
| 134 | 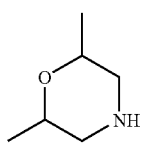 | 99 |

Compound 83

$^1$H-NMR (CDCl$_3$, 400 MHz): 1.32 (s, 9H), 3.47–3.54 (m, 4H), 3.83–3.89 (m, 4H), 3.99 (s, 3H), 4.45–4.50 (m, 2H), 4.83–4.87 (m, 2H), 5.76 (br, 1H), 6.49 (d, J=5.1 Hz, 1H), 7.06 (d, J=8.5 Hz, 2H), 7.06 (d, J=9.0 Hz, 2H), 7.12 (d, J=9.0 Hz, 2H), 7.33 (d, J=8.8 Hz, 2H), 7.49 (s, 1H), 7.58 (s, 1H), 8.49 (d, J=5.4 Hz, 1H)

Compound 84

$^1$H-NMR (CDCl$_3$, 400 MHz): 1.33 (s, 9H), 2.62–2.64 (m, 4H), 2.94 (t, J=5.9 Hz, 2H), 3.74–3.77 (m, 4H), 4.004 (s, 3H), 4.33 (t, J=5.9 Hz, 2H), 5.79 (s, 1H), 6.37 (d, J=5.1 Hz, 1H), 6.79 (d, J=6.6 Hz, 2H), 6.96 (dd, J=2.7, 8.8 Hz, 1H), 7.07–7.12 (m, 1H), 7.17 (d, J=2.7 Hz, 1H), 7.35 (d, J=8.5 Hz, 2H), 7.42 (s, 1H), 7.61 (s, 1H), 8.48 (d, J=5.4 Hz, 1H)

Compound 85

$^1$H-NMR (CDCl$_3$, 400 MHz): 1.32 (s, 9H), 2.89–2.92 (m, 2H), 3.18 (t, J=5.1 Hz, 2H), 3.68–3.71 (m, 2H), 4.03 (s, 3H), 4.23 (t, J=5.1 Hz, 2H), 5.72 (br, 1H), 6.48 (d, J=5.4 Hz, 1H), 7.06 (d, J=8.5 Hz, 2H), 7.07 (d, J=8.5 Hz, 2H), 7.12 (d, J=9.0 Hz, 2H), 7.33 (d, J=8.5 Hz, 2H), 7.42 (s, 1H), 7.58 (s, 1H), 8.48 (d, J=5.4 Hz, 1H)

Compound 86

$^1$H-NMR (CDCl$_3$, 400 MHz): 1.33 (s, 9H), 2.52–2.57 (m, 2H), 2.65–2.74 (m, 4H), 3.73–3.78 (m, 4H), 4.03 (s, 3H), 4.21 (t, J=5.1 Hz, 2H), 4.27–4.32 (m, 1H), 5.71 (s, 1H), 6.51 (d, J=5.4 Hz, 1H), 7.06 (d, J=8.8 Hz, 2H), 7.06 (d, J=8.8 Hz, 2H), 7.12 (d, J=9.0 Hz, 2H), 7.33 (d, J=8.8 Hz, 2H), 7.49 (s, 1H), 7.63 (s, 1H), 8.49 (d, J=5.6 Hz, 1H)

Mass spectrometric value (ESI-MS, m/z): 558 (M$^+$+1)

Compound 88

$^1$H-NMR (CDCl$_3$+CD$_3$OD, 400 MHz): 0.96 (s, 9H), 1.44–1.50 (m, 2H), 2.54–2.61 (m, 2H), 3.04–3.14 (m, 2H), 3.24–3.30 (m, 2H), 3.35–3.42 (m, 2H), 3.56–3.64 (m, 2H), 4.00–4.09 (m, 5H), 4.16–4.25 (m, 2H), 4.47 (t, J=6.1 Hz, 2H), 6.81 (d, J=6.6 Hz, 1H), 6.95–7.12 (m, 2H), 7.32 (s, 1H), 7.63 (s, 1H), 8.40 (t, J=8.8 Hz, 1H), 8.54 (d, J=6.8 Hz, 1H)

Mass spectrometric value (ESI-MS, m/z): 555 (M+1)$^+$

Compound 89

¹H-NMR (CDCl₃+CD₃OD, 400 MHz): 0.97 (s, 9H), 1.44–1.50 (m, 2H), 3.18–3.44 (m, 5H), 3.48–3.68 (m, 2H), 3.80–3.89 (m, 1H), 3.97–4.25 (m, 7H), 4.35–4.46 (m, 2H), 4.85 (br, 1H), 6.82 (d, J=6.6 Hz, 1H), 6.99 (d, J=8.8 Hz, 2H), 7.64 (s, 1H), 7.96 (s, 1H), 8.39 (t, J=8.8 Hz, 1H), 8.53 (d, J=6.6 Hz, 1H)

Mass spectrometric value (ESI-MS, m/z): 571 (M+1)⁺

Compound 90

¹H-NMR (CDCl₃, 400 MHz): δ 0.94 (s, 9H), 1.43–1.48 (m, 2H), 2.63–2.68 (m, 4H), 2.96 (t, J=5.8 Hz, 2H), 3.26–3.33 (m, 2H), 3.73–3.77 (m, 4H), 4.02 (s, 3H), 4.33 (t, J=6.0 Hz, 2H), 4.91–4.96 (m, 1H), 6.44 (d, J=5.4 Hz, 1H), 6.96 (br, 1H), 7.08 (d, J=9.0 Hz, 2H), 7.42–7.47 (m, 3H), 7.59 (s, 1H), 8.42 (d, J=5.6 Hz, 1H)

Mass spectrometric value (ESI-MS, m/z): 523 (M+1)

Compound 91

¹H-NMR (CD₃OD, 400 MHz): 0.97 (s, 9H), 1.48–2.02 (m, 8H), 3.19 (m, 2H), 3.25 (m, 2H), 3.72–3.80 (m, 4H), 4.12 (s, 3H), 4.76 (m, 2H), 6.94 (d, J=6.8 Hz, 1H), 7.24 (d, J=9.0 Hz, 2H), 7.61 (d, J=8.8 Hz, 2H), 7.64 (s, 1H), 7.88 (s, 1H), 8.70 (d, J=6.6 Hz, 1H)

Mass spectrometric value (ESI-MS, m/z): 521 (M⁺−1)

Compound 94

¹H-NMR (CDCl₃+CD₃OD, 400 MHz): 0.95 (s, 9H), 1.32–1.41 (m, 1H), 1.44–1.46 (m, 2H), 1.74–1.77 (m, 4H), 2.03–2.08 (m, 2H), 2.13–2.19 (m, 2H), 2.61–2.64 (m, 2H), 3.03–3.07 (m, 2H), 3.27–3.32 (m, 2H), 3.51 (t, J=6.1 Hz, 2H), 4.00 (s, 3H), 4.25 (t, J=6.6 Hz, 2H), 4.83 (br, 1H), 6.43 (d, J=5.4 Hz, 1H), 6.78 (s, 1H), 7.11 (d, J=9.0 Hz, 2H), 7.42 (s, 1H), 7.43 (d, J=9.0 Hz, 2H), 7.53 (s, 1H), 8.44 (d, J=5.4 Hz, 1H)

Mass spectrometric value (ESI-MS, m/z): 555 (M+1)⁺

Compound 96

¹H-NMR (CDCl₃, 400 MHz): 0.95 (s, 9H), 1.44–1.48 (m, 2H), 1.58–1.67 (m, 2H), 1.93–2.30 (m, 6H), 2.61 (t, J=7.6 Hz, 2H), 2.78–2.86 (m, 2H), 3.27–3.35 (m, 2H), 3.72–3.83 (m, 1H), 4.01 (s, 3H), 4.25 (t, J=6.6 Hz, 3H), 4.93 (t, J=5.4 Hz, 1H), 6.43 (d, J=5.4 Hz, 1H), 6.92 (s, 1H), 7.10 (d, J=8.8 Hz, 2H), 7.41 (s, 1H), 7.44 (d, J=9.0 Hz, 2H), 7.57 (s, 1H), 8.43 (d, J=5.4 Hz, 1H)

Compound 97

¹H-NMR (CDCl₃, 400 MHz): δ 0.96 (s, 9H), 1.18 (d, J=6.3 Hz, 6H), 1.45–1.51 (m, 2H), 1.95–2.05 (m, 2H), 2.90–3.00 (m, 4H), 3.28–3.35 (m, 2H), 3.73–3.81 (m, 2H), 4.01 (s, 3H), 4.37 (t, J=5.8 Hz, 2H), 4.79–4.84 (m, 1H), 6.49 (d, J=5.4 Hz, 1H), 6.56–6.60 (m, 1H), 6.91 (dd, J=2.4, 11.2 Hz, 1H), 6.96 (d, J=9.0 Hz, 1H), 7.44 (s, 1H), 7.50 (s, 1H), 8.18 (t, J=9.0 Hz, 1H), 8.49 (d, J=5.4 Hz, 1H)

Mass spectrometric value (ESI-MS, m/z): 567 (M−1)

Compound 98

¹H-NMR (CDCl₃, 400 MHz): δ 0.95 (s, 9H), 1.44–1.49 (m, 2H), 2.63–2.68 (m, 4H), 2.96 (t, J=5.8 Hz, 2H), 3.26–3.34 (m, 2H), 3.74–3.78 (m, 4H), 4.03 (s, 3H), 4.35 (t, J=5.8 Hz, 2H), 4.90–4.95 (m, 1H), 6.40 (d, J=5.4 Hz, 1H), 7.04–7.14 (m, 3H), 7.45 (s, 1H), 7.50–7.55 (m, 1H), 7.58 (s, 1H), 8.43 (d, J=5.4 Hz, 1H)

Mass spectrometric value (ESI-MS, m/z): 539 (M−1)

Compound 100

1-{2-Chloro-4-[6-methoxy-7-(2-piperidin-1-yl-ethoxy)-quinolin-4-yloxy]-phenyl}-3-(3,3-dimethyl-butyl)-urea ¹H-NMR (CDCl₃, 400 MHz): 0.97 (s, 9H), 1.42–1.54 (m, 4H), 1.58–1.68 (m, 4H), 2.57 (br, 4H), 2.93 (t, J=6.3 Hz, 2H), 3.28–3.36 (m, 2H), 4.01 (s, 3H), 4.34 (t, J=6.3 Hz, 2H), 4.74 (s, 1H), 6.47 (d, J=5.4 Hz, 1H), 6.70 (s, 1H), 7.10 (dd, J=2.7, 9.0 Hz, 1H), 7.21 (d, J=2.7 Hz, 1H), 7.41 (s, 1H), 7.49 (s, 1H), 8.25 (d, J=9.0 Hz, 1H), 8.49 (d, J=5.1 Hz, 1H)

Mass spectrometric value (ESI-MS, m/z): 555 (M)⁺

Compound 102

¹H-NMR (CDCl₃, 400 MHz): 0.92 (s, 9H), 1.41–1.45 (m, 2H), 3.26–3.32 (m, 2H), 4.02 (s, 3H), 4.04 (s, 3H), 5.36 (br, 1H), 6.39 (d, J=5.4 Hz, 1H), 7.07–7.13 (m, 2H), 7.40 (s, 1H), 7.49–7.52 (m, 1H), 7.58 (s, 1H), 7.86 (br, 1H), 8.44 (d, J=5.4 Hz, 1H)

Compound 103

¹H-NMR (CDCl₃, 400 MHz): 0.95 (s, 9H), 1.45–1.50 (m, 2H), 3.27–3.35 (m, 2H), 4.04 (s, 3H), 4.04 (s, 3H), 5.61 (br, 1H), 6.48 (d, J=5.4 Hz, 1H), 7.10 (dd, J=2.7, 9.0 Hz, 1H), 7.17 (br, 1H), 7.18 (d, J=2.7 Hz, 1H), 7.43 (s, 1H), 7.51 (s, 1H), 8.29 (d, J=9.0 Hz, 1H), 8.49 (d, J=5.4 Hz, 1H)

Mass spectrometric value (ESI-MS, m/z): 458 (M⁺+1)

Compound 105

¹H-NMR (CDCl₃, 400 MHz): 0.53–2.09 (m, 7H), 0.85 (d, J=6.4 Hz, 3H), 0.90 (s, 3H), 0.95 (s, 3H), 3.81–3.89 (m, 1H), 4.02 (s, 6H), 4.71 (d, J=7.8 Hz), 6.42 (d, J=5.4 Hz, 1H), 6.80 (s, 1H), 7.08 (d, J=8.8 Hz, 2H), 7.38 (s, 1H), 7.39 (d, J=8.8 Hz, 2H), 7.53 (s, 1H), 8.44 (d, J=5.4 Hz, 1H)

Mass spectrometric value (ESI-MS, m/z): 464 (M⁺+1)

Compound 106

¹H-NMR (CDCl₃, 400 MHz): 0.51–2.05 (m, 7H), 0.82 (d, J=6.6 Hz, 3H), 0.86 (s, 3H), 0.90 (s, 3H), 3.76–3.83 (m, 1H), 3.97 (s, 6H), 4.90 (d, J=8.1 Hz, 1H), 6.41 (d, J=5.4 Hz, 1H), 6.73–6.74 (m, 1H), 6.83–6.93 (m, 2H), 7.35 (s, 1H), 7.44 (s, 1H), 8.13 (t, J=9.1 Hz, 1H), 8.42 (d, J=5.4 Hz, 1H)

Mass spectrometric value (ESI-MS, m/z): 482 (M⁺+1)

Compound 107

¹H-NMR (CDCl₃, 400 MHz): 0.58–2.05 (m, 7H), 0.87 (d, J=6.6 Hz, 3H), 0.91 (s, 3H), 0.95 (s, 3H), 3.78–3.87 (m, 1H), 4.01 (s, 3H), 4.02 (s, 3H), 5.12 (d, J=7.4 Hz, 1H), 6.44 (d, J=5.4 Hz, 1H), 6.98 (s, 1H), 7.07 (dd, J=2.7, 9.0 Hz, 1H), 7.16 (d, J=2.7 Hz, 1H), 7.39 (s, 1H), 7.49 (s, 1H), 8.27 (d, J=9.0 Hz, 1H), 8.46 (d, J=5.4 Hz, 1H)

Mass spectrometric value (ESI-MS, m/z): 498, 500 (M⁺+1)

Compound 108

¹H-NMR (CDCl₃, 400 MHz): 0.84–2.15 (m, 8H), 0.87 (s, 3H), 0.93 (s, 3H), 3.77–3.83 (m, 1H), 4.00 (s, 3H), 4.01 (s, 3H), 5.01 (d, J=7.8 Hz, 1H), 6.40 (d, J=5.4 Hz, 1H), 7.01 (d, J=9.0 Hz, 2H), 7.22 (s, 1H), 7.33 (s, 1H), 7.35 (d, J=9.0 Hz, 2H), 8.38 (d, J=5.4 Hz, 1H)

Mass spectrometric value (ESI-MS, m/z): 450 (M⁺+1)

Compound 109

¹H-NMR (CDCl₃, 400 MHz): 0.81–2.03 (m, 8H), 0.86 (s, 3H), 0.90 (s, 3H), 3.72–3.80 (m, 1H), 3.97 (s, 3H), 3.98 (s, 3H), 5.02 (d, J=7.8 Hz, 1H), 6.41 (d, J=5.4 Hz, 1H), 6.82–6.93 (m, 3H), 7.35 (s, 1H), 7.44 (s, 1H), 8.13 (t, J=9.0 Hz, 1H), 8.41 (d, J=5.4 Hz, 1H)

Mass spectrometric value (ESI-MS, m/z): 468 (M⁺+1)

Compound 110

¹H-NMR (CDCl₃, 400 MHz): 0.85–2.07 (m, 8H), 3.72–3.83 (m, 1H), 4.01 (s, 3H), 4.02 (s, 3H), 5.01 (d, J=7.6 Hz, 1H), 6.44 (d, J=5.4 Hz, 1H), 7.07 (dd, J=2.7, 9.0 Hz, 1H), 7.16 (d, J=2.7 Hz, 1H), 7.40 (s, 1H), 7.49 (s, 1H), 8.27 (d, J=9.0 Hz, 1H), 8.46 (d, J=5.4 Hz, 1H)

Mass spectrometric value (ESI-MS, m/z): 484, 486 (M⁺+1)

Compound 111

¹H-NMR (CDCl₃, 400 MHz): 0.96 (s, 9H), 1.45–1.51 (m, 2H), 3.28–3.35 (m, 2H), 4.04 (s, 3H), 4.05 (s, 3H), 4.74 (t, J=5.4 Hz, 1H), 6.48–6.53 (m, 2H), 6.92–7.00 (m, 2H), 7.42 (s, 1H), 7.51 (s, 1H), 8.17 (t, J=9.0 Hz, 1H), 8.50 (d, J=5.4 Hz, 1H)

Compound 112

¹H-NMR (CD₃OD, 400 MHz): 0.85 (s, 9H), 1.32–1.38 (m, 2H), 2.54–2.57 (m, 4H), 2.85–2.88 (m, 2H), 3.17–3.23 (m, 2H), 3.64–3.69 (m, 4H), 3.93 (s, 3H), 4.23–4.26 (m, 2H), 5.36–5.38 (m, 1H), 6.34 (d, J=5.2 Hz, 1H), 6.99 (d, J=8.8 Hz, 2H), 7.39 (s, 1H), 7.40 (d, J=5.2 Hz, 1H), 7.47 (s, 1H), 7.71 (brs, 1H), 8.36 (d, J=5.2 Hz, 1H)

Mass spectrometric value (ESI-MS, m/z): 523 (M⁺+1)

Compound 113

¹H-NMR (CD₃OD, 400 MHz): 0.97 (s, 9H), 1.48 (m, 2H), 3.06 (s, 3H), 3.24 (m, 2H), 3.80–4.02 (m, 10H), 4.12 (s, 3H), 4.86 (m, 2H), 6.94 (d, J=6.6 Hz, 1H), 7.25 (d, J=8.3 Hz, 2H), 7.61 (d, J=8.8 Hz, 2H), 7.62 (s, 1H), 7.87 (s, 1H), 8.70 (d, J=6.6 Hz, 1H)

Mass spectrometric value (ESI-MS, m/z): 536 (M⁺−1)

Compound 114

1-{2-Chloro-4-[6-methoxy-7-(2-morpholin-4-yl-ethoxy)-quinolin-4-yloxy]-phenyl}-3-(3,3-dimethyl-butyl)-urea ¹H-NMR (CDCl₃, 400 MHz): 0.97 (s, 9H), 1.46–1.53 (m, 2H), 2.62–2.67 (m, 4H), 2.95 (t, J=6.1 Hz, 2H), 3.29–3.36 (m, 2H), 3.73–3.78 (m, 4H), 4.01 (s, 3H), 4.34 (t, J=6.1 Hz, 2H), 4.75 (t, J=5.6 Hz, 1H), 6.48 (d, J=5.1 Hz, 1H), 6.70 (s, 1H), 7.10 (dd, J=2.7, 9.0 Hz, 1H), 7.21 (d, J=2.9 Hz, 1H), 7.42 (s, 1H), 7.50 (s, 1H), 8.26 (d, J=9.0 Hz, 1H), 8.50 (d, J=5.1 Hz, 1H)

Mass spectrometric value (ESI-MS, m/z): 557 (M)⁺

Compound 115

¹H-NMR (CDCl₃, 400 MHz): 0.97 (s, 9H), 1.48–1.52 (m, 2H), 1.81 (br, 4H), 2.31 (s, 3H), 2.51 (br, 2H), 2.68 (br, 2H), 2.97 (t, J=6.1 Hz, 2H), 3.29–3.35 (m, 2H), 4.01 (s, 3H), 4.33 (t, J=6.1 Hz, 2H), 4.75 (br, 1H), 6.47 (d, J=5.4 Hz, 1H), 6.71 (s, 1H), 7.11 (dd, J=2.7, 9.0 Hz, 1H), 7.21 (d, J=2.7 Hz, 1H), 7.41 (s, 1H), 7.49 (s, 1H), 8.26 (d, J=9.0 Hz, 1H), 8.49 (d, J=5.4 Hz, 1H)

Mass spectrometric value (ESI-MS, m/z): 570 (M⁺+1)

Compound 116

¹H-NMR (CDCl₃, 400 MHz): 0.96 (s, 9H), 1.18 (d, J=6.3 Hz, 6H), 1.47–1.52 (m, 2H), 1.92–1.97 (m, 2H), 2.88–2.96 (m, 4H), 3.29–3.35 (m, 2H), 3.70–3.77 (m, 2H), 4.01 (s, 3H), 4.33 (t, J=6.1 Hz, 2H), 4.97 (t, J=5.4 Hz, 1H), 6.48 (d, J=5.4 Hz, 1H), 6.82 (s, 1H), 7.10 (dd, J=2.7, 9.0 Hz, 1H), 7.42 (s, 1H), 7.50 (s, 1H), 8.27 (d, J=9.0 Hz, 1H), 8.49 (d, J=5.1 Hz, 1H)

Compound 117

¹H-NMR (CDCl₃, 400 MHz): 0.94 (d, J=6.1 Hz, 3H), 0.96 (s, 9H), 1.23–1.26 (m, 2H), 1.47–1.51 (m, 2H), 1.64–1.67 (m, 2H), 2.12–2.18 (m, 2H), 2.95 (t, J=6.1 Hz, 2H), 3.01–3.04 (m, 2H), 3.29–3.33 (m, 2H), 4.01 (s, 3H), 4.32 (t, J=6.1 Hz, 2H), 5.09 (t, J=5.4 Hz, 1H), 6.47 (d, J=5.4 Hz, 1H), 6.89 (s, 1H), 7.10 (dd, J=2.7, 9.0 Hz, 1H), 7.19 (d, J=2.7 Hz, 1H), 7.41 (s, 1H), 7.50 (s, 1H), 8.27 (d, J=9.0 Hz, 1H), 8.49 (d, J=5.4 Hz, 1H)

Compound 119

¹H-NMR (CDCl₃, 400 MHz): δ 0.95 (s, 9H), 1.19 (d, J=6.3 Hz, 6H), 1.43–1.49 (m, 2H), 2.02 (t, J=9.7 Hz, 2H), 2.93–3.01 (m, 4H), 3.26–3.33 (m, 2H), 3.74–3.84 (m, 2H), 4.02 (s, 3H), 4.38 (t, J=5.7 Hz, 2H), 4.90–4.96 (m, 1H), 6.44 (d, J=5.6 Hz, 1H), 6.97 (br, 1H), 7.08 (d, J=8.8 Hz, 2H), 7.47 (d, J=8.8 Hz, 2H), 7.51 (s, 1H), 7.56 (s, 1H), 8.40 (d, J=5.6 Hz, 1H)

Mass spectrometric value (ESI-MS, m/z): 551 (M+1), 549 (M−1)

Compound 120

¹H-NMR (CDCl₃, 400 MHz): δ 0.90 (d, J=6.1 Hz, 6H), 0.95 (s, 9H), 0.94–1.10 (m, 2H), 1.42–1.48 (m, 2H), 1.74–1.95 (m, 3H), 3.04–3.16 (m, 3H), 3.26–3.33 (m, 2H), 4.00 (s, 3H), 4.39–4.45 (m, 2H), 4.93 (br, 1H), 6.39 (d, J=5.1 Hz, 1H), 6.91 (br, 1H), 7.05 (d, J=9.0 Hz, 2H), 7.39–7.44 (m, 3H), 7.54 (s, 1H), 8.43 (d, J=5.4 Hz, 1H)

Mass spectrometric value (ESI-MS, m/z): 549 (M+1), 547 (M−1)

Compound 121

¹H-NMR (CDCl₃, 400 MHz): δ 0.94 (s, 9H), 1.43–1.49 (m, 2H), 1.88–2.06 (m, 4H), 2.38–2.50 (m, 2H), 2.53–2.62 (m, 1H), 3.09–3.14 (m, 2H), 3.26–3.34 (m, 4H), 4.01 (s, 3H), 4.41–4.46 (m, 2H), 4.87–4.93 (m, 1H), 6.40 (d, J=5.1 Hz, 1H), 6.88 (br, 1H), 7.07 (d, J=9.0 Hz, 2H), 7.18–7.33 (m, 5H), 7.42–7.50 (m, 3H), 7.55 (s, 1H), 8.42 (d, J=5.4 Hz, 1H)

Mass spectrometric value (ESI-MS, m/z): 597 (M+1), 595 (M−1)

Compound 122

¹H-NMR (CDCl₃, 400 MHz): δ 0.95 (s, 9H), 1.42–1.49 (m, 2H), 1.88–2.09 (m, 4H), 2.26–2.47 (m, 4H), 2.55–2.66 (m, 1H), 2.83–2.92 (m, 2H), 3.24–3.37 (m, 4H), 4.01 (s, 3H), 4.27 (t, J=6.3 Hz, 2H), 6.41 (d, J=5.4 Hz, 1H), 7.08 (d, J=9.0 Hz, 2H), 7.19–7.34 (m, 5H), 7.38 (s, 1H), 7.47 (d, J=8.8 Hz, 2H), 7.54 (s, 1H), 8.39 (d, J=5.1 Hz, 1H)

Mass spectrometric value (ESI-MS, m/z): 611 (M+1)

Compound 123

¹H-NMR (CDCl₃, 400 MHz): δ 0.94 (s, 9H), 1.42–1.50 (m, 4H), 1.62–1.74 (m, 6H), 1.83–1.90 (m, 2H), 2.11–2.20 (m, 2H), 2.43 (br, 1H), 2.61 (br, 4H), 2.93 (t, J=6.1 Hz, 2H), 3.08–3.15 (m, 2H), 3.25–3.33 (m, 2H), 4.00 (s, 3H), 4.30 (t, J=6.1 Hz, 2H), 4.88–4.93 (m, 1H), 6.43 (d, J=5.4 Hz, 1H), 6.88 (br, 1H), 7.10 (d, J=9.0 Hz, 2H), 7.40 (s, 1H), 7.43 (d, J=8.8 Hz, 2H), 7.52 (s, 1H), 8.45 (d, J=5.4 Hz, 1H)

Mass spectrometric value (ESI-MS, m/z): 604 (M+1)

Compound 124

¹H-NMR (CDCl₃, 400 MHz): δ 0.94 (s, 9H), 1.42–1.49 (m, 2H), 1.61–1.73 (m, 2H), 1.76–1.98 (m, 4H), 2.13–2.25 (m, 2H), 2.64–2.71 (m, 3H), 2.93 (t, J=6.0 Hz, 2H), 3.02–3.09 (m, 2H), 3.26–3.32 (m, 2H), 4.00 (s, 3H), 4.31 (t, J=6.0 Hz, 2H), 4.90–4.95 (m, 1H), 6.42 (d, J=5.4 Hz, 1H), 6.88 (br, 1H), 7.09 (d, J=9.0 Hz, 2H), 7.41 (d, J=5.6 Hz, 2H), 7.44 (s, 1H), 7.52 (s, 1H), 8.44 (d, J=5.1 Hz, 1H)

Mass spectrometric value (ESI-MS, m/z): 590 (M+1)

Compound 125

¹H-NMR (CDCl₃, 400 MHz): 0.97 (s, 9H), 1.17 (s, 3H), 1.19 (s, 3H), 1.46–1.54 (m, 2H), 1.91–1.99 (m, 2H), 2.84–2.96 (m, 4H), 3.28–3.36 (m, 2H), 3.68–3.78 (m, 2H), 4.01 (s, 3H), 4.33 (t, J=6.1 Hz, 2H), 4.76 (br, 1H), 6.48 (d,

J=5.4 Hz, 1H), 6.72 (br, 1H), 7.10 (dd, J=2.7, 9.0 Hz, 1H), 7.21 (d, J=2.7 Hz, 1H), 7.42 (s, 1H), 7.50 (s, 1H), 8.26 (d, J=9.0 Hz, 1H), 8.05 (d, J=5.4 Hz, 1H)

Mass spectrometric value (ESI-MS, m/z): 607 (M+Na)$^+$

Compound 126

$^1$H-NMR (CDCl$_3$, 400 MHz): 0.93 (s, 9H), 1.40–1.48 (m, 2H), 2.60–2.66 (m, 4H), 2.94 (t, J=6.1 Hz, 2H), 3.25–3.34 (m, 2H), 3.72–3.78 (m, 4H), 4.02 (s, 3H), 4.32 (t, J=5.9 Hz, 2H), 5.13 (br, 1H), 6.29 (d, J=6.1 Hz, 1H), 7.11 (d, J=8.8 Hz, 1H), 7.31 (dd, J=2.7, 8.8 Hz, 1H), 7.40 (s, 1H), 7.42 (br, 1H), 7.59 (s, 1H), 7.63 (d, J=2.7 Hz, 1H), 8.44 (d, J=5.1 Hz, 1H)

Mass spectrometric value (ESI-MS, m/z): 579 (M+Na)$^+$

Compound 127

$^1$H-NMR (CDCl$_3$, 400 MHz): 0.95 (s, 9H), 1.17 (s, 3H), 1.18 (s, 3H), 1.42–1.50 (m, 2H), 1.90–1.98 (m, 2H), 2.85–2.95 (m, 4H), 3.26–3.35 (m, 2H), 3.67–3.77 (m, 2H), 4.03 (s, 3H), 4.33 (t, J=5.9 Hz, 2H), 4.82 (br, 1H), 6.30 (d, J=5.4 Hz, 1H), 6.88 (br, 1H), 7.14 (d, J=8.8 Hz, 1H), 7.31 (dd, J=2.7, 8.8 Hz, 1H), 7.42 (s, 1H), 7.59 (s, 1H), 7.64 (d, J=2.7 Hz, 1H), 8.45 (d, J=5.1 Hz, 1H)

Mass spectrometric value (ESI-MS, m/z): 607 (M+Na)$^+$

Compound 128

$^1$H-NMR (CDCl$_3$, 400 MHz): δ 0.95 (s, 9H), 1.18 (d, J=6.3 Hz, 6H), 1.44–1.50 (m, 2H), 1.99 (t, J=10.9 Hz, 2H), 2.90–2.98 (m, 4H), 3.24–3.33 (m, 2H), 3.71–3.80 (m, 2H), 4.02 (s, 3H), 4.36 (t, J=6.0 Hz, 2H), 4.90–4.95 (m, 1H), 6.39 (d, J=5.4 Hz, 1H), 7.04–7.13 (m, 3H), 7.44 (s, 1H), 7.50–7.55 (m, 1H), 7.58 (s, 1H), 8.42 (d, J=5.4 Hz, 1H)

Mass spectrometric value (ESI-MS, m/z): 569 (M+1)

Compound 129

$^1$H-NMR (CDCl$_3$, 400 MHz): δ 0.93 (s, 9H), 1.41–1.51 (m, 4H), 1.63–1.70 (m, 4H), 2.57–2.64 (m, 4H), 2.96 (t, J=6.0 Hz, 2H), 3.25–3.32 (m, 2H), 4.00 (s, 3H), 4.34 (t, J=6.0 Hz, 2H), 5.21–5.26 (m, 1H), 6.36 (d, J=5.4 Hz, 1H), 7.04–7.07 (m, 2H), 7.40 (s, 1H), 7.49–7.55 (m, 2H), 7.57 (s, 1H), 8.43 (d, J=5.4 Hz, 1H)

Mass spectrometric value (ESI-MS, m/z): 539 (M+1)

Compound 130

$^1$H-NMR (CDCl$_3$, 400 MHz): 0.92 (s, 9H), 1.18 (d, J=6.3 Hz, 6H), 1.19–1.75 (m, 8H), 2.55–2.61 (m, 2H), 3.17–3.31 (m, 4H), 3.98 (s, 3H), 4.16–4.19 (m, 2H), 5.07–5.09 (m, 1H), 6.44 (d, J=5.3 Hz, 1H), 6.82–6.95 (m, 3H), 7.39 (s, 1H), 7.46 (s, 1H), 8.18 (t, J=9.0 Hz, 1H), 8.46 (d, J=5.3 Hz, 1H)

Mass spectrometric value (ESI-MS, m/z): 567 (M$^+$+1)

Compound 131

$^1$H-NMR (CDCl$_3$, 400 MHz): 0.88 (s, 9H), 1.12 (s, 12H), 1.32–1.52 (m, 8H), 2.95–3.00 (m, 2H), 3.21–3.27 (m, 2H), 3.96 (s, 3H), 4.00-4.17 (m, 2H), 5.03–5.06 (m, 1H), 6.39 (d, J=5.4 Hz, 1H), 6.77–6.93 (m, 3H), 7.36 (s, 1H), 7.42 (s, 1H), 8.11 (t, J=9.0 Hz, 1H), 8.41 (d, J=5.4 Hz, 1H)

Mass spectrometric value (ESI-MS, m/z): 595 (M$^+$+1)

Compound 132

$^1$H-NMR (CDCl$_3$, 400 MHz): 0.90 (s, 9H), 1.17 (d, J=6.3 Hz, 6H), 1.27–1.67 (m, 8H), 2.54–2.61 (m, 2H), 3.16–3.23 (m, 2H), 3.24–3.29 (m, 2H), 3.99 (s, 3H), 4.02–4.18 (m, 2H), 5.15–5.18 (m, 1H), 6.36 (d, J=5.4 Hz, 1H), 7.03–7.09 (m, 2H), 7.37 (s, 1H), 7.54 (s, 1H), 7.46–7.50 (m, 1H), 7.64 (brs, 1H), 8.42 (d, J=5.4 Hz, 1H)

Mass spectrometric value (ESI-MS, m/z): 567 (M$^+$+1)

Compound 133

$^1$H-NMR (CDCl$_3$, 400 MHz): δ 0.94 (s, 3H), 0.98 (s, 3H), 0.95–1.12 (m, 2H), 1.33–1.40 (m, 1H), 1.50–1.65 (m, 2H), 1.71–1.77 (m, 1H), 2.03–2.10 (m, 1H), 2.61–2.66 (m, 4H), 2.95 (t, J=5.9 Hz, 2H), 3.70–3.88 (m, 6H), 4.00 (s, 3H), 4.33 (t, J=5.9 Hz, 2H), 4.94 (d, J=7.8 Hz, 1H), 6.48 (d, J=5.1 Hz, 1H), 6.79 (d, J=2.6 Hz, 1H), 6.91 (dd, J=2.6, 11.5 Hz, 1H), 6.96 (d, J=9.0 Hz, 1H), 7.41 (s, 1H), 7.50 (s, 1H), 8.20 (t, J=9.0 Hz, 1H), 8.48 (d, J=5.1 Hz, 1H)

Mass spectrometric value (ESI-MS, m/z): 565 (M−1)

Compound 134

$^1$H-NMR (CDCl$_3$, 400 MHz): δ 0.93 (s, 3H), 0.98 (s, 3H), 0.94–1.11 (m, 2H), 1.17 (d, J=9.3 Hz, 6H), 1.33–1.38 (m, 1H), 1.46–1.65 (m, 2H), 1.70–1.76 (m, 1H), 1.94 (t, J=10.7 Hz, 2H), 2.04–2.14 (m, 2H), 2.86–2.95 (m, 4H), 3.68–3.87 (m, 3H), 4.01 (s, 3H), 4.32 (t, J=5.9 Hz, 2H), 5.05 (d, J=8.1 Hz, 1H), 6.47 (d, J=5.1 Hz, 1H), 6.86–6.98 (m, 3H), 7.41 (s, 1H), 7.51 (s, 1H), 8.21 (t, J=9.0 Hz, 1H), 8.48 (d, J=5.1 Hz, 1H)

Mass spectrometric value (ESI-MS, m/z): 595 (M+1)

The following compounds were synthesized in the same manner as in the Synthesis Examples of the above compounds.

Compound No. Name of Compound

135: 1-[4-(6,7-Dimethoxy-quinolin-4-yloxy)-2-nitro-phenyl]-3-(3,3-dimethyl-butyl)-urea 136: 1-[4-(6,7-Dimethoxy-quinolin-4-yloxy)-2-methyl-phenyl]-3-(3,3-dimethyl-butyl)-urea 137: 1-[4-(6,7-Dimethoxy-quinolin-4-yloxy)-3-methyl-phenyl]-3-(3,3-dimethyl-butyl)-urea 138: 1-[4-(6,7-Dimethoxy-quinolin-4-yloxy)-2-methoxy-phenyl]-3-(3,3-dimethyl-butyl)-urea 139: 1-[4-(6,7-Dimethoxy-quinolin-4-yloxy)-3-methoxy-phenyl]-3-(3,3-dimethyl-butyl)-urea 140: 1-[3,5-Dichloro-4-(6,7-dimethoxy-quinolin-4-yloxy)-phenyl]-3-(3,3-dimethyl-butyl)-urea 141: 1-[4-(6,7-Dimethoxy-quinolin-4-yloxy)-2,3-dimethyl-phenyl]-3-(3,3-dimethyl-butyl)-urea 142: 1-[4-(6,7-Dimethoxy-quinolin-4-yloxy)-2,5-dimethyl-phenyl]-3-(3,3-dimethyl-butyl)-urea 143: 1-[4-(6,7-Dimethoxy-quinolin-4-yloxy)-phenyl]-3-(1,1,3,3-tetramethyl-butyl)-urea 144: 1-[2-Chloro-4-(6,7-dimethoxy-quinolin-4-yloxy)-phenyl]-3-(1,1,3,3-tetramethyl-butyl)-urea 145: 1-[4-(7-Benzyloxy-6-methoxy-quinolin-4-yloxy)-phenyl]-3-(3,3-dimethyl-butyl)-urea 146: 1-{4-[7-(2-Bromo-ethoxy)-6-methoxy-quinolin-4-yloxy]-phenyl}-3-(3,3-dimethyl-butyl)-urea 147: 1-{4-[7-(3-Bromo-propoxy)-6-methoxy-quinolin-4-yloxy]-phenyl}-3-(3,3-dimethyl-butyl)-urea 148: 1-{4-[7-(4-Bromo-butoxy)-6-methoxy-quinolin-4-yloxy]-phenyl}-3-(3,3-dimethyl-butyl)-urea 149: 1-[4-(6,7-Dimethoxy-quinolin-4-yloxy)-2-fluoro-phenyl]-3-(3,3,5,5-tetramethyl-hexyl)-urea 150: 1-[4-(6,7-Dimethoxy-quinolin-4-yloxy)-2-trifluoromethyl-phenyl]-3-(3,3-dimethyl-butyl)-urea 151: 1-{4-[7-(3-Chloro-propoxy)-6-methoxy-quinolin-4-yloxy]-phenyl}-3-(3,3-dimethyl-butyl)-urea 152: 1-{4-[7-(2-Chloro-ethoxy)-6-methoxy-quinolin-4-yloxy]-phenyl}-3-(3,3-dimethyl-butyl)-urea 153: 1-{4-[7-(4-Chloro-butoxy)-6-methoxy-quinolin-4-yloxy]-phenyl}-3-(3,3-dimethyl-butyl)-urea 154: 1-(3,3-Dimethyl-butyl)-3-{4-[6-methoxy-7-(3-piperidin-1-yl-propoxy)-quinolin-4-yloxy]-phenyl}-urea hydrochloride 155: 1-(3,3-Dimethyl-butyl)-3-{4-[6-methoxy-7-(3-morpholin-4-yl-propoxy)-quinolin-4-yloxy]-phenyl}-urea hydrochloride 156: 1-(3,3-Dimethyl-butyl)-3-(4-{6-methoxy-7-[3-(4-methyl-piperazin-1-yl)-propoxy]-quinolin-4-yloxy}-phenyl)-urea hydrochloride 157: 1-(3,3-Dimethyl-butyl)-3-{4-[6-methoxy-7-(4-piperidin-1-yl-butoxy)-quinolin-4-yloxy]-phenyl}-urea hydrochloride 158: 1-(3,3-Dimethyl-butyl)-3-{4-[6-methoxy-7-(4-morpholin-4-yl-butoxy)-quinolin-4-yloxy]-phenyl}-urea hydrochloride 159: 1-(3,3-Dimethyl-butyl)-3-(4-{6-methoxy-7-[4-(4-methyl-piperazin-1-yl)-butoxy]-quinolin-4-yloxy}-phenyl)-urea hydrochloride 160: 1-{2-Chloro-4-[7-(2-chloro-ethoxy)-6-methoxy-quinolin-4-yloxy]-phenyl}-3-(3,3-dimethyl-butyl)-urea 161: 1-{2-Chloro-4-[7-(3-chloro-propoxy)-6-methoxy-quinolin-4-yloxy]-phenyl}-3-(3,3-dimethyl-butyl)-urea 162: 1-{2-Chloro-4-[7-(4-chloro-butoxy)-6-methoxy-quinolin-4-yloxy]-phenyl}-3-(3,3-dimethyl-butyl)-urea 163: 1-[4-(7-Benzyloxy-6-methoxy-quinolin-4-yloxy)-2-chloro-phenyl]-3-(3,3-dimethyl-butyl)-urea 164: 1-(2-Chloro-4-{7-[4-(1,3-dioxo-1,3-dihydro-isoindol-2-yl)-butoxy]-6-methoxy-quinolin-4-yloxy}-phenyl)-3-(3,3-dimethyl-butyl)-urea 165: 1-{2-Chloro-4-[6-methoxy-7-(2-pyrrolidin-1-yl-ethoxy)-quinolin-4-yloxy]-phenyl}-3-(3,3-dimethyl-butyl)-urea 166: 1-{2-Chloro-4-[7-(2-dimethylamino-ethoxy)-6-methoxy-quinolin-4-yloxy]-phenyl}-3-(3,3-dimethyl-butyl)-urea 167: 1-{2-Chloro-4-[7-(2-diethylamino-ethoxy)-6-methoxy-quinolin-4-yloxy]-phenyl}-3-(3,3-dimethyl-butyl)-urea 168: 1-{2-Chloro-4-[6-methoxy-7-(piperidin-4-ylmethoxy)-quinolin-4-yloxy]-phenyl}-3-(3,3-dimethyl-butyl)-urea 169: 1-{2-Chloro-4-[6-methoxy-7-(1-methyl-piperidin-4-ylmethoxy)-quinolin-4-yloxy]-phenyl}-3-(3,3-dimethyl-butyl)-urea 170: 1-(2-Chloro-4-{7-[1-(2-hydroxy-ethyl)-piperidin-4-ylmethoxy]-6-methoxy-quinolin-4-yloxy}-phenyl)-3-(3,3-dimethyl-butyl)-urea 171: 1-(2-Chloro-4-{6-methoxy-7-[1-(2-methoxy-ethyl)-piperidin-4-ylmethoxy]-quinolin-4-yloxy}-phenyl)-3-(3,3-dimethyl-butyl)-urea 172: 1-{2-Chloro-4-[7-(3-dimethylamino-propoxy)-6-methoxy-quinolin-4-yloxy]-phenyl}-3-(3,3-dimethyl-butyl)-urea 173: 1-(2-Chloro-4-{7-[2-(1,3-dioxo-1,3-dihydro-isoindol-2-yl)-ethoxy]-6-methoxy-quinolin-4-yloxy}-phenyl)-3-(3,3-dimethyl-butyl)-urea 174: 1-(2-Chloro-4-{7-[3-(1,3-dioxo-1,3-dihydro-isoindol-2-yl)-propoxy]-6-methoxy-quinolin-4-yloxy}-phenyl)-3-(3,3-dimethyl-butyl)-urea 175: 1-{4-[7-(4-Amino-butoxy)-6-methoxy-quinolin-4-yloxy]-2-chloro-phenyl}-3-(3,3-dimethyl-butyl)-urea 176: 1-[4-(7-{2-[Bis-(2-hydroxy-ethyl)-amino]-ethoxy}-6-methoxy-quinolin-4-yloxy)-2-chloro-phenyl]-3-(3,3-dimethyl-butyl)-urea 177: 1-[2-Chloro-4-(7-{2-[(2-hydroxy-ethyl)-methyl-amino]-ethoxy}-6-methoxy-quinolin-4-yloxy)-phenyl]-3-(3,3-dimethyl-butyl)-urea 178: 1-[2-Chloro-4-(7-{3-[(2-hydroxy-ethyl)-methyl-amino]-propoxy}-6-methoxy-quinolin-4-yloxy)-phenyl]-3-(3,3-dimethyl-butyl)-urea 179: 1-{2-Chloro-4-[6-methoxy-7-(3-pyrrolidin-1-yl-propoxy)-quinolin-4-yloxy]-phenyl}-3-(3,3-dimethyl-butyl)-urea 180: 1-{2-Chloro-4-[6-methoxy-7-(3-piperidin-1-yl-propoxy)-quinolin-4-yloxy]-phenyl}-3-(3,3-dimethyl-butyl)-urea 181: 1-{4-[7-(3-Azepan-1-yl-propoxy)-6-methoxy-quinolin-4-yloxy]-2-chloro-phenyl}-3-(3,3-dimethyl-butyl)-urea 182: 1-{2-Chloro-4-[6-methoxy-7-(3-morpholin-4-yl-propoxy)-quinolin-4-yloxy]-phenyl}-3-(3,3-dimethyl-butyl)-urea 183: 1-{2-Chloro-4-[7-(3-diethylamino-propoxy)-6-methoxy-quinolin-4-yloxy]-phenyl}-3-(3,3-dimethyl-butyl)-urea 184: 1-[4-(7-{3-[Bis-(2-hydroxy-ethyl)-amino]-propoxy}-6-methoxy-quinolin-4-yloxy)-2-chloro-phenyl]-3-(3,3-dimethyl-butyl)-urea 185: 1-{4-[7-(2-Azepan-1-yl-ethoxy)-6-methoxy-quinolin-4-yloxy]-2-chloro-phenyl}-3-(3,3-dimethyl-butyl)-urea 186: 1-(2-Chloro-4-{6-methoxy-7-[2-(4-methyl-[1,4]diazepan-1-yl)-ethoxy]-quinolin-4-yloxy}-phenyl)-3-(3,3-dimethyl-butyl)-urea 187: 1-(2-Chloro-4-{6-methoxy-7-[3-(4-methyl-piperazin-1-yl)-propoxy]-quinolin-4-yloxy}-phenyl)-3-(3,3-dimethyl-butyl)-urea 188: 1-(2-Chloro-4-{6-methoxy-7-[3-(4-methyl-[1,4]diazepan-1-yl)-propoxy]-quinolin-4-yloxy}-phenyl)-3-(3,3-dimethyl-butyl)-urea 189: Tert-butyl 3-(4-{3-chloro-4-[3-(3,3-dimethyl-butyl)-ureido]-phenoxy}-6-methoxy-quinolin-7-yloxymethyl)-piperidin-1-carboxylate 190: 1-{2-Chloro-4-[6-methoxy-7-(piperidin-3-ylmethoxy)-quinolin-4-yloxy]-phenyl}-3-(3,3-dimethyl-butyl)-urea 191: 1-{2-Chloro-4-[7-(3-diethylamino-2-hydroxy-propoxy)-6-methoxy-quinolin-4-yloxy]-phenyl}-3-(3,3-dimethyl-butyl)-urea 192: 1-{2-Chloro-4-[7-(2-hydroxy-3-pyrrolidin-1-yl-propoxy)-6-methoxy-quinolin-4-yloxy]-phenyl}-3-(3,3-dimethyl-butyl)-urea 193: 1-{2-Chloro-4-[7-(2-hydroxy-3-piperidin-1-yl-propoxy)-6-methoxy-quinolin-4-yloxy]-phenyl}-3-(3,3-dimethyl-butyl)-urea 194: 1-{4-[7-(3-Azepan-1-yl-2-hydroxy-propoxy)-6-methoxy-quinolin-4-yloxy]-2-chloro-phenyl}-3-(3,3-dimethyl-butyl)-urea 195: 1-{2-Chloro-4-[7-(2-hydroxy-3-morpholin-4-yl-propoxy)-6-methoxy-quinolin-4-yloxy]-phenyl}-3-(3,3-dimethyl-butyl)-urea 196: 1-(2-Chloro-4-{7-[2-hydroxy-3-(4-methyl-[1,4]diazepan-1-yl)-propoxy]-6-methoxy-quinolin-4-yloxy}-phenyl)-3-(3,3-dimethyl-butyl)-urea 197: 1-{2-Chloro-4-[7-(2-hydroxy-3-morpholin-4-yl-propoxy)-6-methoxy-quinolin-4-yloxy]-phenyl}-3-(3,3-dimethyl-butyl)-urea 198: 1-{2-Chloro-4-[7-(3-ethylamino-2-hydroxy-propoxy)-6-methoxy-quinolin-4-yloxy]-phenyl}-3-(3,3-dimethyl-butyl)-urea 199: 1-{2-Chloro-4-[7-(3-dimethylamino-2-hydroxy-propoxy)-6-methoxy-quinolin-4-yloxy]-phenyl}-3-(3,3-dimethyl-butyl)-urea 200: 1-(3,3-Dimethyl-butyl)-3-(4-{7-[3-(2,6-dimethyl-morpholin-4-yl)-propoxy]-6-methoxy-quinolin-4-yloxy}-phenyl)-urea 201: 1-{2-Chloro-4-[7-(2-hydroxy-3-morpholin-4-yl-propoxy)-6-methoxy-quinolin-4-yloxy]-phenyl}-3-(3,3-dimethyl-butyl)-urea 202: 1-{2-Chloro-4-[6-methoxy-7-(2-piperidin-4-yl-ethoxy)-quinolin-4-yloxy]-phenyl}-3-(3,3-dimethyl-butyl)-urea 203: 1-{2-Chloro-4-[6-methoxy-7-(2-piperidin-2-yl-ethoxy)-quinolin-4-yloxy]-phenyl}-3-(3,3-dimethyl-butyl)-urea
204: 1-{4-[7-(3-Chloro-propoxy)-6-methoxy-quinolin-4-yloxy]-2-fluoro-phenyl}-3-(3,3-dimethyl-butyl)-urea
205: 1-{2-Chloro-4-[6-methoxy-7-(3-morpholin-4-yl-propoxy)-quinolin-4-yloxy]-phenyl}-3-(3,3-dimethyl-butyl)-urea
206: 1-{2-Chloro-4-[7-(2-hydroxy-3-morpholin-4-yl-propoxy)-6-methoxy-quinolin-4-yloxy]-phenyl}-3-(3,3-dimethyl-butyl)-urea
207: 1-(2-Chloro-4-{6-methoxy-7-[3-(4-methyl-piperidin-1-yl)-propoxy]-quinolin-4-yloxy}-phenyl)-3-(3,3-dimethyl-butyl)-urea
208: 1-(2-Chloro-4-{7-[3-(2-hydroxymethyl-pyrrolidin-1-yl)-propoxy]-6-methoxy-quinolin-4-yloxy}-phenyl)-3-(3,3-dimethyl-butyl)-urea
209: 1-(3,3-Dimethyl-butyl)-3-{2-fluoro-4-[7-(2-hydroxy-3-morpholin-4-yl-propoxy)-6-methoxy-quinolin-4-yloxy]-phenyl}-urea
210: 1-(3,3-Dimethyl-butyl)-3-{2-fluoro-4-[6-methoxy-7-(3-morpholin-4-yl-propoxy)-quinolin-4-yloxy]-phenyl}-urea
211: 1-{2-Chloro-4-[7-(2-hydroxy-ethoxy)-6-methoxy-quinolin-4-yloxy]-phenyl}-3-(3,3-dimethyl-butyl)-urea
212: (4-Tert-butyl-phenyl)-{4-[7-methoxy-6-(2-morpholin-4-yl-ethoxy)-quinolin-4-yloxy]-phenyl}-amine
213: 1-{4-[4-(4-Tert-butyl-phenylamino)-phenoxy]-7-methoxy-quinolin-6-yloxy}-3-morpholin-4-yl-propan-2-ol
214: 4-[4-(4-Tert-butyl-phenylamino)-phenoxy]-7-methoxy-quinolin-6-ol
215: Methyl (4-{4-[3-(3,3-dimethyl-butyl)-ureido]-phenoxy}-6-methoxy-quinolin-7-yloxy)-acetate
216: 1-(3-{4-[4-(4-Tert-butyl-phenylamino)-phenoxy]-6-methoxy-quinolin-7-yloxy}-propyl)-piperidin-4-ol
217: [1-(3-{4-[4-(4-Tert-butyl-phenylamino)-phenoxy]-6-methoxy-quinolin-7-yloxy}-propyl)-piperidin-4-yl]-methanol
218: 2-[1-(3-{4-[4-(4-Tert-butyl-phenylamino)-phenoxy]-6-methoxy-quinolin-7-yloxy}-propyl)-piperidin-4-yl]-ethanol
219: 1-(3,3-Dimethyl-butyl)-3-[4-(7-{2-[4-(2-hydroxy-ethyl)-piperidin-1-yl]-ethoxy}-6-methoxy-quinolin-4-yloxy)-phenyl]-urea
220: 1-(3,3-Dimethyl-butyl)-3-[4-(7-{3-[4-(2-hydroxy-ethyl)-piperidin-1-yl]-propoxy}-6-methoxy-quinolin-4-yloxy)-phenyl]-urea
221: (4-{4-[3-(3,3-Dimethyl-butyl)-ureido]-phenoxy}-6-methoxy-quinolin-7-yloxy)-acetic acid
222: 1-{4-[6-(2-Dimethylamino-ethoxy)-7-methoxy-quinolin-4-yloxy]-phenyl}-3-(3,3-dimethyl-butyl)-urea
223: 1-(3,3-Dimethyl-butyl)-3-{4-[7-methoxy-6-(3-morpholin-4-yl-propoxy)-quinolin-4-yloxy]-phenyl}-urea
224: 1-{4-[6-(3-Dimethylamino-propoxy)-7-methoxy-quinolin-4-yloxy]-phenyl}-3-(3,3-dimethyl-butyl)-urea
225: 1-(3,3-Dimethyl-butyl)-3-{4-[6-(2-hydroxy-3-morpholin-4-yl-propoxy)-7-methoxy-quinolin-4-yloxy]-phenyl}-urea
226: 1-{4-[6-(3-Dimethylamino-2-hydroxy-propoxy)-7-methoxy-quinolin-4-yloxy]-phenyl}-3-(3,3-dimethyl-butyl)-urea
227: 1-(3,3-Dimethyl-butyl)-3-{4-[7-methoxy-6-(4-morpholin-4-yl-butoxy)-quinolin-4-yloxy]-phenyl}-urea
228: 1-{4-[6-(4-Dimethylamino-butoxy)-7-methoxy-quinolin-4-yloxy]-phenyl}-3-(3,3-dimethyl-butyl)-urea
229: 2-{4-[4-(4-Isopropyl-phenylamino)-phenoxy]-6-methoxy-quinolin-7-yloxy}-1-morpholin-4-yl-ethanone
230: 4-{4-[3-(3,3-Dimethyl-butyl)-ureido]-3-fluoro-phenoxy}-6-methoxy-quinolin-7-yl [1,4']bipiperidineyl-1'-carboxylate
231: 1-(3,3-Dimethyl-butyl)-3-(4-{6-[3-(2,6-dimethyl-morpholin-4-yl)-propoxy]-7-methoxy-quinolin-4-yloxy}-3-fluoro-phenyl)-urea
232: (4-Tert-butyl-phenyl)-(4-{7-[3-(2,6-dimethyl-morpholin-4-yl)-propoxy]-6-methoxy-quinolin-4-yloxy}-phenyl)-amine
233: (4-Tert-butyl-phenyl)-(4-{7-[3-(3,5-dimethyl-piperidin-1-yl)-propoxy]-6-methoxy-quinolin-4-yloxy}-phenyl)-amine
234: (4-Tert-butyl-phenyl)-(4-{6-methoxy-7-[3-(4-phenyl-piperidin-1-yl)-propoxy]-quinolin-4-yloxy}-phenyl)-amine
235: (4-{7-[3-(4-Benzyl-piperidin-1-yl)-propoxy]-6-methoxy-quinolin-4-yloxy}-phenyl)-(4-tert-butyl-phenyl)-amine
236: {4-[7-(3-[1,4']Bipiperidineyl-1'-yl-propoxy)-6-methoxy-quinolin-4-yloxy]-phenyl}-(4-tert-butyl-phenyl)-amine
237: (4-Tert-butyl-phenyl)-(4-{6-methoxy-7-[3-(4-pyrrolidin-1-yl-piperidin-1-yl)-propoxy]-quinolin-4-yloxy}-phenyl)-amine
238: (4-Tert-butyl-phenyl)-(4-{7-[2-(2,6-dimethyl-morpholin-4-yl)-ethoxy]-6-methoxy-quinolin-4-yloxy}-phenyl)-amine
239: (4-Tert-butyl-phenyl)-(4-{7-[2-(3,5-dimethyl-piperidin-1-yl)-ethoxy]-6-methoxy-quinolin-4-yloxy}-phenyl)-amine
240: (4-Tert-butyl-phenyl)-(4-{6-methoxy-7-[2-(4-phenyl-piperidin-1-yl)-ethoxy]-quinolin-4-yloxy}-phenyl)-amine
241: (4-{7-[2-(4-Benzyl-piperidin-1-yl)-ethoxy]-6-methoxy-quinolin-4-yloxy}-phenyl)-(4-tert-butyl-phenyl)-amine
242: {4-[7-(2-[1,4']Bipiperidineyl-1'-yl-ethoxy)-6-methoxy-quinolin-4-yloxy]-phenyl}-(4-tert-butyl-phenyl)-amine
243: (4-Tert-butyl-phenyl)-(4-{6-methoxy-7-[2-(4-pyrrolidin-1-yl-piperidin-1-yl)-ethoxy]-quinolin-4-yloxy}-phenyl)-amine
244: 1-(3,3-Dimethyl-butyl)-3-(4-{7-[3-(2,6-dimethyl-morpholin-4-yl)-propoxy]-6-methoxy-quinolin-4-yloxy}-phenyl)-urea
245: 1-(3,3-Dimethyl-butyl)-3-(4-{7-[3-(3,5-dimethyl-piperidin-1-yl)-propoxy]-6-methoxy-quinolin-4-yloxy}-phenyl)-urea
246: 1-(3,3-Dimethyl-butyl)-3-(4-{6-methoxy-7-[3-(4-phenyl-piperidin-1-yl)-propoxy]-quinolin-4-yloxy}-phenyl)-urea
247: 1-(4-{7-[3-(4-Benzyl-piperidin-1-yl)-propoxy]-6-methoxy-quinolin-4-yloxy}-phenyl)-3-(3,3-dimethyl-butyl)-urea
248: 1-{4-[7-(3-[1,4']Bipiperidinyl-1'-yl-propoxy)-6-methoxy-quinolin-4-yloxy]-phenyl}-3-(3,3-dimethyl-butyl)-urea
249: 1-(3,3-Dimethyl-butyl)-3-(4-{6-methoxy-7-[3-(4-pyrrolidin-1-yl-piperidin-1-yl)-propoxy]-quinolin-4-yloxy}-phenyl)-urea
250: 1-(3,3-Dimethyl-butyl)-3-(4-{7-[3-(2,6-dimethyl-morpholin-4-yl)-2-hydroxy-propoxy]-6-methoxy-quinolin-4-yloxy}-phenyl)-urea
251: 1-(3,3-Dimethyl-butyl)-3-(4-{7-[3-(3,5-dimethyl-piperidin-1-yl)-2-hydroxy-propoxy]-6-methoxy-quinolin-4-yloxy}-phenyl)-urea 252: 1-(3,3-Dimethyl-butyl)-3-(4-{7-[2-hydroxy-3-(4-phenyl-piperidin-1-yl)-propoxy]-6-methoxy-quinolin-4-yloxy}-phenyl)-urea
253: 1-{4-[4-(4-Tert-butyl-phenylamino)-phenoxy]-6-methoxy-quinolin-7-yloxy}-3-(2,6-dimethyl-morpholin-4-yl)-propan-2-ol
254: 1-{4-[4-(4-Tert-butyl-phenylamino)-phenoxy]-6-methoxy-quinolin-7-yloxy}-3-(3,5-dimethyl-piperidin-1-yl)-propan-2-ol
256: 1-{4-[4-(4-Tert-butyl-phenylamino)-phenoxy]-6-methoxy-quinolin-7-yloxy}-3-(4-phenyl-piperidin-1-yl)-propan-2-ol
257: 1-(4-Benzyl-piperidin-1-yl)-3-{4-[4-(4-tert-butyl-phenylamino)-phenoxy]-6-methoxy-quinolin-7-yloxy}-propan-2-ol
258: 1-[1,4']Bipiperidineyl-1'-yl-3-{4-[4-(4-tert-butyl-phenylamino)-phenoxy]-6-methoxy-quinolin-7-yloxy}-propan-2-ol
259: 1-{4-[4-(4-Tert-butyl-phenylamino)-phenoxy]-6-methoxy-quinolin-7-yloxy}-3-(4-pyrrolidin-1-yl-piperidin-1-yl)-propan-2-ol
260: 1-(4-{7-[3-(4-Benzyl-piperidin-1-yl)-2-hydroxy-propoxy]-6-methoxy-quinolin-4-yloxy}-phenyl)-3-(3,3-dimethyl-butyl)-urea
261: 1-{4-[7-(3-[1,4']Bipiperidineyl-1'-yl-2-hydroxy-propoxy)-6-methoxy-quinolin-4-yloxy]-phenyl}-3-(3,3-dimethyl-butyl)-urea
262: 1-(3,3-Dimethyl-butyl)-3-(4-{7-[2-hydroxy-3-(4-pyrrolidin-1-yl-piperidin-1-yl)-propoxy]-6-methoxy-quinolin-4-yloxy}-phenyl)-urea
263: 1-(3,3-Dimethyl-butyl)-3-(4-{7-[3-(2-hydroxymethyl-pyrrolidin-1-yl)-propoxy]-6-methoxy-quinolin-4-yloxy}-phenyl)-urea
265: 1-(3,3-Dimethyl-butyl)-3-(4-{7-[3-(4-hydroxymethyl-piperidin-1-yl)-propoxy]-6-methoxy-quinolin-4-yloxy}-phenyl)-urea
266: 1-(2-Chloro-4-{7-[3-(4-hydroxymethyl-piperidin-1-yl)-propoxy]-6-methoxy-quinolin-4-yloxy}-phenyl)-3-(3,3-dimethyl-butyl)-urea
267: 1-[2-Chloro-4-(7-{3-[4-(2-hydroxy-ethyl)-piperidin-1-yl]-propoxy}-6-methoxy-quinolin-4-yloxy)-phenyl]-3-(3,3-dimethyl-butyl)-urea
268: 1-(2-Chloro-4-{7-[3-(4-hydroxy-piperidin-1-yl)-propoxy]-6-methoxy-quinolin-4-yloxy}-phenyl)-3-(3,3-dimethyl-butyl)-urea
269: 1-(3,3-Dimethyl-butyl)-3-[4-(7-{3-[(2-hydroxy-ethyl)-methyl-amino]-propoxy}-6-methoxy-quinolin-4-yloxy)-phenyl]-urea
270: [1-(3-{4-[4-(4-Tert-butyl-phenylamino)-2-fluoro-phenoxy]-6-methoxy-quinolin-7-yloxy}-propyl)-piperidin-4-yl]-methanol
271: 1-(3,3-Dimethyl-butyl)-3-(4-{6-methoxy-7-[3-(2-methoxy-ethylamino)-propoxy]-quinolin-4-yloxy}-phenyl)-urea
272: 2-[1-(3-{4-[4-(4-Tert-butyl-phenylamino)-2-fluoro-phenoxy]-6-methoxy-quinolin-7-yloxy}-propyl)-piperidin-4-yl]-ethanol
273: 1-(3-{4-[4-(4-Tert-butyl-phenylamino)-2-fluoro-phenoxy]-6-methoxy-quinolin-7-yloxy}-propyl)-piperidin-4-ol
274: 1-(2-Chloro-4-{7-[2-(4-hydroxy-piperidin-1-yl)-ethoxy]-6-methoxy-quinolin-4-yloxy}-phenyl)-3-(3,3-dimethyl-butyl)-urea
275: 1-(2-Chloro-4-{7-[2-(4-hydroxymethyl-piperidin-1-yl)-ethoxy]-6-methoxy-quinolin-4-yloxy}-phenyl)-3-(3,3-dimethyl-butyl)-urea
276: 1-(3-{4-[4-(4-Tert-butyl-phenylamino)-3-chloro-phenoxy]-6-methoxy-quinolin-7-yloxy}-propyl)-piperidin-4-ol
277: [1-(3-{4-[4-(4-Tert-butyl-phenylamino)-3-chloro-phenoxy]-6-methoxy-quinolin-7-yloxy}-propyl)-piperidin-4-yl]-methanol
278: 1-(2-{4-[4-(4-Tert-butyl-phenylamino)-3-chloro-phenoxy]-6-methoxy-quinolin-7-yloxy}-ethyl)-piperidin-4-ol
279: [1-(2-{4-[4-(4-Tert-butyl-phenylamino)-3-chloro-phenoxy]-6-methoxy-quinolin-7-yloxy}-ethyl)-piperidin-4-yl]-methanol
280: (4-Tert-butyl-phenyl)-(4-{6-methoxy-7-[2-(4-methoxy-piperidin-1-yl)-ethoxy]-quinolin-4-yloxy}-phenyl)-amine
281: (4-Tert-butyl-phenyl)-(4-{6-methoxy-7-[2-(4-methoxymethyl-piperidin-1-yl)-ethoxy]-quinolin-4-yloxy}-phenyl)-amine
282: 1-(3,3-Dimethyl-butyl)-3-(4-{6-methoxy-7-[3-(4-methoxymethyl-piperidin-1-yl)-propoxy]-quinolin-4-yloxy}-phenyl)-urea
283: [1-(2-{4-[4-(4-Tert-butyl-phenylamino)-2-fluoro-phenoxy]-6-methoxy-quinolin-7-yloxy}-ethyl)-piperidin-4-yl]-methanol
284: 1-(2-{4-[4-(4-Tert-butyl-phenylamino)-2-fluoro-phenoxy]-6-methoxy-quinolin-7-yloxy}-ethyl)-piperidin-4-ol
285: 1-(3,3-Dimethyl-butyl)-3-(3-fluoro-4-{7-[3-(4-hydroxymethyl-piperidin-1-yl)-propoxy]-6-methoxy-quinolin-4-yloxy}-phenyl)-urea
286: 1-(3,3-Dimethyl-butyl)-3-(3-fluoro-4-{7-[3-(4-hydroxy-piperidin-1-yl)-propoxy]-6-methoxy-quinolin-4-yloxy}-phenyl)-urea
287: 1-(2-{4-[4-(4-Tert-butyl-phenylamino)-3-fluoro-phenoxy]-6-methoxy-quinolin-7-yloxy}-ethyl)-piperidin-4-ol
288: [1-(2-{4-[4-(4-Tert-butyl-phenylamino)-3-fluoro-phenoxy]-6-methoxy-quinolin-7-yloxy}-ethyl)-piperidin-4-yl]-methanol
289: 1-(3-{4-[4-(4-Tert-butyl-phenylamino)-3-fluoro-phenoxy]-6-methoxy-quinolin-7-yloxy}-propyl)-piperidin-4-ol
290: [1-(3-{4-[4-(4-Tert-butyl-phenylamino)-3-fluoro-phenoxy]-6-methoxy-quinolin-7-yloxy}-propyl)-piperidin-4-yl]-methanol
292: 1-[2-Chloro-4-(7-{2-[4-(2-hydroxy-ethyl)-piperidin-1-yl]-ethoxy}-6-methoxy-quinolin-4-yloxy)-phenyl]-3-(3,3-dimethyl-butyl)-urea
293: 2-[1-(2-{4-[4-(4-Tert-butyl-phenylamino)-3-chloro-phenoxy]-6-methoxy-quinolin-7-yloxy}-ethyl)-piperidin-4-yl]-ethanol
294: 2-[1-(3-{4-[4-(4-Tert-butyl-phenylamino)-3-chloro-phenoxy]-6-methoxy-quinolin-7-yloxy}-propyl)-piperidin-4-yl]-ethanol
295: 1-(3,3-Dimethyl-butyl)-3-(3-fluoro-4-{7-[2-(4-hydroxymethyl-piperidin-1-yl)-ethoxy]-6-methoxy-quinolin-4-yloxy}-phenyl)-urea
296: 1-(3,3-Dimethyl-butyl)-3-(3-fluoro-4-{7-[2-(4-hydroxy-piperidin-1-yl)-ethoxy]-6-methoxy-quinolin-4-yloxy}-phenyl)-urea
297: 1-(3,3-Dimethyl-butyl)-3-[3-fluoro-4-(7-{2-[4-(2-hydroxy-ethyl)-piperidin-1-yl]-ethoxy}-6-methoxy-quinolin-4-yloxy)-phenyl]-urea
298: 1-(3,3-Dimethyl-butyl)-3-[3-fluoro-4-(7-{3-[4-(2-hydroxy-ethyl)-1-piperidin-1-yl]-propoxy}-6-methoxy-quinolin-4-yloxy)-phenyl]-urea 299: 1-(3,3-Dimethyl-butyl)-3-(2-fluoro-4-{7-[2-(4-hydroxy-piperidin-1-yl)-ethoxy]-6-methoxy-quinolin-4-yloxy}-phenyl)-urea
300: 1-(3,3-Dimethyl-butyl)-3-(2-fluoro-4-{7-[2-(4-hydroxymethyl-piperidin-1-yl)-ethoxy]-6-methoxy-quinolin-4-yloxy}-phenyl)-urea
301: 1-(3,3-Dimethyl-butyl)-3-[2-fluoro-4-(7-{2-[4-(2-hydroxy-ethyl)-piperidin-1-yl]-ethoxy}-6-methoxy-quinolin-4-yloxy)-phenyl]-urea
302: 1-(3,3-Dimethyl-butyl)-3-(2-fluoro-4-{7-[3-(4-hydroxy-piperidin-1-yl)-propoxy]-6-methoxy-quinolin-4-yloxy}-phenyl)-urea
303: 1-(3,3-Dimethyl-butyl)-3-(2-fluoro-4-{7-[3-(4-hydroxymethyl-piperidin-1-yl)-propoxy]-6-methoxy-quinolin-4-yloxy}-phenyl)-urea
304: 1-(3,3-Dimethyl-butyl)-3-[2-fluoro-4-(7-{3-[4-(2-hydroxy-ethyl)-piperidin-1-yl]-propoxy}-6-methoxy-quinolin-4-yloxy)-phenyl]-urea
305: 2-[1-(2-{4-[4-(4-Tert-butyl-phenylamino)-3-fluoro-phenoxy]-6-methoxy-quinolin-7-yloxy}-ethyl)-piperidin-4-yl]-ethanol
306: 2-[1-(3-{4-[4-(4-Tert-butyl-phenylamino)-3-fluoro-phenoxy]-6-methoxy-quinolin-7-yloxy}-propyl)-piperidin-4-yl]-ethanol
307: 1-(2-{4-[4-(4-Tert-butyl-phenylamino)-2-chloro-phenoxy]-6-methoxy-quinolin-7-yloxy}-ethyl)-piperidin-4-ol
308: [1-(2-{4-[4-(4-Tert-butyl-phenylamino)-2-chloro-phenoxy]-6-methoxy-quinolin-7-yloxy}-ethyl)-piperidin-4-yl]-methanol
309: 1-(3-{4-[4-(4-Tert-butyl-phenylamino)-2-chloro-phenoxy]-6-methoxy-quinolin-7-yloxy}-propyl)-piperidin-4-ol
310: [1-(3-{4-[4-(4-Tert-butyl-phenylamino)-2-chloro-phenoxy]-6-methoxy-quinolin-7-yloxy}-propyl)-piperidin-4-yl]-methanol
311: 1-(3-Chloro-4-{7-[2-(4-hydroxy-piperidin-1-yl)-ethoxy]-6-methoxy-quinolin-4-yloxy}-phenyl)-3-(3,3-dimethyl-butyl)-urea
312: 1-(3-Chloro-4-{7-[2-(4-hydroxymethyl-piperidin-1-yl)-ethoxy]-6-methoxy-quinolin-4-yloxy}-phenyl)-3-(3,3-dimethyl-butyl)-urea
313: 2-[1-(2-{4-[4-(4-Tert-butyl-phenylamino)-2-chloro-phenoxy]-6-methoxy-quinolin-7-yloxy}-ethyl)-piperidin-4-yl]-ethanol
314: 2-[1-(3-{4-[4-(4-Tert-butyl-phenylamino)-2-chloro-phenoxy]-6-methoxy-quinolin-7-yloxy}-propyl)-piperidin-4-yl]-ethanol
315: 1-[3-Chloro-4-(7-{2-[4-(2-hydroxy-ethyl)-piperidin-1-yl]-ethoxy}-6-methoxy-quinolin-4-yloxy)-phenyl]-3-(3,3-dimethyl-butyl)-urea
316: 1-[3-Chloro-4-(7-{3-[4-(2-hydroxy-ethyl)-piperidin-1-yl]-propoxy}-6-methoxy-quinolin-4-yloxy)-phenyl]-3-(3,3-dimethyl-butyl)-urea
317: 1-(2-Chloro-4-{7-[3-(2,6-dimethyl-morpholin-4-yl)-propoxy]-6-methoxy-quinolin-4-yloxy}-phenyl)-3-(3,3-dimethyl-butyl)-urea
318: 1-{3-Chloro-4-[6-methoxy-7-(3-morpholin-4-yl-propoxy)-quinolin-4-yloxy]-phenyl}-3-(3,3-dimethyl-butyl)-urea
319: 1-(3-Chloro-4-{7-[3-(2,6-dimethyl-morpholin-4-yl)-propoxy]-6-methoxy-quinolin-4-yloxy}-phenyl)-3-(3,3-dimethyl-butyl)-urea
320: 1-{2-Chloro-4-[6-methoxy-7-(4-morpholin-4-yl-butoxy)-quinolin-4-yloxy]-phenyl}-3-(3,3-dimethyl-butyl)-urea
321: 1-(2-Chloro-4-{7-[4-(2,6-dimethyl-morpholin-4-yl)-butoxy]-6-methoxy-quinolin-4-yloxy}-phenyl)-3-(3,3-dimethyl-butyl)-urea
322: 1-(3,3-Dimethyl-butyl)-3-(4-{6-[3-(4-hydroxy-piperidin-1-yl)-propoxy]-7-methoxy-quinolin-4-yloxy}-phenyl)-urea
323: 1-(3,3-Dimethyl-butyl)-3-(4-{6-[3-(4-hydroxymethyl-piperidin-1-yl)-propoxy]-7-methoxy-quinolin-4-yloxy}-phenyl)-urea
324: 1-(3,3-Dimethyl-butyl)-3-[4-(6-{3-[4-(2-hydroxy-ethyl)-piperidin-1-yl]-propoxy}-7-methoxy-quinolin-4-yloxy)-phenyl]-urea
325: 1-(3,3-Dimethyl-butyl)-3-(4-{7-[3-(2,6-dimethyl-morpholin-4-yl)-propoxy]-6-methoxy-quinolin-4-yloxy}-2-fluoro-phenyl)-urea
326: 1-(3,3-Dimethyl-butyl)-3-{3-fluoro-4-[6-methoxy-7-(3-morpholin-4-yl-propoxy)-quinolin-4-yloxy]-phenyl}-urea
327: 1-(3,3-Dimethyl-butyl)-3-(4-{7-[3-(2,6-dimethyl-morpholin-4-yl)-propoxy]-6-methoxy-quinolin-4-yloxy}-3-fluoro-phenyl)-urea
328: 1-(3,3-Dimethyl-butyl)-3-[4-(7-{2-[(2-hydroxy-ethyl)-methyl-amino]-ethoxy}-6-methoxy-quinolin-4-yloxy)-phenyl]-urea
329: 1-(3,3-Dimethyl-butyl)-3-(2-fluoro-4-{7-[2-(2-hydroxy-ethylamino)-ethoxy]-6-methoxy-quinolin-4-yloxy}-phenyl)-urea
330: 1-(3,3-Dimethyl-butyl)-3-[2-fluoro-4-(7-{2-[(2-hydroxy-ethyl)-methyl-amino]-ethoxy}-6-methoxy-quinolin-4-yloxy)-phenyl]-urea
331: 1-(2-Chloro-4-{7-[2-(2-hydroxy-ethylamino)-ethoxy]-6-methoxy-quinolin-4-yloxy}-phenyl)-3-(3,3-dimethyl-butyl)-urea
332: 1-(3,3-Dimethyl-butyl)-3-(2-fluoro-4-{7-[3-(2-hydroxy-ethylamino)-propoxy]-6-methoxy-quinolin-4-yloxy}-phenyl)-urea
333: 1-(3,3-Dimethyl-butyl)-3-[2-fluoro-4-(7-{3-[(2-hydroxy-ethyl)-methyl-amino]-propoxy}-6-methoxy-quinolin-4-yloxy)-phenyl]-urea
334: 1-(2-Chloro-4-{7-[3-(2-hydroxy-ethylamino)-propoxy]-6-methoxy-quinolin-4-yloxy}-phenyl)-3-(3,3-dimethyl-butyl)-urea
335: 2-[(2-{4-[4-(4-Tert-butyl-phenylamino)-3-fluoro-phenoxy]-6-methoxy-quinolin-7-yloxy}-ethyl)-(2-hydroxy-ethyl)-amino]-ethanol
336: 2-[(2-{4-[4-(4-Tert-butyl-phenylamino)-2-fluoro-phenoxy]-6-methoxy-quinolin-7-yloxy}-ethyl)-(2-hydroxy-ethyl)-amino]-ethanol
337: 2-[(2-{4-[4-(4-Tert-butyl-phenylamino)-3-chloro-phenoxy]-6-methoxy-quinolin-7-yloxy}-ethyl)-(2-hydroxy-ethyl)-amino]-ethanol
338: 1-(3-Chloro-4-{7-[3-(4-hydroxy-piperidin-1-yl)-propoxy]-6-methoxy-quinolin-4-yloxy}-phenyl)-3-(3,3-dimethyl-butyl)-urea
339: 1-(3-Chloro-4-{7-[3-(4-hydroxymethyl-piperidin-1-yl)-propoxy]-6-methoxy-quinolin-4-yloxy}-phenyl)-3-(3,3-dimethyl-butyl)-urea
340: 1-(3,3-Dimethyl-butyl)-3-[4-(7-{2-[ethyl-(2-hydroxy-ethyl)-amino]-ethoxy}-6-methoxy-quinolin-4-yloxy)-phenyl]-urea
341: 1-(3,3-Dimethyl-butyl)-3-[4-(7-{2-[ethyl-(2-hydroxy-ethyl)-amino]-ethoxy}-6-methoxy-quinolin-4-yloxy)-2-fluoro-phenyl]-urea
342: 1-[2-Chloro-4-(7-{2-[ethyl-(2-hydroxy-ethyl)-amino]-ethoxy}-6-methoxy-quinolin-4-yloxy)-phenyl]-3-(3,3-dimethyl-butyl)-urea 343: 1-(3,3-Dimethyl-butyl)-3-[4-(7-{3-[ethyl-(2-hydroxy-ethyl)-amino]-propoxy}-6-methoxy-quinolin-4-yloxy)-phenyl]-urea 344: 1-(3,3-Dimethyl-butyl)-3-[4-(7-{3-[ethyl-(2-hydroxy-ethyl)-amino]-propoxy}-6-methoxy-quinolin-4-yloxy)-2-fluoro-phenyl]-urea 345: 1-[2-Chloro-4-(7-{3-[ethyl-(2-hydroxy-ethyl)-amino]-propoxy}-6-methoxy-quinolin-4-yloxy)-phenyl]-3-(3,3-dimethyl-butyl)-urea 346: 2-[(2-{4-[4-(4-Tert-butyl-phenylamino)-2-chloro-phenoxy]-6-methoxy-quinolin-7-yloxy}-ethyl)-(2-hydroxy-ethyl)-amino]-ethanol 347: N1-[4-(Tert-butyl)phenyl]-4-[(6-methoxy-7-{2-[(tetrahydro-2-furanylmethyl)amino]ethoxy}-4-quinolyl)oxy]aniline 348: 2-[(2-{4-[4-(4-Tert-butyl-phenylamino)-phenoxy]-6-methoxy-quinolin-7-yloxy}-ethyl)-methyl-amino]-ethanol hydrochloride 349: 2-[(2-{4-[4-(4-Tert-butyl-phenylamino)-phenoxy]-6-methoxy-quinolin-7-yloxy}-ethyl)-(2-hydroxy-ethyl)-amino]-ethanol hydrochloride 350: [1-(2-{4-[4-(4-Tert-butyl-phenylamino)-phenoxy]-6-methoxy-quinolin-7-yloxy}-ethylamino)-cyclopenthyl]-methanol 351: 2-(2-{4-[4-(4-Tert-butyl-phenylamino)-phenoxy]-6-methoxy-quinolin-7-yloxy}-ethylamino)-2-ethyl-propan-1,3-diol 352: 1-[(2-{4-[4-(4-Tert-butyl-phenylamino)-phenoxy]-6-methoxy-quinolin-7-yloxy}-ethyl)-(2-hydroxy-propyl)-amino]-propan-2-ol 353: 2-(2-{4-[4-(4-Tert-butyl-phenylamino)-phenoxy]-6-methoxy-quinolin-7-yloxy}-ethylamino)-propan-1-ol 354: 1-(4-{7-[2-(1,1-Bis-hydroxymethyl-propylamino)-ethoxy]-6-methoxy-quinolin-4-yloxy}-phenyl)-3-(3,3-dimethyl-butyl)-urea 355: [1-(2-{4-[4-(4-Tert-butyl-phenylamino)-phenoxy]-7-methoxy-quinolin-6-yloxy}-ethyl)-piperidin-4-yl]-methanol 356: 2-(2-{4-[4-(4-Tert-butyl-phenylamino)-phenoxy]-7-methoxy-quinolin-6-yloxy}-ethylamino)-ethanol 357: 2-[(2-{4-[4-(4-Tert-butyl-phenylamino)-phenoxy]-7-methoxy-quinolin-6-yloxy}-ethyl)-methyl-amino]-ethanol 358: 2-[(2-{4-[4-(4-Tert-butyl-phenylamino)-phenoxy]-7-methoxy-quinolin-6-yloxy}-ethyl)-(2-hydroxy-ethyl)-amino]-ethanol 359: 1-(3,3-Dimethyl-butyl)-3-(4-{7-[2-(1-hydroxymethyl-cyclopenthylamino)-ethoxy]-6-methoxy-quinolin-4-yloxy}-phenyl)-urea 360: 1-[4-(7-{2-[Bis-(2-hydroxy-propyl)-amino]-ethoxy}-6-methoxy-quinolin-4-yloxy)-phenyl]-3-(3,3-dimethyl-butyl)-urea 361: 1-(3,3-Dimethyl-butyl)-3-(4-{7-[2-(2-hydroxy-1-methyl-ethylamino)-ethoxy]-6-methoxy-quinolin-4-yloxy}-phenyl)-urea 362: 1-[4-(7-{2-[Cyclohexyl-(2-hydroxy-ethyl)-amino]-ethoxy}-6-methoxy-quinolin-4-yloxy)-phenyl]-3-(3,3-dimethyl-butyl)-urea 363: N1-[4-(Tert-butyl)phenyl]-4-[(6-methoxy-7-{2-[(2-methoxy-1-methylethyl)amino]ethoxy}-4-quinolyl)oxy]aniline 364: 2-[(2-{4-[4-(4-Tert-butyl-phenylamino)-phenoxy]-6-methoxy-quinolin-7-yloxy}-ethyl)-cyclohexyl-amino]-ethanol 365: 2-[Benzyl-(2-{4-[4-(4-tert-butyl-phenylamino)-phenoxy]-6-methoxy-quinolin-7-yloxy}-ethyl)-amino]-ethanol 366: 2-[(2-{4-[4-(4-Tert-butyl-phenylamino)-phenoxy]-6-methoxy-quinolin-7-yloxy}-ethyl)-propyl-amino]-ethanol 367: 2-[(2-{4-[4-(4-Tert-butyl-phenylamino)-phenoxy]-6-methoxy-quinolin-7-yloxy}-ethyl)-isopropyl-amino]-ethanol 368: 1-[4-(7-{2-[Benzyl-(2-hydroxy-ethyl)-amino]-ethoxy}-6-methoxy-quinolin-4-yloxy)-phenyl]-3-(3,3-dimethyl-butyl)-urea 369: 1-(3,3-Dimethyl-butyl)-3-[4-(7-{2-[(2-hydroxy-ethyl)-propyl-amino]-ethoxy}-6-methoxy-quinolin-4-yloxy)-phenyl]-urea 370: 1-(3,3-Dimethyl-butyl)-3-[4-(7-{2-[(2-hydroxy-ethyl)-isopropyl-amino]-ethoxy}-6-methoxy-quinolin-4-yloxy)-phenyl]-urea 371: 1-(3,3-Dimethyl-butyl)-3-(4-{7-[2-(4-hydroxymethyl-piperidin-1-yl)-ethoxy]-6-methoxy-quinolin-4-yloxy}-phenyl)-urea 372: 1-(3,3-Dimethyl-butyl)-3-(4-{7-[2-(2-hydroxy-ethylamino)-ethoxy]-6-methoxy-quinolin-4-yloxy}-phenyl)-urea 373: 1-(3,3-Dimethyl-butyl)-3-(4-{7-[2-(4-hydroxy-piperidin-1-yl)-ethoxy]-6-methoxy-quinolin-4-yloxy}-phenyl)-urea 374: 1-[3-Chloro-4-(6,7-dimethoxy-quinolin-4-yloxy)-phenyl]-3-(3,3-dimethyl-butyl)-urea 375: 1-(3,3-Dimethyl-butyl)-3-{4-[6-methoxy-7-(2-morpholin-4-yl-2-oxo-ethoxy)-quinolin-4-yloxy]-phenyl}-urea Compounds 135 to 141, 165, 179, 180, 183, 202, 207, and 245 were analyzed by mass spectrometry. The results were as follows.

| Compound No. | Mass spectrometric value (m/z) |
| --- | --- |
| 135 | 469 [M + 1] |
| 136 | 438 [M + 1] |
| 137 | 438 [M + 1] |
| 138 | 454 [M + 1] |
| 139 | 454 [M + 1] |
| 140 | 492 [M + 1] |
| 141 | 452 [M + 1] |
| 165 | 541 [M + 1] |
| 179 | 555 [M + 1] |
| 180 | 569 [M + 1] |
| 183 | 557 [M + 1] |
| 202 | 555 [M + 1] |
| 207 | 583 [M + 1] |
| 245 | 563 [M + 1] |

Compounds 135 to 375 had the following respective chemical structures.
| Compound No. | structure of compound |
|---|---|
| 135 | 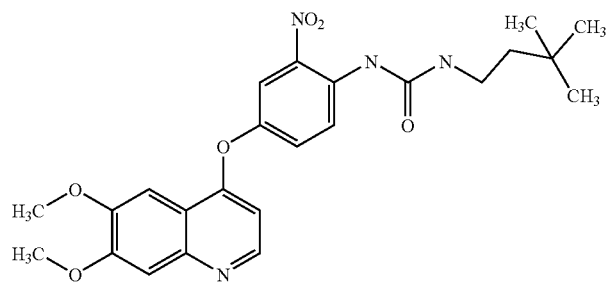 |
| 136 | 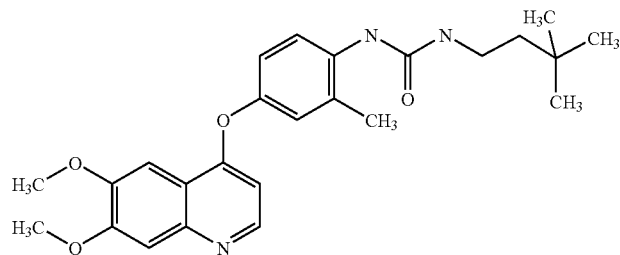 |
| 137 | 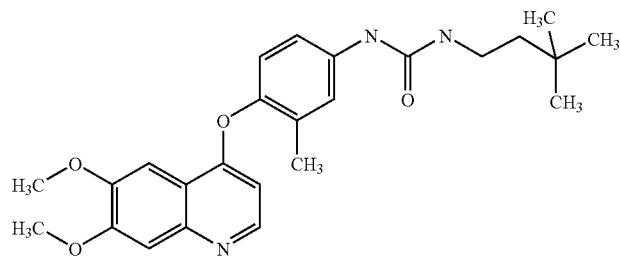 |
| 138 | 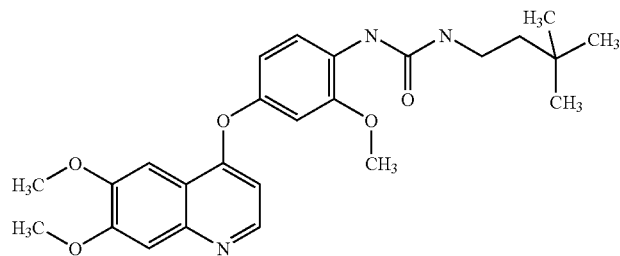 |
| 139 | 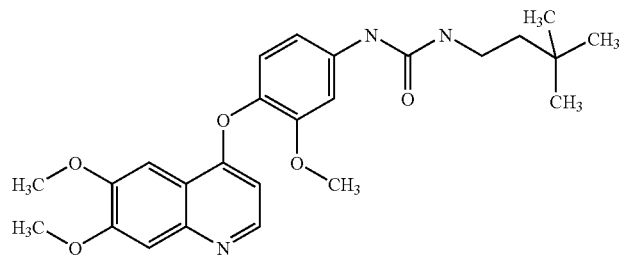 |

140 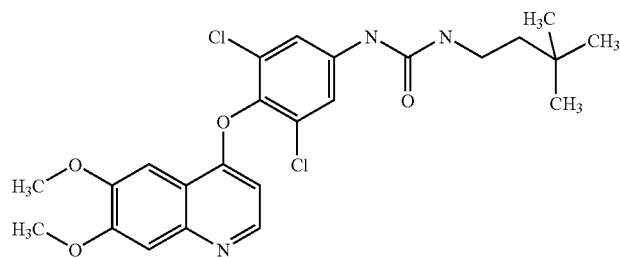
141 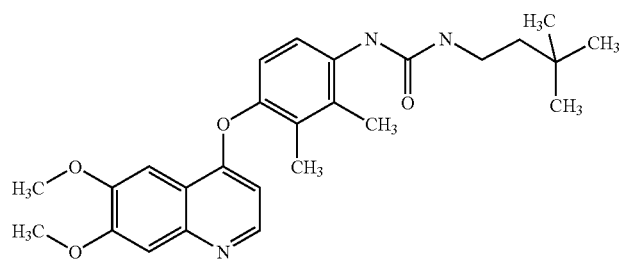
142 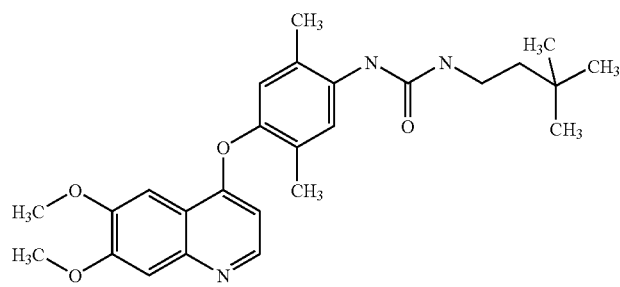
143 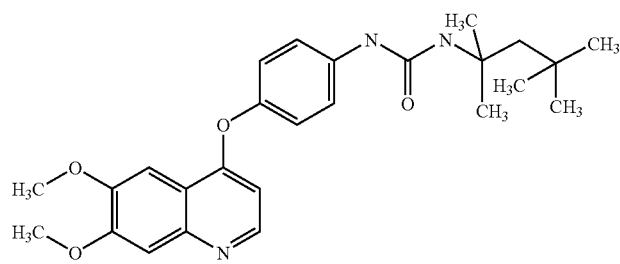
144 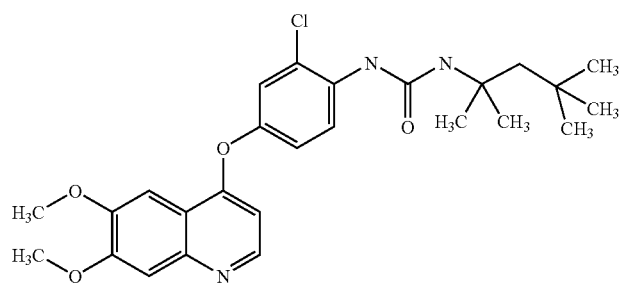

| | |
|---|---|
| 145 | 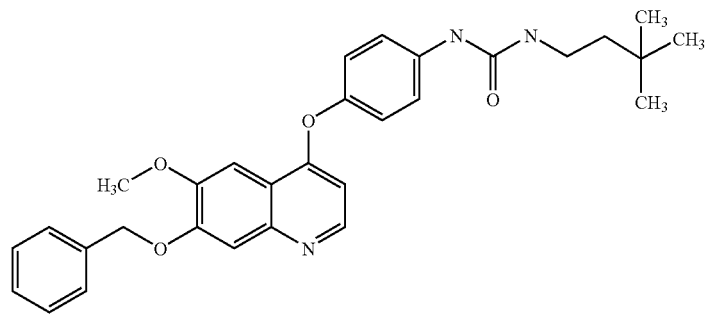 |
| 146 | 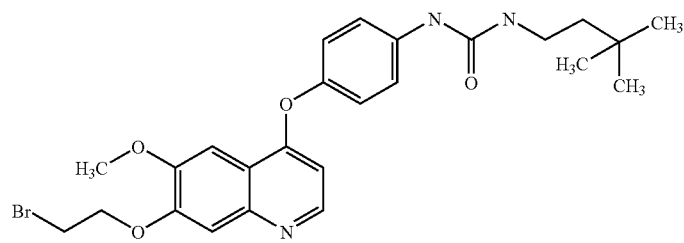 |
| 147 | 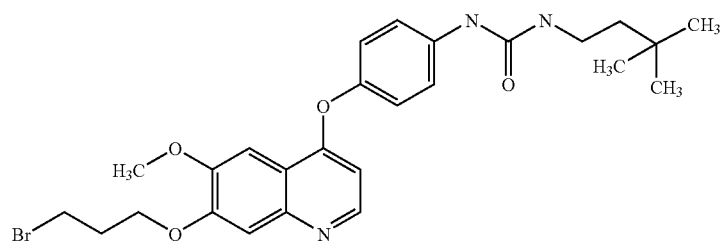 |
| 148 | 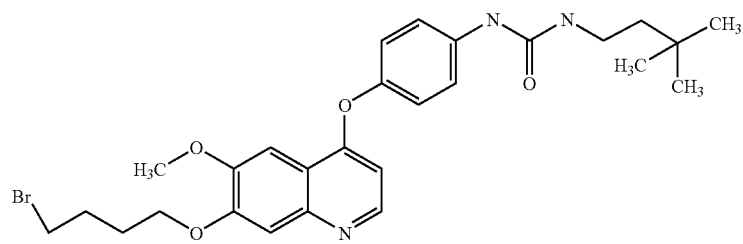 |
| 149 | 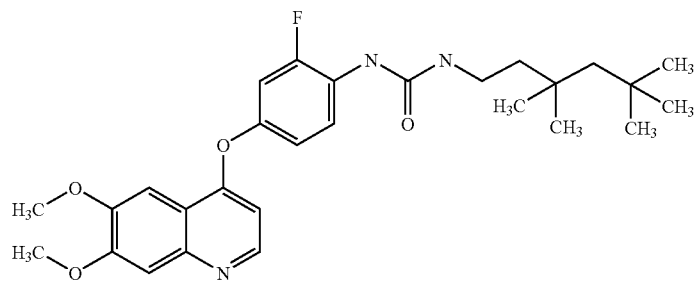 |
| 150 | 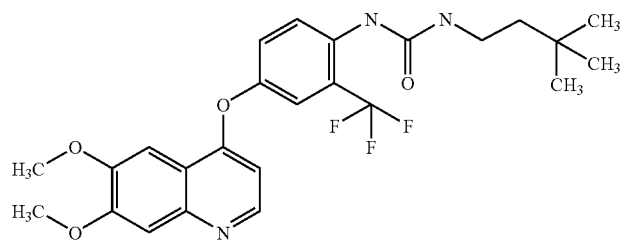 |

| | |
|---|---|
| 151 | 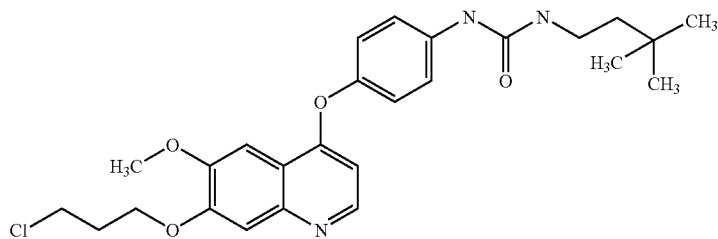 |
| 152 | 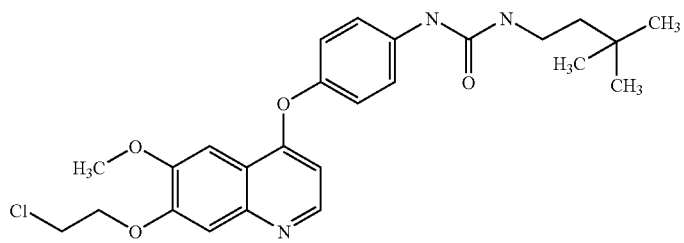 |
| 153 | 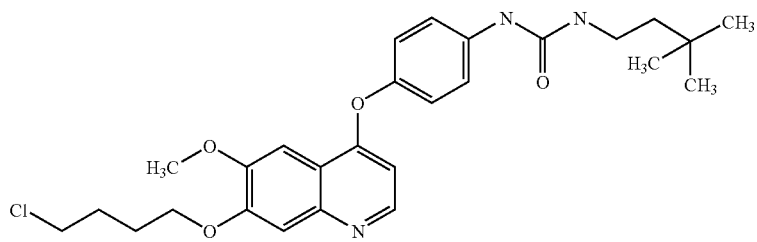 |
| 154 | 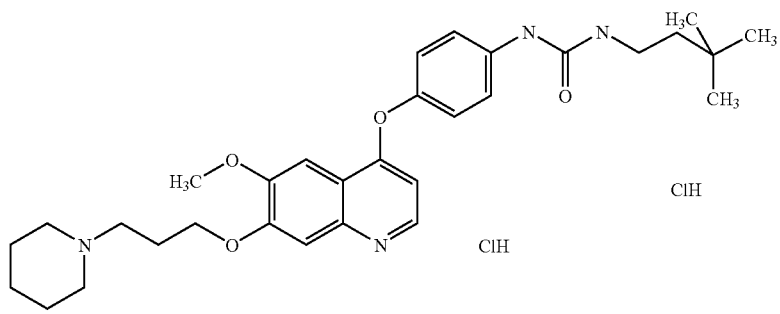 |
| 155 | 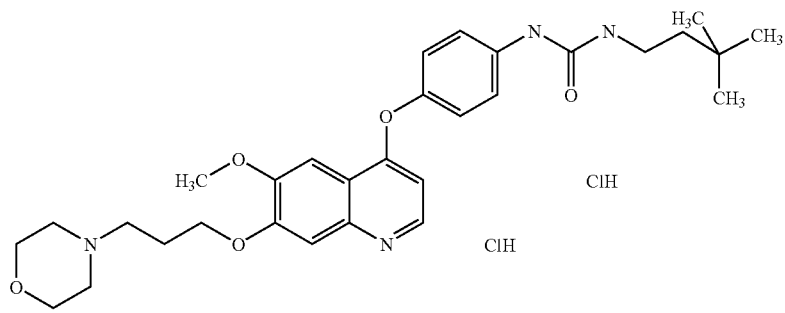 |

-continued
156
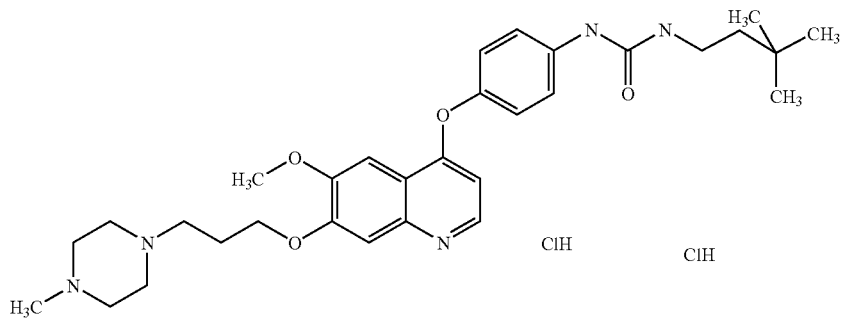
157
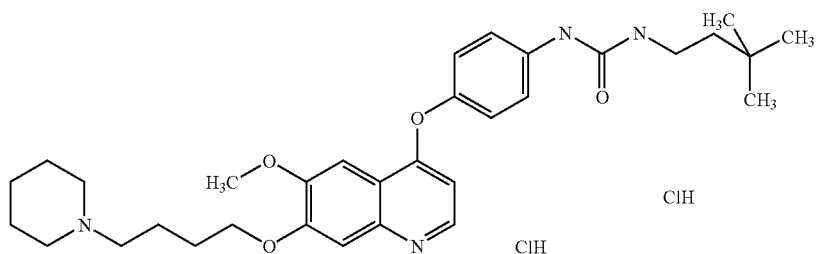
158
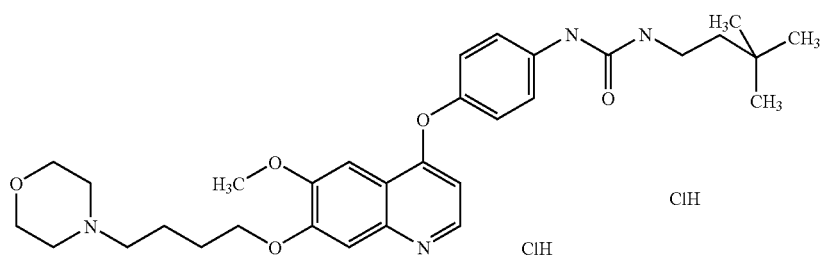
159
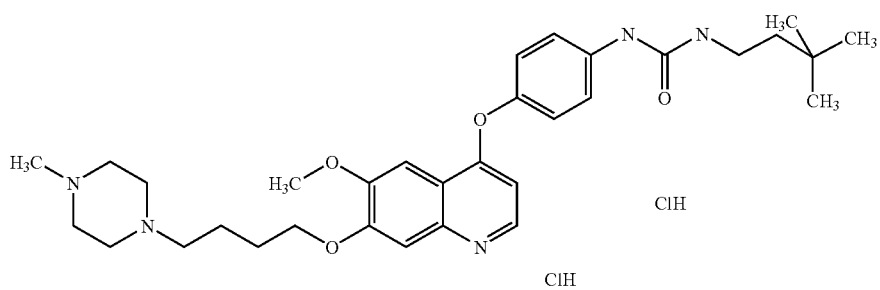
160
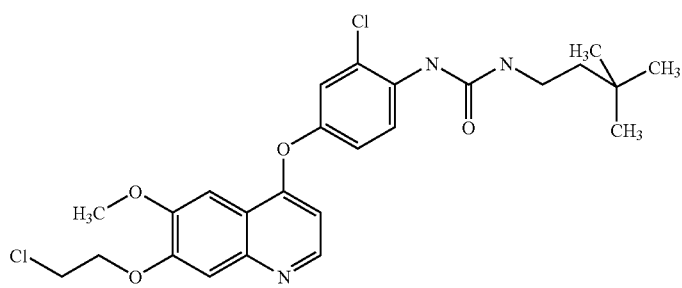

-continued
161
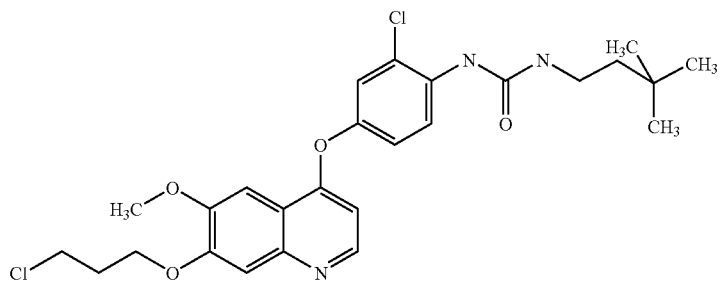
162
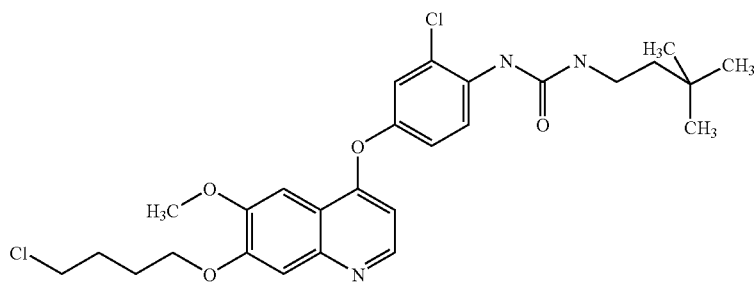
163
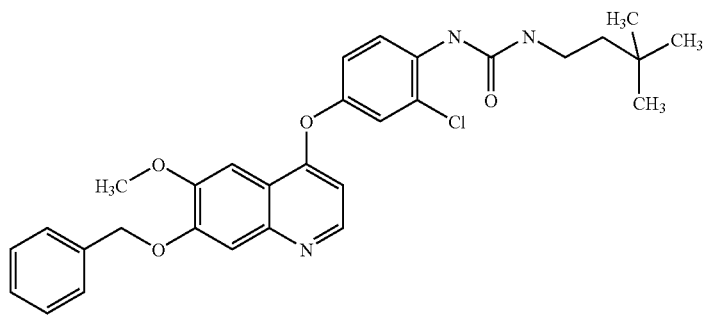
164
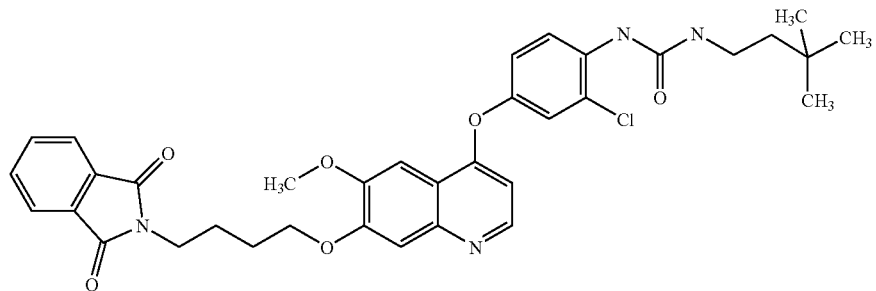
165
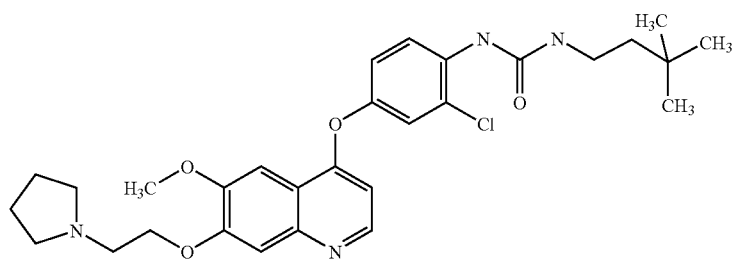

-continued
166
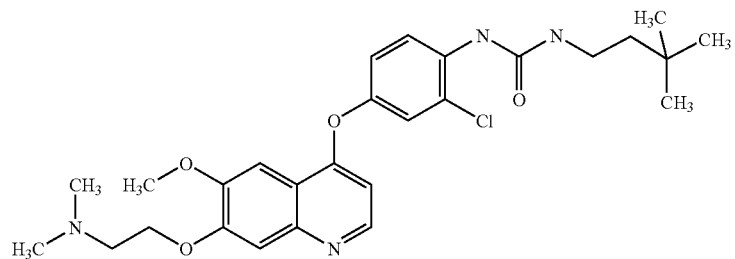
167
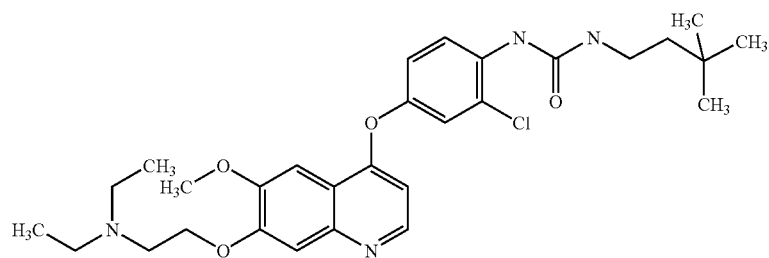
168
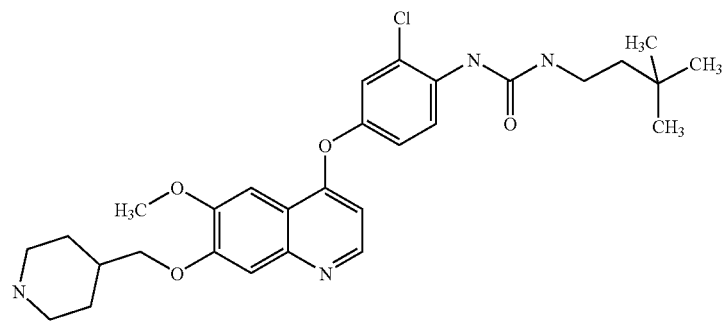
169
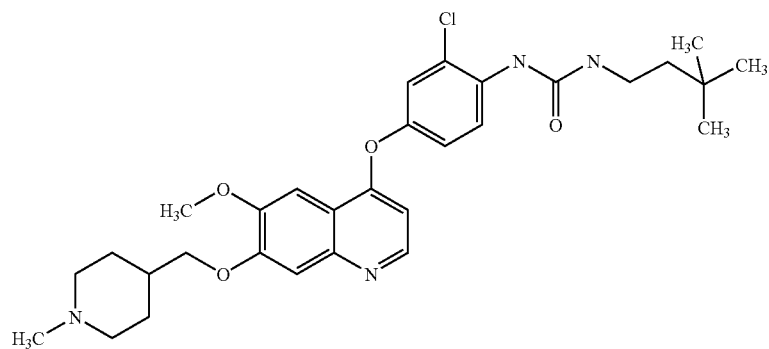
170
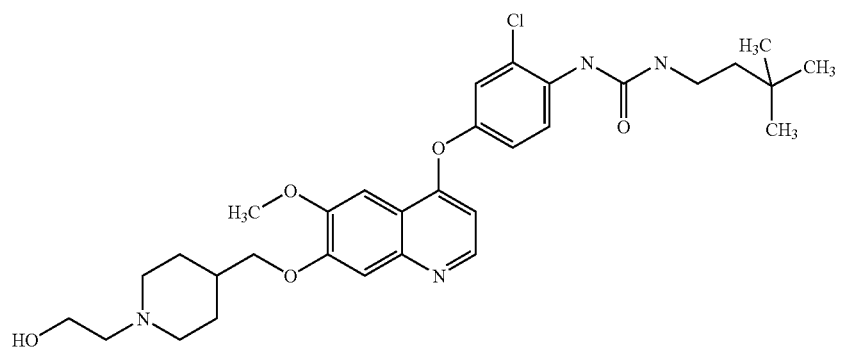

171 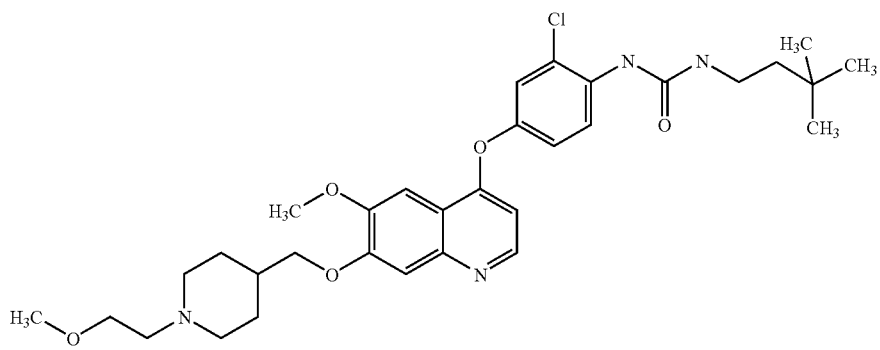
172 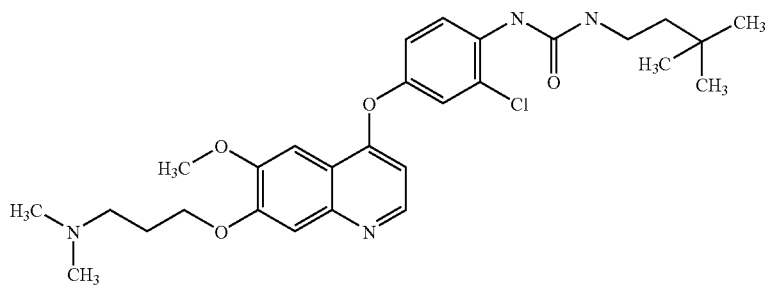
173 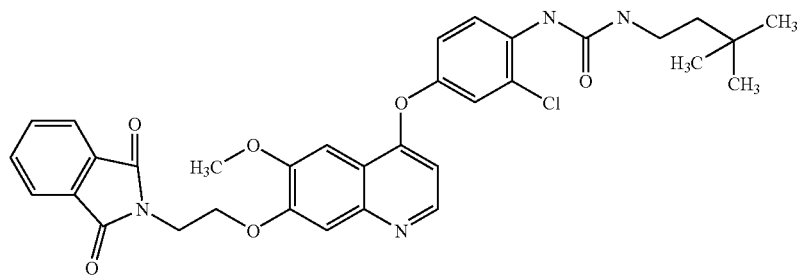
174 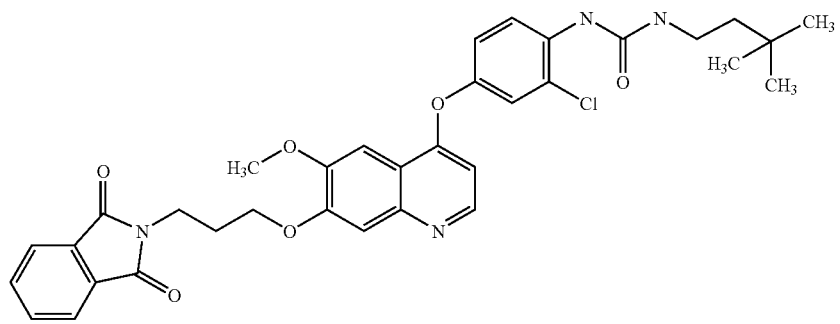
175 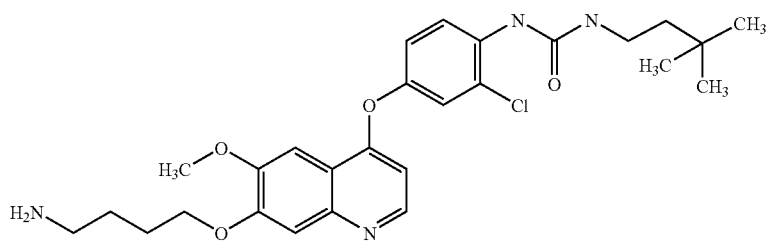

176 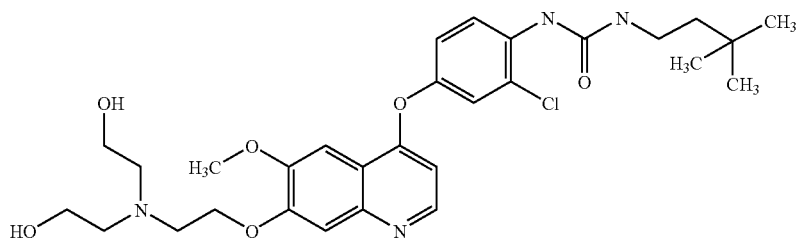
177 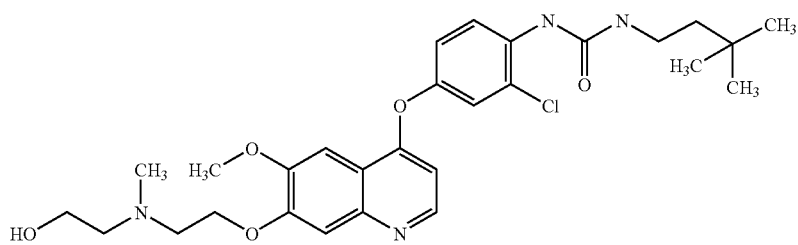
178 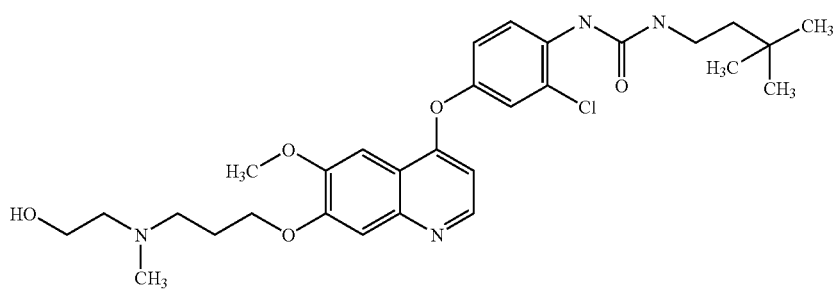
179 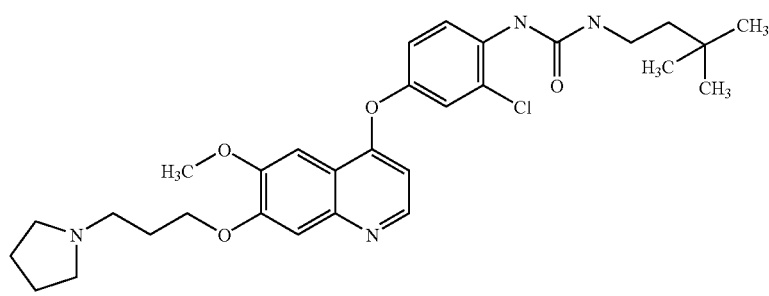
180 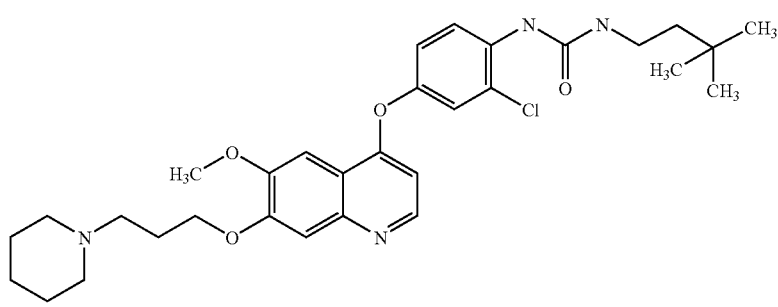

-continued
181
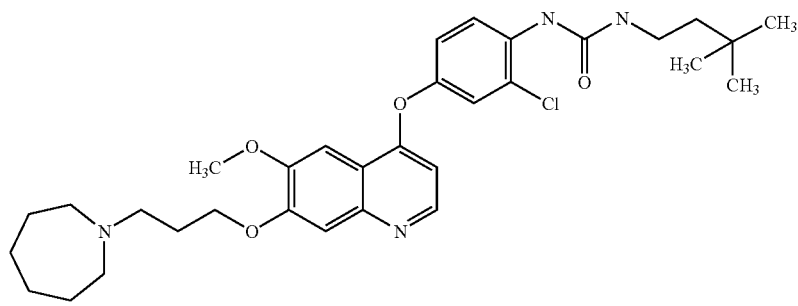
182
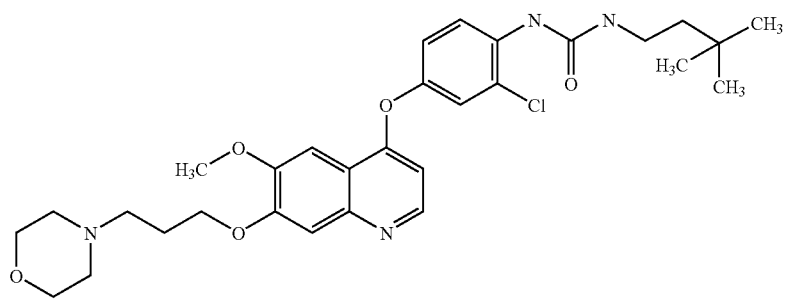
183
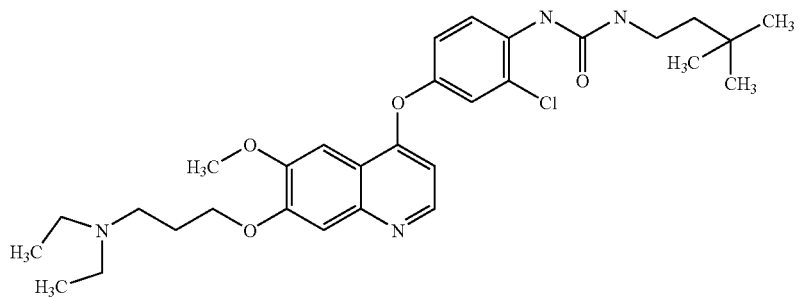
184
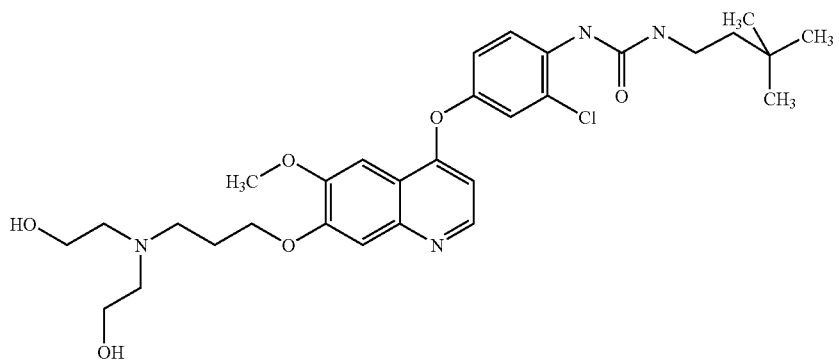
185
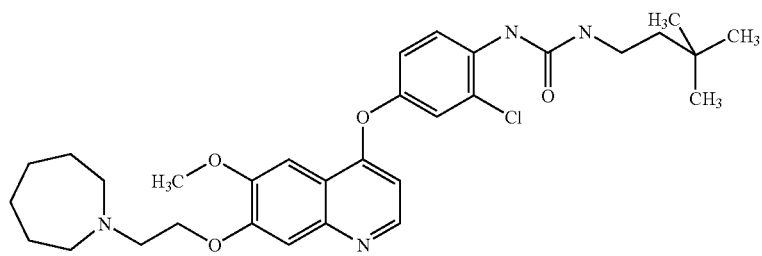

-continued
186
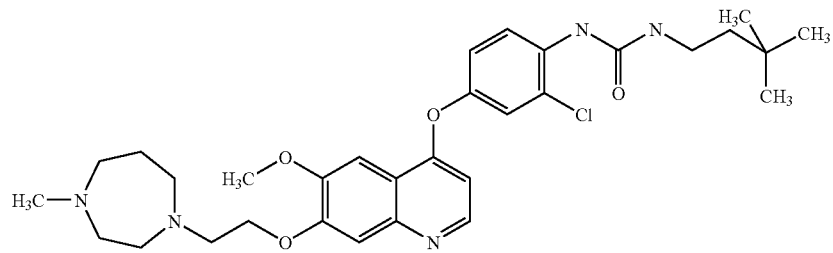
187
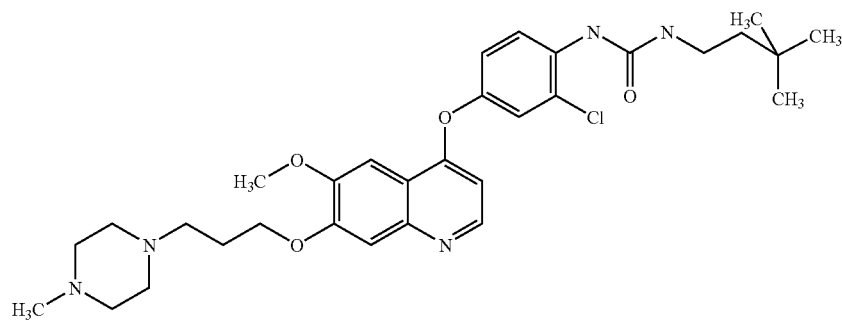
188
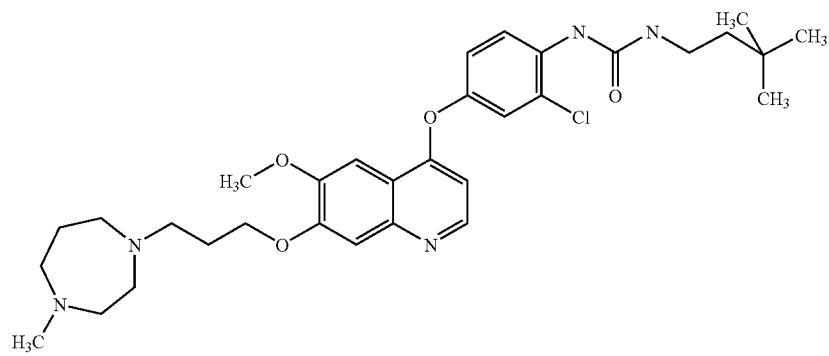
189
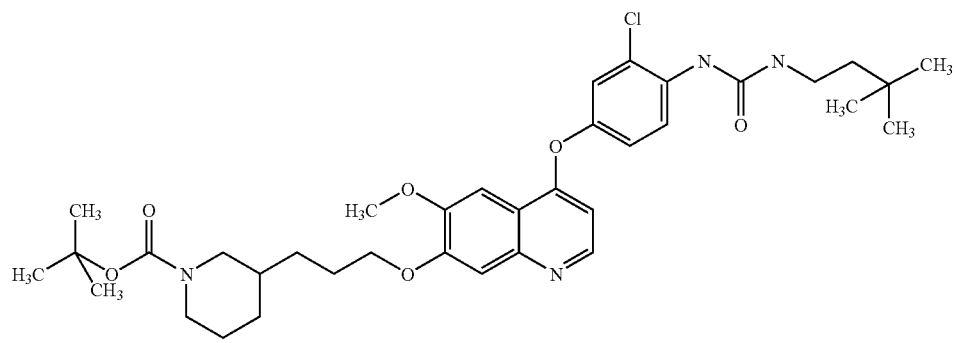
190
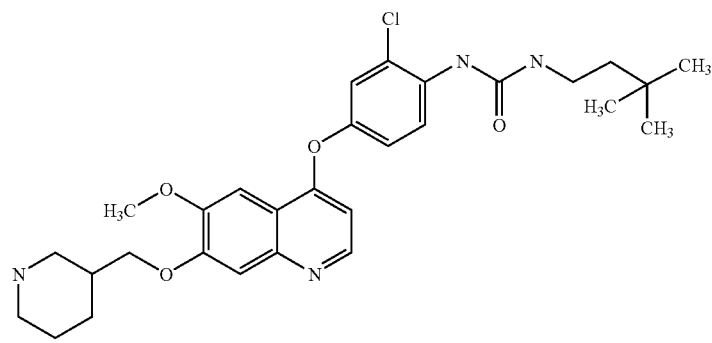

-continued
191
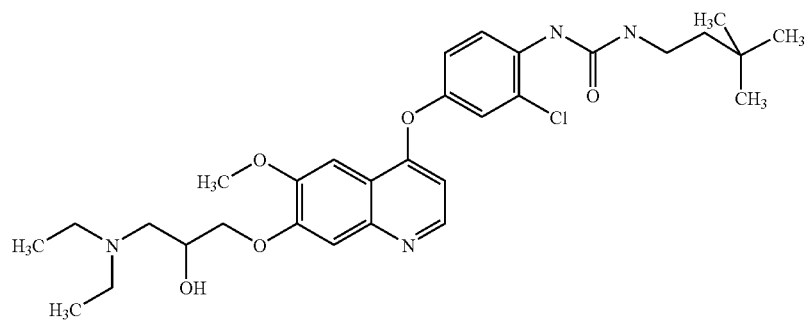
192
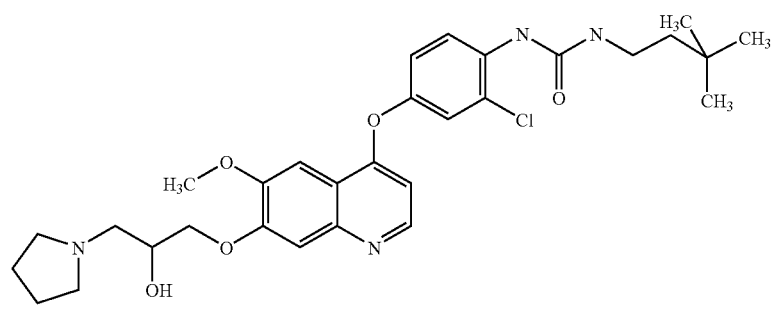
193
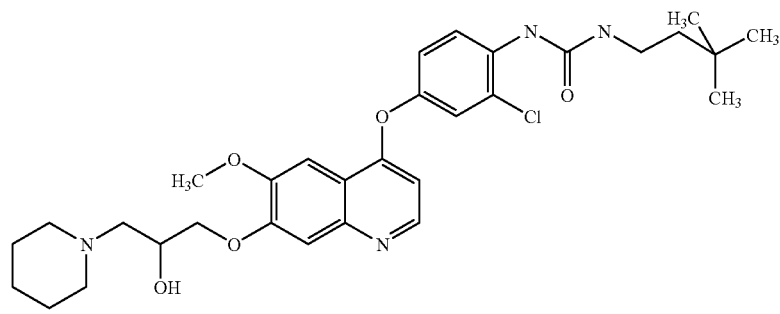
194
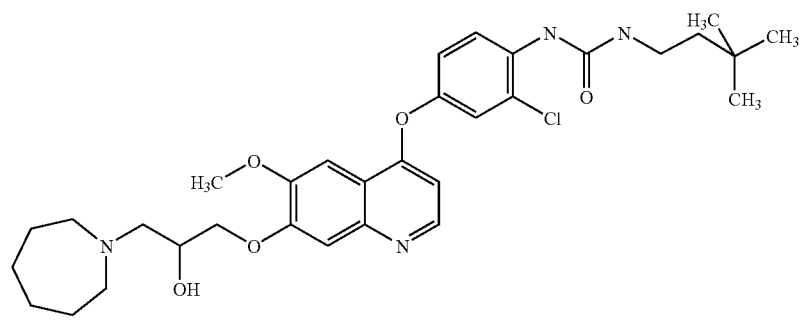
195
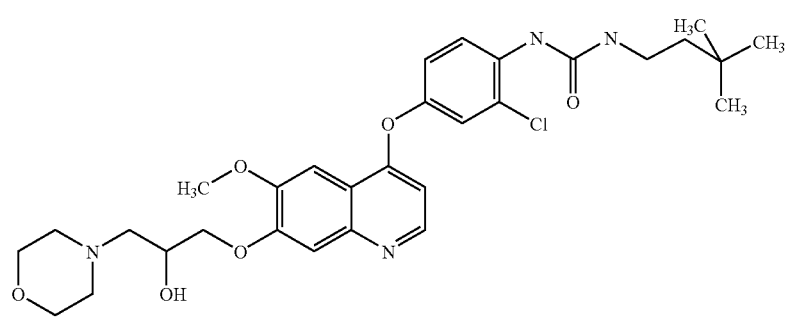

-continued
| | |
|---|---|
| 196 | 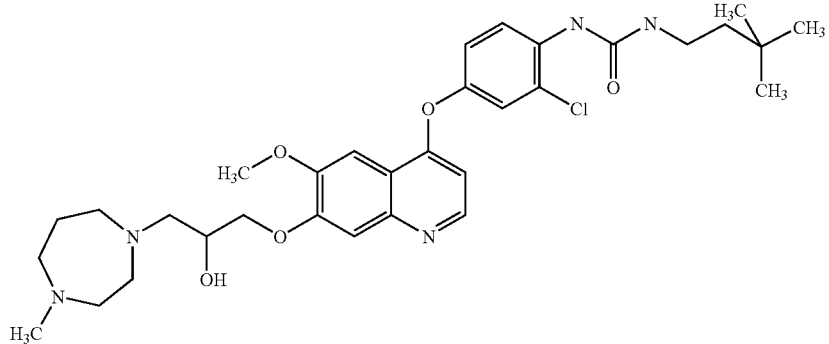 |
| 197 | 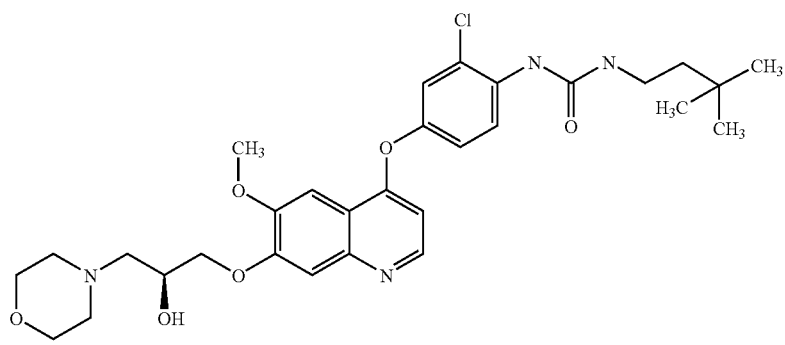 |
| 198 | 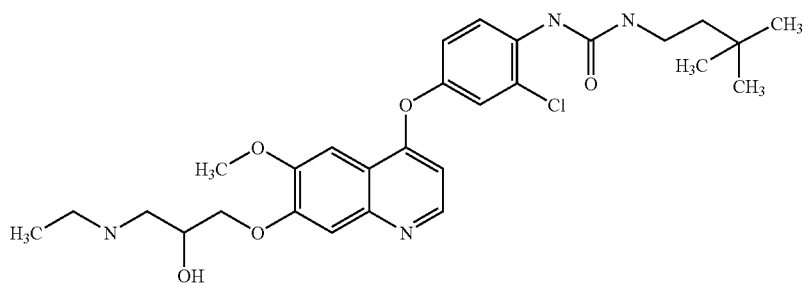 |
| 199 | 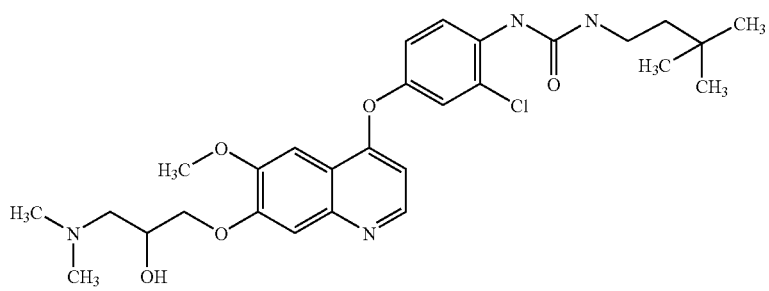 |
| 200 | 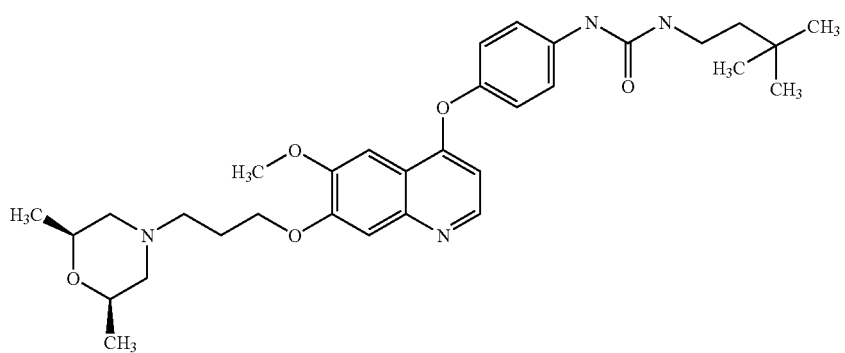 |

-continued
201
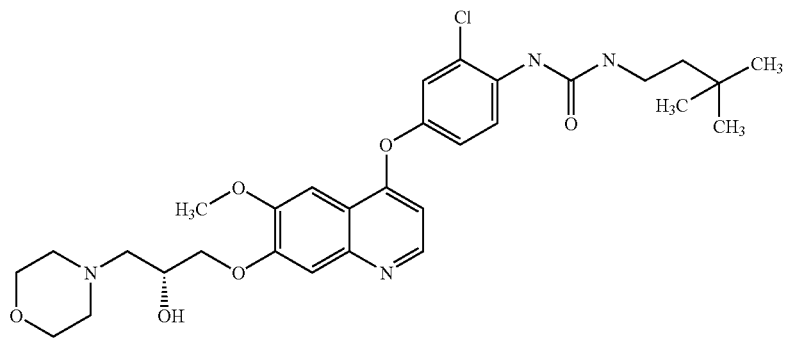
202
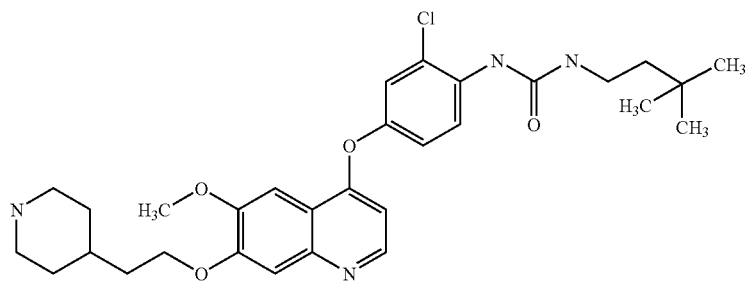
203
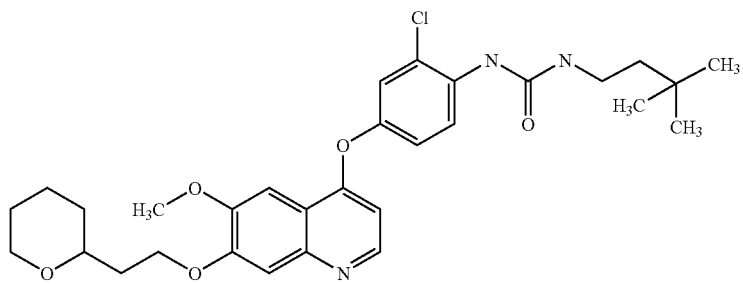
204
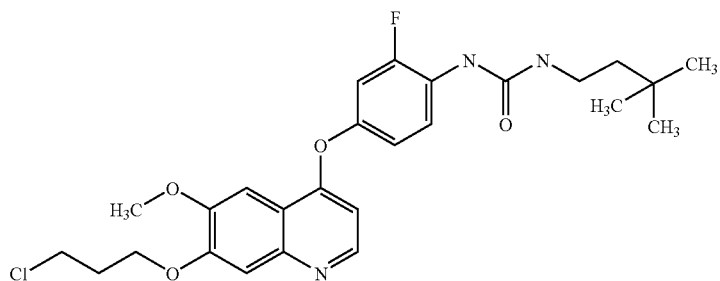
205
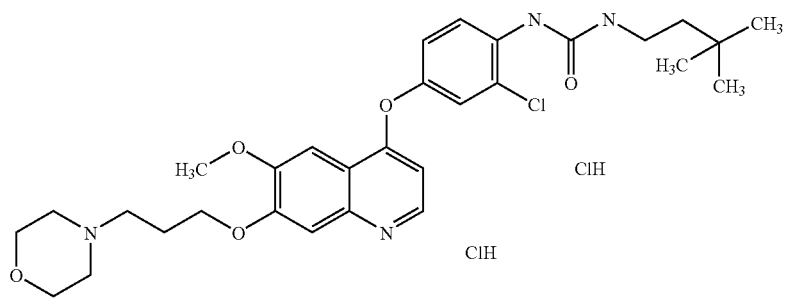

-continued
| | |
|---|---|
| 206 | 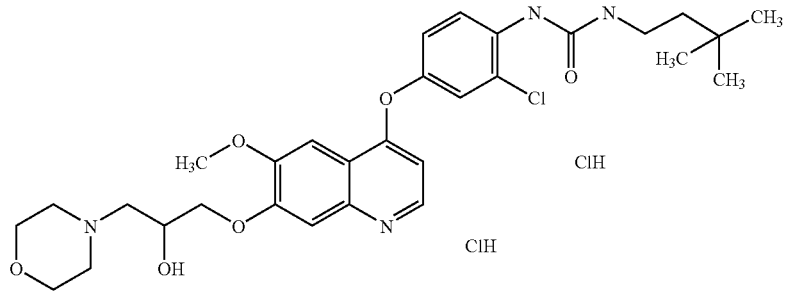 |
| 207 | 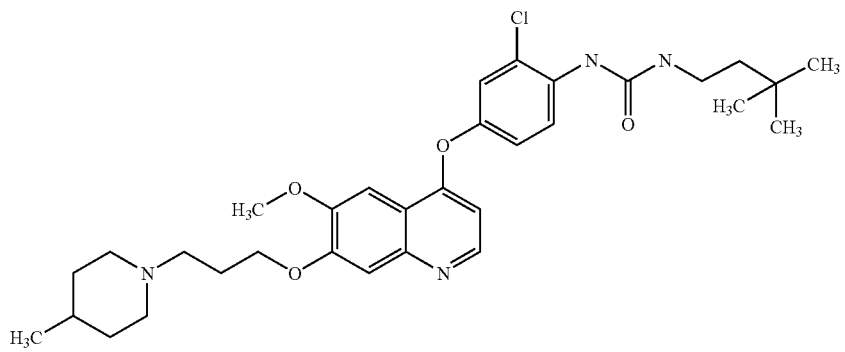 |
| 208 | 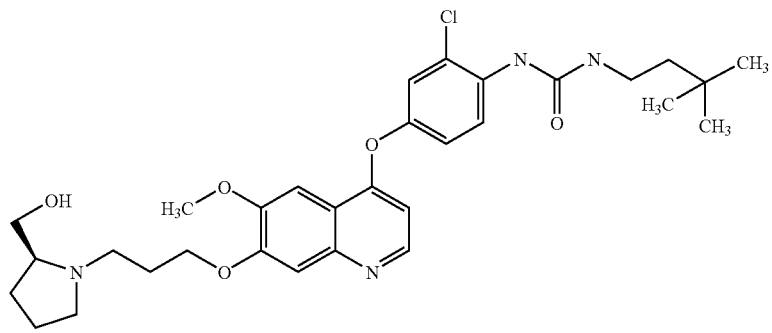 |
| 209 | 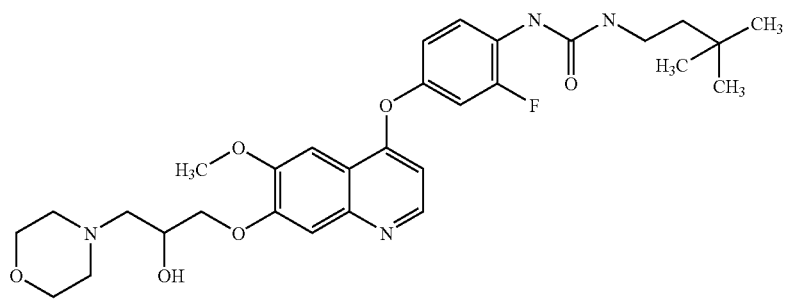 |
| 210 | 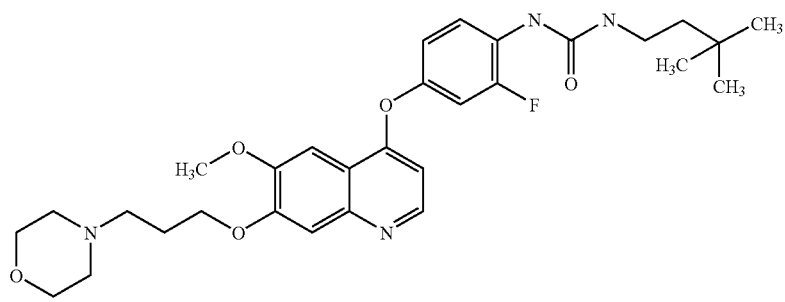 |

211 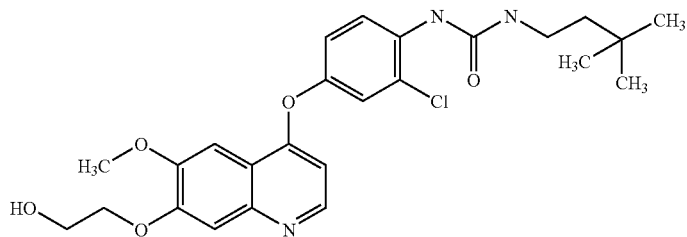
212 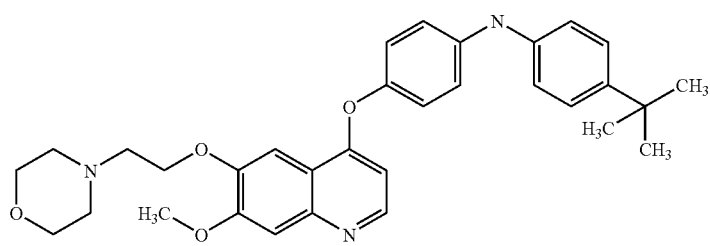
213 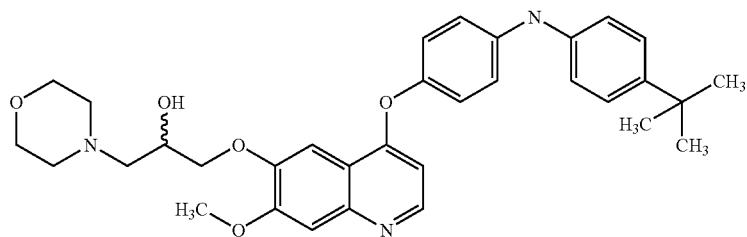
214 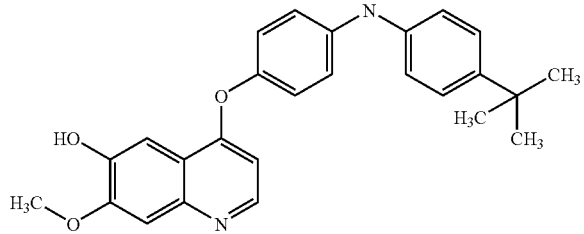
215 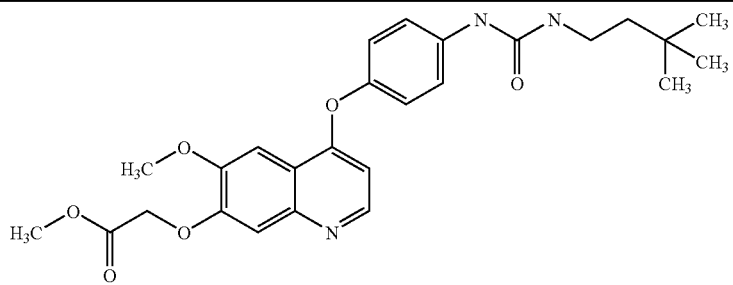

216 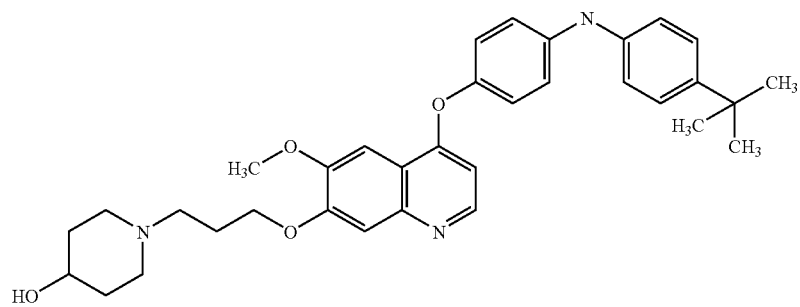
217 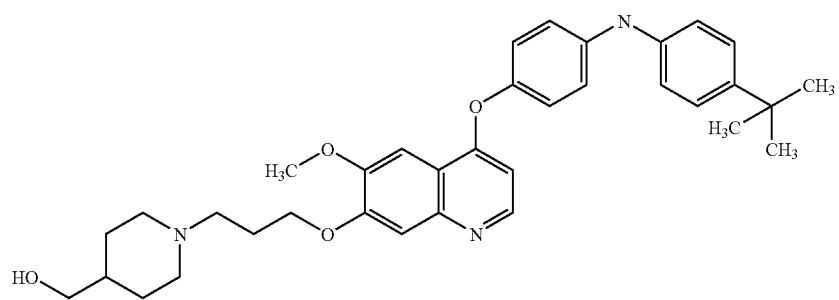
218 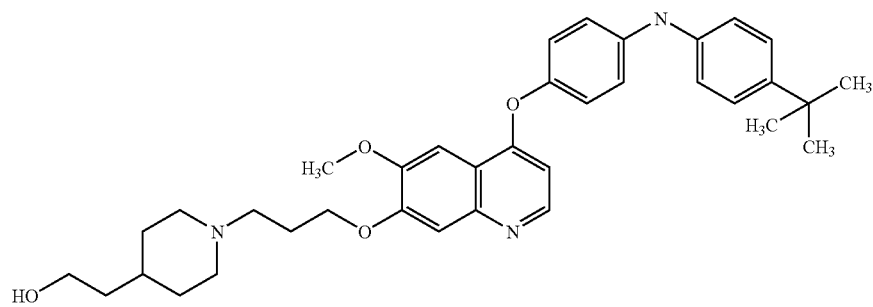
219 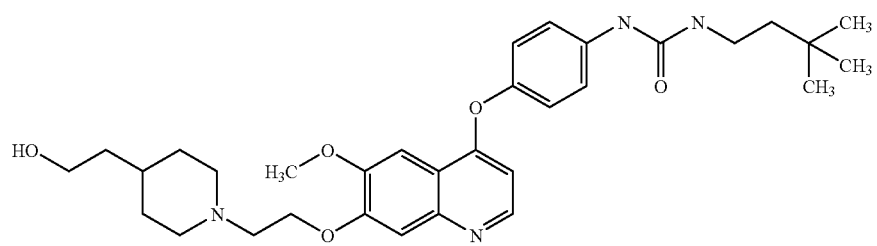
220 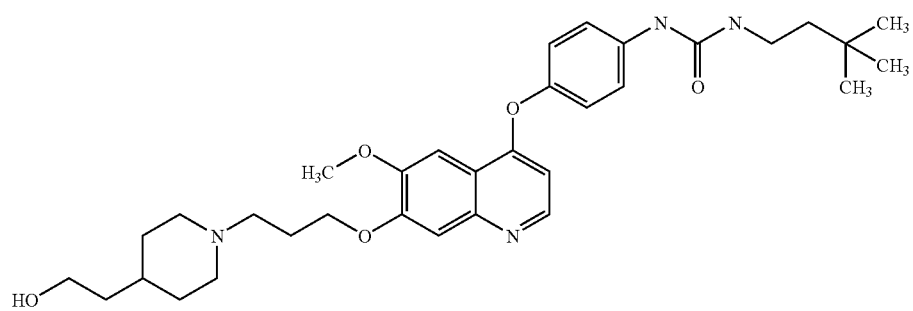

-continued
221 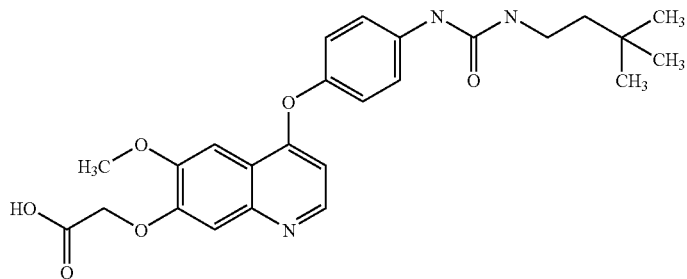
222 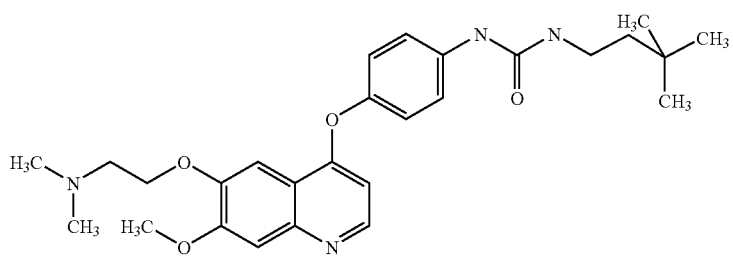
223 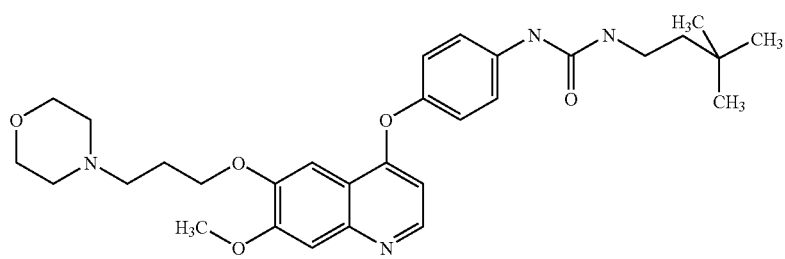
224 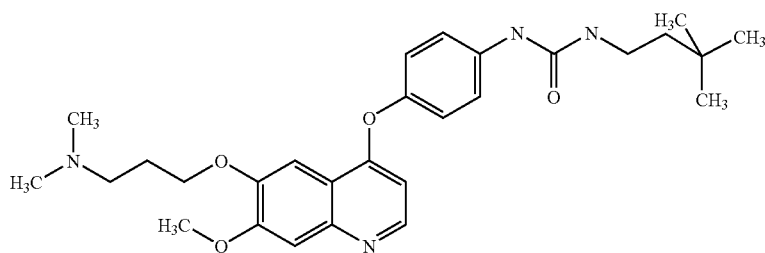
225 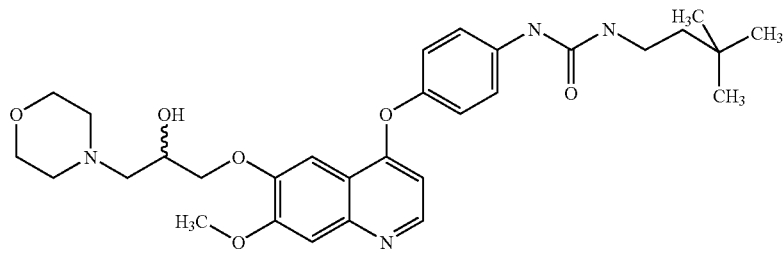
226 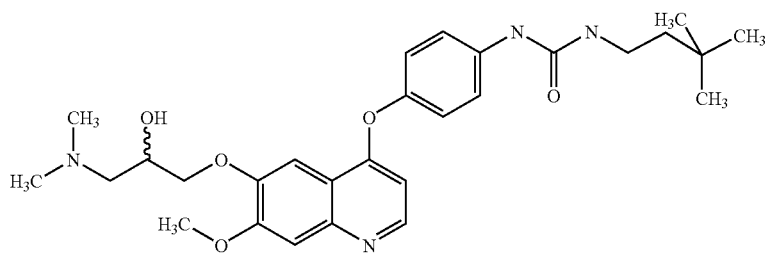

227 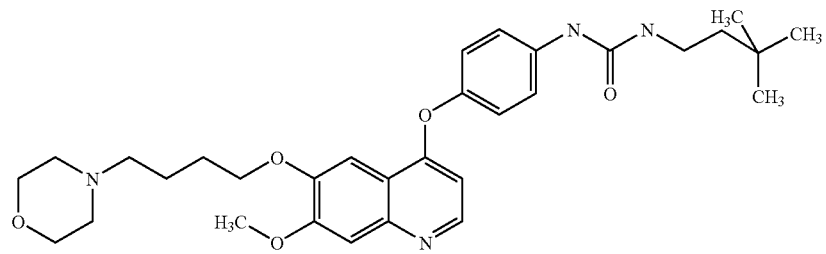
228 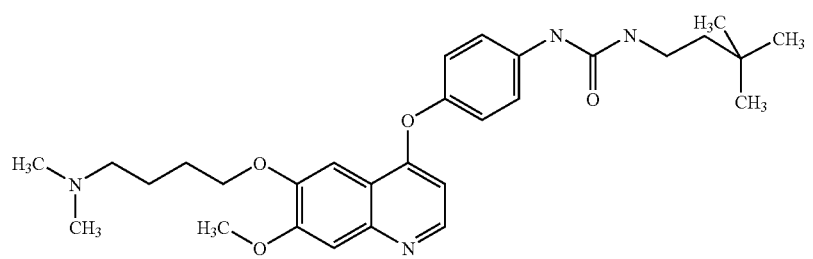
229 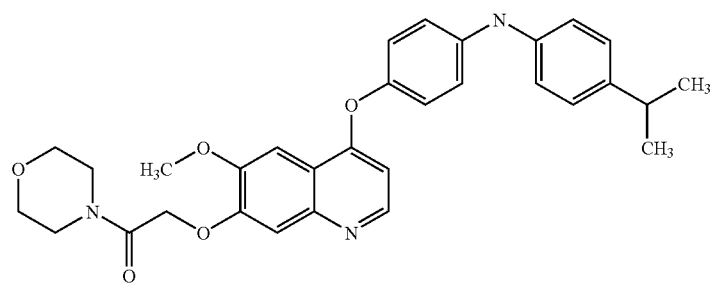
230 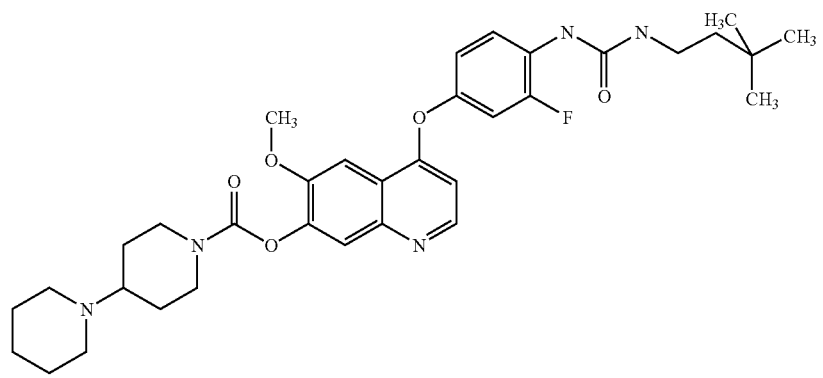
231 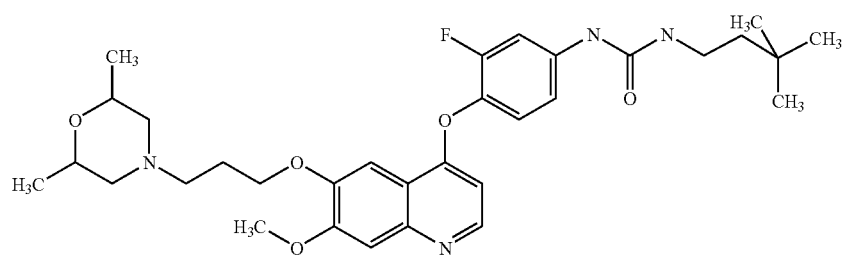

232 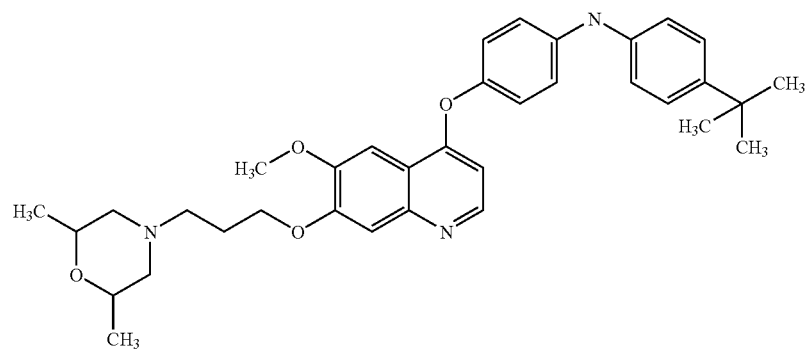
233 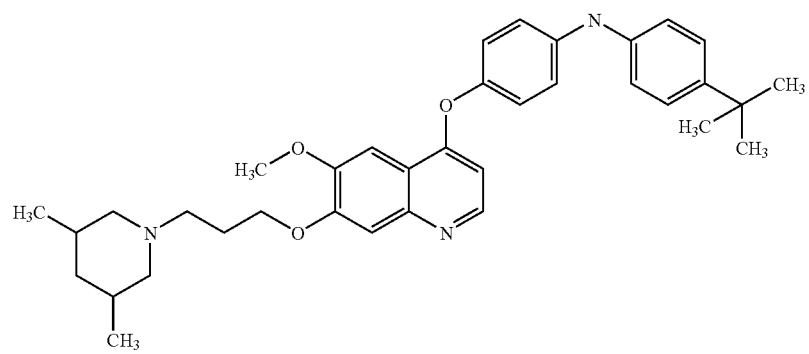
234 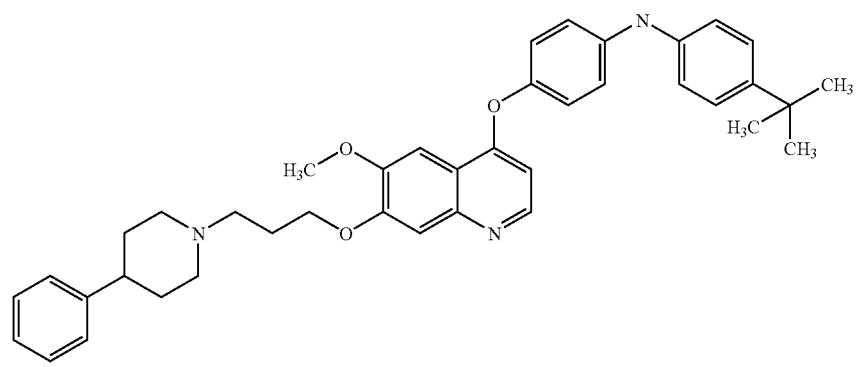
235 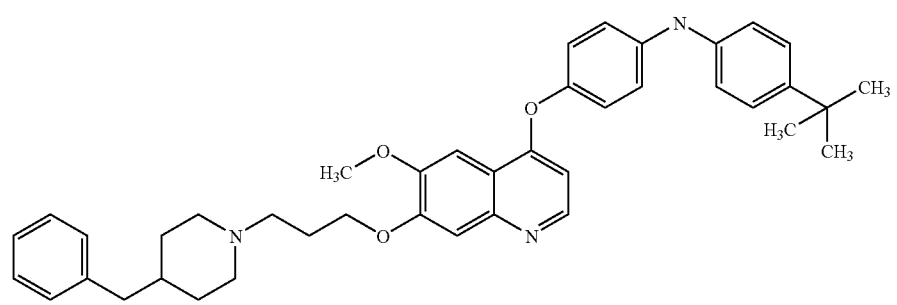

-continued
236
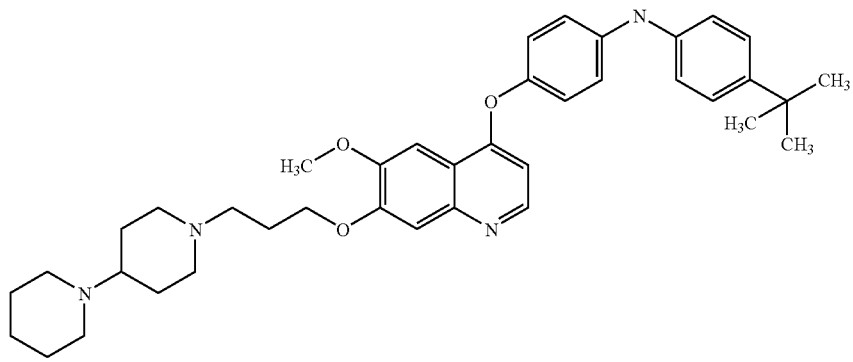
237
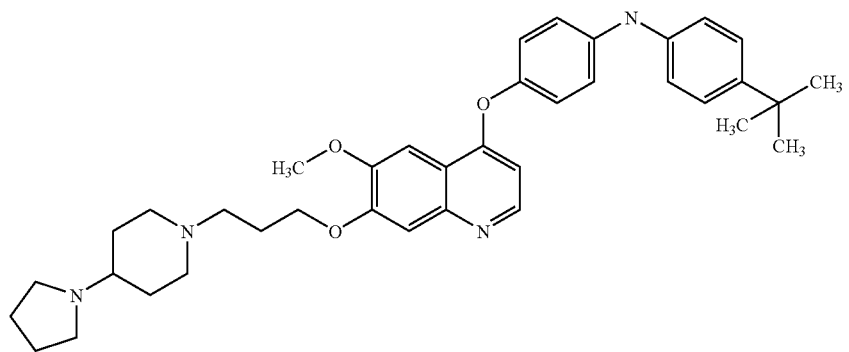
238
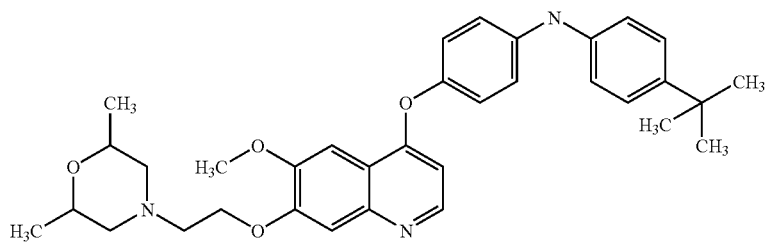
239
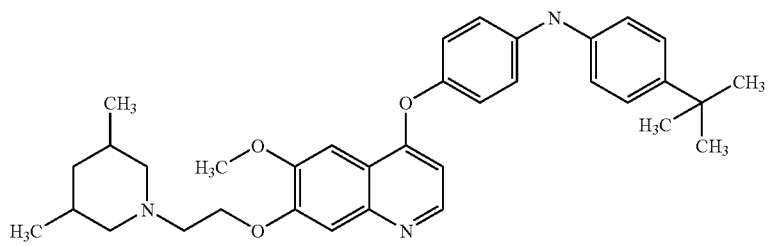
240
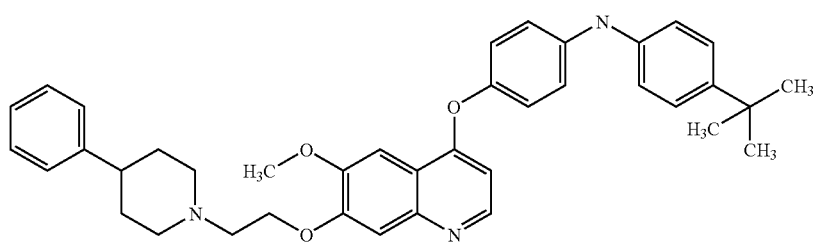

-continued
241
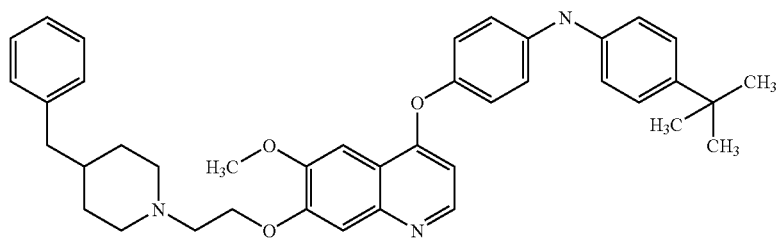
242
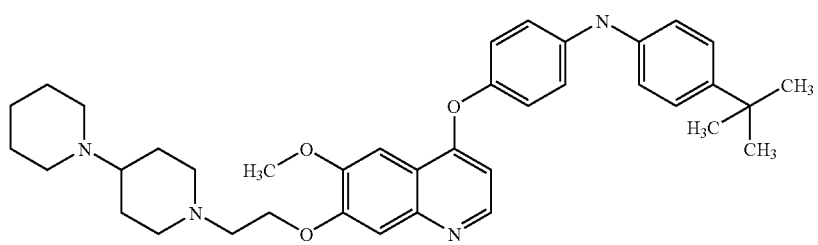
243
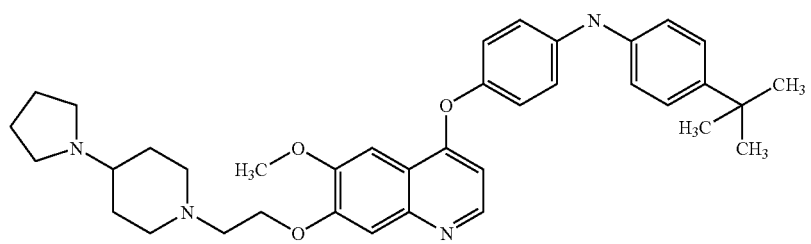
244
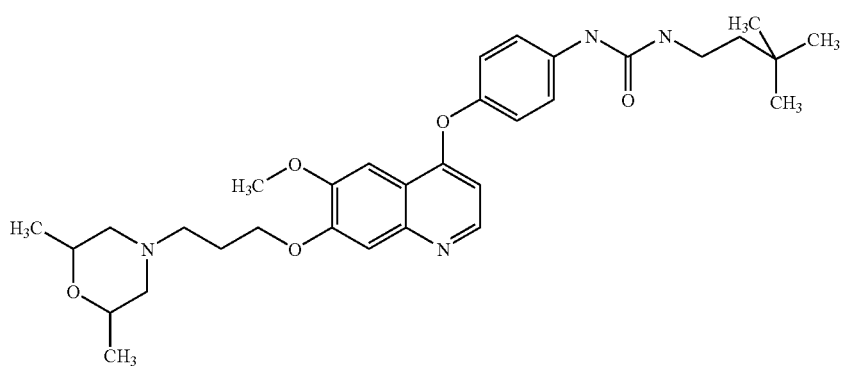
245
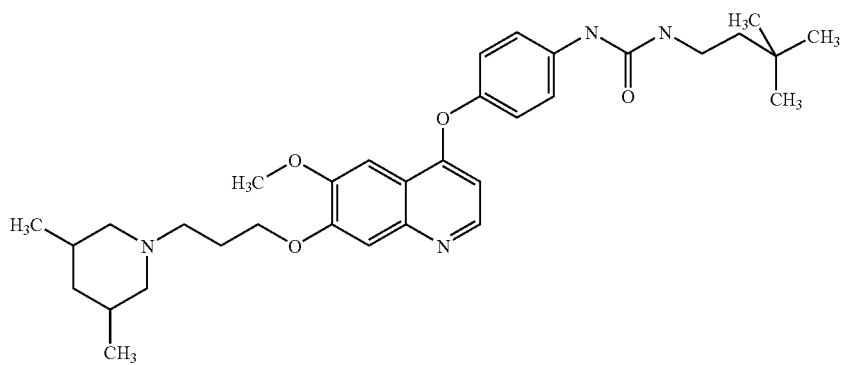

246 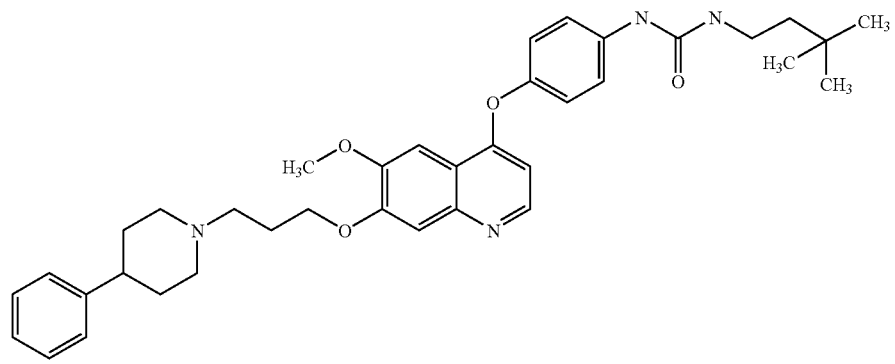
247 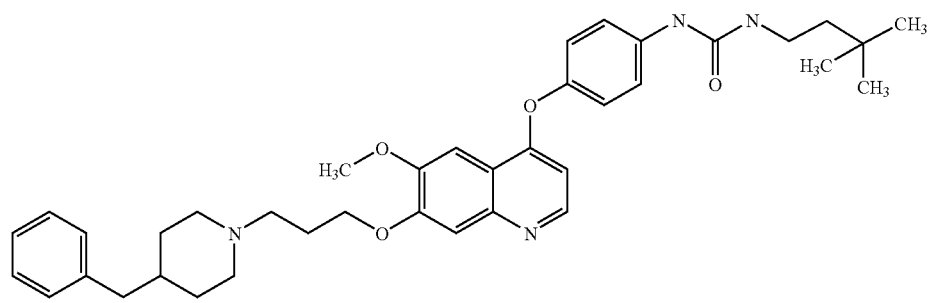
248 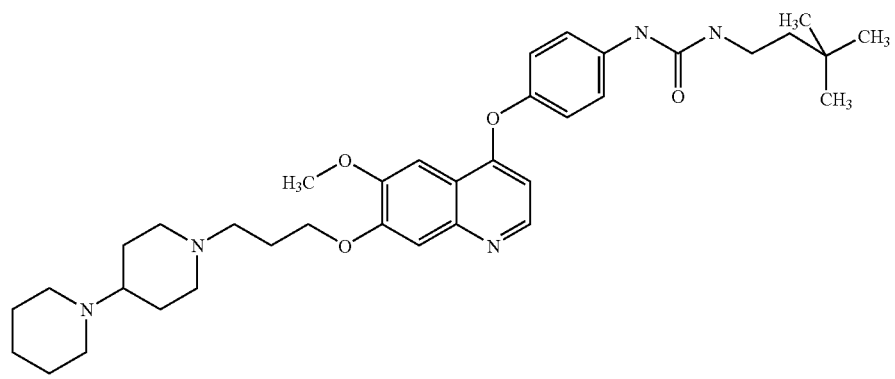
249 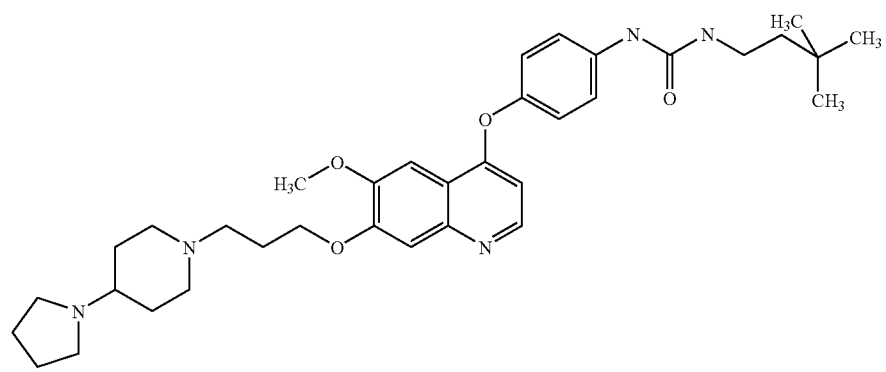

250 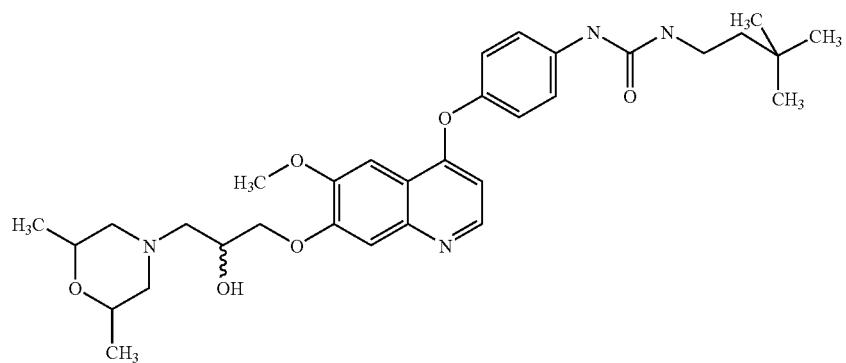
251 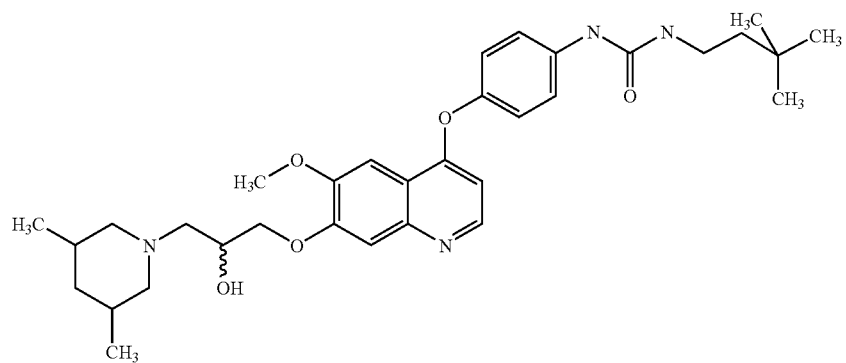
252 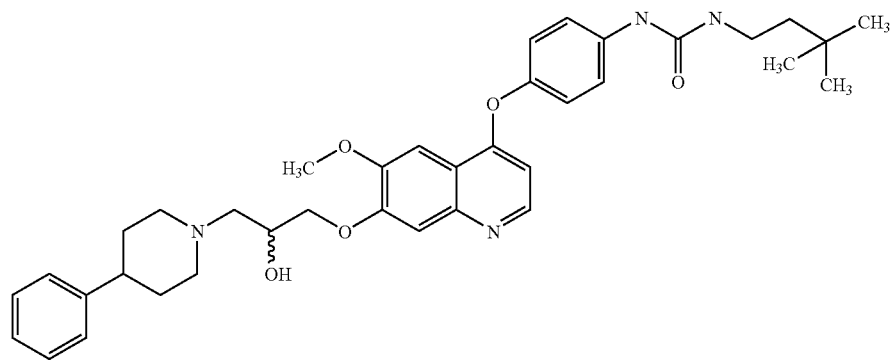
253 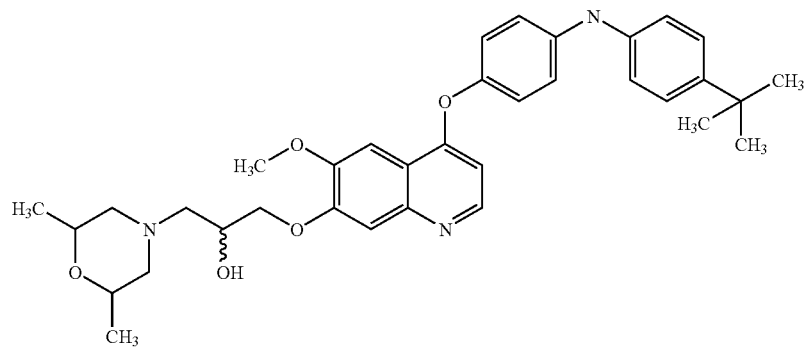

-continued
254
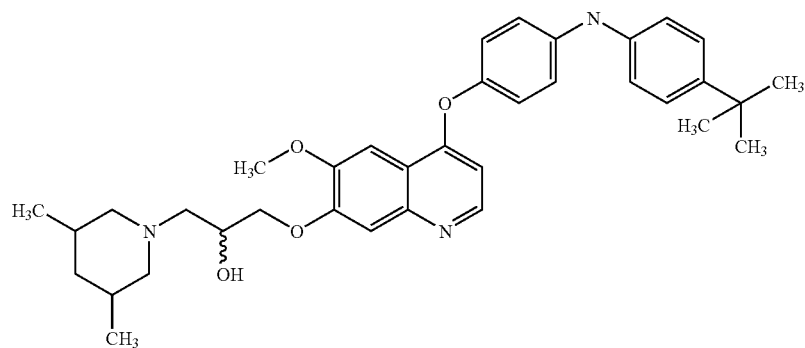
256
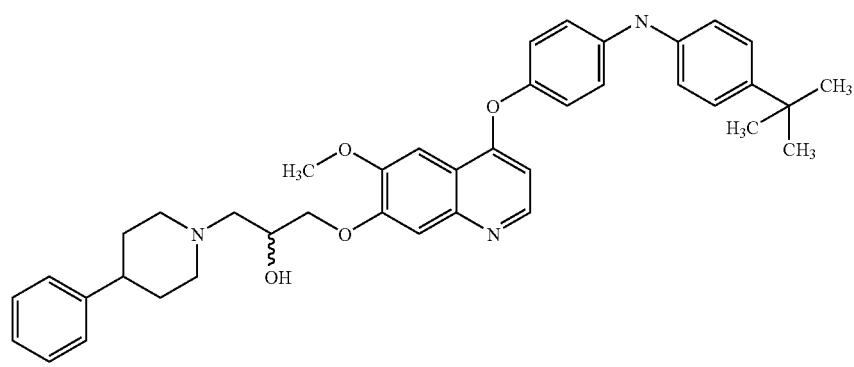
257
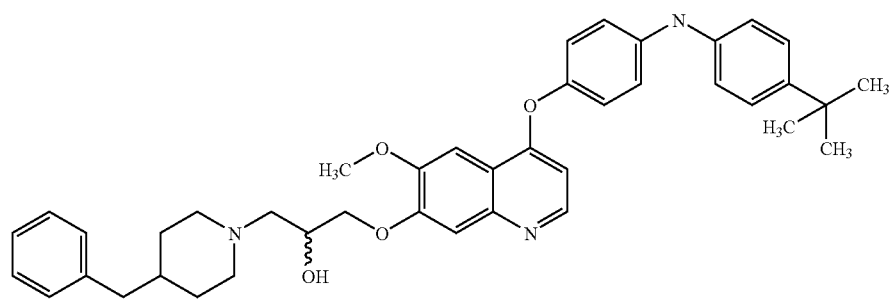
258
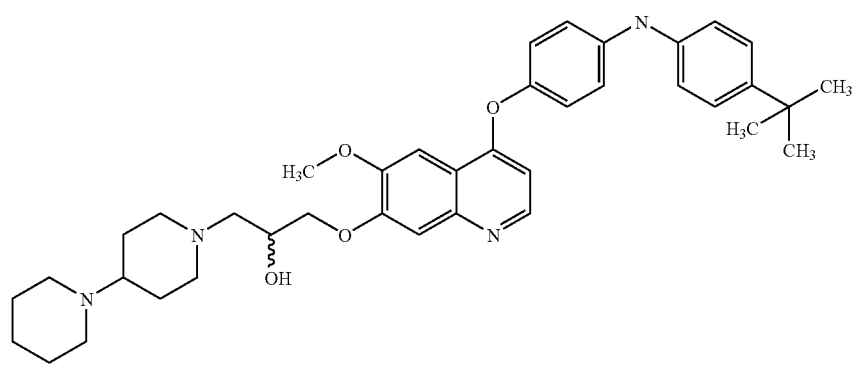

-continued
259
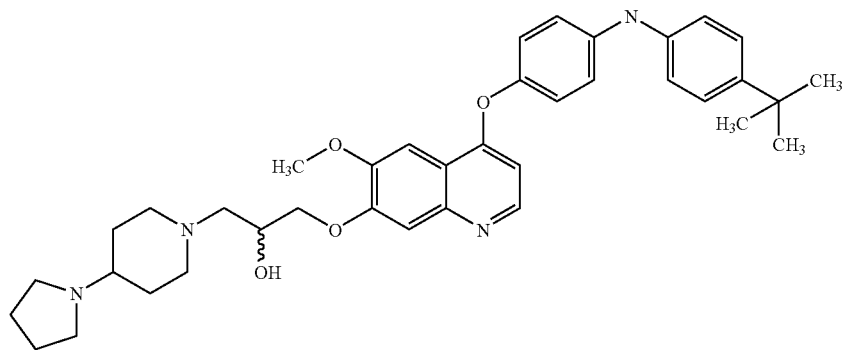
260
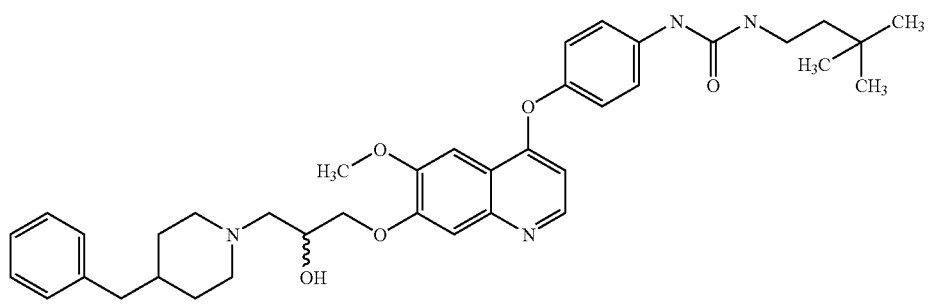
261
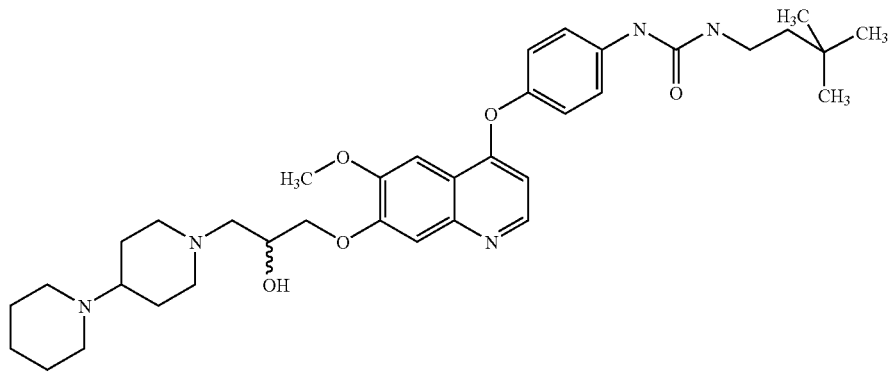
262
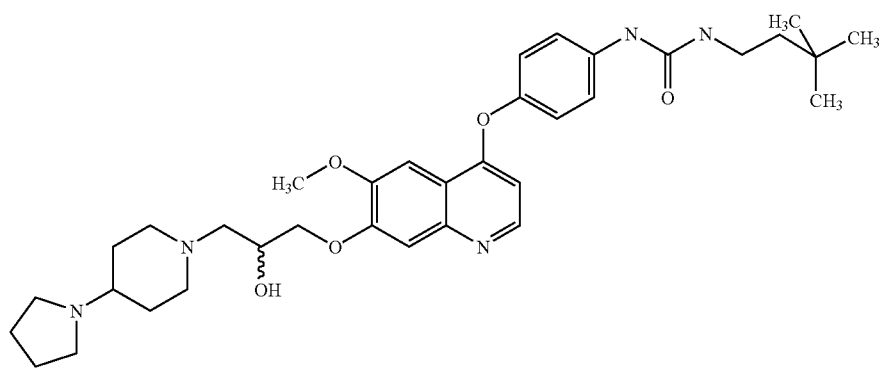

263 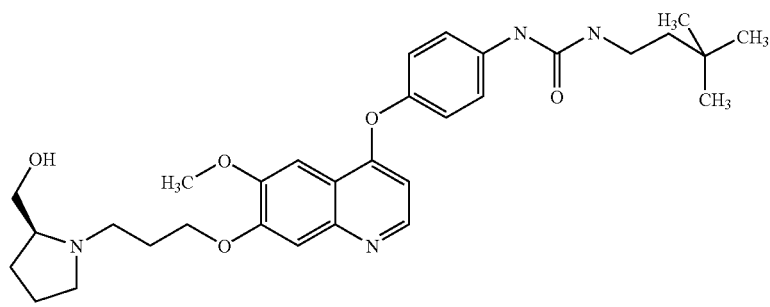
265 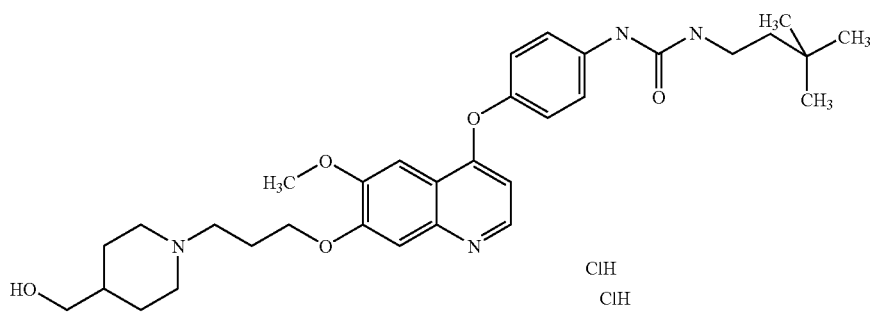
ClH
ClH
266 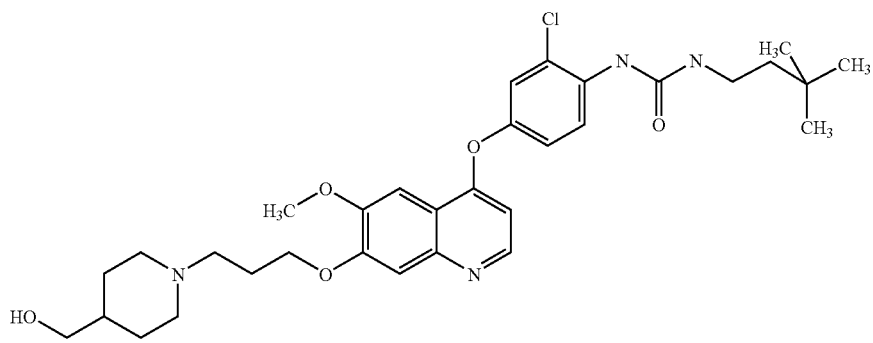
267 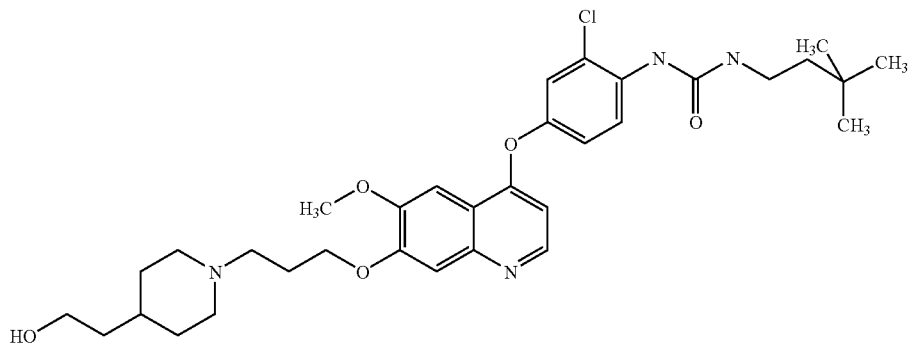

-continued
268
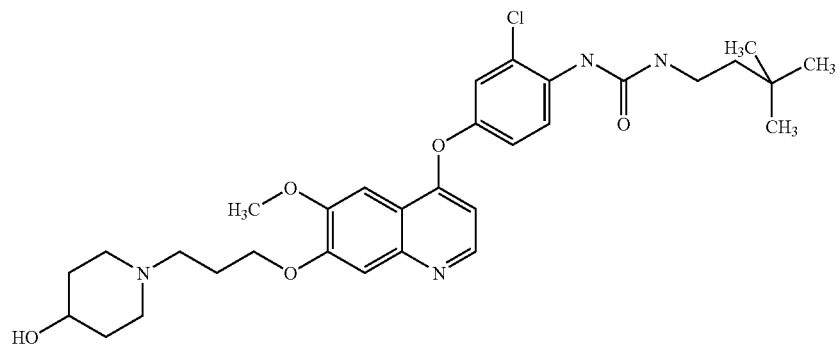
269
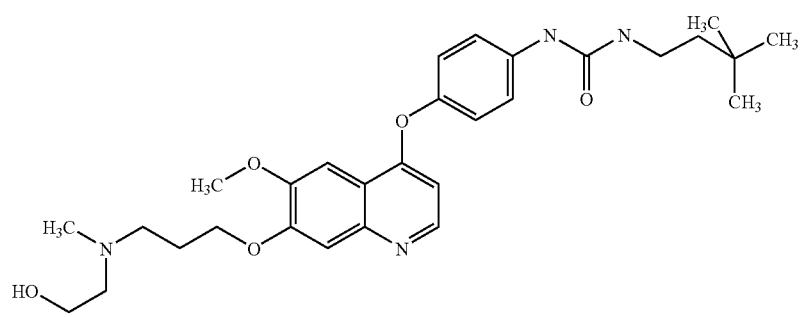
270
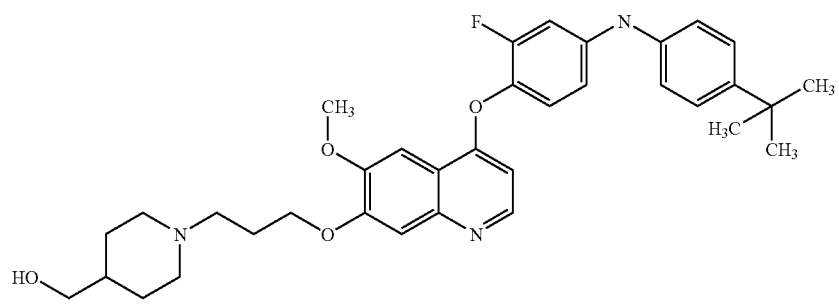
271
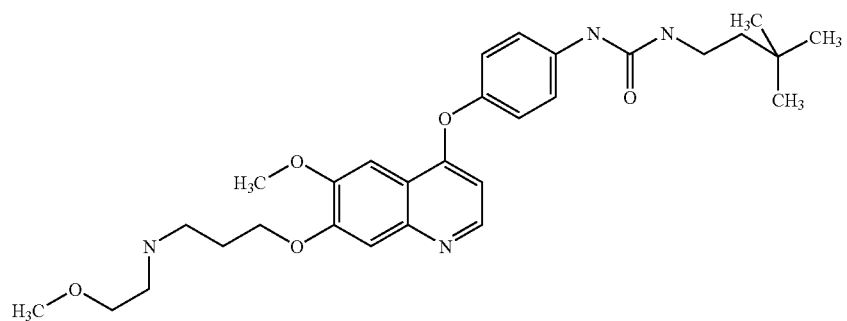
272
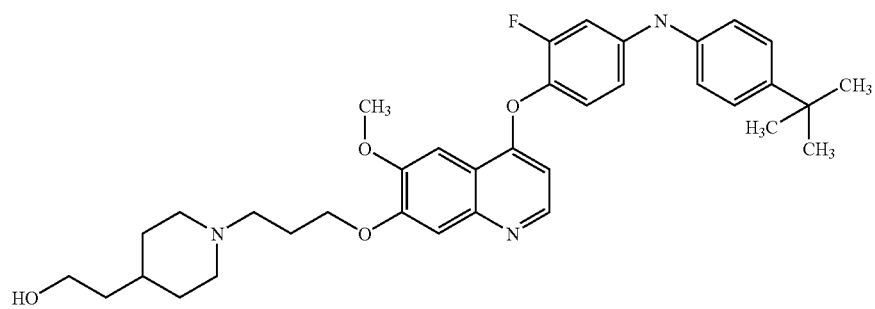

273 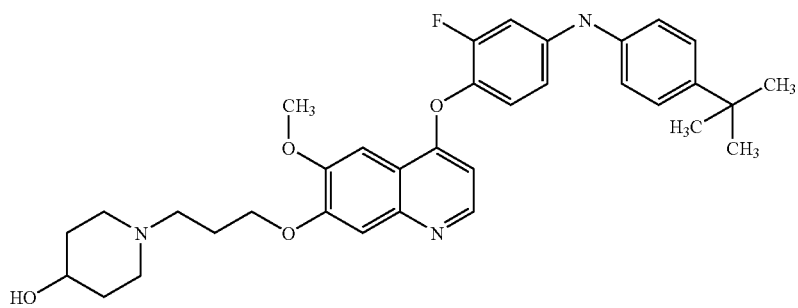
274 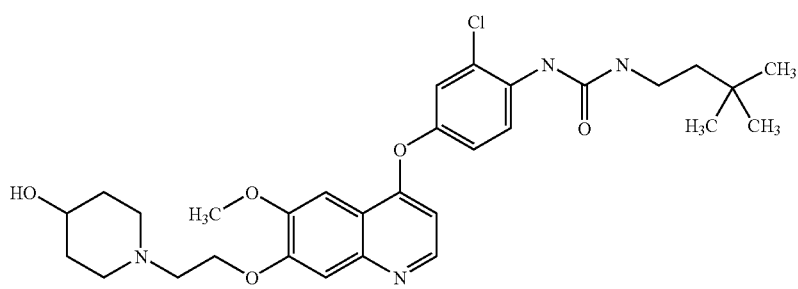
275 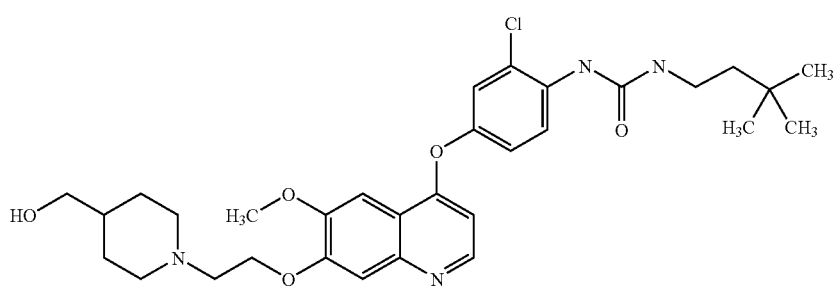
276 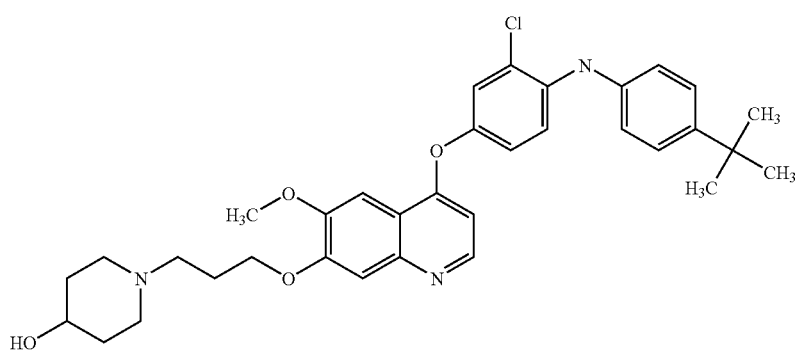
277 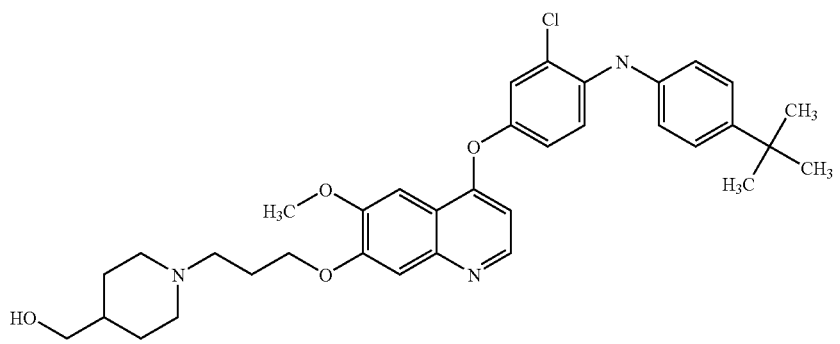

-continued
278 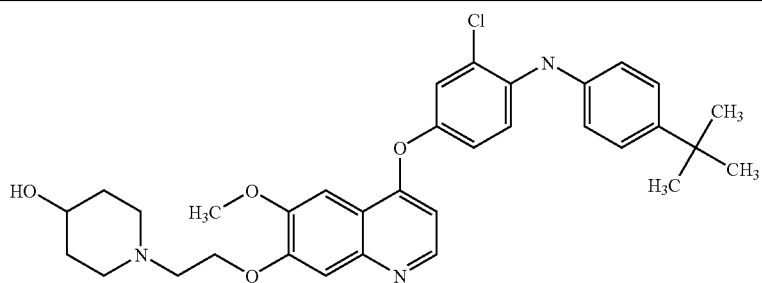
279 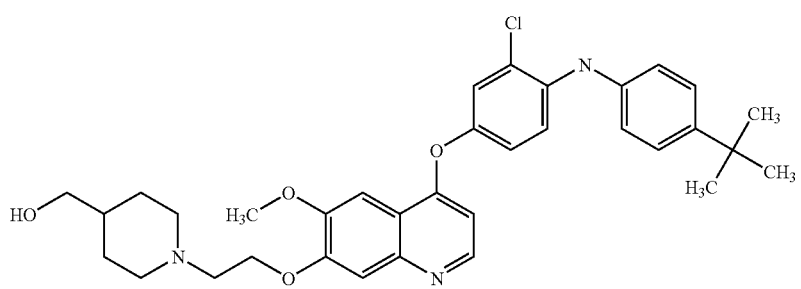
280 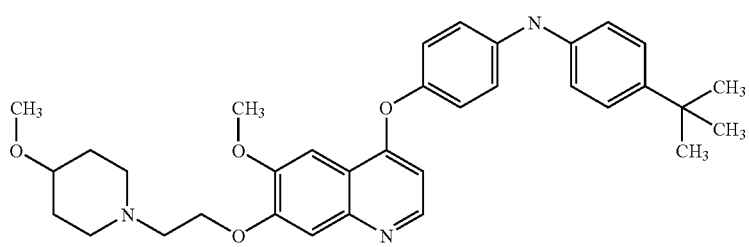
281 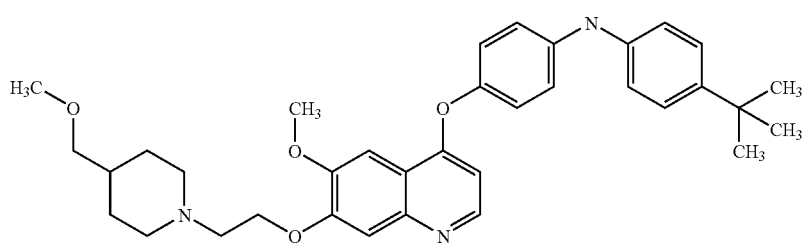
282 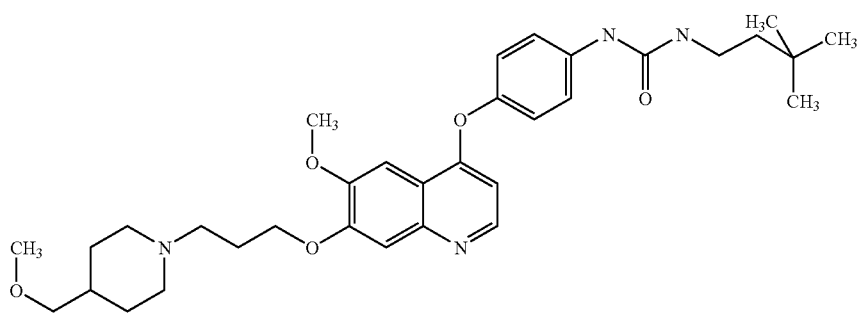
283 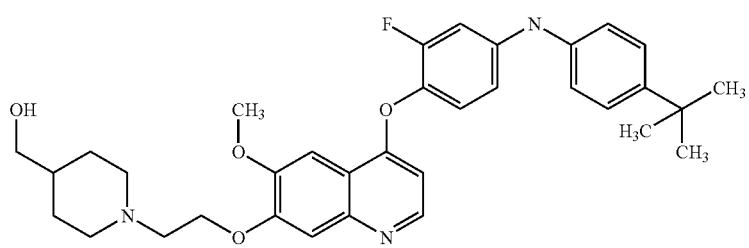

-continued
284
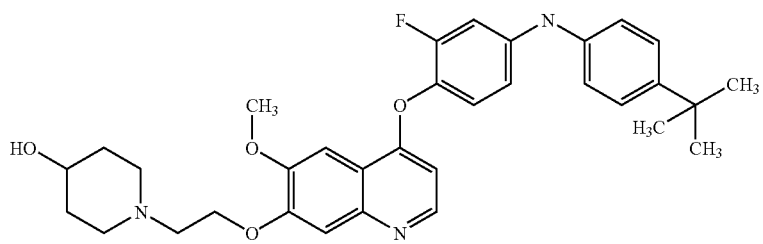
285
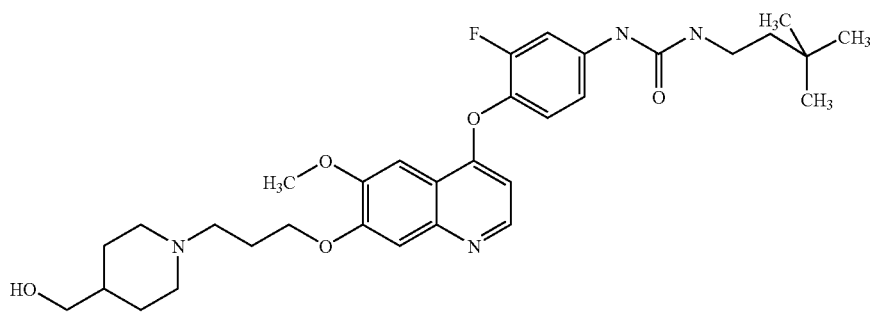
286
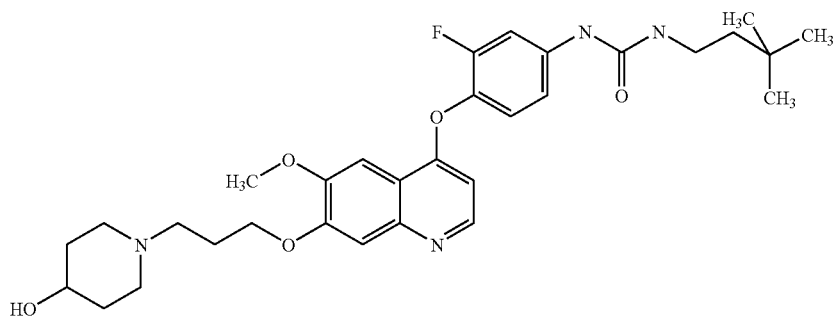
287
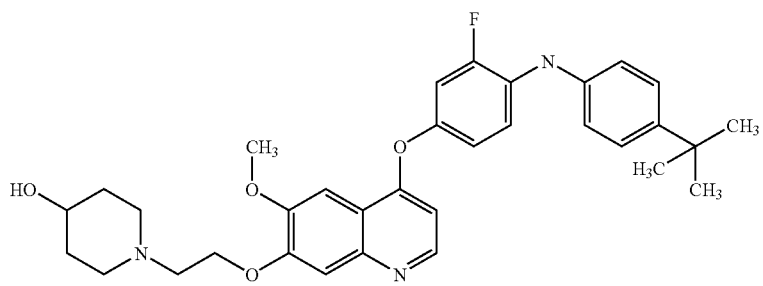
288
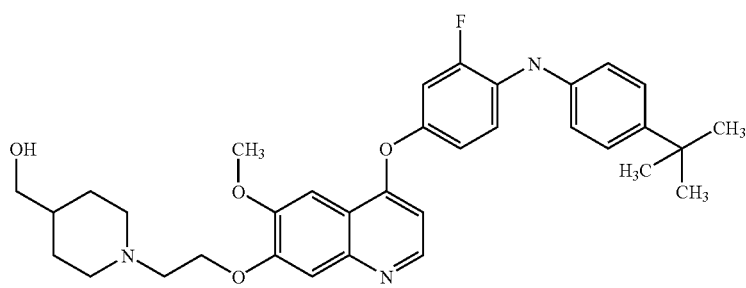

-continued
289
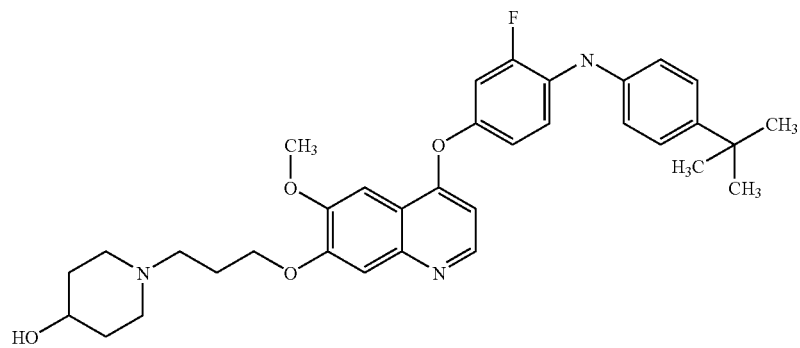
290
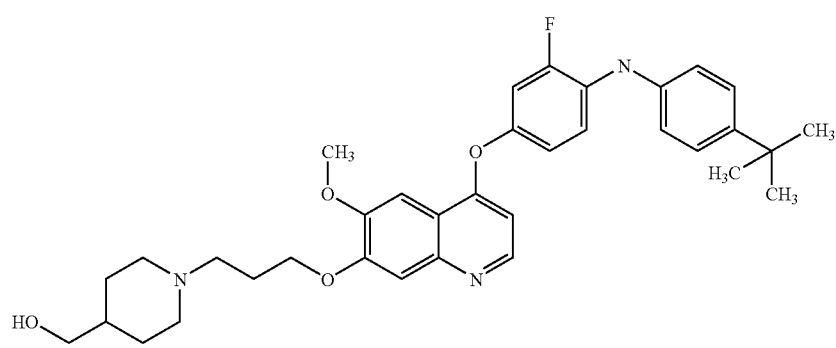
292
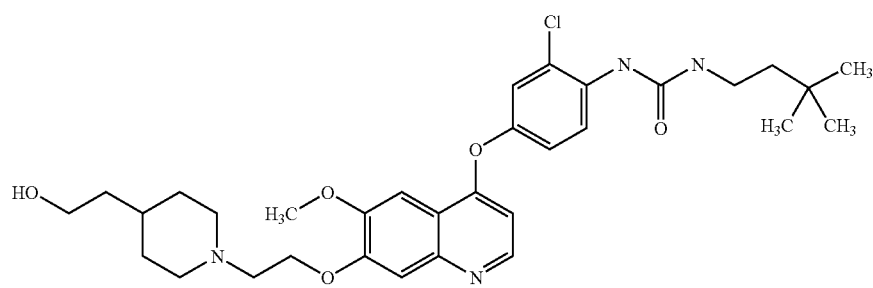
293
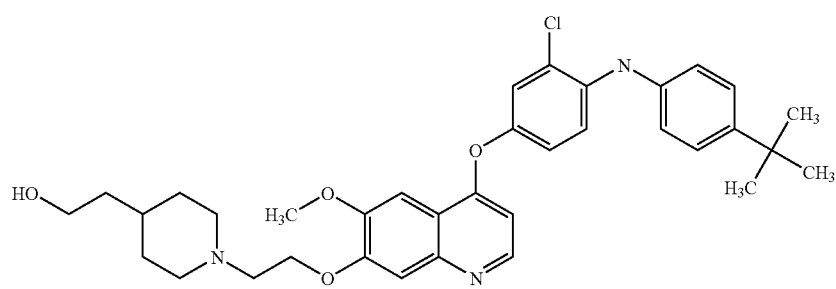
294
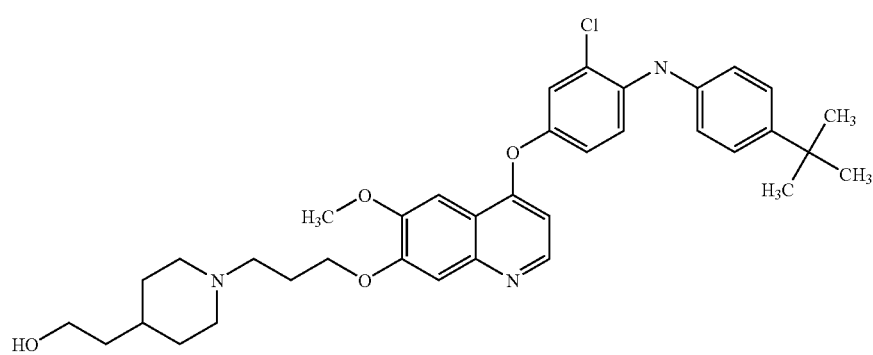

295 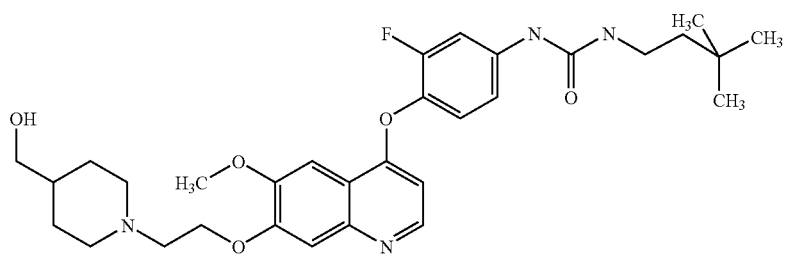
296 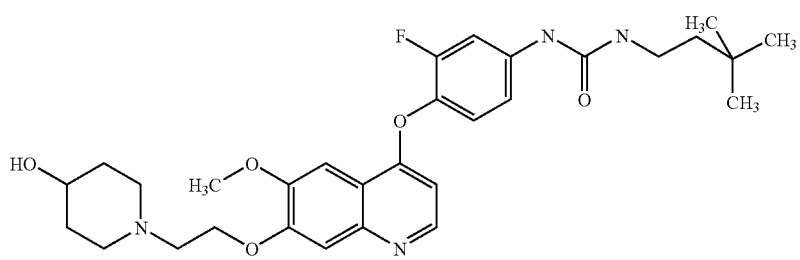
297 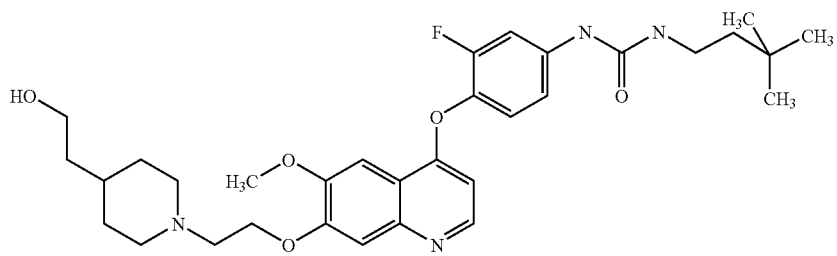
298 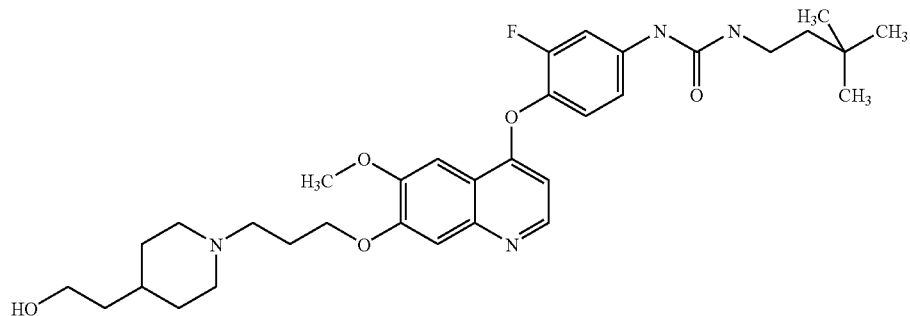
299 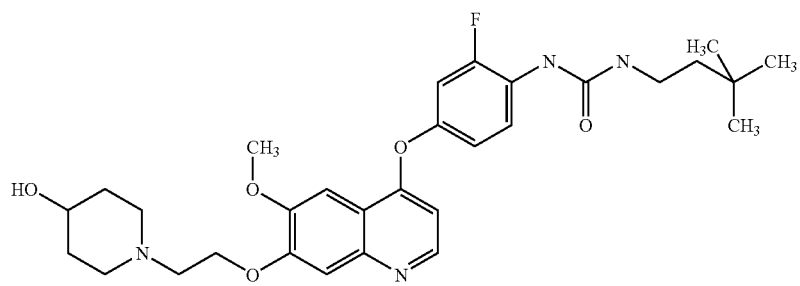

-continued
300
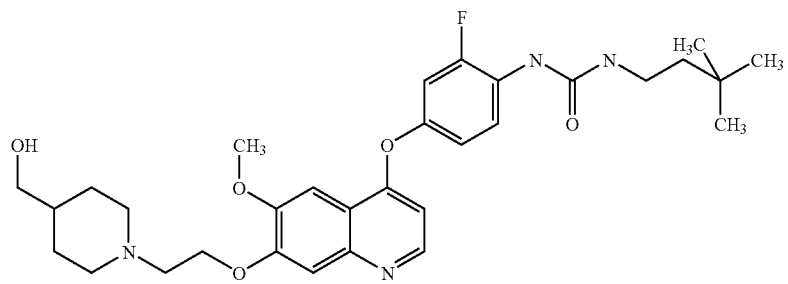
301
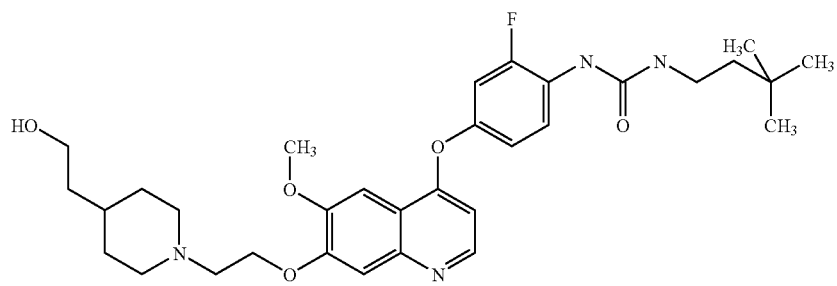
302
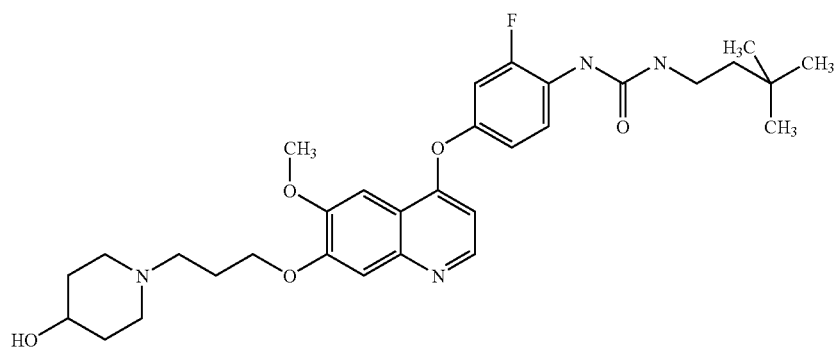
303
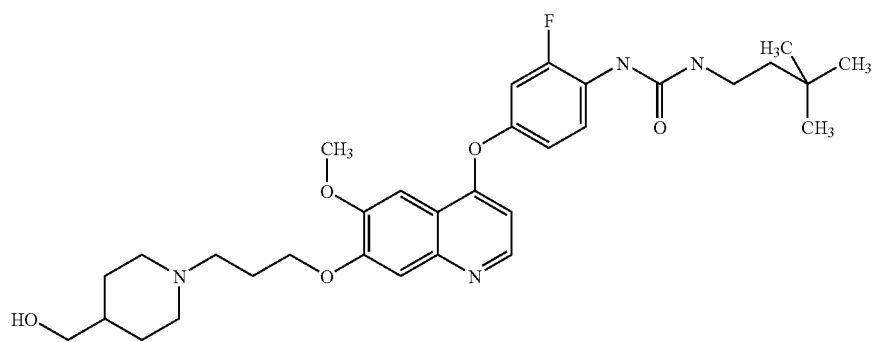
304
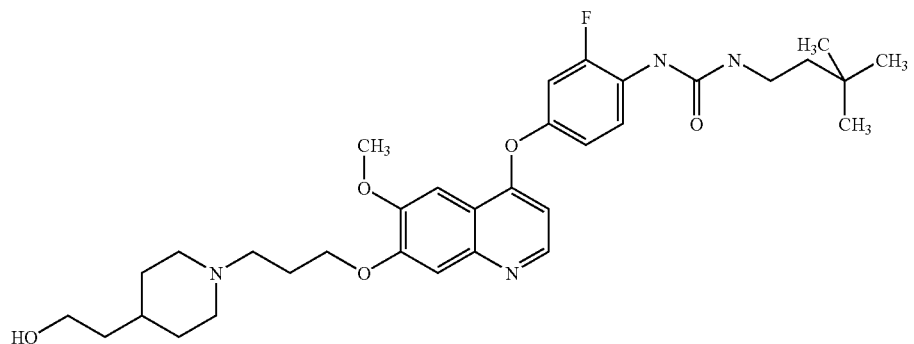

-continued
305
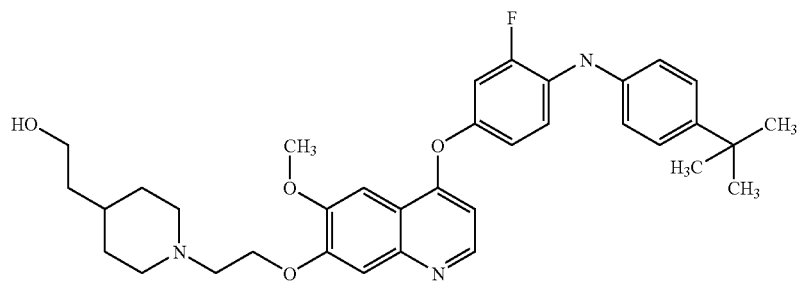
306
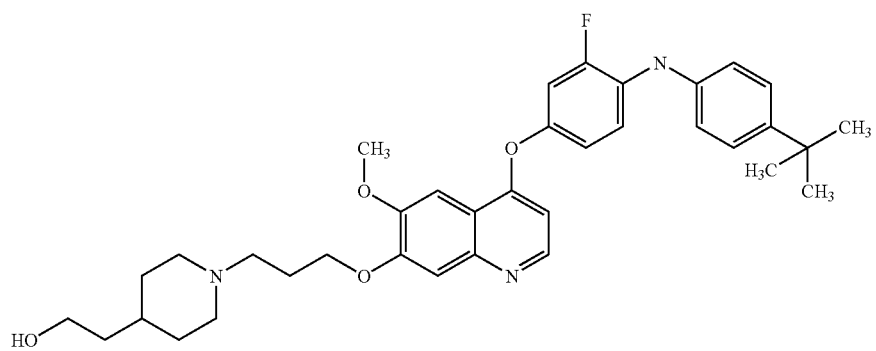
307
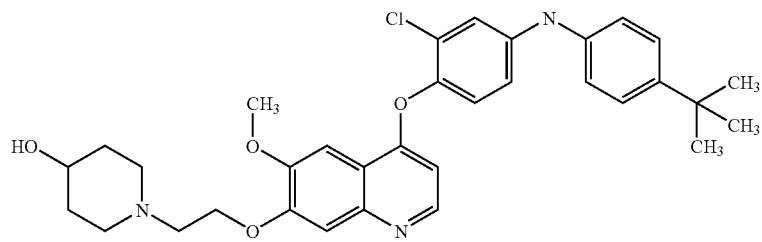
308
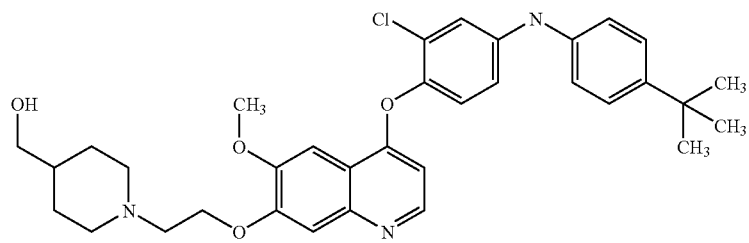
309
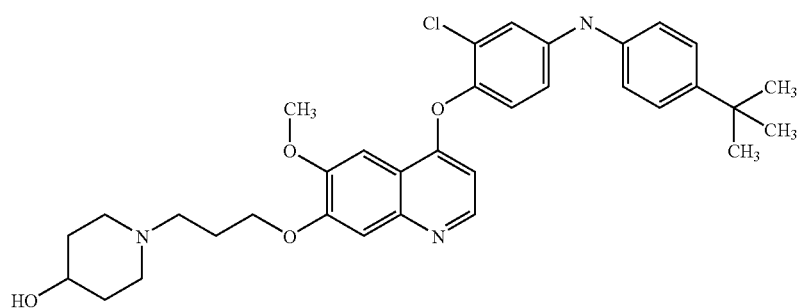

-continued
310 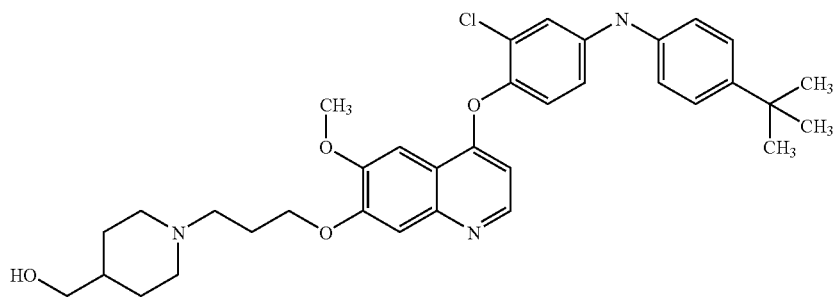
311 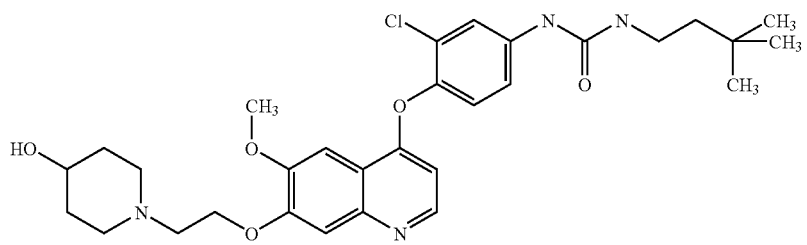
312 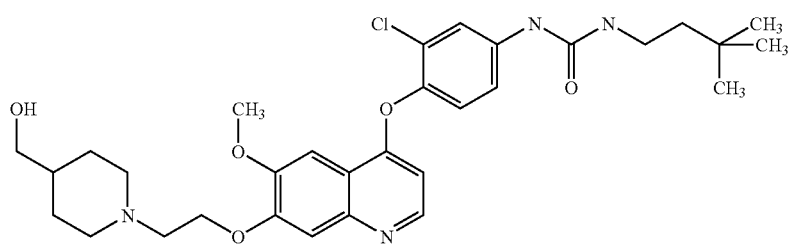
313 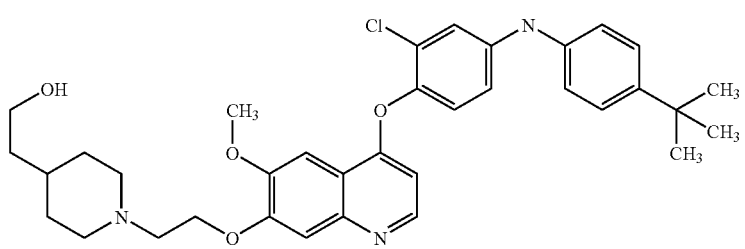
314 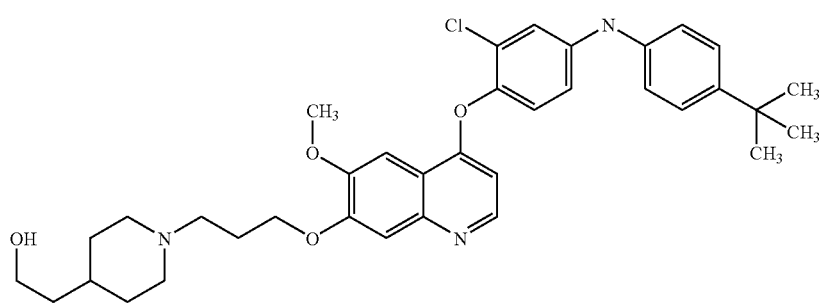
315 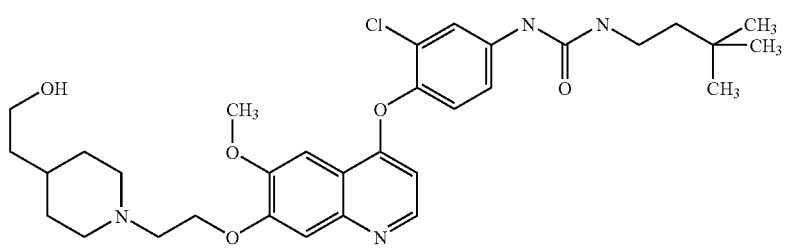

-continued
316 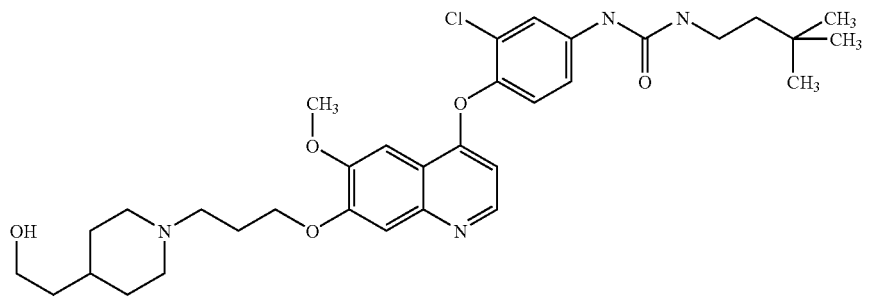
317 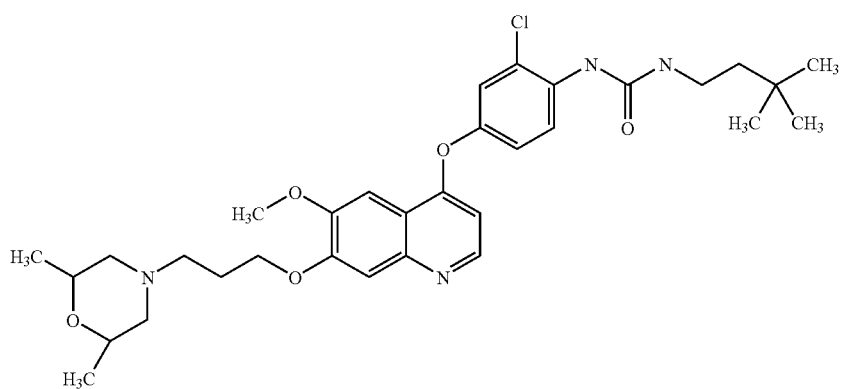
318 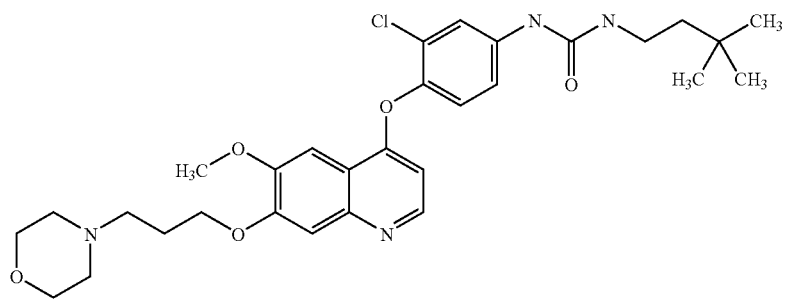
319 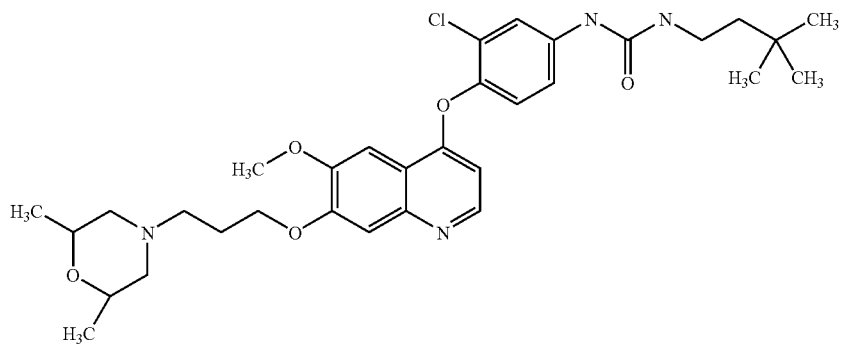
320 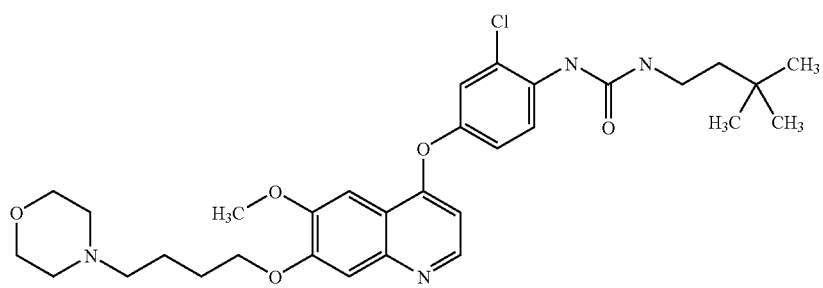

321 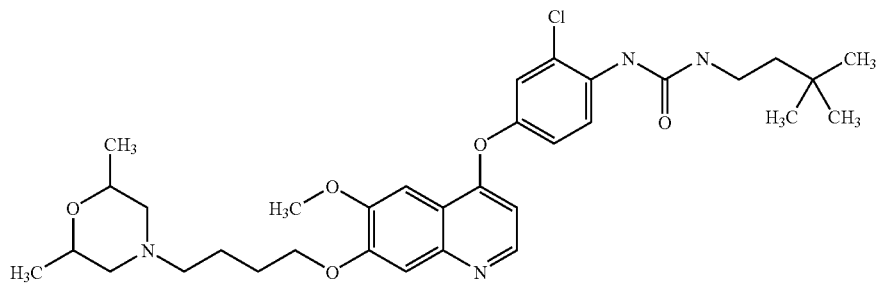
322 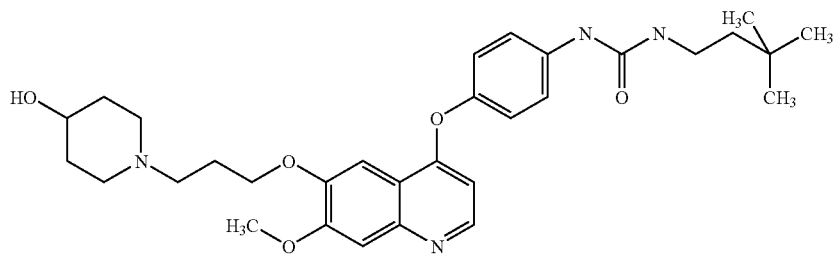
323 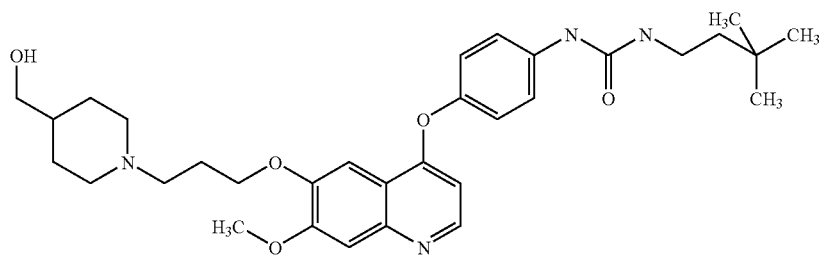
324 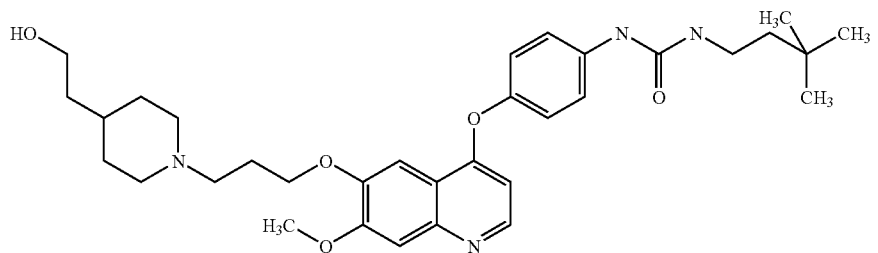
325 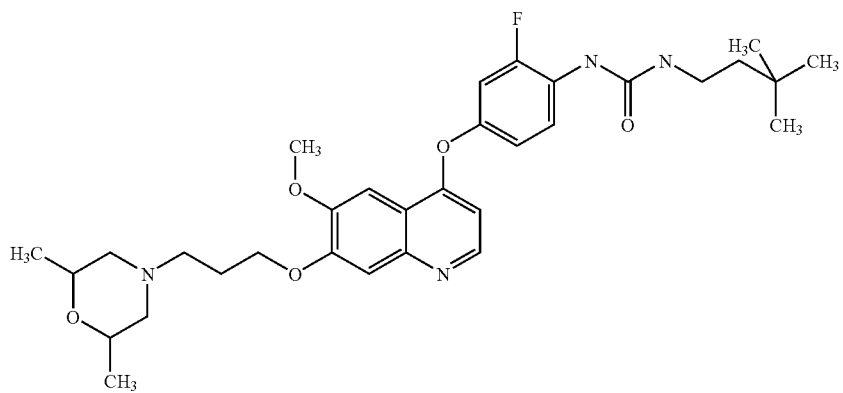

326 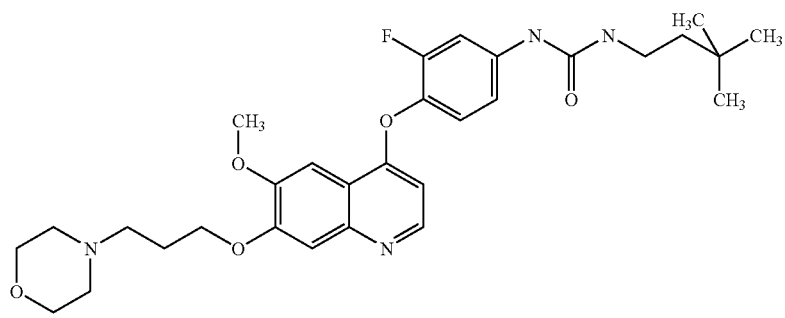
327 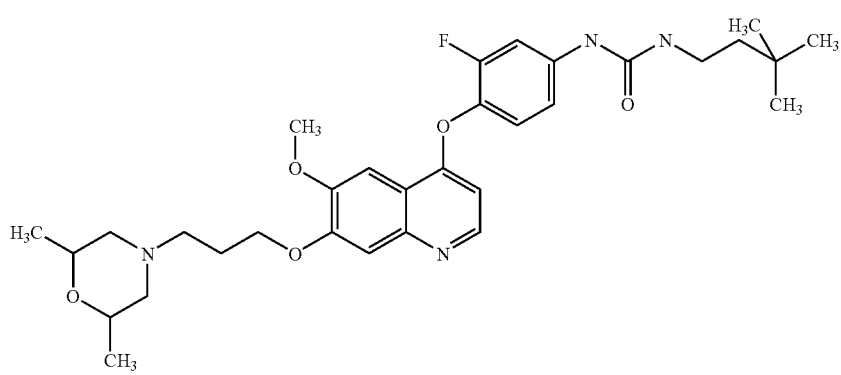
328 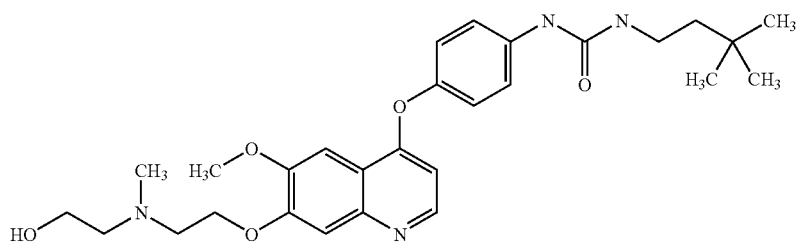
329 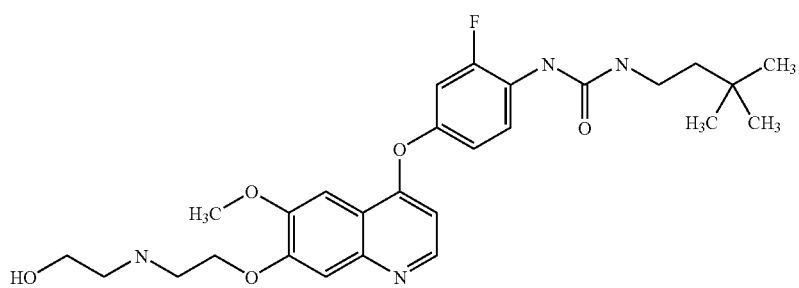
330 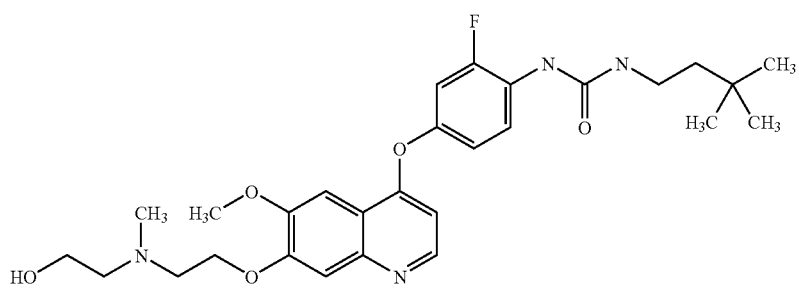

-continued
331
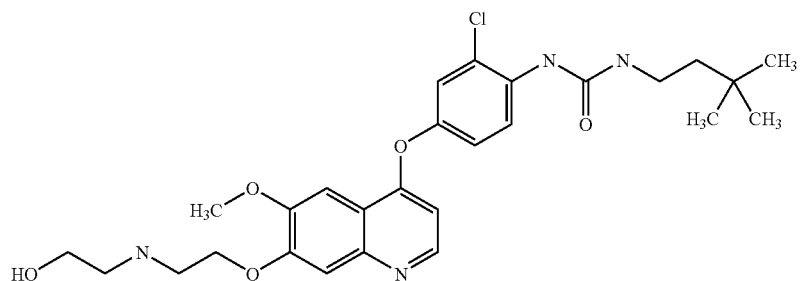
332
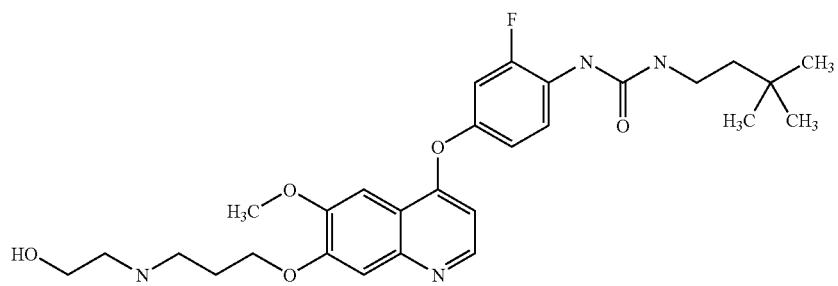
333
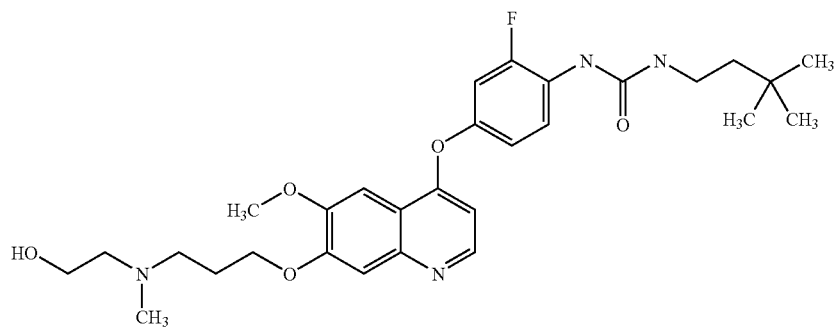
334
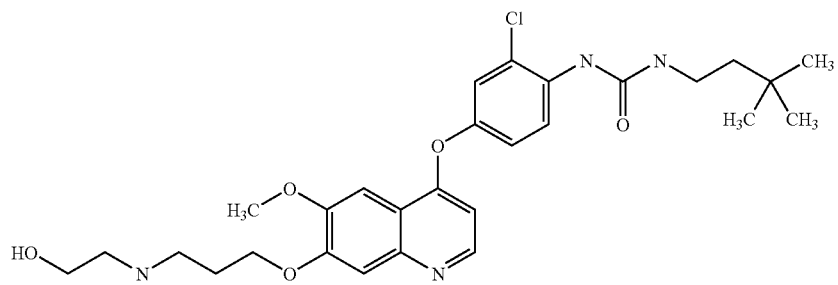
335
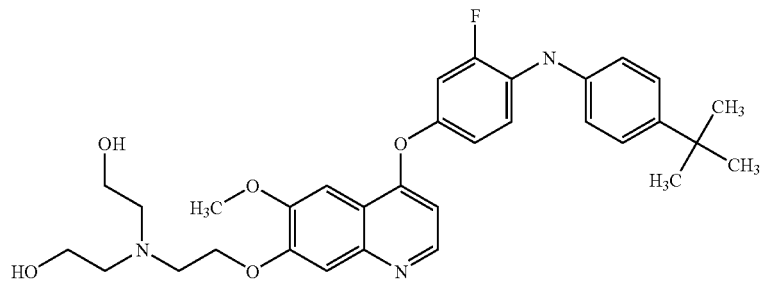

336 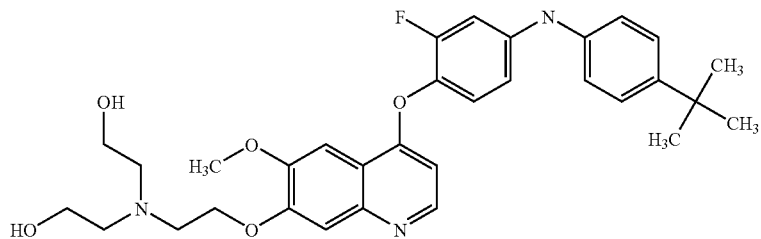
337 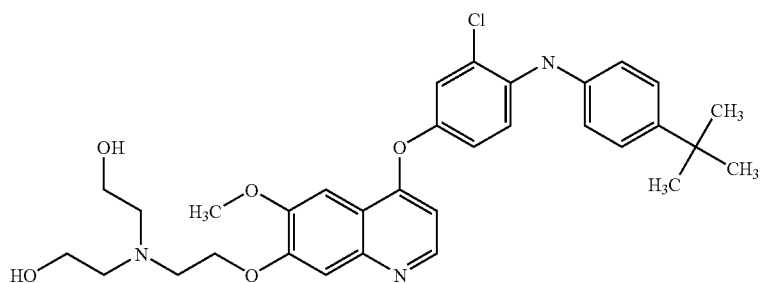
338 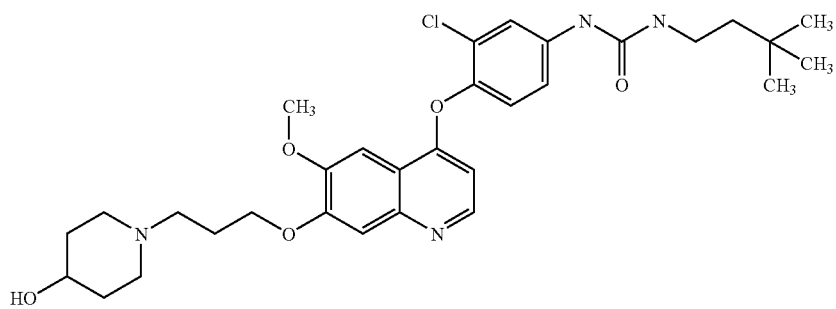
339 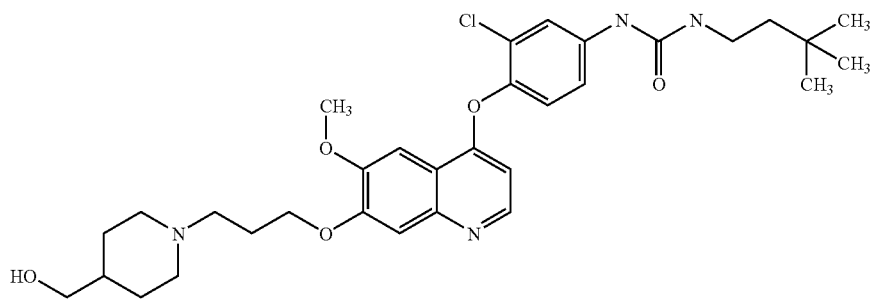
340 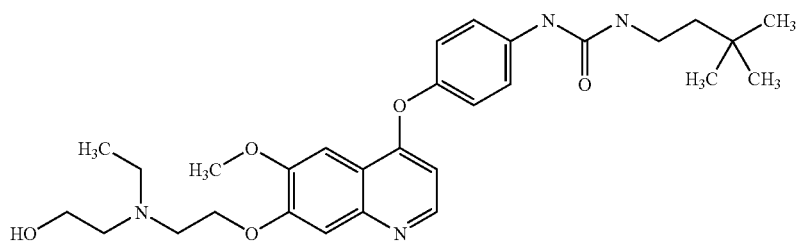

-continued
341 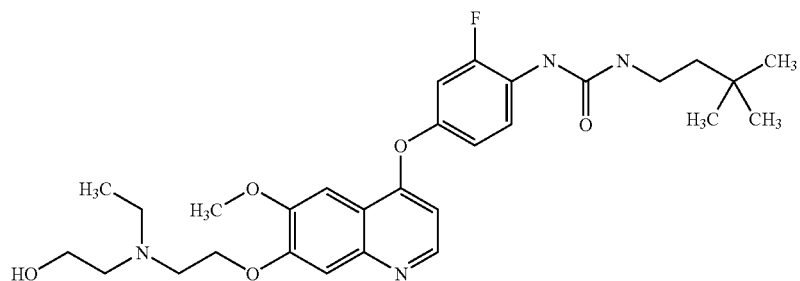
342 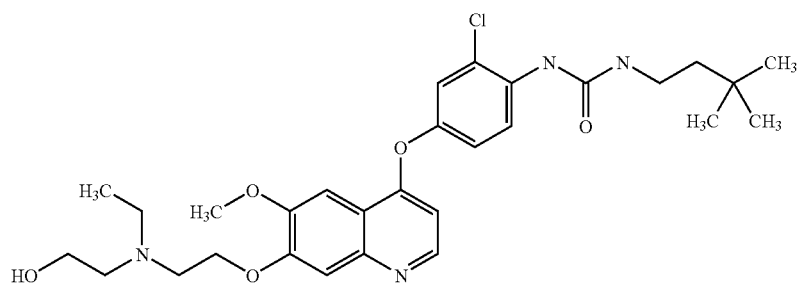
343 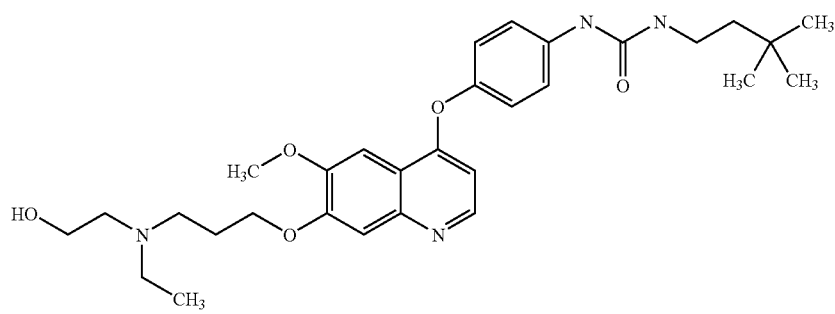
344 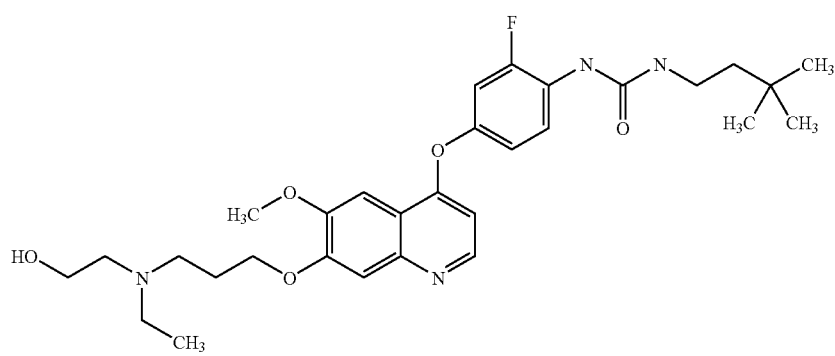
345 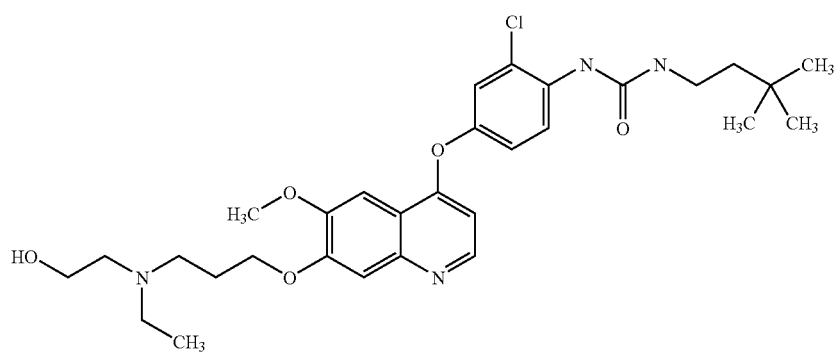

-continued
346
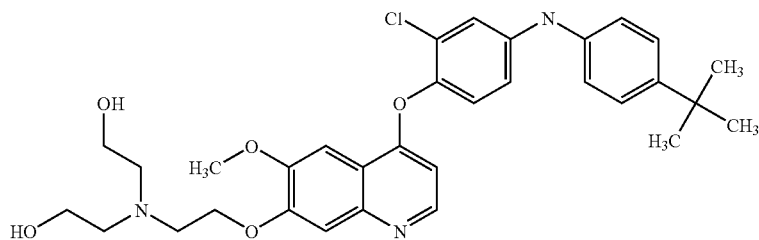
347
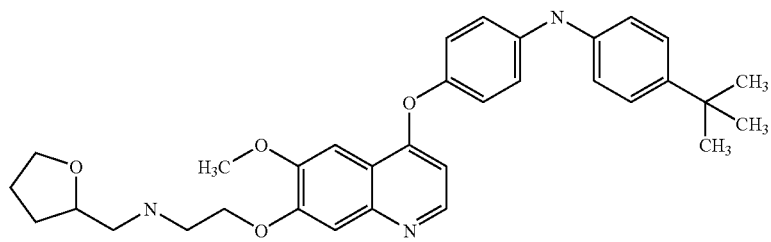
348
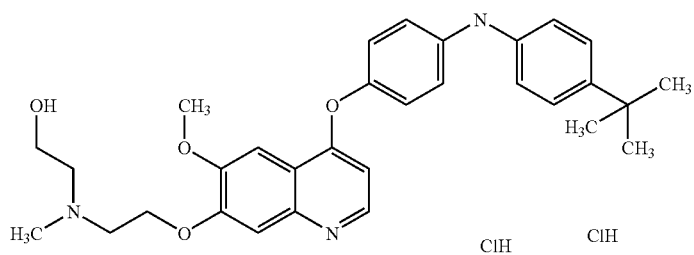
349
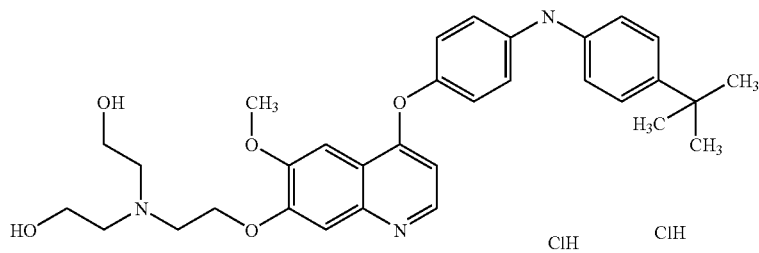
350
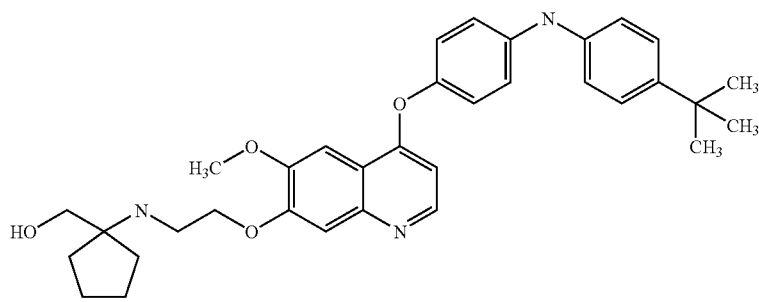

351 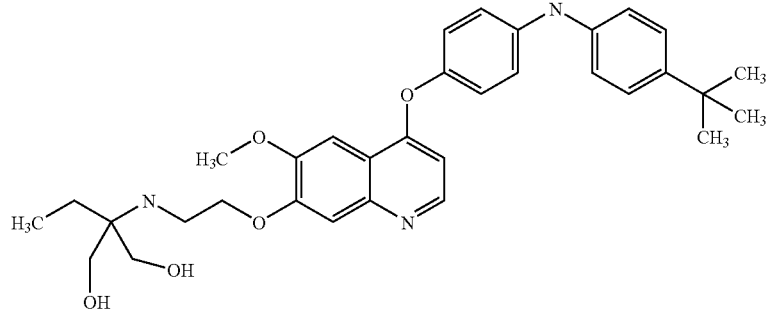
352 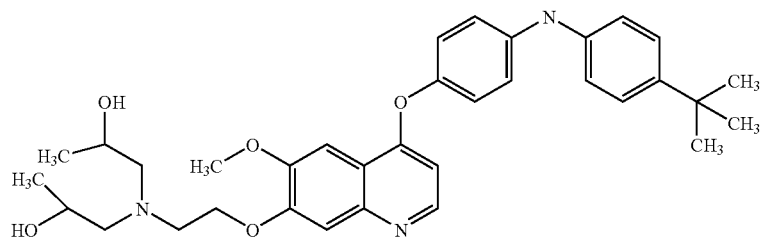
353 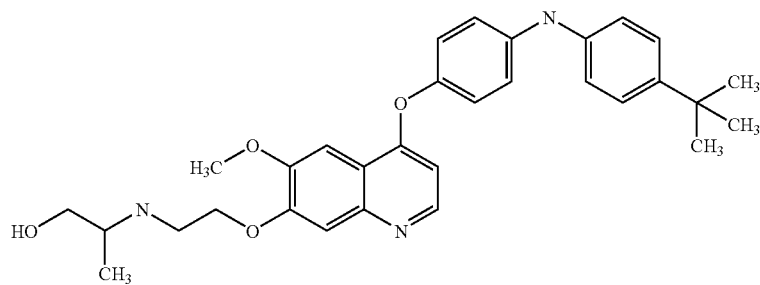
354 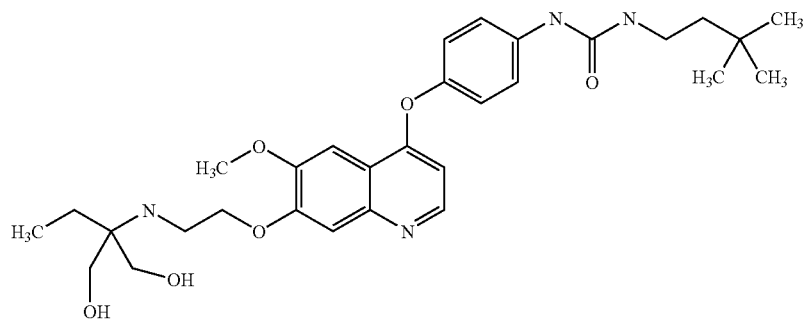
355 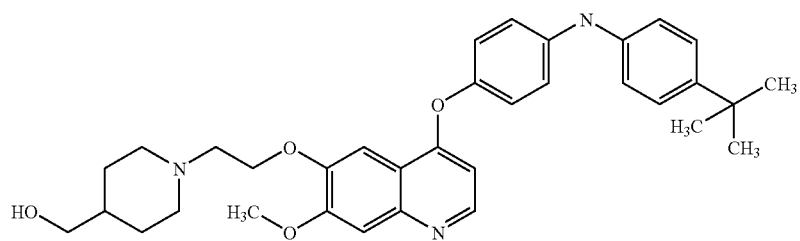

356 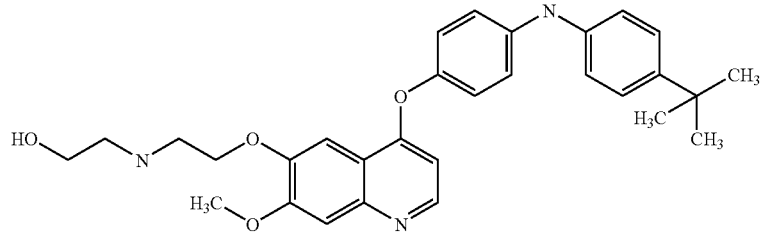
357 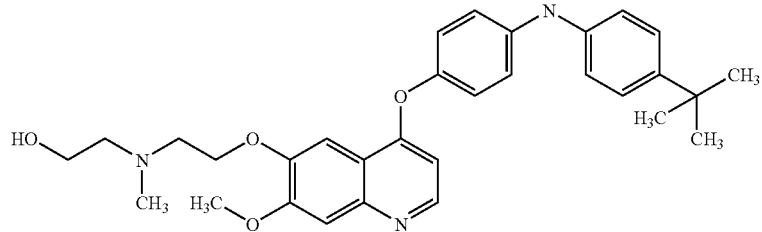
358 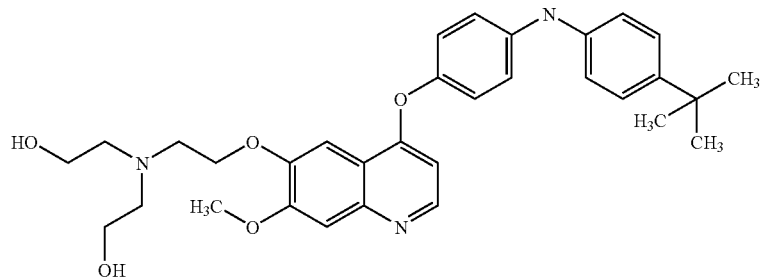
359 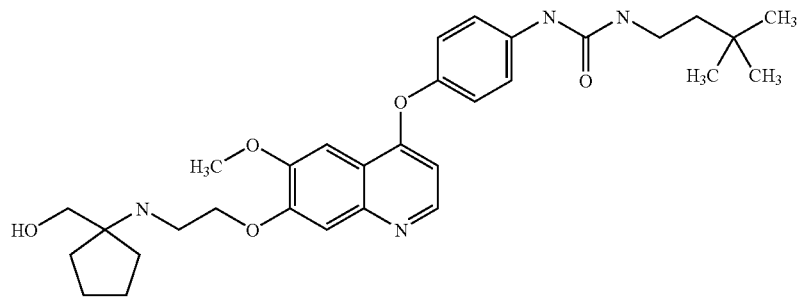
360 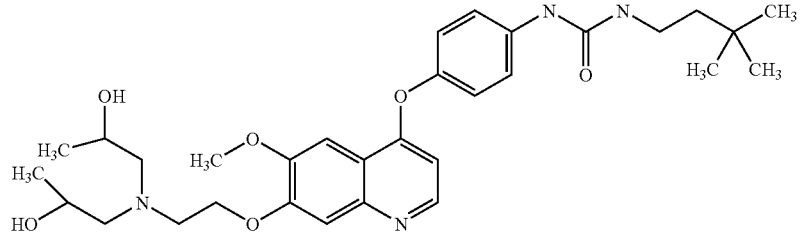
361 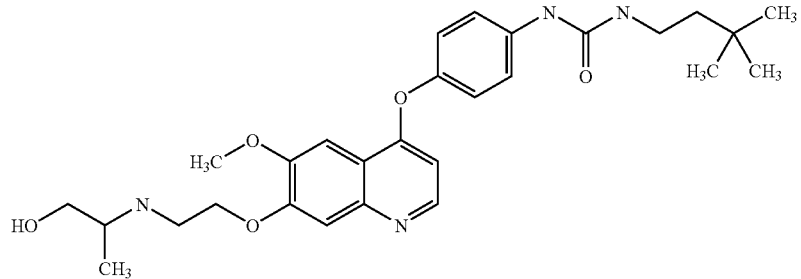

-continued
362
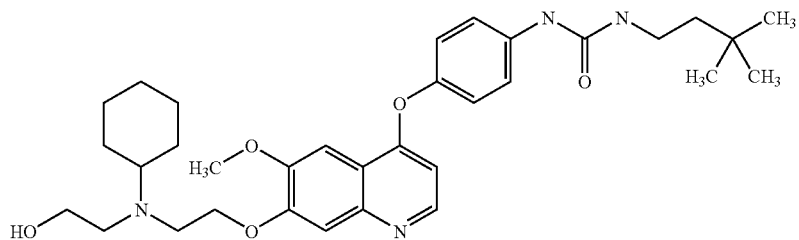
363
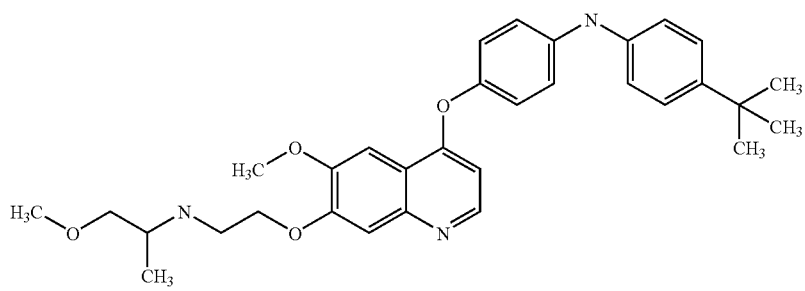
364
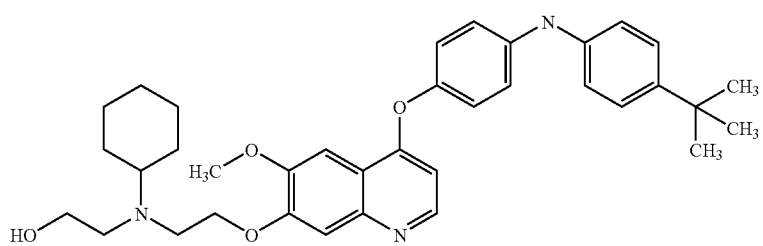
365
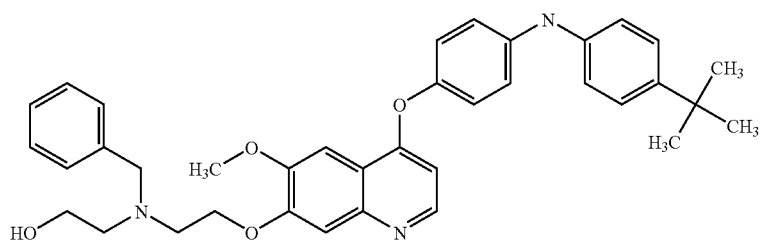
366
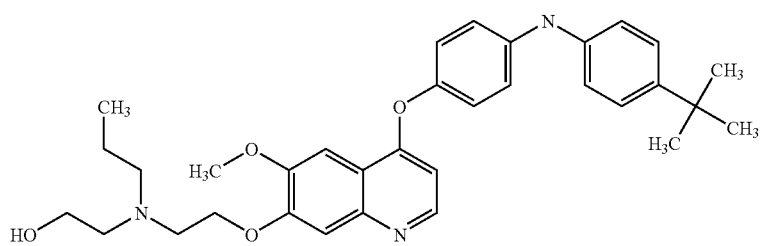
367
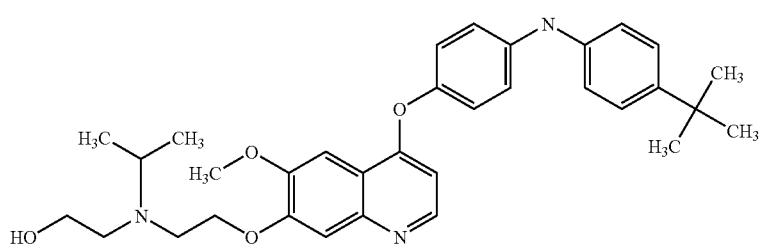

368 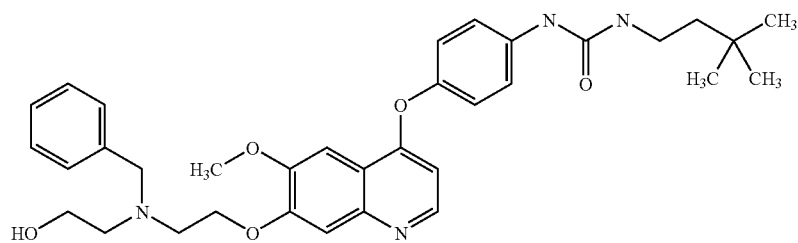
369 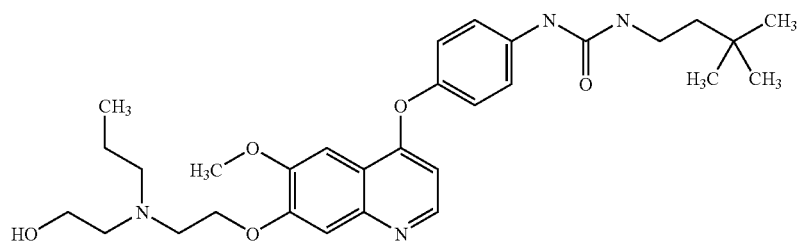
370 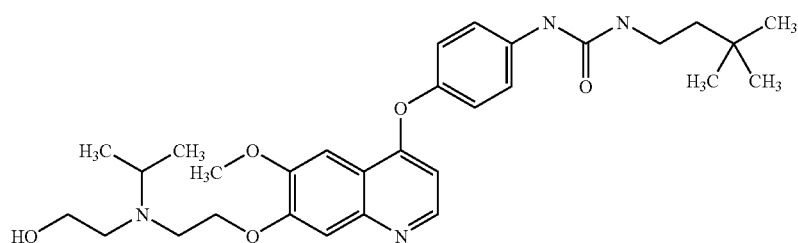
371 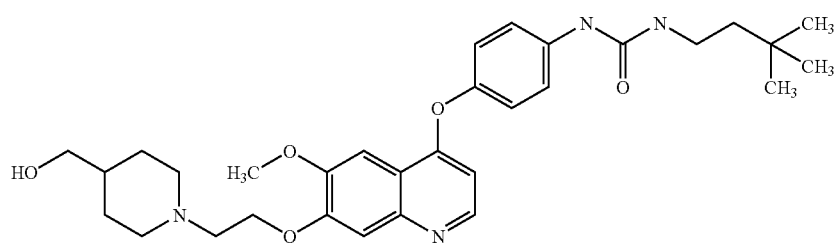
372 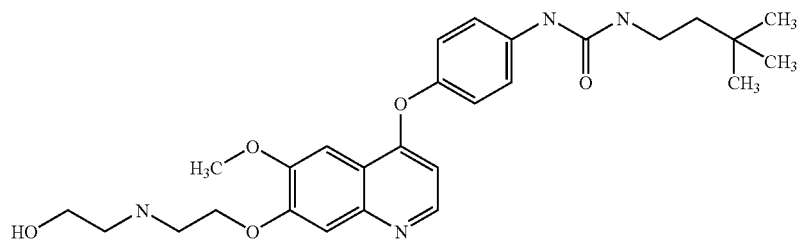
373 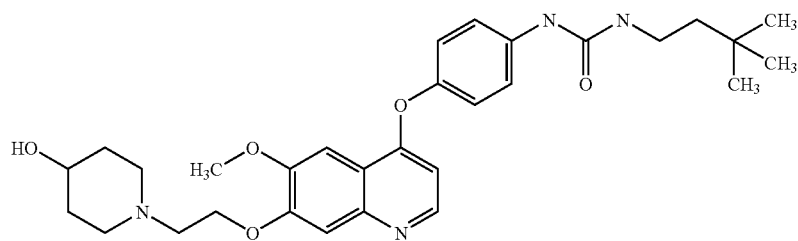

| | |
|---|---|
| 374 | 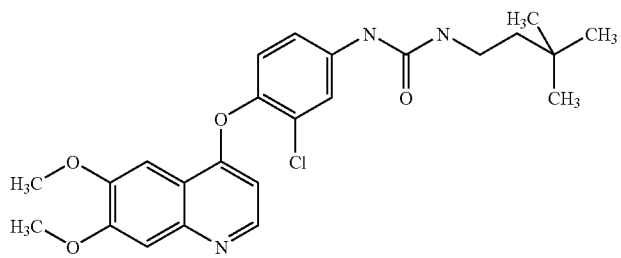 |
| 375 | 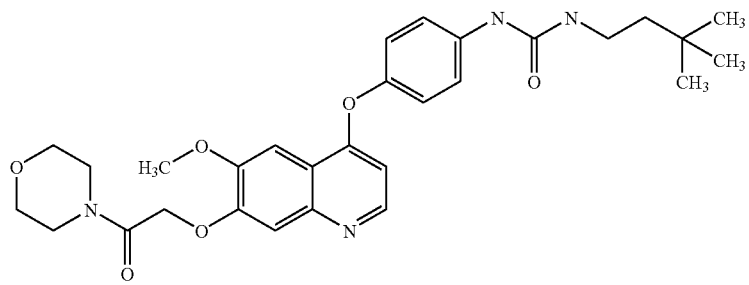 |

The following compounds were synthesized in the same manner as in the Synthesis Examples of the above compounds.

| Compound No. | Name of compound |
|---|---|
| 376: | 1-[4-(6,7-Dimethoxy-quinolin-4-yloxy)-3-fluoro-phenyl]-3-(3,3-dimethyl-butyl)-urea hydrochloride |
| 377: | 1-[3-Chloro-4-(6,7-dimethoxy-quinolin-4-yloxy)-phenyl]-3-(3,3-dimethyl-cyclohexyl)-urea |
| 378: | 1-[4-(6,7-Dimethoxy-quinolin-4-yloxy)-3-fluoro-phenyl]-3-(3,3-dimethyl-cyclohexyl)-urea |
| 379: | 1-[4-(6,7-Dimethoxy-quinolin-4-yloxy)-3-fluoro-phenyl]-3-(3,3-dimethyl-cyclohexyl)-urea |
| 380: | 1-[4-(6,7-Dimethoxy-quinolin-4-yloxy)-phenyl]-3-pentyl-urea |
| 381: | 1-Cyclohexyl-3-[4-(6,7-dimethoxy-quinolin-4-yloxy)-phenyl]-urea |
| 382: | 1-[4-(6,7-Dimethoxy-quinolin-4-yloxy)-phenyl]-3-(4,4-dimethyl-pentyl)-urea |
| 383: | 1-[4-(6,7-Dimethoxy-quinazolin-4-yloxy)-phenyl]-3-(3,3-dimethyl-butyl)-urea |
| 384: | 1-(3,3-Dimethyl-cyclohexyl)-3-{3-fluoro-4-[6-methoxy-7-(2-piperidin-1-yl-ethoxy)-quinolin-4-yloxy]-phenyl}-urea |
| 385: | 1-{3-Fluoro-4-[6-methoxy-7-(2-piperidin-1-yl-ethoxy)-quinolin-4-yloxy]-phenyl}-3-(3,3,5-trimethyl-cyclohexyl)-urea |
| 386: | 1-{2-Fluoro-4-[6-methoxy-7-(2-piperidin-1-yl-ethoxy)-quinolin-4-yloxy]-phenyl}-3-(3,3,5-trimethyl-cyclohexyl)-urea |
| 387: | 1-{4-[7-(2-Azepan-1-yl-ethoxy)-6-methoxy-quinolin-4-yloxy]-2-chloro-phenyl}-3-(3,3-dimethyl-butyl)-urea |
| 388: | 1-(3,3-Dimethyl-butyl)-3-(4-{6-methoxy-7-[3-(4-methyl-piperazin-1-yl)-propoxy]-quinolin-4-yloxy}-phenyl)-urea hydrochloride |
| 389: | 1-(3,3-Dimethyl-butyl)-3-(2-fluoro-4-{6-methoxy-7-[3-(4-methyl-piperazin-1-yl)-propoxy]-quinolin-4-yloxy}-phenyl)-urea |
| 390: | 1-(3,3-Dimethyl-butyl)-3-(3-chloro-4-{6-methoxy-7-[3-(4-methyl-piperazin-1-yl)-propoxy]-quinolin-4-yloxy}-phenyl)-urea |

For these compounds, chemical structures, starting compounds, synthesis methods, and data for identifying the compounds are as follows. The numeral described in the column of the synthesis method indicates that the indicated compound has been synthesized according to the Synthesis Example of the indicated compound number.

| Compound No | Structure of compound | Starting compound A |
|---|---|---|
| 376 | 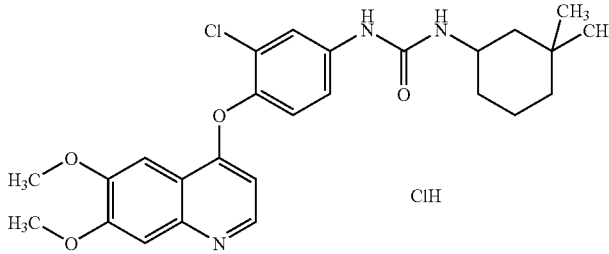 | 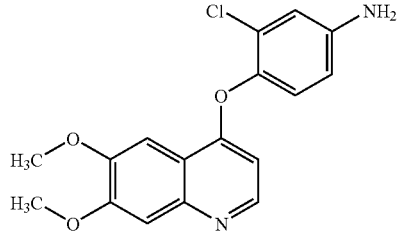 |
| 377 | 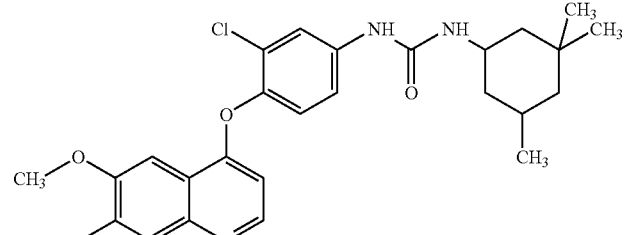 | 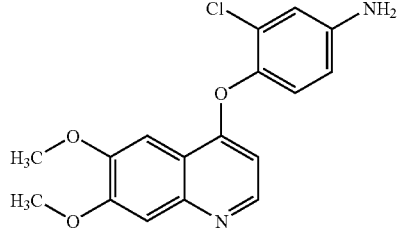 |
| 378 | 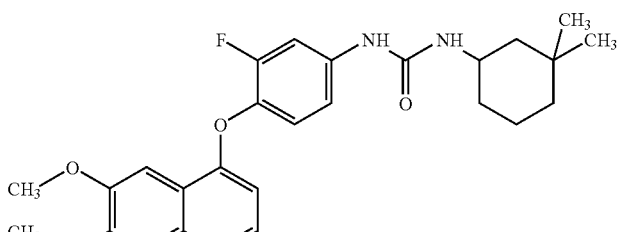 | 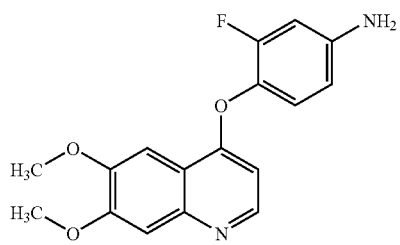 |
| 379 | 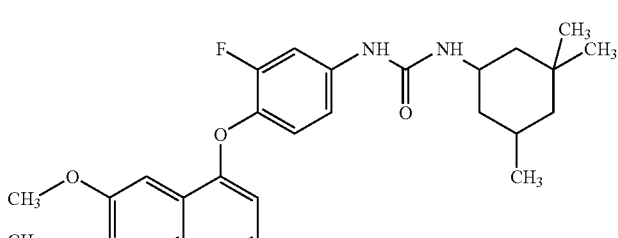 | 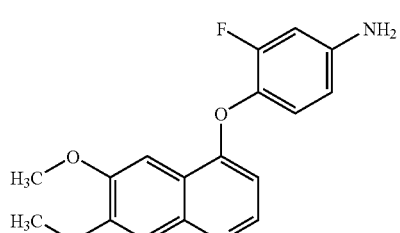 |
| 380 | 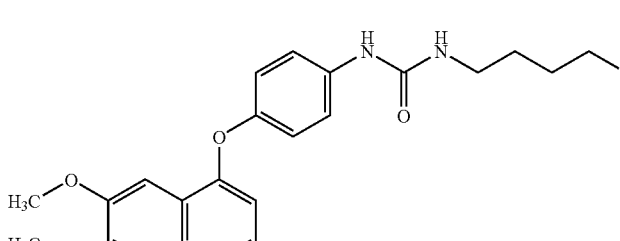 | 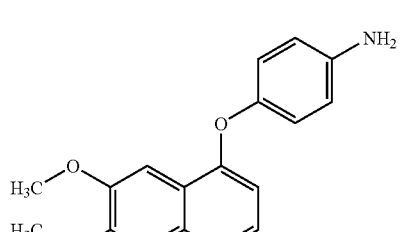 |
| Compound No. | Starting compound B | Synthesis method | Mass spectrometric value (m/z) |
|---|---|---|---|
| 376 | 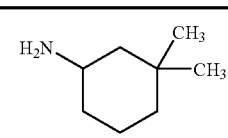 | 101 | 482 [M − 1]<br>484 [M + 1] |

| | -continued | | | |
|---|---|---|---|---|
| 377 | H2N-cyclohexyl with 3 CH3 groups (1,1,3-trimethyl) | 101 | 496 [M − 1] | |
| | | | 498 [M + 1] | |
| 378 | H2N-cyclohexyl with 2 CH3 (1,1-dimethyl) | 101 | 468 [M + 1] | |
| | | | 466 [M − 1] | |
| 379 | H2N-cyclohexyl with 3 CH3 (1,1,3-trimethyl isomer) | 101 | 482 [M + 1] | |
| | | | 480 [M − 1] | |
| 380 | H2N-(CH2)4-CH3 | 101 | 410 [M + 1] | |

| Compound No. | Structure of compound | Starting compound A |
|---|---|---|
| 381 | 6,7-dimethoxyquinoline-4-oxy-phenyl-NHC(O)NH-cyclohexyl | 6,7-dimethoxy-4-(4-aminophenoxy)quinoline |
| 382 | 6,7-dimethoxyquinoline-4-oxy-phenyl-NHC(O)NH-(CH2)3-C(CH3)3 | 6,7-dimethoxy-4-(4-aminophenoxy)quinoline |
| 383 | 6,7-dimethoxyquinazoline-4-oxy-phenyl-NHC(O)NH-(CH2)2-C(CH3)3 | 6,7-dimethoxy-4-(4-aminophenoxy)quinazoline |
| 384 | 7-(2-piperidinoethoxy)-6-methoxyquinoline-4-oxy-(2-fluorophenyl)-NHC(O)NH-(3,3-dimethylcyclohexyl) | 7-(2-chloroethoxy)-6-methoxyquinoline-4-oxy-(2-fluorophenyl)-NHC(O)NH-(3,3-dimethylcyclohexyl) |

-continued
385 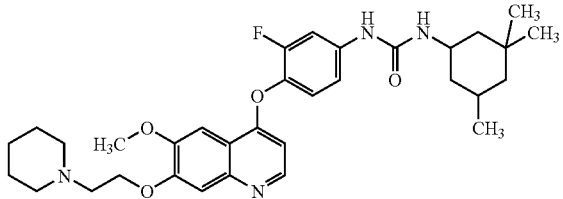 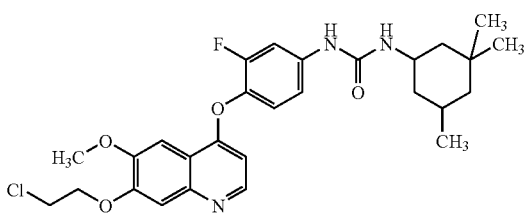
| Compound No. | Starting compound B | Synthesis method | Mass spectrometric value (m/z) |
|---|---|---|---|
| 381 | H₂N-cyclohexyl | 101 | 422 [M + 1] |
| 382 | H₂N(CH₂)₃C(CH₃)₃ | 101 | 438 [M + 1] |
| 383 | H₂N(CH₂)₂C(CH₃)₃ | 101 | 425 [M + 1] |
| 384 | piperidine (NH) | 99 | 565 [M + 1] |
| 385 | piperidine (NH) | 99 | 579 [M + 1] |
| Compound No. | Structure of compound |
|---|---|
| 386 | |
| 387 | |

| 388 | 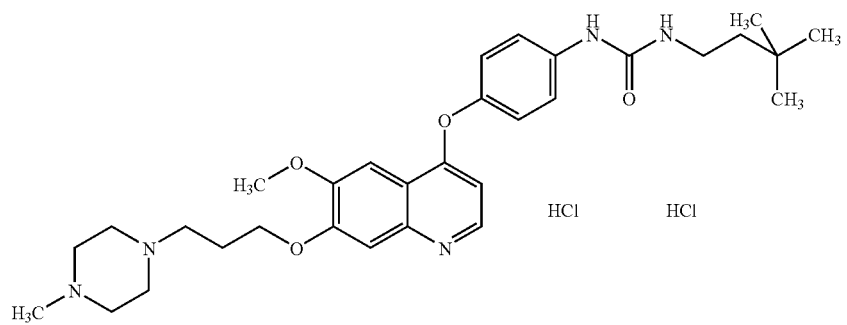 |
| --- | --- |
| 389 | 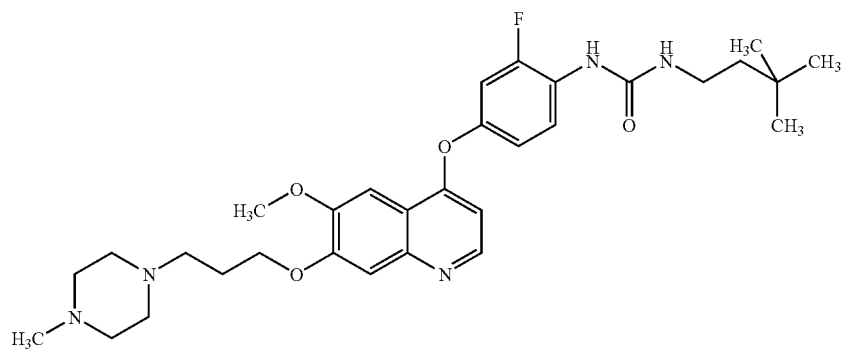 |
| 390 | 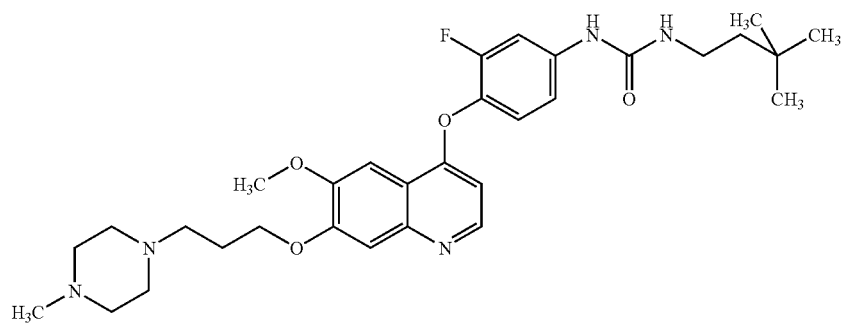 |
| Compound No. | Starting compound A |
| --- | --- |
| 386 | 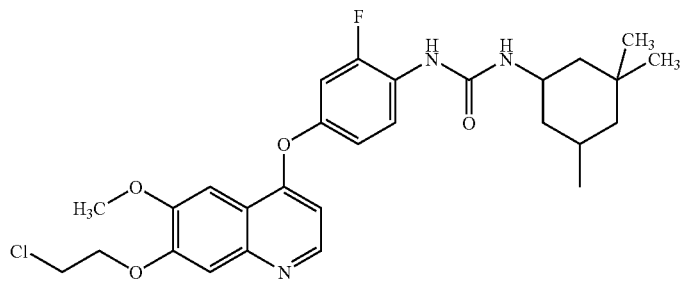 |

-continued
387 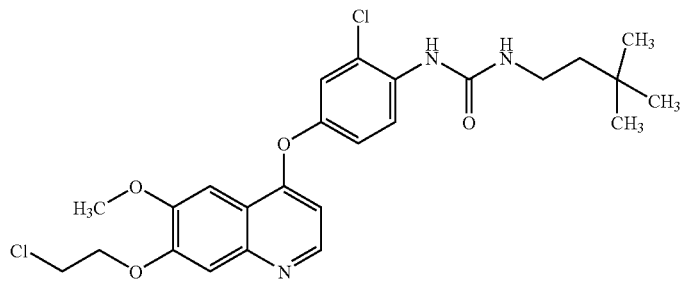
388 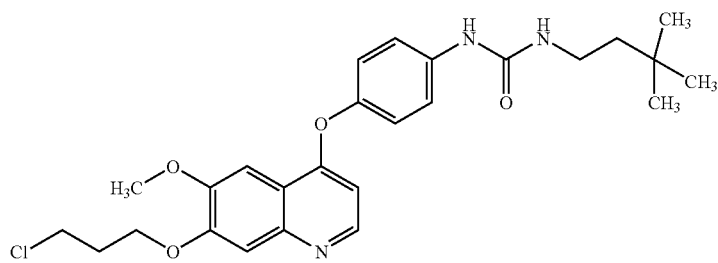
389 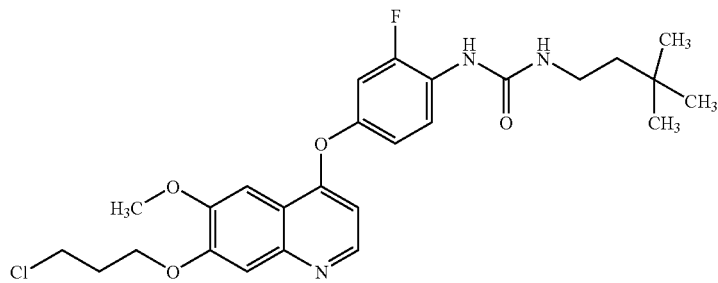
390 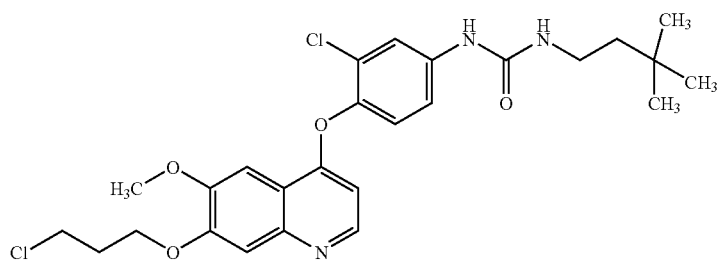
| Compound No. | Starting compound B | Synthesis method | Mass spectrometric value (m/z) |
| --- | --- | --- | --- |
| 386 | 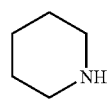 | 99 | 579 [M + 1] |
| 387 | 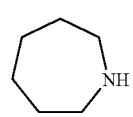 | 99 | 569 [M + 1] |
| 388 | 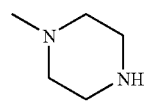 | 99 | 550 [M + 1] |

| | | | |
|---|---|---|---|
| 389 | 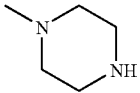 | 99 | 568 [M + 1] |
| 390 | 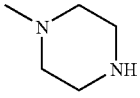 | 99 | 584 [M + 1] |

Pharmacological Test Example 1

Measurement of Inhibitory Activity against Bek-Autophosphorylation Using ELISA Method Human scirrhus stomach cancer cells OCUM-2MD3 (kindly provided by Dr. Kosei Hirakawa, Osaka City University) were cultured in an RPMI medium containing 10% fetal calf serum (purchased from ICN) within a 5% carbon dioxide incubator until 50 to 90% confluent. The harvested cells were seeded onto 96-well flat-bottom plate in RPMI containing 0.1% fetal calf serum at $3.5 \times 10^4$ cells per well, followed by cultivation at 37° C. overnight. A solution of the test compound in dimethyl sulfoxide was added to each well, and the cultivation was continued at 37° C. for additional one hr. The medium was removed, and 50 µl of lysis buffer (20 mM HEPES (pH 7.4), 150 mM NaCl, 0.2% Triton X-100, 10% glycerol, 5 mM sodium orthovanadylate, 5 mM disodium ethylenediaminetetraacetate, and 2 mM $Na_4P_2O_7$) was then added thereto. The mixture was shaken at 4° C. for 2 hr to prepare cell extracts.

Separately, phosphate buffered saline (50 µl, pH 7.4) containing 5 µg/ml of anti-phospho-tyrosine antibody (PY20; purchased from Transduction Laboratories) was added to a microplate for ELISA (Maxisorp; purchased from NUNC), followed by standing at 4° C. overnight to form a solid phase on the wells. After washing of the plate, 300 µl of a blocking solution was added, followed by standing at room temperature for 2 hr to perform blocking. After washing, the whole quantity of the cell extracts was transferred to the wells, and the plate was then allowed to stand at 4° C. overnight. After washing, an anti-Bek antibody (Bek (C-17), purchased from Santa Cruz Biotechnology) or Anti-Human K-sam Rabbit IgG Affinity Purity (purchased from IBL Co., Ltd.) was allowed to react at room temperature for one hr, and, after washing, a peroxidase-labeled anti-rabbit Ig antibody (purchased from Amersham) was allowed to react at room temperature for one hr. After washing, a chromophoric substrate for peroxidase (purchased from Sumitomo Bakelite Co., Ltd.) was added thereto to initiate a reaction. After a suitable level of color development, a reaction termination solution was added to stop the reaction, and the absorbance at 450 nm was measured with a microplate reader. The Bek-phosphorylation activity for each well was determined by presuming the absorbance without the addition of the medicament to be 100% Bek-phosphorylation activity and the absorbance with the addition of a large excess of a positive control (N-{4-[(6, 7-dimethoxy-4-quinolyl)oxy]phenyl}-N'-(3,3-dimethylbutyl)urea, 1000 nM) to be 0% Bek-phosphorylation activity. The concentration of the test compound was varied on several levels, the Bek-phosphorylation inhibitory activity was determined for each case, and the concentration of the test compound necessary for inhibiting 50% of Bek-phosphorylation ($IC_{50}$) was calculated. The results were as shown in Table 1.

TABLE 1

| Compound No. | IC50, uM |
|---|---|
| 1 | 3.9286 |
| 2 | 7.9407 |
| 3 | 4.5819 |
| 4 | 3.7268 |
| 5 | 0.3209 |
| 6 | 0.8753 |
| 7 | 1.7965 |
| 8 | 1.5028 |
| 9 | 0.3127 |
| 10 | 0.6314 |
| 11 | 0.3199 |
| 12 | 0.2853 |
| 13 | 0.2791 |
| 14 | 1.9230 |
| 15 | 0.4298 |
| 16 | 0.2418 |
| 17 | 5.6149 |
| 18 | 0.1554 |
| 19 | 0.1946 |
| 20 | 0.3254 |
| 21 | 0.3279 |
| 22 | 0.1891 |
| 23 | 0.7617 |
| 24 | 0.1831 |
| 25 | 0.1994 |
| 26 | 0.3176 |
| 27 | 2.5210 |
| 28 | 2.4043 |
| 29 | 0.9310 |
| 30 | 3.2615 |
| 31 | 1.0087 |
| 32 | 0.6935 |
| 33 | 0.1554 |
| 34 | 0.2188 |
| 35 | 0.2205 |
| 36 | 0.2469 |
| 37 | 0.3449 |
| 38 | 0.4626 |
| 39 | 0.5703 |
| 40 | 0.9242 |
| 41 | 0.4799 |
| 42 | 0.3989 |
| 43 | 3.3410 |
| 44 | 0.0765 |
| 45 | 0.2403 |
| 46 | 0.2300 |
| 47 | 0.2433 |
| 48 | 0.0335 |
| 49 | 0.0339 |
| 50 | 0.0350 |
| 51 | 0.0306 |
| 52 | 0.0330 |
| 53 | 0.0380 |
| 54 | 0.3242 |
| 55 | 8.0027 |
| 56 | 0.4054 |
| 57 | 3.8267 |
| 58 | 1.1998 |
| 59 | 0.1427 |
| 60 | 0.2034 |

TABLE 1-continued

| Compound No. | IC50, uM |
|---|---|
| 61 | 0.1865 |
| 62 | 0.2494 |
| 63 | 0.2466 |
| 64 | 0.1782 |
| 65 | 0.1845 |
| 66 | 0.1986 |
| 67 | 0.1885 |
| 68 | 0.2483 |
| 69 | 0.2477 |
| 70 | 0.0685 |
| 71 | 0.0611 |
| 72 | 0.8359 |
| 73 | 3.5085 |
| 74 | 0.5206 |
| 75 | 5.1890 |
| 76 | 7.5605 |
| 77 | 3.4479 |
| 78 | 0.2737 |
| 79 | 0.1587 |
| 80 | 0.1512 |
| 81 | 0.0101 |
| 82 | 0.0701 |
| 87 | <0.0100 |
| 88 | 0.0108 |
| 89 | <0.0100 |
| 90 | 0.0126 |
| 91 | 0.0184 |
| 94 | <0.0100 |
| 96 | <0.0100 |
| 97 | <0.0100 |
| 98 | <0.0100 |
| 99 | 0.0286 |
| 100 | 0.1753 |
| 101 | <0.0100 |
| 102 | 0.0278 |
| 103 | 0.0298 |
| 105 | 0.0306 |
| 106 | 0.0197 |
| 107 | <0.0100 |
| 108 | <0.0100 |
| 109 | <0.0100 |
| 110 | <0.0100 |
| 111 | <0.0100 |
| 112 | 0.0521 |
| 113 | 0.01 |
| 114 | 0.0201 |
| 115 | <0.0100 |
| 116 | 0.0144 |
| 117 | 0.1778 |
| 119 | <0.0100 |
| 120 | 0.021 |
| 121 | 0.088 |
| 122 | 0.1509 |
| 123 | <0.0100 |
| 124 | <0.0100 |
| 125 | 0.013 |
| 126 | 0.0133 |
| 127 | 0.0094 |
| 128 | <0.0100 |
| 129 | 0.0481 |
| 130 | 0.1623 |
| 131 | 0.1607 |
| 132 | 0.1463 |
| 133 | 0.0092 |
| 134 | 0.0118 |
| 136 | 0.0562 |
| 137 | 0.0667 |
| 138 | 0.3166 |
| 139 | 1.1584 |
| 140 | 0.1723 |
| 141 | 0.0586 |
| 142 | 0.2653 |
| 143 | 0.1925 |
| 144 | 0.2018 |
| 147 | 0.6539 |
| 148 | 1.6713 |
| 149 | 0.2182 |

TABLE 1-continued

| Compound No. | IC50, uM |
|---|---|
| 150 | 0.0638 |
| 151 | 0.2214 |
| 152 | 0.025 |
| 153 | 0.2408 |
| 154 | 0.0244 |
| 155 | 0.0287 |
| 156 | 0.0191 |
| 157 | 0.0285 |
| 158 | 0.0321 |
| 159 | 0.0262 |
| 160 | 0.0235 |
| 161 | 0.1887 |
| 162 | 0.2522 |
| 163 | 0.3696 |
| 164 | 0.2598 |
| 165 | 0.0689 |
| 166 | 0.039 |
| 167 | 0.095 |
| 168 | 0.024 |
| 169 | 0.0252 |
| 170 | 0.0244 |
| 171 | 0.0324 |
| 172 | <0.0100 |
| 173 | 0.1526 |
| 175 | 0.0217 |
| 176 | <0.0100 |
| 177 | 0.0106 |
| 178 | <0.0100 |
| 179 | 0.0173 |
| 180 | 0.0227 |
| 181 | 0.0262 |
| 182 | 0.0095 |
| 183 | 0.0154 |
| 184 | 0.0092 |
| 185 | 0.0548 |
| 186 | 0.0183 |
| 187 | 0.0223 |
| 188 | 0.0299 |
| 189 | 0.0833 |
| 190 | 0.0335 |
| 191 | 0.0106 |
| 192 | 0.0091 |
| 193 | 0.0174 |
| 194 | 0.0197 |
| 195 | <0.0100 |
| 196 | 0.0173 |
| 197 | <0.0100 |
| 198 | 0.0123 |
| 199 | <0.0100 |
| 200 | 0.0211 |
| 201 | <0.0100 |
| 202 | 0.0285 |
| 203 | 0.0297 |
| 204 | 0.2343 |
| 205 | 0.0255 |
| 206 | 0.0185 |
| 207 | 0.06 |
| 208 | 0.027 |
| 209 | <0.0100 |
| 210 | <0.0100 |
| 211 | <0.0100 |
| 212 | 0.1374 |
| 213 | 0.1255 |
| 214 | 0.0261 |
| 215 | 0.341 |
| 216 | 0.1741 |
| 217 | 0.0409 |
| 218 | 0.096 |
| 219 | <0.0100 |
| 220 | 0.012 |
| 221 | 0.7625 |
| 222 | 0.0243 |
| 223 | 0.0498 |
| 224 | 0.0704 |
| 225 | 0.0199 |
| 226 | 0.0279 |
| 227 | 0.0239 |

TABLE 1-continued

| Compound No. | IC50, uM |
|---|---|
| 228 | 0.0385 |
| 229 | 0.1559 |
| 230 | 0.0321 |
| 231 | 0.1133 |
| 232 | 0.1029 |
| 233 | 0.3711 |
| 236 | 0.2688 |
| 237 | 0.2072 |
| 238 | 0.0472 |
| 239 | 0.8949 |
| 242 | 0.4007 |
| 243 | 0.3415 |
| 244 | <0.0100 |
| 245 | 0.0165 |
| 246 | 0.0309 |
| 247 | 0.0819 |
| 248 | 0.0126 |
| 249 | <0.0100 |
| 250 | <0.0100 |
| 251 | 0.0207 |
| 252 | 0.0426 |
| 253 | 0.0285 |
| 254 | 0.0942 |
| 258 | 0.11 |
| 259 | 0.0466 |
| 260 | 0.0267 |
| 261 | <0.0100 |
| 262 | <0.0100 |
| 263 | <0.0100 |
| 264 | 1.4351 |
| 265 | <0.0100 |
| 266 | 0.011 |
| 267 | 0.0267 |
| 268 | 0.0157 |
| 269 | 0.0356 |
| 270 | 0.303 |
| 271 | 0.0332 |
| 272 | 0.1512 |
| 273 | 0.1612 |
| 274 | 0.0278 |
| 275 | 0.0316 |
| 276 | 1.1253 |
| 277 | 0.617 |
| 278 | 1.1247 |
| 279 | 0.3699 |
| 280 | 0.2784 |
| 281 | 0.2443 |
| 282 | 0.0316 |
| 283 | 0.167 |
| 284 | 0.2467 |
| 285 | 0.0228 |
| 286 | 0.0172 |
| 287 | 0.2541 |
| 288 | 0.1095 |
| 289 | 0.2482 |
| 290 | 0.2329 |
| 292 | 0.0496 |
| 293 | 2.3564 |
| 294 | 1.1001 |
| 295 | 0.0144 |
| 296 | 0.0198 |
| 297 | 0.0424 |
| 298 | 0.0417 |
| 299 | 0.0274 |
| 300 | 0.0227 |
| 301 | 0.0384 |
| 302 | 0.0266 |
| 303 | 0.022 |
| 304 | 0.0312 |
| 305 | 0.3593 |
| 306 | 0.2865 |
| 307 | 0.3792 |
| 308 | 0.2045 |
| 309 | 0.2111 |
| 310 | 0.1837 |
| 311 | 0.0231 |
| 312 | 0.0205 |

TABLE 1-continued

| Compound No. | IC50, uM |
|---|---|
| 313 | 0.3674 |
| 314 | 0.2772 |
| 315 | 0.1328 |
| 316 | 0.0851 |
| 317 | 0.0204 |
| 318 | 0.0187 |
| 319 | 0.022 |
| 320 | 0.0214 |
| 321 | 0.0254 |
| 322 | 0.247 |
| 323 | 0.3733 |
| 324 | 0.2868 |
| 325 | 0.0342 |
| 326 | <0.0100 |
| 327 | 0.0206 |
| 328 | 0.037 |
| 329 | 0.0208 |
| 330 | 0.0178 |
| 331 | 0.0301 |
| 332 | 0.0108 |
| 333 | 0.0094 |
| 334 | 0.0165 |
| 335 | 0.0953 |
| 336 | 0.053 |
| 337 | 0.252 |
| 338 | 0.0166 |
| 339 | 0.0164 |
| 340 | 0.0183 |
| 341 | 0.0289 |
| 342 | 0.0116 |
| 343 | <0.0100 |
| 344 | <0.0100 |
| 345 | 0.0098 |
| 346 | 0.2941 |
| 347 | 0.3541 |
| 348 | 0.1862 |
| 349 | 0.0959 |
| 350 | 0.3342 |
| 351 | 0.2323 |
| 352 | 0.0547 |
| 353 | 0.3741 |
| 354 | 0.0384 |
| 355 | 0.4027 |
| 356 | 0.3467 |
| 357 | 0.2131 |
| 358 | 0.0517 |
| 359 | 0.2542 |
| 360 | 0.0195 |
| 361 | 0.0298 |
| 362 | 0.0492 |
| 363 | 0.3636 |
| 364 | 0.2301 |
| 365 | 7.1303 |
| 366 | 0.2571 |
| 367 | 0.4681 |
| 368 | 0.1566 |
| 369 | 0.0423 |
| 370 | 0.1303 |
| 371 | <0.0100 |
| 372 | <0.0100 |
| 373 | <0.0100 |
| 374 | 0.0328 |
| 375 | 0.028 |

Pharmacological Test Example 2

Tumor Growth Inhibitory Activity against Human Gastric Cancer Cells (OCUM-2MD3)

Human gastric cancer cells (OCUM-2MD3) (kindly provided by Dr. Kosei Hirakawa, Osaka City University) were transplanted into nude mice. When the tumor volume became about 100 to 200 mm$^3$, the mice were grouped so that the groups each consisted of four mice and had an even average tumor volume. The test compound suspended in 0.5% methylcellulose was orally administered every day twice a day for 5 days (except for the first day on which the suspension was administered once a day).

Only 0.5% methylcellulose was administered to the control group in the manner as in the test groups. The tumor growth inhibition rate (TGIR) was calculated as follows: The tumor growth inhibition rate (TGIR)=(1−TX/CX)×100 wherein CX represents the volume of tumor at day X for the control group when the tumor volume at the day of the start of the administration was presumed to be 1; and TX represents the volume of tumor for test compound administration groups.

The tumor growth inhibition rate for representative examples of a group of compounds according to the present invention is shown in Table 2.

TABLE 2

| | Unit dose, mg/kg | TGIR, % |
|---|---|---|
| Compound 37 (hydrochloride) | 10 | 35 |
| Compound 59 (hydrochloride) | 10 | 16 |

Pharmacological Test Example 3

Tumor Growth Inhibitory Activity against Human Gastric Cancer Cells (OCUM-2MD3)

Tumor growth inhibitory activity was measured in the same manner as in Pharmacological Test Example 2, except that oral administration was carried out once a day or twice a day (except for the first day on which the suspension was administered once a day).

The tumor growth inhibition rate for representative examples of a group of compounds according to the present invention is shown in Table 3.

TABLE 3

| | Dose per day | TGIR, % |
|---|---|---|
| Compound 83 | 10 mg × 2 | 34 |
| Compound 84 | 10 mg × 2 | 33 |
| Compound 85 | 10 mg × 2 | 43 |
| Compound 86 | 10 mg × 2 | 30 |
| Compound 87 | 10 mg × 2 | 33 |
| Compound 87 | 25 mg × 1 | 54 |
| Compound 88 | 10 mg × 2 | 35 |
| Compound 89 | 10 mg × 2 | 29 |
| Compound 90 | 10 mg × 2 | 36 |
| Compound 91 | 25 mg × 1 | 28 |
| Compound 94 | 10 mg × 2 | 40 |
| Compound 97 | 25 mg × 1 | 48 |
| Compound 98 | 25 mg × 1 | 48 |
| Compound 99 | 25 mg × 1 | 63 |
| Compound 100 | 25 mg × 1 | 43 |
| Compound 114 | 30 mg × 2 | 48 |

The invention claimed is:
1. A compound represented by formula (100):

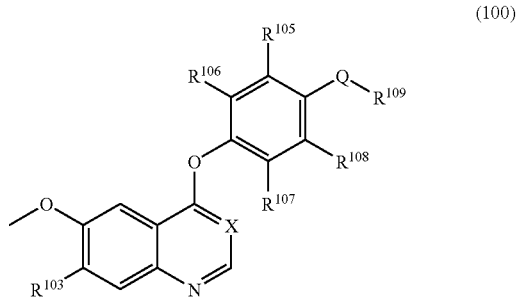

(100)

wherein
X represents CH or N;
Q represents
a) —N(—$R^{110}$)- wherein $R^{110}$ represents a hydrogen atom or $C_{1-4}$ alkyl,
b) —C($R^{111}$)(—$R^{112}$)- wherein $R^{111}$ and $R^{112}$, which may be the same or different, represent a hydrogen atom or $C_{1-4}$ alkylcarbonyloxy, or
c) —O—;
$R^{103}$ represents $C_{1-6}$ alkoxy in which the $C_{1-6}$ alkoxy group is optionally substituted by hydroxyl; a halogen atom; $C_{1-6}$ alkoxy; $C_{1-6}$ alkylcarbonyl; carboxyl; $C_{1-6}$ alkoxycarbonyl; —(C=O)—$NR^{14}R^{15}$ wherein $R^{14}$ and $R^{15}$, which may be the same or different, represent a hydrogen atom or $C_{1-4}$ alkyl optionally substituted by hydroxyl, or alternatively $R^{14}$ and $R^{15}$ may combine with the nitrogen atom attached thereto to form a saturated five- or six-membered heterocyclic group; amino in which one or two hydrogen atoms on the amino group are optionally substituted by $C_{1-6}$ alkyl or a saturated or unsaturated three- to eight-membered carbocyclic or heterocyclic group, and the $C_{1-6}$ alkyl group is optionally substituted by hydroxyl, $C_{1-6}$ alkoxy, or a saturated or unsaturated three- to eight-membered carbocyclic or heterocyclic group; or a saturated or unsaturated three- to eight-membered carbocyclic or heterocyclic group in which the carbocyclic or heterocyclic group is optionally substituted by hydroxyl, an oxygen atom, $C_{1-6}$ alkyl, $C_{2-6}$ alkenyl, $C_{2-6}$ alkynyl, $C_{1-6}$ alkoxy, $C_{1-6}$ alkoxycarbonyl, or a saturated or unsaturated three- to eight-membered carbocyclic or heterocyclic group; the $C_{1-6}$ alkyl, $C_{2-6}$ alkenyl, and $C_{2-6}$ alkynyl groups are optionally substituted by hydroxyl, $C_{1-6}$ alkoxy, or a saturated or unsaturated three- to eight-membered carbocyclic or heterocyclic group; when the carbocyclic or heterocyclic group is substituted by two $C_{1-6}$ alkyl groups, the two alkyl groups may combine together to form an alkylene chain; and the carbocyclic or heterocyclic group may be condensed with another saturated or unsaturated five- to seven-membered carbocyclic or heterocyclic group to form a bicyclic group;
all of $R^{105}$, $R^{106}$, $R^{107}$, and $R^{108}$ represent a hydrogen atom, or any one or two of $R^{105}$, $R^{106}$, $R^{107}$, and $R^{108}$ represent a halogen atom, $C_{1-4}$ alkyl, $C_{1-4}$ alkoxy, nitro, or amino with all the remaining groups representing a hydrogen atom; and
$R^{109}$ represents a saturated or unsaturated four- to seven-membered carbocyclic or heterocyclic group in which the four- to seven-membered carbocyclic or heterocyclic group is optionally substituted by an oxygen atom, $C_{1-4}$ alkyl, $C_{2-4}$ alkenyl, $C_{1-4}$ alkoxy, a halogen atom, or a saturated or unsaturated four- to seven-membered carbocyclic or heterocyclic group, and the $C_{1-4}$ alkyl, $C_{2-4}$ alkenyl, and $C_{1-4}$ alkoxy groups are optionally substituted by a halogen atom or saturated or unsaturated four- to seven-membered carbocyclic or heterocyclic group, or a pharmaceutically acceptable salt thereof.

2. A compound represented by formula (200):

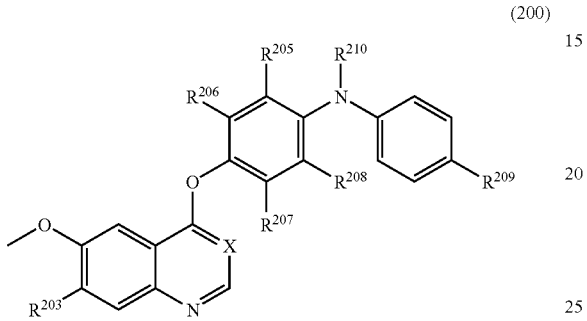

(200)

wherein

X represents CH or N;

$R^{203}$ represents —O—$(CH_2)$p-$R^{13}$ wherein p is an integer of 1 to 6, —$(CH_2)$p- is optionally substituted by $C_{1-6}$ alkyl, hydroxyl, or a halogen atom, and $R^{13}$ represents hydroxyl; a halogen atom; $C_{1-6}$ alkoxy; $C_{1-6}$ alkylcarbonyl; carboxyl; $C_{1-6}$ alkoxycarbonyl; —(C=O)—$NR^{14}R^{15}$ wherein $R^{14}$ and $R^{15}$, which may be the same or different, represent a hydrogen atom or $C_{1-4}$ alkyl optionally substituted by hydroxyl, or alternatively $R^{14}$ and $R^{15}$ may combine with the nitrogen atom attached thereto to form a saturated five- or six-membered heterocyclic group; $C_{1-6}$ alkoxycarbonyl; amino in which one or two hydrogen atoms on the amino group are optionally substituted by $C_{1-6}$ alkyl or a saturated or unsaturated three- to eight-membered carbocyclic or heterocyclic group, and the $C_{1-6}$ alkyl group is optionally substituted by hydroxyl, $C_{1-6}$ alkoxy, or a saturated or unsaturated three- to eight-membered carbocyclic or heterocyclic group; or a saturated or unsaturated three- to eight-membered carbocyclic or heterocyclic group in which the carbocyclic or heterocyclic group is optionally substituted by hydroxyl, an oxygen atom, $C_{1-6}$ alkyl, $C_{2-6}$ alkenyl, $C_{2-6}$ alkynyl, $C_{1-6}$ alkoxy, $C_{1-6}$ alkoxycarbonyl, or a saturated or unsaturated three- to eight-membered carbocyclic or heterocyclic group; the $C_{1-6}$ alkyl, $C_{2-6}$ alkenyl, and $C_{2-6}$ alkynyl groups are optionally substituted by hydroxyl, $C_{1-6}$ alkoxy, or a saturated or unsaturated three- to eight-membered carbocyclic or heterocyclic group; when the carbocyclic or heterocyclic group is substituted by two $C_{1-6}$ alkyl groups, the two alkyl groups may combine together to form an alkylene chain; and the carbocyclic or heterocyclic group may be condensed with another saturated or unsaturated five- to seven-membered carbocyclic or heterocyclic group to form a bicyclic group;

all of $R^{205}$, $R^{206}$, $R^{207}$, and $R^{208}$ represent a hydrogen atom, or any one or two of $R^{205}$, $R^{206}$, $R^{207}$, and $R^{208}$ represent a halogen atom, $C_{1-4}$ alkyl, $C_{1-4}$ alkoxy, nitro, or amino with all the remaining groups representing a hydrogen atom; and $R^{209}$ represents $C_{1-4}$ alkyl or a saturated or unsaturated four- to seven-membered carbocyclic or heterocyclic group and $R^{210}$ represents a hydrogen atom or $C_{1-4}$ alkyl, or a pharmaceutically acceptable salt thereof.

3. A compound represented by formula (300):

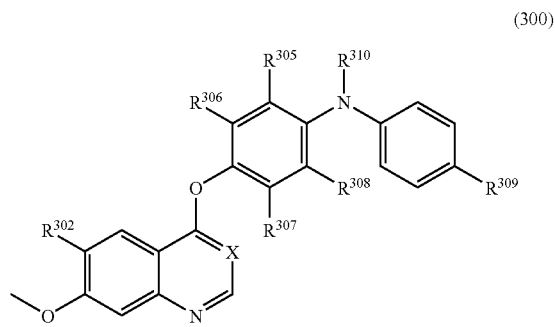

(300)

wherein

X represents CH or N;

$R^{302}$ represents —O—$(CH_2)$p-$R^{13}$ wherein p is an integer of 1 to 6, —$(CH_2)$p- is optionally substituted by $C_{1-6}$ alkyl, hydroxyl, or a halogen atom, and $R^{13}$ represents hydroxyl; a halogen atom; $C_{1-6}$ alkoxy; $C_{1-6}$ alkylcarbonyl; carboxyl; $C_{1-6}$ alkoxycarbonyl; —(C=O)-$NR^{14}R^{15}$ wherein $R^{14}$ and $R^{15}$, which may be the same or different, represent a hydrogen atom or $C_{1-4}$ alkyl optionally substituted by hydroxyl, or alternatively $R^{14}$ and $R^{15}$ may combine with the nitrogen atom attached thereto to form a saturated five- or six-membered heterocyclic group; $C_{1-6}$ alkoxycarbonyl; amino in which one or two hydrogen atoms on the amino group are optionally substituted by $C_{1-6}$ alkyl or a saturated or unsaturated three- to eight-membered carbocyclic or heterocyclic group, and the $C_{1-6}$ alkyl group is optionally substituted by hydroxyl, $C_{1-6}$ alkoxy, or a saturated or unsaturated three- to eight-membered carbocyclic or heterocyclic group; or a saturated or unsaturated three- to eight-membered carbocyclic or heterocyclic group in which the carbocyclic or heterocyclic group is optionally substituted by hydroxyl, an oxygen atom, $C_{1-6}$ alkyl, $C_{2-6}$ alkenyl, $C_{2-6}$ alkynyl, $C_{1-6}$ alkoxy, $C_{1-6}$ alkoxycarbonyl, or a saturated or unsaturated three- to eight-membered carbocyclic or heterocyclic group; the $C_{1-6}$ alkyl, $C_{2-6}$ alkenyl, and $C_{2-6}$ alkynyl groups are optionally substituted by hydroxyl, $C_{1-6}$ alkoxy, or a saturated or unsaturated three- to eight-membered carbocyclic or heterocyclic group; when the carbocyclic or heterocyclic group is substituted by two $C_{1-6}$ alkyl groups, the two alkyl groups may combine together to form an alkylene chain; and the carbocyclic or heterocyclic group may be condensed with another saturated or unsaturated five- to seven-membered carbocyclic or heterocyclic group to form a bicyclic group;

all of $R^{305}$, $R^{306}$, $R^{307}$, and $R^{308}$ represent a hydrogen atom, or any one or two of $R^{305}$, $R^{306}$, $R^{307}$, and $R^{308}$ represent a halogen atom, $C_{1-4}$ alkyl, $C_{1-4}$ alkoxy, nitro, or amino with all the remaining groups representing a hydrogen atom; and $R^{309}$ represents $C_{1-4}$ alkyl or a saturated or unsaturated four- to seven-membered carbocyclic or heterocyclic group and $R^{310}$ represents a hydrogen atom or $C_{1-4}$ alkyl, or a pharmaceutically acceptable salt thereof.

4. A compound represented by formula (400):

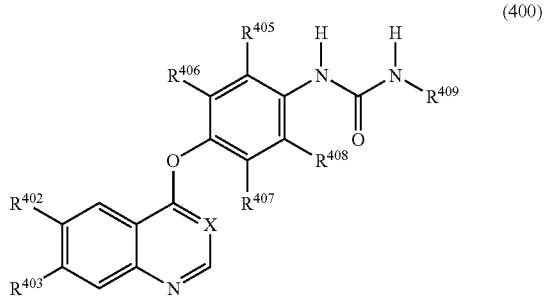

(400)

wherein

X represents CH or N;

$R^{402}$ and $R^{403}$, which may be the same or different, represent —O—$(CH_2)$p-$R^{13}$ wherein p is an integer of 0 to 6, —$(CH_2)$p- is optionally substituted by $C_{1-6}$ alkyl, hydroxyl, or a halogen atom, and $R^{13}$ represents a hydrogen atom; hydroxyl; a halogen atom; $C_{1-6}$ alkoxy; $C_{1-6}$ alkylcarbonyl; carboxyl; $C_{1-6}$ alkoxycarbonyl; —(C=O)—$NR^{14}R^{15}$ wherein $R^{14}$ and $R^{15}$, which may be the same or different, represent a hydrogen atom or $C_{1-4}$ alkyl optionally substituted by hydroxyl, or alternatively $R^{14}$ and $R^{15}$ may combine with the nitrogen atom attached thereto to form a saturated five- or six-membered heterocyclic group; $C_{1-6}$ alkoxycarbonyl; amino in which one or two hydrogen atoms on the amino group are optionally substituted by $C_{1-6}$ alkyl or a saturated or unsaturated three- to eight-membered carbocyclic or heterocyclic group, and the $C_{1-6}$ alkyl group is optionally substituted by hydroxyl, $C_{1-6}$ alkoxy, or a saturated or unsaturated three- to eight-membered carbocyclic or heterocyclic group; or a saturated or unsaturated three- to eight-membered carbocyclic or heterocyclic group in which the carbocyclic or heterocyclic group is optionally substituted by hydroxyl, an oxygen atom, $C_{1-6}$ alkyl, $C_{2-6}$ alkenyl, $C_{2-6}$ alkynyl, $C_{1-6}$ alkoxy, $C_{1-6}$ alkoxycarbonyl, or a saturated or unsaturated three- to eight-membered carbocyclic or heterocyclic group; the $C_{1-6}$ alkyl, $C_{2-6}$ alkenyl, and $C_{2-6}$ alkynyl groups are optionally substituted by hydroxyl, $C_{1-6}$ alkoxy, or a saturated or unsaturated three- to eight-membered carbocyclic or heterocyclic group; when the carbocyclic or heterocyclic group is substituted by two $C_{1-6}$ alkyl groups, the two alkyl groups may combine together to form an alkylene chain; and the carbocyclic or heterocyclic group may be condensed with another saturated or unsaturated five-, to seven-membered carbocyclic or heterocyclic group to form a bicyclic group;

all of $R^{405}$, $R^{406}$, $R^{407}$, and $R^{408}$ represent a hydrogen atom, or any one or two of $R^{405}$, $R^{406}$, $R^{407}$, and $R^{408}$ represent a halogen atom, $C_{1-4}$ alkyl, $C_{1-4}$ alkoxy, nitro, or amino with all the remaining groups representing a hydrogen atom; and $R^{409}$ represents 3,3-dimethyl-butyl; or a saturated five- to seven-membered carbocyclic group substituted by one, two, or three of $C_{1-4}$ alkyl groups, or a pharmaceutically acceptable salt thereof.

5. A pharmaceutical composition comprising the compound according to any one of claims 1 to 4 or a pharmaceutically acceptable salt thereof.

6. The compound according to claim 1, which is selected from the group consisting of:
- (4-Tert-butylphenyl)-{4-[7-(2-chloroethoxy)-6-methoxyquinolin-4-yloxy]phenyl}amine,
- (4-Tert-butylphenyl)-{4-[7-(3-chloropropoxy)-6-methoxyquinolin-4-yloxy]phenyl}amine,
- (4-Tert-butylphenyl)-{4-[6-methoxy-7-(3-morpholin-4-ylpropoxy)quinolin-4-yloxy]phenyl}amine,
- (4-Tert-butylphenyl)-{4-[6-methoxy-7-(4-morpholin-4-ylbutoxy)-quinolin-4-yloxy]phenyl}amine,
- 3-{4-[4-(4-Tert-butylphenylamino)phenoxy]-6-methoxyquinolin-7-yloxy}propionamide,
- (4-Tert-butylphenyl)-(4-{6-methoxy-7-[2-(1-methylpyrrolidin-2-yl)ethoxy]quinolin-4-yloxy}phenyl)amine,
- (4-Tert-butylphenyl)-{4-[6-methoxy-7-(2-methylthiazol-4-ylmethoxy)quinolin-4-yloxy]phenyl}amine,
- (4-Tert-butylphenyl)-(4-{6-methoxy-7-[4-(4-methylpiperazin-1-yl)butoxy]quinolin-4-yloxy}phenyl)amine,
- (4-Tert-butylphenyl)-(4-{6-methoxy-7-[2-(4-methylpiperazin-1-yl)ethoxy]quinolin-4-yloxy}phenyl)amine,
- (4-Tert-butylphenyl)-{4-[6-methoxy-7-(3-piperidin-1-yl-propoxy)-quinolin-4-yloxy]phenyl}amine,
- (4-Tert-butylphenyl)-(4-{6-methoxy-7-[3-(4-methylpiperazin-1-yl)propoxy]quinolin-4-yloxy}phenyl)amine,
- (4-Tert-butylphenyl)-{4-[6-methoxy-7-(4-piperidin-1-ylbutoxy)-quinolin-4-yloxy]phenyl}amine,
- (4-Tert-butylphenyl)-{4-[6-methoxy-7-(2-morpholin-4-ylethoxy)quinolin-4-yloxy]phenyl}amine,
- (4-Tert-butylphenyl)-{4-[6-methoxy-7-(2-piperidin-1-ylethoxy)-quinolin-4-yloxy]phenyl}amine,
- (4-Tert-butylphenyl)-{4-[6-methoxy-7-(2-pyrrolidin-1-ylethoxy)-quinolin-4-yloxy]phenyl}amine,
- N1-[4-(Tert-butyl)phenyl]-4-({7-[2-(dimethylamino)ethoxy]-6-methoxy-4-quinolyl}oxy)aniline,
- N1-[4-(Tert-butyl)phenyl]-4-({7-[2-(diethylamino)ethoxy]-6-methoxy-4-quinolyl}oxy)aniline,
- (4-Tert-butylphenyl)-{4-[6-methoxy-7-(1-propylpiperidin-4-ylmethoxy)quinolin-4-yloxy]phenyl}amine,
- (4-Tert-butylphenyl)-(4-{6-methoxy-7-[2-(4-methyl-[1,4]diazepin-1-yl)ethoxy]quinolin-4-yloxy}phenyl)amine,
- N1-[4-(Tert-butyl)phenyl]-4-({7-[3-(dimethylamino)propoxy]-6-methoxy-4-quinolyl}oxy)aniline,
- N1-[4-(Tert-butyl)phenyl]-4-({7-[3-(diethylamino)propoxy]-6-methoxy-4-quinolyl}oxy)aniline,
- 2-[(2-{4-[4-(4-Tert-butyl-phenylamino)phenoxy]-6-methoxy-quinolin-7-yloxy}ethyl)-(2-hydroxyethyl)amino]ethanol,
- 2-[(2-{4-[4-(4-Tert-butyl-phenylamino)phenoxy]-6-methoxy-quinolin-7-yloxy}ethyl)methylamino]ethanol,
- {4-[7-(2-Azepan-1-ylethoxy)-6-methoxyquinolin-4-yloxy]phenyl}-(4-tert-butylphenyl)amine,
- 2-[(3-{4-[4-(4-Tert-butylphenylamino)phenoxy]-6-methoxy-quinolin-7-yloxy}propyl)-(2-hydroxyethyl)amino]ethanol,
- 2-[(3-{4-[4-(4-Tert-butylphenylamino)phenoxy]-6-methoxy-quinolin-7-yloxy}propyl)methylamino]ethanol,
- (4-Tert-butylphenyl)-{4-[6-methoxy-7-(3-pyrrolidin-1-ylpropoxy)-quinolin-4-yloxy]phenyl}amine,
- {4-[7-(3-Azepan-1-ylpropoxy)-6-methoxyquinolin-4-yloxy]-phenyl}-(4-tert-butylphenyl)amine,
- (4-Tert-butylphenyl)-{4-[6-methoxy-7-(1-methylpiperidin-2-ylmethoxy)quinolin-4-yloxy]phenyl}amine, (4-Tert-butylphenyl)-{4-[6-methoxy-7-(1-methylpiperidin-3-ylmethoxy)quinolin-4-yloxy]phenyl}amine,
(4-Tert-butylphenyl)-{4-[6-methoxy-7-(5-vinyl-1-azabicyclo-[2.2.2]oct-2-ylmethoxy)quinolin-4-yloxy]phenyl}amine,
(4-Tert-butylphenyl)-{4-[6-methoxy-7-(1-methylpyrrolidin-2-ylmethoxy)quinolin-4-yloxy]phenyl}amine,
1-{4-[4-(4-Tert-butyl-phenylamino)phenoxy]-6-methoxyquinolin-7-yloxy}-3-morpholin-4-ylpropan-2-ol,
1-{4-[4-(4-Tert-butyl-phenylamino)phenoxy]-6-methoxyquinolin-7-yloxy}-3-diethylaminopropan-2-ol,
1-{4-[4-(4-Tert-butyl-phenylamino)phenoxy]-6-methoxyquinolin-7-yloxy}-3-pyrrolidin-1-ylpropan-2-ol,
1-{4-[4-(4-Tert-butyl-phenylamino)phenoxy]-6-methoxyquinolin-7-yloxy}-3-piperidin-1-ylpropan-2-ol,
1-Azepan-1-yl-3-{4-[4-(4-tert-butylphenylamino)phenoxy]-6-methoxyquinolin-7-yloxy}propan-2-ol,
1-{4-[4-(4-Tert-butylphenylamino)phenoxy]-6-methoxyquinolin-7-yloxy}-3-(4-methylpiperazin-1-yl)propan-2-ol,
1-{4-[4-(4-Tert-butylphenyl-amino)phenoxy]-6-methoxyquinolin-7-yloxy}-3-(4-methyl-[1,4]diazepin-1-yl)propan-2-ol,
1-{4-[4-(4-Tert-butylphenyl-amino)phenoxy]-6-methoxyquinolin-7-yloxy}-3-ethylaminopropan-2-ol,
1-{4-[4-(4-Tert-butylphenyl-amino)phenoxy]-6-methoxyquinolin-7-yloxy}-3-dimethylaminopropan-2-ol,
(4-Tert-butylphenyl)-(4-{7-[2-(2,6-dimethylmorpholin-4-yl)ethoxy]-6-methoxyquinolin-4-yloxy}phenyl)amine,
(4-Tert-butylphenyl)-(4-{7-[3-(2,6-dimethylmorpholin-4-yl)propoxy]-6-methoxyquinolin-4-yloxy}phenyl)amine,
(R)-1-{4-[4-(4-Tert-butylphenylamino)phenoxy]-6-methoxyquinolin-7-yloxy}-3-morpholin-4-ylpropan-2-ol,
(s)-1-{4-[4-(4-Tert-butylphenylamino)phenoxy]-6-methoxyquinolin-7-yloxy}-3-morpholin-4-ylpropan-2-ol,
(4-Tert-butylphenyl)-{4-[6-methoxy-7-(2-morpholin-4-ylethoxy)quinazolin-4-yloxy]phenyl}amine,
(4-Tert-butylphenyl)-{2-fluoro-4-[6-methoxy-7-(2-morpholin-4-ylethoxy)quinolin-4-yloxy]phenyl}amine,
(4-Tert-butylphenyl)-{4-[6-methoxy-7-(3-morpholin-4-ylbutoxy)-quinolin-4-yloxy]phenyl}amine,
[1-(2-{4-[4-(4-Tert-butylphenylamino)phenoxy]-6-methoxy-quinolin-7-yloxy}ethyl)piperidin-4-yl]methanol,
1-(2-{4-[4-(4-Tert-butylphenylamino)phenoxy]-6-methoxy-quinolin-7-yloxy}ethyl)piperidin-4-ol,
4-{2-[(4-{4-[4-(Tert-butyl)anilino]phenoxy}-6-methoxy-7-quinolyl)-oxy]ethyl}-1,4-oxazinan-4-ium-4-oleate,
N-[4-(Tert-butyl)phenyl]-N-(3-chloro-4-{[6-methoxy-7-(2-morpholinoethoxy)-4-quinolyl]oxy}phenyl)amine,
2-({2-[(4-{4-[4-(Tert-butyl)anilino]phenoxy}-6-methoxy-7-quinolyl)oxy]ethyl}amino)-1-ethanol,
1-(3-{4-[4-(4-Tert-butyl-phenylamino)-phenoxy]-6-methoxy-quinolin-7-yloxy}-propyl)-piperidin-4-ol,
[1-(3-{4-[4-(4-Tert-butyl-phenylamino)-phenoxy]-6-methoxy-quinolin-7-yloxy}-propyl)-piperidin-4-yl]-methanol,
2-[1-(3-{4-[4-(4-Tert-butyl-phenylamino)-phenoxy]-6-methoxy-quinolin-7-yloxy}-propyl)-piperidin-4-yl]-ethanol,
2-{4-[4-(4-Isopropyl-phenylamino)-phenoxy]-6-methoxy-quinolin-7-yloxy}-1-morpholin-4-yl-ethanone,
(4-Tert-butyl-phenyl)-(4-{7-[3-(2,6-dimethyl-morpholin-4-yl)-propoxy]-6-methoxy-quinolin-4-yloxy}-phenyl)-amine,
(4-Tert-butyl-phenyl)-(4-{7-[3-(3,5-dimethyl-piperidin-1-yl)-propoxy]-6-methoxy-quinolin-4-yloxy}-phenyl)-amine,
(4-Tert-butyl-phenyl)-(4-{6-methoxy-7-[3-(4-phenyl-piperidin-1-yl)-propoxy]-quinolin-4-yloxy}-phenyl)-amine,
(4-{7-[3-(4-Benzyl-piperidin-1-yl)-propoxy]-6-methoxy-quinolin-4-yloxy}-phenyl)-(4-tert-butyl-phenyl)-amine,
{4-[7-(3-[1,4']Bipiperidineyl-1'-yl-propoxy)-6-methoxy-quinolin-4-yloxy]-phenyl}-(4-tert-butyl-phenyl)-amine,
(4-Tert-butyl-phenyl)-(4-{6-methoxy-7-[3-(4-pyrrolidin-1-yl-piperidin-1-yl)-propoxy]-quinolin-4-yloxy}-phenyl)-amine,
(4-Tert-butyl-phenyl)-(4-{7-[2-(2,6-dimethyl-morpholin-4-yl)-ethoxy]-6-methoxy-quinolin-4-yloxy}-phenyl)-amine,
(4-Tert-butyl-phenyl)-(4-{7-[2-(3,5-dimethyl-piperidin-1-yl)-ethoxy]-6-methoxy-quinolin-4-yloxy}-phenyl)-amine,
(4-Tert-butyl-phenyl)-(4-{6-methoxy-7-[2-(4-phenyl-piperidin-1-yl)-ethoxy]-quinolin-4-yloxy}-phenyl)-amine,
(4-{7-[2-(4-Benzyl-piperidin-1-yl)-ethoxy]-6-methoxy-quinolin-4-yloxy}-phenyl)-(4-tert-butyl-phenyl)-amine,
{4-[7-(2-[1,4']Bipiperidineyl-1'-yl-ethoxy)-6-methoxy-quinolin-4-yloxy]-phenyl}-(4-tert-butyl-phenyl)-amine,
(4-Tert-butyl-phenyl)-(4-{6-methoxy-7-[2-(4-pyrrolidin-1-yl-piperidin-1-yl)-ethoxy]-quinolin-4-yloxy}-phenyl)-amine,
1-{4-[4-(4-Tert-butyl-phenylamino)-phenoxy]-6-methoxy-quinolin-7-yloxy}-3-(2,6-dimethyl-morpholin-4-yl)-propan-2-ol,
1-{4-[4-(4-Tert-butyl-phenylamino)-phenoxy]-6-methoxy-quinolin-7-yloxy}-3-(3,5-dimethyl-piperidin-1-yl)-propan-2-ol,
1-{4-[4-(4-Tert-butyl-phenylamino)-phenoxy]-6-methoxy-quinolin-7-yloxy}-3-(4-phenyl-piperidin-1-yl)-propan-2-ol,
1-(4-Benzyl-piperidin-1-yl)-3-{4-[4-(4-tert-butyl-phenylamino)-phenoxy]-6-methoxy-quinolin-7-yloxy}-propan-2-ol,
1-[1,4']Bipiperidineyl-1'-yl-3-{4-[4-(4-tert-butyl-phenylamino)-phenoxy]-6-methoxy-quinolin-7-yloxy}-propan-2-ol,
1-{4-[4-(4-Tert-butyl-phenylamino)-phenoxy]-6-methoxy-quinolin-7-yloxy}-3-(4-pyrrolidin-1-yl-piperidin-1-yl)-propan-2-ol,
[1-(3-{4-[4-(4-Tert-butyl-phenylamino)-2-fluoro-phenoxy]-6-methoxy-quinolin-7-yloxy}-propyl)-piperidin-4-yl]-methanol,
2-[1-(3-{4-[4-(4-Tert-butyl-phenylamino)-2-fluoro-phenoxy]-6-methoxy-quinolin-7-yloxy}-propyl)-piperidin-4-yl]-ethanol,
1-(3-{4-[4-(4-Tert-butyl-phenylamino)-2-fluoro-phenoxy]-6-methoxy-quinolin-7-yloxy}-propyl)-piperidin-4-ol,
1-(3-{4-[4-(4-Tert-butyl-phenylamino)-3-chloro-phenoxy]-6-methoxy-quinolin-7-yloxy}-propyl)-piperidin-4-ol,
[1-(3-{4-[4-(4-Tert-butyl-phenylamino)-3-chloro-phenoxy]-6-methoxy-quinolin-7-yloxy}-propyl)-piperidin-4-yl]-methanol, 1-(2-{4-[4-(4-Tert-butyl-phenylamino)-3-chloro-phenoxy]-6-methoxy-quinolin-7-yloxy}-ethyl)-piperidin-4-ol,

[1-(2-{4-[4-(4-Tert-butyl-phenylamino)-3-chloro-phenoxy]-6-methoxy-quinolin-7-yloxy}-ethyl)-piperidin-4-yl]-methanol, (4-Tert-butyl-phenyl)-(4-{6-methoxy-7-[2-(4-methoxy-piperidin-1-yl)-ethoxy]-quinolin-4-yloxy}-phenyl)-amine, (4-Tert-butyl-phenyl)-(4-{6-methoxy-7-[2-(4-methoxymethyl-piperidin-1-yl)-ethoxy]-quinolin-4-yloxy}-phenyl)-amine,

[1-(2-{4-[4-(4-Tert-butyl-phenylamino)-2-fluoro-phenoxy]-6-methoxy-quinolin-7-yloxy}-ethyl)-piperidin-4-yl]-methanol, 1-(2-{4-[4-(4-Tert-butyl-phenylamino)-2-fluoro-phenoxy]-6-methoxy-quinolin-7-yloxy}-ethyl)-piperidin-4-ol, 1-(2-{4-[4-(4-Tert-butyl-phenylamino)-3-fluoro-phenoxy]-6-methoxy-quinolin-7-yloxy}-ethyl)-piperidin-4-ol,

[1-(2-{4-[4-(4-Tert-butyl-phenylamino)-3-fluoro-phenoxy]-6-methoxy-quinolin-7-yloxy}-ethyl)-piperidin-4-yl]-methanol, 1-(3-{4-[4-(4-Tert-butyl-phenylamino)-3-fluoro-phenoxy]-6-methoxy-quinolin-7-yloxy}-propyl)-piperidin-4-ol,

[1-(3-{4-[4-(4-Tert-butyl-phenylamino)-3-fluoro-phenoxy]-6-methoxy-quinolin-7-yloxy}-propyl)-piperidin-4-yl]-methanol, 2-[1-(2-{4-[4-(4-Tert-butyl-phenylamino)-3-chloro-phenoxy]-6-methoxy-quinolin-7-yloxy}-ethyl)-piperidin-4-yl]-ethanol, 2-[1-(3-{4-[4-(4-Tert-butyl-phenylamino)-3-chloro-phenoxy]-6-methoxy-quinolin-7-yloxy}-propyl)-piperidin-4-yl]-ethanol, 2-[1-(2-{4-[4-(4-Tert-butyl-phenylamino)-3-fluoro-phenoxy]-6-methoxy-quinolin-7-yloxy}-ethyl)-piperidin-4-yl]-ethanol, 2-[1-(3-{4-[4-(4-Tert-butyl-phenylamino)-3-fluoro-phenoxy]-6-methoxy-quinolin-7-yloxy}-propyl)-piperidin-4-yl]-ethanol, 1-(2-{4-[4-(4-Tert-butyl-phenylamino)-2-chloro-phenoxy]-6-methoxy-quinolin-7-yloxy}-ethyl)-piperidin-4-ol,

[1-(2-{4-[4-(4-Tert-butyl-phenylamino)-2-chloro-phenoxy]-6-methoxy-quinolin-7-yloxy}-ethyl)-piperidin-4-yl]-methanol, 1-(3-{4-[4-(4-Tert-butyl-phenylamino)-2-chloro-phenoxy]-6-methoxy-quinolin-7-yloxy}-propyl)-piperidin-4-ol,

[1-(3-{4-[4-(4-Tert-butyl-phenylamino)-2-chloro-phenoxy]-6-methoxy-quinolin-7-yloxy}-propyl)-piperidin-4-yl]-methanol, 2-[1-(2-{4-[4-(4-Tert-butyl-phenylamino)-2-chloro-phenoxy]-6-methoxy-quinolin-7-yloxy}-ethyl)-piperidin-4-yl]-ethanol, 2-[1-(3-{4-[4-(4-Tert-butyl-phenylamino)-2-chloro-phenoxy]-6-methoxy-quinolin-7-yloxy}-propyl)-piperidin-4-yl]-ethanol, 2-[(2-{4-[4-(4-Tert-butyl-phenylamino)-3-fluoro-phenoxy]-6-methoxy-quinolin-7-yloxy}-ethyl)-(2-hydroxy-ethyl)-amino]-ethanol, 2-[(2-{4-[4-(4-Tert-butyl-phenylamino)-2-fluoro-phenoxy]-6-methoxy-quinolin-7-yloxy}-ethyl)-(2-hydroxy-ethyl)-amino]-ethanol, 2-[(2-{4-[4-(4-Tert-butyl-phenylamino)-3-chloro-phenoxy]-6-methoxy-quinolin-7-yloxy}-ethyl)-(2-hydroxy-ethyl)-amino]-ethanol, 2-[(2-{4-[4-(4-Tert-butyl-phenylamino)-2-chloro-phenoxy]-6-methoxy-quinolin-7-yloxy}-ethyl)-(2-hydroxy-ethyl)-amino]-ethanol, N1-[4-(Tert-butyl)phenyl]-4-[(6-methoxy-7-{2-[(tetrahydro-2-furanylmethyl)amino]ethoxy}-4-quinolyl)oxy]aniline, 2-[(2-{4-[4-(4-Tert-butyl-phenylamino)-phenoxy]-6-methoxy-quinolin-7-yloxy}-ethyl)-methyl-amino]-ethanol hydrochloride, 2-[(2-{4-[4-(4-Tert-butyl-phenylamino)-phenoxy]-6-methoxy-quinolin-7-yloxy}-ethyl)-(2-hydroxy-ethyl)-amino]-ethanol hydrochloride,

[1-(2-{4-[4-(4-Tert-butyl-phenylamino)-phenoxy]-6-methoxy-quinolin-7-yloxy}-ethylamino)-cyclopenthyl]-methanol, 2-(2-{4-[4-(4-Tert-butyl-phenylamino)-phenoxy]-6-methoxy-quinolin-7-yloxy}-ethylamino)-2-ethyl-propan-1,3-diol, 1-[(2-{4-[4-(4-Tert-butyl-phenylamino)-phenoxy]-6-methoxy-quinolin-7-yloxy}-ethyl)-(2-hydroxy-propyl)-amino]-propan-2-ol, 2-(2-{4-[4-(4-Tert-butyl-phenylamino)-phenoxy]-6-methoxy-quinolin-7-yloxy}-ethylamino)-propan-1-ol, N1-[4-(Tert-butyl)phenyl]-4-[(6-methoxy-7-{2-[(2-methoxy-1-methylethyl)amino]ethoxy}-4-quinolyl)oxy]aniline, 2-[(2-{4-[4-(4-Tert-butyl-phenylamino)-phenoxy]-6-methoxy-quinolin-7-yloxy}-ethyl)-cyclohexyl-amino]-ethanol, 2-[Benzyl-(2-{4-[4-(4-tert-butyl-phenyl amino)-phenoxy]-6-methoxy-quinolin-7-yloxy}-ethyl)-amino]-ethanol, 2-[(2-{4-[4-(4-Tert-butyl-phenylamino)-phenoxy]-6-methoxy-quinolin-7-yloxy}-ethyl)-propyl-amino]-ethanol, and 2-[(2-{4-[4-(4-Tert-butyl-phenylamino)-phenoxy]-6-methoxy-quinolin-7-yloxy}-ethyl)-isopropyl-amino]-ethanol.

7. The compound according to claim 3, which is selected from the group consisting of:

1-[(4-{4-[4-(Tert-butyl)anilino]phenoxy}-7-methoxy-6-quinolyl)-oxy]-3-morpholino-2-propanol, (4-Tert-butyl-phenyl)-{4-[7-methoxy-6-(2-morpholin-4-yl-ethoxy)-quinolin-4-yloxy]-phenyl}-amine, 1-{4-[4-(4-Tert-butyl-phenylamino)-phenoxy]-7-methoxy-quinolin-6-yloxy}-3-morpholin-4-yl-propan-2-ol, 4-[4-(4-Tert-butyl-phenylamino)-phenoxy]-7-methoxy-quinolin-6-ol,

[1-(2-{4-[4-(4-Tert-butyl-phenylamino)-phenoxy]-7-methoxy-quinolin-6-yloxy}-ethyl)-piperidin-4-yl]-methanol, 2-(2-{4-[4-(4-Tert-butyl-phenylamino)-phenoxy]-7-methoxy-quinolin-6-yloxy}-ethylamino)-ethanol, 2-[(2-{4-[4-(4-Tert-butyl-phenylamino)-phenoxy]-7-methoxy-quinolin-6-yloxy}-ethyl)-methyl-amino]-ethanol, and 2-[(2-{4-[4-(4-Tert-butyl-phenylamino)-phenoxy]-7-methoxy-quinolin-6-yloxy}-ethyl)-(2-hydroxy-ethyl)-am mo]-ethanol.

8. The compound according to claim 4, which is selected from the group consisting of:

1-(3,3-Dimethyl-butyl)-3-{2-fluoro-4-[6-methoxy-7-(2-morpholin-4-yl-ethoxy)-quinolin-4-yloxy]-phenyl}-urea, 1-(3,3-Dimethyl-butyl)-3-{2-fluoro-4-[6-methoxy-7-(3-morpholin-4-yl-propoxy)-quinolin-4-yloxy]-phenyl}-urea, hydrochloride, 1-(3,3-Dimethyl-butyl)-3-{2-fluoro-4-[7-(2-hydroxy-3-morpholin-4-yl-propoxy)-6-methoxy-quinolin-4-yloxy]-phenyl}-urea, hydrochloride, 1-(3,3-Dimethyl-butyl)-3-{4-[7-methoxy-6-(2-morpholin-4-yl-ethoxy)-quinolin-4-yloxy]-phenyl}-urea, 1-(3,3-Dimethyl-butyl)-3-{4-[6-methoxy-7-(2-piperidin-1-yl-ethoxy)-quinolin-4-yloxy]-phenyl}-urea, hydrochloride, 1-(3,3-Dimethyl-butyl)-3-(4-{7-[3-(4-hydroxymethyl-piperidin-1-yl)-propoxy]-6-methoxy-quinolin-4-yloxy}-phenyl)-urea, 1-(3,3-Dimethyl-butyl)-3-(4-{7-[3-(4-hydroxy-piperidin-1-yl)-propoxy]-6-methoxy-quinolin-4-yloxy}-phenyl)-urea, 1-(3,3-Dimethyl-butyl)-3-(4-{7-[2-(2,6-dimethyl-morpholin-4-yl)-ethoxy]-6-methoxy-quinolin-4-yloxy}-2-fluoro-phenyl)-urea, 1-(3,3-Dimethyl-butyl)-3-{3-fluoro-4-[6-methoxy-7-(2-morpholin-4-yl-ethoxy)-quinolin-4-yloxy]-phenyl}-urea, 1-(3,3-Dimethyl-butyl)-3-{2-fluoro-4-[6-methoxy-7-(2-piperidin-1-yl-ethoxy)-quinolin-4-yloxy]-phenyl}-urea, 1-{2-Chloro-4-[6-methoxy-7-(2-piperidin-1-yl-ethoxy)-quinolin-4-yloxy]-phenyl}-3-(3,3-dimethyl-butyl)-urea, 1-[4-(6,7-Dimethoxy-quinolin-4-yloxy)-phenyl]-3-(3,3-dimethyl-butyl)-urea, 1-[4-(6,7-Dimethoxy-quinolin-4-yloxy)-3-fluorophenyl]-3-(3,3-dimethyl-butyl)-urea, 1-[2-Chloro-4-(6,7-dimethoxyquinolin-4-yloxy)-phenyl]-3-(3,3-dimethyl-butyl)-urea, 1-[4-(6,7-Dimethoxy-quinolin-4-yloxy)-phenyl]-3-(3,3,5-trimethyl-cyclohexyl)-urea, 1-[4-(6,7-Dimethoxy-quinolin-4-yloxy)-2-fluoro-phenyl]-3-(3,3,5-trimethyl-cyclohexyl)-urea, 1-[2-Chloro-4-(6,7-dimethoxy-quinolin-4-yloxy)-phenyl]-3-(3,3,5-trimethyl-cyclohexyl)-urea, 1-[4-(6,7-Dimethoxy-quinolin-4-yloxy)-phenyl]-3-(3,3-dimethyl-cyclohexyl)-urea, 1-[4-(6,7-Dimethoxy-quinolin-4-yloxy)-2-fluoro-phenyl]-3-(3,3-dimethyl-cyclohexyl)-urea, 1-[2-Chloro-4-(6,7-dimethoxy-quinolin-4-yloxy)-phenyl]-3-(3,3-dimethyl-cyclohexyl)-urea, 1-[4-(6,7-Dimethoxy-quinolin-4-yloxy)-2-fluoro-phenyl]-3-(3,3-dimethyl-butyl)-urea, 1-(3,3-Dimethyl-butyl)-3-{4-[6-methoxy-7-(2-morpholin-4-yl-ethoxy)-quinolin-4-yloxy]-phenyl}-urea, hydrochloride, 1-(3,3-Dimethyl-butyl)-3-(4-{6-methoxy-7-[2-(4-methyl-piperazin-1-yl)-ethoxy]-quinolin-4-yloxy}-phenyl)-urea, hydrochloride, 1-{2-Chloro-4-[6-methoxy-7-(2-morpholin-4-yl-ethoxy)-quinolin-4-yloxy]-phenyl}-3-(3,3-dimethyl-butyl)-urea, 1-(2-Chloro-4-{6-methoxy-7-[2-(4-methyl-piperazin-1-yl)-ethoxy]-quinolin-4-yloxy}-phenyl)-3-(3,3-dimethyl-butyl)-urea, 1-(2-Chloro-4-{7-[2-(2,6-dimethyl-morpholin-4-yl)-ethoxy]-6-methoxy-quinolin-4-yloxy}-phenyl)-3-(3,3-dimethyl-butyl)-urea, 1-(2-Chloro-4-{6-methoxy-7-[2-(4-methyl-piperidin-1-yl)-ethoxy]-quinolin-4-yloxy}-phenyl)-3-(3,3-dimethyl-butyl)-urea, 1-(3,3-Dimethyl-butyl)-3-(4-{7-[2-(2,6-dimethyl-morpholin-4-yl)-ethoxy]-6-methoxy-quinolin-4-yloxy}-phenyl)-urea, 1-(3,3-Dimethyl-butyl)-3-(4-{7-[2-(3,5-dimethyl-piperidin-1-yl)-ethoxy]-6-methoxy-quinolin-4-yloxy}-phenyl)-urea, 1-(3,3-Dimethyl-butyl)-3-(4-{6-methoxy-7-[2-(4-phenyl-piperidin-1-yl)-ethoxy]-quinolin-4-yloxy}-phenyl)-urea, 1-(4-{7-[2-(4-Benzyl-piperidin-1-yl)-ethoxy]-6-methoxy-quinolin-4-yloxy}-phenyl)-3-(3,3-dimethyl-butyl)-urea, 1-{4-[7-(2-[1,4']bipiperidineyl-1'-yl-ethoxy)-6-methoxy-quinolin-4-yloxy]-phenyl}-3-(3,3-dimethyl-butyl)-urea, 1-(3,3-Dimethyl-butyl)-3-(4-{6-methoxy-7-[2-(4-pyrrolidin-1-yl-piperidin-1-yl)-ethoxy]-quinolin-4-yloxy}-phenyl)-urea, 1-(2-Chloro-4-{7-[2-(2,6-dimethyl-morpholin-4-yl)-ethoxy]-6-methoxy-quinolin-4-yloxy}-phenyl)-3-(3,3-dimethyl-butyl)-urea, 1-{3-Chloro-4-[6-methoxy-7-(2-morpholin-4-yl-ethoxy)-quinolin-4-yloxy]-phenyl}-3-(3,3-dimethyl-butyl)-urea, 1-(3-Chloro-4-{7-[2-(2,6-dimethyl-morpholin-4-yl)-ethoxy]-6-methoxy-quinolin-4-yloxy}-phenyl)-3-(3,3-dimethyl-butyl)-urea, 1-(3,3-Dimethyl-butyl)-3-(4-{7-[2-(2,6-dimethyl-morpholin-4-yl)-ethoxy]-6-methoxy-quinolin-4-yloxy}-3-fluoro-phenyl)-urea, 1-(3,3-Dimethyl-butyl)-3-{3-fluoro-4-[6-methoxy-7-(2-piperidin-1-yl-ethoxy)-quinolin-4-yloxy]-phenyl}-urea, 1-(3,3-Dimethyl-butyl)-3-(4-{7-[2-(2,6-dimethyl-piperidin-1-yl)-ethoxy]-6-methoxy-quinolin-4-yloxy}-2-fluoro-phenyl)-urea, 1-(3,3-Dimethyl-butyl)-3-(2-fluoro-4-{6-methoxy-7-[2-(2,2,6,6-tetramethyl-piperidin-1-yl)-ethoxy]-quinolin-4-yloxy}-phenyl)-urea, 1-(3,3-Dimethyl-butyl)-3-(4-{7-[2-(2,6-dimethyl-piperidin-1-yl)-ethoxy]-6-methoxy-quinolin-4-yloxy}-3-fluoro-phenyl)-urea, 1-(3,3-Dimethyl-cyclohexyl)-3-{2-fluoro-4-[6-methoxy-7-(2-morpholin-4-yl-ethoxy)-quinolin-4-yloxy]-phenyl}-urea, 1-(3,3-Dimethyl-cyclohexyl)-3-(4-{7-[2-(2,6-dimethyl-morpholin-4-yl)-ethoxy]-6-methoxy-quinolin-4-yloxy}-2-fluoro-phenyl)-urea, 1-[4-(6,7-Dimethoxy-quinolin-4-yloxy)-2-nitro-phenyl]-3-(3,3-dimethyl-butyl)-urea, 1-[4-(6,7-Dimethoxy-quinolin-4-yloxy)-2-methyl-phenyl]-3-(3,3-dimethyl-butyl)-urea, 1-[4-(6,7-Dimethoxy-quinolin-4-yloxy)-3-methyl-phenyl]-3-(3,3-dimethyl-butyl)-urea, 1-[4-(6,7-Dimethoxy-quinolin-4-yloxy)-2-methoxy-phenyl]-3-(3,3-dimethyl-butyl)-urea, 1-[4-(6,7-Dimethoxy-quinolin-4-yloxy)-3-methoxy-phenyl]-3-(3,3-dimethyl-butyl)-urea, 1-[3,5-Dichloro-4-(6,7-dimethoxy-quinolin-4-yloxy)-phenyl]-3-(3,3-dimethyl-butyl)-urea, 1-[4-(6,7-Dimethoxy-quinolin-4-yloxy)-2,3-dimethyl-phenyl]-3-(3,3-dimethyl-butyl)-urea, 1-[4-(6,7-Dimethoxy-quinolin-4-yloxy)-2,5-dimethyl-phenyl]-3-(3,3-dimethyl-butyl)-urea, 1-[4-(7-Benzyloxy-6-methoxy-quinolin-4-yloxy)-phenyl]-3-(3,3-dimethyl-butyl)-urea, 1-{4-[7-(2-Bromo-ethoxy)-6-methoxy-quinolin-4-yloxy]-phenyl}-3-(3,3-dimethyl-butyl)-urea,
1-{4-[7-(3-Bromo-propoxy)-6-methoxy-quinolin-4-yloxy]-phenyl}-3-(3,3-dimethyl-butyl)-urea,
1-{4-[7-(4-Bromo-butoxy)-6-methoxy-quinolin-4-yloxy]-phenyl}-3-(3,3-dimethyl-butyl)-urea,
1-[4-(6,7-Dimethoxy-quinolin-4-yloxy)-2-fluoro-phenyl]-3-(3,3,5,5-tetramethyl-hexyl)-urea,
1-[4-(6,7-Dimethoxy-quinolin-4-yloxy)-2-trifluoromethyl-phenyl]-3-(3,3-dimethyl-butyl)-urea,
1-{4-[7-(3-Chloro-propoxy)-6-methoxy-quinolin-4-yloxy]-phenyl}-3-(3,3-dimethyl-butyl)-urea,
1-{4-[7-(2-Chloro-ethoxy)-6-methoxy-quinolin-4-yloxy]-phenyl}-3-(3,3-dimethyl-butyl)-urea,
1-{4-[7-(4-Chloro-butoxy)-6-methoxy-quinolin-4-yloxy]-phenyl}-3-(3,3-dimethyl-butyl)-urea,
1-(3,3-Dimethyl-butyl)-3-{4-[6-methoxy-7-(3-piperidin-1-yl-propoxy)-quinolin-4-yloxy]-phenyl}-urea, hydrochloride,
1-(3,3-Dimethyl-butyl)-3-{4-[6-methoxy-7-(3-morpholin-4-yl-propoxy)-quinolin-4-yloxy]-phenyl}-urea, hydrochloride,
1-(3,3-Dimethyl-butyl)-3-(4-{6-methoxy-7-[3-(4-methyl-piperazin-1-yl)-propoxy]-quinolin-4-yloxy}-phenyl)-urea, hydrochloride,
1-(3,3-Dimethyl-butyl)-3-{4-[6-methoxy-7-(4-pipendin-1-yl-butoxy)-quinolin-4-yloxy]-phenyl}-urea, hydrochloride,
1-(3,3-Dimethyl-butyl)-3-{4-[6-methoxy-7-(4-morpholin-4-yl-butoxy)-quinolin-4-yloxy]-phenyl}-urea, hydrochloride,
1-(3,3-Dimethyl-butyl)-3-(4-{6-methoxy-7-[4-(4-methyl-piperazin-1-yl)-butoxy]-quinolin-4-yloxy}-phenyl)-urea, hydrochloride,
1-{2-Chloro-4-[7-(2-chloro-ethoxy)-6-methoxy-quinolin-4-yloxy]-phenyl}-3-(3,3dimethyl-butyl)-urea,
1-{2-Chloro-4-[7-(3-chloro-propoxy)-6-methoxy-quinolin-4-yloxy]-phenyl}-3-(3,3dimethyl-butyl)-urea,
1-{2-Chloro-4-[7-(4-chloro-butoxy)-6-methoxy-quinolin-4-yloxy]-phenyl}-3-(3,3-dimethyl-butyl)-urea,
1-[4-(7-Benzyloxy-6-methoxy-quinolin-4-yloxy)-2-chloro-phenyl]-3-(3,3-dimethyl-butyl)-urea,
1-(2-Chloro-4-{7-[4-(1,3-dioxo-1,3-dihydro-isoindol-2-yl)-butoxy]-6-methoxy-quinolin-4-yloxy}-phenyl)-3-(3,3-dimethyl-butyl)-urea,
1-{2-Chloro-4-[6-methoxy-7-(2-pyrrolidin-1-yl-ethoxy)-quinolin-4-yloxy]-phenyl}-3-(3,3-dimethyl-butyl)-urea,
1-{2-Chloro-4-[7-(2-dimethylamino-ethoxy)-6-methoxy-quinolin-4-yloxy]-phenyl}-3-(3,3-dimethyl-butyl)-urea,
1-{2-Chloro-4-[7-(2-diethylamino-ethoxy)-6-methoxy-quinolin-4-yloxy]-phenyl}-3-(3,3-dimethyl-butyl)-urea,
1-{2-Chloro-4-[6-methoxy-7-(piperidin-4-ylmethoxy)-quinolin-4-yloxy]-phenyl}-3-(3,3-dimethyl-butyl)-urea,
1-{2-Chloro-4-[6-methoxy-7-(1-methyl-piperidin-4-ylmethoxy)-quinolin-4-yloxy]-phenyl}-3-(3,3-dimethyl-butyl)-urea,
1-(2-Chloro-4-{7-[1-(2-hydroxy-ethyl)-piperidin-4-ylmethoxy]-6-methoxy-quinolin-4-yloxy}-phenyl)-3-(3,3-dimethyl-butyl)-urea,
1-(2-Chloro-4-{6-methoxy-7-[1-(2-methoxy-ethyl)-piperidin-4-ylmethoxy]-quinolin-4-yloxy}-phenyl)-3-(3,3-dimethyl-butyl)-urea,
1-{2-Chloro-4-[7-(3-dimethylamino-propoxy)-6-methoxy-quinolin-4-yloxy]-phenyl}-3-(3,3-dimethyl-butyl)-urea,
1-(2-Chloro-4-{7-[2-(1,3-dioxo-1,3-dihydro-isoindol-2-yl)-ethoxy]-6-methoxy-quinolin-4-yloxy}-phenyl)-3-(3,3-dimethyl-butyl)-urea,
1-(2-Chloro-4-{7-[3-(1,3-dioxo-1,3-dihydro-isoindol-2-yl)-propoxy]-6-methoxy-quinolin-4-yloxy}-phenyl)-3-(3,3-dimethyl-butyl)-urea,
1-{4-[7-(4-Amino-butoxy)-6-methoxy-quinolin-4-yloxy]-2-chloro-phenyl}-3-(3,3-dimethyl-butyl)-urea,
1-[4-(7-{2-[Bis-(2-hydroxy-ethyl)-amino]-ethoxy}-6-methoxy-quinolin-4-yloxy)-2-chloro-phenyl]-3-(3,3-dimethyl-butyl)-urea,
1-[2-Chloro-4-(7-{2-[(2-hydroxy-ethyl)-methyl-amino]-ethoxy}-6-methoxy-quinolin-4-yloxy)-phenyl]-3-(3,3-dimethyl-butyl)-urea,
1-[2-Chloro-4-(7-{3-[(2-hydroxy-ethyl)-methyl-amino]-propoxy}-6-methoxy-quinolin-4-yloxy)-phenyl]-3-(3,3-dimethyl-butyl)-urea,
1-{2-Chloro-4-[6-methoxy-7-(3-pyrrolidin-1-yl-propoxy)-quinolin-4-yloxy]-phenyl}-3-(3,3-dimethyl-butyl)-urea,
1-{2-Chloro-4-[6-methoxy-7-(3-piperidin-1-yl-propoxy)-quinolin-4-yloxy]-phenyl}-3-(3,3-dimethyl-butyl)-urea,
1-{4-[7-(3-Azepan-1-yl-propoxy)-6-methoxy-quinolin-4-yloxy]-2-chloro-phenyl}-3-(3,3-dimethyl-butyl)-urea,
1-{2-Chloro-4-[6-methoxy-7-(3-morpholin-4-yl-propoxy)-quinolin-4-yloxy]-phenyl}-3-(3,3-dimethyl-butyl)-urea,
1-{2-Chloro-4-[7-(3-diethylamino-propoxy)-6-methoxy-quinolin-4-yloxy]-phenyl}-3-(3,3-dimethyl-butyl)-urea,
1-[4-(7-{3-[Bis-(2-hydroxy-ethyl)-amino]-propoxy}-6-methoxy-quinolin-4-yloxy)-2-chloro-phenyl]-3-(3,3-dimethyl-butyl)-urea,
1-{4-[7-(2-Azepan-1-yl-ethoxy)-6-methoxy-quinolin-4-yloxy]-2-chloro-phenyl}-3-(3,3-dimethyl-butyl)-urea,
1-(2-Chloro-4-{6-methoxy-7-[2-(4-methyl-[1,4]diazepan-1-yl)-ethoxy]-quinolin-4-yloxy}-phenyl)-3-(3,3-dimethyl-butyl)-urea,
1-(2-Chloro-4-{6-methoxy-7-[3-(4-methyl-piperazin-1-yl)-propoxy]-quinolin-4-yloxy}-phenyl)-3-(3,3-dimethyl-butyl)-urea,
1-(2-Chloro-4-{6-methoxy-7-[3-(4-methyl-[1,4]diazepan-1-yl)-propoxy]-quinolin-yloxy}-phenyl)-3-(3,3-dimethyl-butyl)-urea,
Tert-butyl 3-(4-{3-chloro-4-[3-(3,3-dimethyl-butyl)-ureido]-phenoxy}-6-methoxy-quinolin-7-yloxymethyl)-piperidin-1-carboxylate,
1-{2-Chloro-4-[6-methoxy-7-(piperidin-3-ylmethoxy)-quinolin-4-yloxy]-phenyl}-3-(3,3-dimethyl-butyl)-urea,
1-{2-Chloro-4-[7-(3-diethylamino-2-hydroxy-propoxy)-6-methoxy-quinolin-4-yloxy]-phenyl}-3-(3,3-dimethyl-butyl)-urea,
1-{2-Chloro-4-[7-(2-hydroxy-3-pyrrolidin-1-yl-propoxy)-6-methoxy-quinolin-4-yloxy]-phenyl}-3-(3,3-dimethyl-butyl)-urea,
1-{2-Chloro-4-[7-(2-hydroxy-3-piperidin-1-yl-propoxy)-6-methoxy-quinolin-4-yloxy]-phenyl}-3-(3,3-dimethyl-butyl)-urea,
1-{4-[7-(3-Azepan-1-yl-2-hydroxy-propoxy)-6-methoxy-quinolin-4-yloxy]-2-chloro-phenyl}-3-(3,3-dimethyl-butyl)-urea, 1-{2-Chloro-4-[7-(2-hydroxy-3-morpholin-4-yl-propoxy)-6-methoxy-quinolin-4-yloxy]-phenyl}-3-(3,3-dimethyl-butyl)-urea,
1-(2-Chloro-4-{7-[2-hydroxy-3-(4-methyl-[1,4]diazepan-1-yl)-propoxy]-6-methoxy-quinolin-4-yloxy}-phenyl)-3-(3,3-dimethyl-butyl)-urea,
1-{2-Chloro-4-[7-(2-hydroxy-3-morpholin-4-yl-propoxy)-6-methoxy-quinolin-4-yloxy]-phenyl}-3-(3,3-dimethyl-butyl)-urea,
1-{2-Chloro-4-[7-(3-ethylamino-2-hydroxy-propoxy)-6-methoxy-quinolin-4-yloxy]-phenyl}-3-(3,3-dimethyl-butyl)-urea,
1-{2-Chloro-4-[7-(3-dimethylamino-2-hydroxy-propoxy)-6-methoxy-quinolin-4-yloxy]-phenyl}-3-(3,3-dimethyl-butyl)-urea,
1-(3,3-Dimethyl-butyl)-3-(4-{7-[3-(2,6-dimethyl-morpholin-4-yl)-propoxy]-6-methoxy-quinolin-4-yloxy}-phenyl)-urea,
1-{2-Chloro-4-[7-(2-hydroxy-3-morpholin-4-yl-propoxy)-6-methoxy-quinolin-4-yloxy]-phenyl}-3-(3,3-dimethyl-butyl)-urea,
1-{2-Chloro-4-[6-methoxy-7-(2-piperidin-4-yl-ethoxy)-quinolin-4-yloxy]-phenyl}-3-(3,3-dimethyl-butyl)-urea,
1-{2-Chloro-4-[6-methoxy-7-(2-piperidin-2-yl-ethoxy)-quinolin-4-yloxy]-phenyl}-3-(3,3-dimethyl-butyl)-urea,
1-{4-[7-(3-Chloro-propoxy)-6-methoxy-quinolin-4-yloxy]-2-fluoro-phenyl-3-(3,3-dimethyl-butyl)-urea,
1-{2-Chloro-4-[6-methoxy-7-(3-morpholin-4-yl-propoxy)-quinolin-4-yloxy]-phenyl}-3-(3,3-dimethyl-butyl)-urea,
1-{2-Chloro-4-[7-(2-hydroxy-3-morpholin-4-yl-propoxy)-6-methoxy-quinolin-4-yloxy]-phenyl}-3-(3,3-dimethyl-butyl)-urea,
1-(2-Chloro-4-{6-methoxy-7-[3-(4-methyl-piperidin-1-yl)-propoxy]-quinolin-4-yloxy}-phenyl)-3-(3,3-dimethyl-butyl)-urea,
1-(2-Chloro-4-{7-[3-(2-hydroxymethyl-pyrrolidin-1-yl)-propoxy]-6-methoxy-quinolin-4-yloxy}-phenyl)-3-(3,3-dimethyl-butyl)-urea,
1-(3,3-Dimethyl-butyl)-3-{2-fluoro-4-[7-(2-hydroxy-3-morpholin-4-yl-propoxy)-6-methoxy-quinolin-4-yloxy]-phenyl}-urea,
1-(3,3-Dimethyl-butyl)-3-{2-fluoro-4-[6-methoxy-7-(3-morpholin-4-yl-propoxy)-quinolin-4-yloxy]-phenyl}-urea,
1-{2-Chloro-4-[7-(2-hydroxy-ethoxy)-6-methoxy-quinolin-4-yloxy]-phenyl}-3-(3,3-dimethyl-butyl)-urea,
Methyl (4-{4-[3-(3,3-dimethyl-butyl)-ureido]-phenoxy}-6-methoxy-quinolin-7-yloxy)-acetate,
(4-{4-[3-(3,3-Dimethyl-butyl)-ureido]-phenoxy}-6-methoxy-quinolin-7-yloxy)-acetic acid,
4-{4-[3-(3,3-Dimethyl-butyl)-ureido]-3-fluoro-phenoxyl-6-methoxy-quinolin-7-yl [1,4']bipiperidineyl-1'-carboxylate,
1-(3-Chloro-4-{7-[2-(4-hydroxy-piperidin-1-yl)-ethoxy]-6-methoxy-quinolin-4-yloxy}-phenyl)-3-(3,3-dimethyl-butyl)-urea,
1-(3-Chloro-4-{7-[2-(4-hydroxymethyl-piperidin-1-yl)-ethoxy]-6-methoxy-quinolin-4-yloxy}-phenyl)-3-(3,3-dimethyl-butyl)-urea,
1-[3-Chloro-4-(7-2-[4-(2-hydroxy-ethyl)-piperidin-1-yl]-ethoxy}-6-methoxy-quinolin-4-yloxy)-phenyl]-3-(3,3-dimethyl-butyl)-urea,
1-[3-Chloro-4-(7-{3-[4-(2-hydroxy-ethyl)-piperidin-1-yl]-propoxy}-6-methoxy-quinolin-4-yloxy)-phenyl]-3-(3,3-dimethyl-butyl)-urea,
1-(2-Chloro-4-{7-[3-(2,6-dimethyl-morpholin-4-yl)-propoxy]-6-methoxy-quinolin-4-yloxy}-phenyl)-3-(3,3-dimethyl-butyl)-urea,
1-{3-Chloro-4-[6-methoxy-7-(3-morpholin-4-yl-propoxy)-quinolin-4-yloxy]-phenyl}-3-(3,3-dimethyl-butyl)-urea,
1-(3-Chloro-4-{7-[3-(2,6-dimethyl-morpholin-4-yl)-propoxy]-6-methoxy-quinolin-4-yloxy}-phenyl)-3-(3,3-dimethyl-butyl)-urea,
1-{2-Chloro-4-[6-methoxy-7-(4-morpholin-4-yl-butoxy)-quinolin-4-yloxy]-phenyl}-3-(3,3-dimethyl-butyl)-urea,
1-(2-Chloro-4-{7-[4-(2,6-dimethyl-morpholin-4-yl)-butoxy]-6-methoxy-quinolin-4-yloxy}-phenyl)-3-(3,3-dimethyl-butyl)-urea,
1-(3,3-Dimethyl-butyl)-3-(4-{7-[3-(2,6-dimethyl-morpholin-4-yl)-propoxy]-6-methoxy-quinolin-4-yloxy}-2-fluoro-phenyl)-urea,
1-(3,3-Dimethyl-butyl)-3-{3-fluoro-4-[6-methoxy-7-(3-morpholin-4-yl-propoxy)-quinolin-4-yloxy]-phenyl}-urea,
1-(3,3-Dimethyl-butyl)-3-(4-{7-[3-(2,6-dimethyl-morpholin-4-yl)-propoxy]-6-methoxy-quinolin-4-yloxy}-3-fluoro-phenyl)-urea,
1-(3,3-Dimethyl-butyl)-3-[4-(7-{2-[(2-hydroxy-ethyl)-methyl-amino]-ethoxy}-6-methoxy-quinolin-4-yloxy)-phenyl]-urea,
1-(3,3-Dimethyl-butyl)-3-(2-fluoro-4-7-[2-(2-hydroxy-ethylamino)-ethoxyl]-6-methoxy-quinolin-4-yloxy}-phenyl)-urea,
1-(3,3-Dimethyl-butyl)-3-[2-fluoro-4-(7-{2-[(2-hydroxy-ethyl)-methyl-amino]-ethoxy}-6-methoxy-quinolin-4-yloxy)-phenyl]-urea,
1-(2-Chloro-4-{7-[2-(2-hydroxy-ethylamino)-ethoxy]-6-methoxy-quinolin-4-yloxy}-phenyl)-3-(3,3-dimethyl-butyl)-urea,
1-(3,3-Dimethyl-butyl)-3-(2-fluoro-4-{7-[3-(2-hydroxy-ethylamino)-propoxy]-6-methoxy-quinolin-4-yloxy}-phenyl)-urea,
1-(3,3-Dimethyl-butyl)-3-[2-fluoro-4-(7-{3-[(2-hydroxy-ethyl)-methyl-amino]-propoxy}-6-methoxy-quinolin-4-yloxy)-phenyl]-urea,
1-(2-Chloro-4-{7-[3-(2-hydroxy-ethylamino)-propoxy]-6-methoxy-quinolin-4-yloxy}-phenyl)-3-(3,3-dimethyl-butyl)-urea,
1-(3-Chloro-4-{7-[3-(4-hydroxy-piperidin-1-yl)-propoxy]-6-methoxy-quinolin-4-yloxy}-phenyl)-3-(3,3-dimethyl-butyl)-urea,
1-(3-Chloro-4-{7-[3-(4-hydroxymethyl-piperidin-1-yl)-propoxy]-6-methoxy-quinolin-4-yloxy}-phenyl)-3-(3,3-dimethyl-butyl)-urea,
1-(3,3-Dimethyl-butyl)-3-[4-(7-{2-[ethyl-(2-hydroxy-ethyl)-amino]-ethoxy}-6-methoxy-quinolin-4-yloxy)-phenyl]-urea,
1-(3,3-Dimethyl-butyl)-3-[4-(7-{2-[ethyl-(2-hydroxy-ethyl)-amino]-ethoxy}-6-methoxy-quinolin-4-yloxy)-2-fluoro-phenyl]-urea,
1-[2-Chloro-4-(7-{2-[ethyl-(2-hydroxy-ethyl)-amino]-ethoxy}-6-methoxy-quinolin-4-yloxy)-phenyl]-3-(3,3-dimethyl-butyl)-urea,
1-(3,3-Dimethyl-butyl)-3-[4-(7-{3-[ethyl-(2-hydroxy-ethyl)-amino]-propoxy}-6-methoxy-quinolin-4-yloxy)-phenyl]-urea, 1-(3,3-Dimethyl-butyl)-3-[4-(7-{3-[ethyl-(2-hydroxy-ethyl)-amino]-propoxy}-6-methoxy-quinolin-4-yloxy)-2-fluoro-phenyl]-urea,
1-[2-Chloro-4-(7-{3-[ethyl-(2-hydroxy-ethyl)-amino]-propoxy}-6-methoxy-quinolin-4-yloxy)-phenyl]-3-(3,3-dimethyl-butyl)-urea,
1-(3,3-Dimethyl-butyl)-3-[4-(7-{2-[4-(2-hydroxy-ethyl)-piperidin-1-yl]-ethoxy}-6-methoxy-quinolin-4-yloxy)-phenyl]-urea,
1-(3,3-Dimethyl-butyl)-3-[4-(7-{3-[4-(2-hydroxy-ethyl)-piperidin-1-yl]-propoxy}-6-methoxy-quinolin-4-yloxy)-phenyl]-urea,
1-(3,3-Dimethyl-butyl)-3-(4-{6-[3-(4-hydroxy-piperidin-1-yl)-propoxy]-7-methoxy-quinolin-4-yloxy}-phenyl)-urea,
1-(3,3-Dimethyl-butyl)-3-(4-{6-[3-(4-hydroxymethyl-piperidin-1-yl)-propoxy]-7-methoxy-quinolin-4-yloxy}-phenyl)-urea,
1-(3,3-Dimethyl-butyl)-3-[4-(6-{3-[4-(2-hydroxy-ethyl)-piperidin-1-yl]-propoxy}-7-methoxy-quinolin-4-yloxy)-phenyl]-urea,
1-{4-[6-(2-Dimethylamino-ethoxy)-7-methoxy-quinolin-4-yloxy]-phenyl}-3-(3,3-dimethyl-butyl)-urea,
1-(3,3-Dimethyl-butyl)-3-{4-[7-methoxy-6-(3-morpholin-4-yl-propoxy)-quinolin-4-yloxy]-phenyl}-urea,
1-{4-[6-(3-Dimethylamino-propoxy)-7-methoxy-quinolin-4-yloxy]-phenyl}-3-(3,3-dimethyl-butyl)-urea,
1-(3,3-Dimethyl-butyl)-3-{4-[6-(2-hydroxy-3-morpholin-4-yl-propoxy)-7-methoxy-quinolin-4-yloxy]-phenyl}-urea,
1-{4-[6-(3-Dimethylamino-2-hydroxy-propoxy)-7-methoxy-quinolin-4-yloxy]-phenyl}-3-(3,3-dimethyl-butyl)-urea,
1-(3,3-Dimethyl-butyl)-3-{4-[7-methoxy-6-(4-morpholin-4-yl-butoxy)-quinolin-4-yloxy]-phenyl}-urea,
1-{4-[6-(4-Dimethylamino-butoxy)-7-methoxy-quinolin-4-yloxy]-phenyl}-3-(3,3-dimethyl-butyl)-urea,
1-(3,3-Dimethyl-butyl)-3-(4-{6-[3-(2,6-dimethyl-morpholin-4-yl)-propoxy]-7-methoxy-quinolin-4-yloxy}-3-fluoro-phenyl)-urea,
1-(3,3-Dimethyl-butyl)-3-(4-{7-[3-(2,6-dimethyl-morpholin-4-yl)-propoxy]-6-methoxy-quinolin-4-yloxy}-phenyl)-urea,
1-(3,3-Dimethyl-butyl)-3-(4-{7-[3-(3,5-dimethyl-piperidin-1-yl)-propoxy]-6-methoxy-quinolin-4-yloxy}-phenyl)-urea,
1-(3,3-Dimethyl-butyl)-3-(4-{6-methoxy-7-[3-(4-phenyl-piperidin-1-yl)-propoxy]-quinolin-4-yloxy}-phenyl)-urea,
1-(4-{7-[3-(4-Benzyl-piperidin-1-yl)-propoxy]-6-methoxy-quinolin-4-yloxy}-phenyl)-3-(3,3-dimethyl-butyl)-urea,
1-{4-[7-(3-[1,4']Bipiperidinyl-1'-yl-propoxy)-6-methoxy-quinolin-4-yloxy]-phenyl}-3-(3,3-dimethyl-butyl)-urea,
1-(3,3-Dimethyl-butyl)-3-(4-{6-methoxy-7-[3-(4-pyrrolidin-1-yl-piperidin-1-yl)-propoxy]-quinolin-4-yloxy}-phenyl)-urea,
1-(3,3-Dimethyl-butyl)-3-(4-{7-[3-(2,6-dimethyl-morpholin-4-yl)-2-hydroxy-propoxy]-6-methoxy-quinolin-4-yloxy}-phenyl)-urea,
1-(3,3-Dimethyl-butyl)-3-(4-{7-[3-(3,5-dimethyl-piperidin-1-yl)-2-hydroxy-propoxy]-6-methoxy-quinolin-4-yloxy}-phenyl)-urea,
1-(3,3-Dimethyl-butyl)-3-(4-{7-[2-hydroxy-3-(4-phenyl-piperidin-1-yl)-propoxy]-6-methoxy-quinolin-4-yloxy}-phenyl)-urea,
1-(4-{7-[3-(4-Benzyl-piperidin-1-yl)-2-hydroxy-propoxy]-6-methoxy-quinolin-4-yloxy}-phenyl)-3-(3,3-dimethyl-butyl)-urea,
1-{4-[7-(3-[1,4']Bipiperidineyl-1'-yl-2-hydroxy-propoxy)-6-methoxy-quinolin-4-yloxy]-phenyl}-3-(3,3-dimethyl-butyl)-urea,
1-(3,3-Dimethyl-butyl)-3-(4-{7-[2-hydroxy-3-(4-pyrrolidin-1-yl-piperidin-1-yl)-propoxy]-6-methoxy-quinolin-4-yloxy}-phenyl)-urea,
1-(3,3-Dimethyl-butyl)-3-(4-{7-[3-(2-hydroxymethyl-pyrrolidin-1-yl)-propoxy]-6-methoxy-quinolin-4-yloxy}-phenyl)-urea,
1-(3,3-Dimethyl-butyl)-3-(4-{7-[3-(4-hydroxymethyl-piperidin-1-yl)-propoxy]-6-methoxy-quinolin-4-yloxy}-phenyl)-urea,
1-(2-Chloro-4-{7-[3-(4-hydroxymethyl-piperidin-1-yl)-propoxy]-6-methoxy-quinolin-4-yloxy}-phenyl)-3-(3,3-dimethyl-butyl)-urea,
1-[2-Chloro-4-(7-{3-[4-(2-hydroxy-ethyl)-piperidin-1-yl]-propoxy}-6-methoxy-quinolin-4-yloxy)-phenyl]-3-(3,3-dimethyl-butyl)-urea,
1-(2-Chloro-4-{7-[3-(4-hydroxy-piperidin-1-yl)-propoxy]-6-methoxy-quinolin-4-yloxy}-phenyl)-3-(3,3-dimethyl-butyl)-urea,
1-(3,3-Dimethyl-butyl)-3-[4-(7-{3-[(2-hydroxy-ethyl)-methyl-amino]-propoxy}-6-methoxy-quinolin-4-yloxy)-phenyl]-urea,
1-(3,3-Dimethyl-butyl)-3-(4-{6-methoxy-7-[3-(2-methoxy-ethylamino)-propoxy]-quinolin-4-yloxy}-phenyl)-urea,
1-(2-Chloro-4-{7-[2-(4-hydroxy-piperidin-1-yl)-ethoxy]-6-methoxy-quinolin-4-yloxy}-phenyl)-3-(3,3-dimethyl-butyl)-urea,
1-(2-Chloro-4-{7-[2-(4-hydroxymethyl-piperidin-1-yl)-ethoxy]-6-methoxy-quinolin-4-yloxy}-phenyl)-3-(3,3-dimethyl-butyl)-urea,
1-(3,3-Dimethyl-butyl)-3-(4-{6-methoxy-7-[3-(4-methoxymethyl-piperidin-1-yl)-propoxy]-quinolin-4-yloxy}-phenyl)-urea,
1-(3,3-Dimethyl-butyl)-3-(3-fluoro-4-{7-[3-(4-hydroxymethyl-piperidin-1-yl)-propoxy]-6-methoxy-quinolin-4-yloxy}-phenyl)-urea,
1-(3,3-Dimethyl-butyl)-3-(3-fluoro-4-{7-[3-(4-hydroxy-piperidin-1-yl)-propoxy]-6-methoxy-quinolin-4-yloxy}-phenyl)-urea,
1-[2-Chloro-4-(7-{2-[4-(2-hydroxy-ethyl)-piperidin-1-yl]-ethoxy}-6-methoxy-quinolin-4-yloxy)-phenyl]-3-(3,3-dimethyl-butyl)-urea,
1-(3,3-Dimethyl-butyl)-3-(3-fluoro-4-{7-[2-(4-hydroxymethyl-piperidin-1-yl)-ethoxy]-6-methoxy-quinolin-4-yloxy}-phenyl)-urea,
1-(3,3-Dimethyl-butyl)-3-(3-fluoro-4-{7-[2-(4-hydroxy-piperidin-1-yl)-ethoxy]-methoxy-quinolin-4-yloxy}-phenyl)-urea,
1-(3,3-Dimethyl-butyl)-3-[3-fluoro-4-(7-{2-[4-(2-hydroxy-ethyl)-piperidin-1-yl]-ethoxy}-6-methoxy-quinolin-4-yloxy)-phenyl]-urea,
1-(3,3-Dimethyl-butyl)-3-[3-fluoro-4-(7-{3-[4-(2-hydroxy-ethyl)-piperidin-1-yl]-propoxy}-6-methoxy-quinolin-4-yloxy)-phenyl]-urea,
1-(3,3-Dimethyl-butyl)-3-(2-fluoro-4-{7-[2-(4-hydroxy-piperidin-1-yl)-ethoxy]-6-methoxy-quinolin-4-yloxy}-phenyl)-urea,
1-(3,3-Dimethyl-butyl)-3-(2-fluoro-4-{7-[2-(4-hydroxymethyl-piperidin-1-yl)-ethoxy]-6-methoxy-quinolin-4-yloxy}-phenyl)-urea, 1-(3,3-Dimethyl-butyl)-3-[2-fluoro-4-(7-{2-[4-(2-hydroxy-ethyl)-piperidin-1-yl]-ethoxy}-6-methoxy-quinolin-4-yloxy)-phenyl]-urea, 1-(3,3-Dimethyl-butyl)-3-(2-fluoro-4-{7-[3-(4-hydroxy-piperidin-1-yl)-propoxy]-6-methoxy-quinolin-4-yloxy}-phenyl)-urea, 1-(3,3-Dimethyl-butyl)-3-(2-fluoro-4-{7-[3-(4-hydroxymethyl-piperidin-1-yl)-propoxy]-6-methoxy-quinolin-4-yloxy}-phenyl )-urea, 1-(3,3-Dimethyl-butyl)-3-[2-fluoro-4-(7-{3-[4-(2-hydroxy-ethyl)-piperidin-1-yl]-propoxy}-6-methoxy-quinolin-4-yloxy)-phenyl]-urea, 1-(4-{7-[2-(1,1-Bis-hydroxymethyl-propylamino)-ethoxy]-6-methoxy-quinolin-4-yloxy}-phenyl)-3-(3,3-dimethyl-butyl)-urea, 1-(3,3-Dimethyl-butyl)-3-(4-{7-[2-(1-hydroxymethyl-cyclopenthylamino)-ethoxy]-6-methoxy-quinolin-4-yloxy}-phenyl)-urea, 1-[4-(7-{2-[Bis-(2-hydroxy-propyl)-amino]-ethoxy}-6-methoxy-quinolin-4-yloxy)-phenyl]-3-(3,3-dimethyl-butyl)-urea, 1-(3,3-Dimethyl-butyl)-3-(4-{7-[2-(2-hydroxy-1-methyl-ethylamino)-ethoxy]-6-methoxy-quinolin-4-yloxy}-phenyl)-urea, 1-[4-(7-{2-[Cyclohexyl-(2-hydroxy-ethyl)-amino]-ethoxy}-6-methoxy-quinolin-4-yloxy)-phenyl]-3-(3,3-dimethyl-butyl)-urea, 1-[4-(7-{2-[Benzyl-(2-hydroxy-ethyl)-amino]-ethoxy}-6-methoxy-quinolin-4-yloxy)-phenyl]-3-(3,3-dimethyl-butyl)-urea, 1-(3,3-Dimethyl-butyl)-3-[4-(7-{2-[(2-hydroxy-ethyl)-propyl-amino]-ethoxy}-6-methoxy-quinolin-4-yloxy)-phenyl]-urea, 1-(3,3-Dimethyl-butyl)-3-[4-(7-{2-[(2-hydroxy-ethyl)-isopropyl-amino]-ethoxy}-6-methoxy-quinolin-4-yloxy)-phenyl]-urea, 1-(3,3-Dimethyl-butyl)-3-(4-{7-[2-(4-hydroxymethyl-piperidin-1-yl)-ethoxy]-6-methoxy-quinolin-4-yloxy}-phenyl)-urea, 1-(3,3-Dimethyl-butyl)-3-(4-{7-[2-(2-hydroxy-ethylamino)-ethoxy]-6-methoxy-quinolin-4-yloxy}-phenyl)-urea, 1-(3,3-Dimethyl-butyl)-3-(4-{7-[2-(4-hydroxy-piperidin-1-yl)-ethoxy]-6-methoxy-quinolin-4-yloxy}-phenyl)-urea, 1-[3-Chloro-4-(6,7-dimethoxy-quinolin-4-yloxy)-phenyl]-3-(3,3-dimethyl-butyl)-urea, and 1-(3,3-Dimethyl-butyl)-3-{4-[6-methoxy-7-(2-morpholin-4-yl-2-oxo-ethoxy)-quinolin-4-yloxy]-phenyl}-urea.

9. The compound according to claim 4, wherein X represents CH.

10. The compound according to claim 4, wherein $R^{402}$ represents unsubstituted $C_{1-6}$ alkoxy and $R^{403}$ represents substituted $C_{1-6}$ alkoxy.

11. The compound according to claim 10, wherein $R^{402}$ represents unsubstituted methoxy.

12. The compound according to claim 10, wherein $R^{403}$ represents substituted $C_{2-4}$ alkoxy.

13. The compound according to claim 10, wherein $R^{403}$ represents $C_{1-6}$ alokoxy substituted by a saturated five- to seven-membered heterocyclic group containing one or two hetero atoms selected from the group consisting of O, S, and N.

14. The compound according to claim 13, wherein the heterocyclic group is selected from the group consisting of piperazinyl, piperazino, piperidyl, piperidino, morpholinyl, morpholino, homopiperazinyl, homopiperazino, thiomorpholinyl, thiomorpholino, tetrahydropyrrolyl, and azepanyl.

15. The compound according to claim 13, wherein the heterocyclic group is piperazino.

16. The compound according to claim 4, wherein $R^{406}$ represents a halogen atom and $R^{405}$, $R^{407}$, and $R^{408}$ represents a hydrogen atom.

17. The compound according to claim 16, wherein $R^{406}$ represents a fluorine atom.

18. The compound according to claim 4, wherein $R^{409}$ represents 3,3-dimethyl-butyl or 3,3-dimethyl-cyclohexyl.

19. The compound according to claim 18, wherein $R^{409}$ represents 3,3-dimethyl-butyl.

20. The compound of claim 1, wherein $R^{103}$ represents $C_{1-6}$ alkoxy in which the $C_{1-6}$ alkoxy group is substituted by hydroxyl; a halogen atom; $C_{1-6}$ alkoxy; C1-6 alkylcarbonyl; carboxyl; $C_{1-6}$ alkoxycarbonyl; -(C=O)-NR$^{14}$R$^{15}$ wherein $R^{14}$ and $R^{15}$, which may be the same or different, represent a hydrogen atom or $C_{1-4}$ alkyl optionally substituted by hydroxyl, or alternatively $R^{14}$ and $R^{15}$ may combine with the nitrogen atom attached thereto to form a saturated five- or six-membered heterocyclic group; amino in which one or two hydrogen atoms on the amino group are optionally substituted by $C_{1-6}$ alkyl or a saturated or unsaturated three- to eight-membered carbocyclic or heterocyclic group, and the $C_{1-6}$ alkyl group is optionally substituted by hydroxyl, $C_{1-6}$ alkoxy, or a saturated or unsaturated three-to eight-membered carbocyclic or heterocyclic group; or a saturated or unsaturated three- to eight-membered carbocyclic or heterocyclic group in which the carbocyclic or heterocyclic group is optionally substituted by hydroxyl, an oxygen atom, $C_{1-6}$ alkyl, $C_{2-6}$ alkenyl, $C_{2-6}$ alkynyl, $C_{1-6}$ alkoxy, $C_{1-6}$ alkoxycarbonyl, or a saturated or unsaturated three- to eight-membered carbocyclic or heterocyclic group; the $C_{1-6}$ alkyl, $C_{2-6}$ alkenyl, and $C_{2-6}$ alkynyl groups are optionally substituted by hydroxyl, $C_{1-6}$ alkoxy, or a saturated or unsaturated three- to eight-membered carbocyclic or heterocyclic group; when the carbocyclic or heterocyclic group is substituted by two $C_{1-6}$ alkyl groups, the two alkyl groups may combine together to form an alkylene chain; and the carbocyclic or heterocyclic group may be condensed with another saturated or unsaturated five- to seven-membered carbocyclic or heterocyclic group to form a bicyclic group.

21. The compound of claim 4, wherein $R^{402}$ and $R^{403}$, which may be the same or different, represent -O-(CH$_2$)p-R$^{13}$ wherein p is an integer of 0 to 6, -(CH$_2$)p- is substituted by $C_{1-6}$ alkyl, hydroxyl, or a halogen atom, and $R^{13}$ represents hydroxyl; a halogen atom; $C_{1-6}$ alkoxy; $C_{1-6}$alkylcarbonyl; carboxyl; $C_{1-6}$ alkoxycarbonyl; -(C=O)-NR$^{14}$R$^{15}$ wherein $R^{14}$ and $R^{15}$, which may be the same or different, represent a hydrogen atom or $C_{1-4}$ alkyl optionally substituted by hydroxyl, or alternatively $R^{14}$ and $R^{15}$ may combine with the nitrogen atom attached thereto to form a saturated five- or six-membered heterocyclic group; $C_{1-6}$alkoxycarbonyl; amino in which one or two hydrogen atoms on the amino group are optionally substituted by $C_{1-6}$alkyl or a saturated or unsaturated three- to eight-membered carbocyclic or heterocyclic group, and the $C_{1-6}$alkyl group is optionally substituted by hydroxyl, $C_{1-6}$alkoxy, or a saturated or unsaturated three- to eight-membered carbocyclic or heterocyclic group; or a saturated or unsaturated three- to eight-membered carbocyclic or heterocyclic group in which the carbocyclic or heterocyclic group is optionally substituted by hydroxyl, an oxygen atom, $C_{1-6}$alkyl, $C_{2-6}$ alkenyl, $C_{2-6}$ alkynyl, $C_{1-6}$alkoxy, $C_{1-6}$ alkoxycarbonyl, or a saturated or unsaturated three- to eight-membered carbocyclic or heterocyclic group; the $C_{1-6}$alkyl, $C_{2-6}$ alkenyl, and $C_{2-6}$ alkynyl groups are optionally substituted by hydroxyl, $C_{1-6}$alkoxy, or a saturated or unsaturated three- to eight-membered carbocyclic or heterocyclic group; when the carbocyclic or heterocyclic group is substituted by two $C_{1-6}$alkyl groups, the two alkyl groups may combine together to form an alkylene chain; and the carbocyclic or heterocyclic group may be condensed with another saturated or unsaturated five- to seven-membered carbocyclic or heterocyclic group to form a bicyclic group.

* * * * *